US009260701B2

(12) United States Patent
Payne et al.

(10) Patent No.: US 9,260,701 B2
(45) Date of Patent: *Feb. 16, 2016

(54) GLUCOSYLTRANSFERASE ENZYMES FOR PRODUCTION OF GLUCAN POLYMERS

(71) Applicant: E I DU PONT DE NEMOURS AND COMPANY, Wilmington, DE (US)

(72) Inventors: Mark S Payne, Wilmington, DE (US); Yefim Brun, Wilmington, DE (US); Hongxian He, Wilmington, DE (US); Thomas Scholz, Bear, DE (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 14/490,791

(22) Filed: Sep. 19, 2014

(65) Prior Publication Data

US 2015/0004651 A1    Jan. 1, 2015

Related U.S. Application Data

(62) Division of application No. 14/036,049, filed on Sep. 25, 2013, now Pat. No. 8,871,474.

(60) Provisional application No. 61/705,177, filed on Sep. 25, 2012, provisional application No. 61/705,178, filed on Sep. 25, 2012, provisional application No. 61/705,179, filed on Sep. 25, 2012, provisional application No. 61/705,180, filed on Sep. 25, 2012, provisional application No. 61/705,181, filed on Sep. 25, 2012.

(51) Int. Cl.
*C12P 19/18* (2006.01)
*C12N 9/10* (2006.01)
*C08B 37/00* (2006.01)
*C12P 19/04* (2006.01)

(52) U.S. Cl.
CPC .......... *C12N 9/1051* (2013.01); *C08B 37/0009* (2013.01); *C12N 9/1048* (2013.01); *C12P 19/04* (2013.01); *C12P 19/18* (2013.01); *C12Y 204/01005* (2013.01)

(58) Field of Classification Search
None
See application file for complete search history.

(56) References Cited

U.S. PATENT DOCUMENTS

| | | | |
|---|---|---|---|
| 5,952,205 | A | 9/1999 | Catani et al. |
| 6,242,225 | B1 | 6/2001 | Catani et al. |
| 6,660,502 | B2 | 12/2003 | Catani et al. |
| 7,000,000 | B1 | 2/2006 | O'Brien |
| 2013/0244287 | A1 | 9/2013 | O'Brien et al. |
| 2013/0244288 | A1 | 9/2013 | O'Brien et al. |

FOREIGN PATENT DOCUMENTS

| | | |
|---|---|---|
| JP | 2008-75075 A | 4/2008 |
| WO | 2013036918 A2 | 3/2013 |

OTHER PUBLICATIONS

Abo et al., Peptide Sequences for Sucrose Splitting and Glucan Binding Within Streptococcus Sobrinus Glucosyltransferase (Water-Insoluble Glucan Synthetase), Journal of Bacteriology, vol. 173, No. 3 (1991), pp. 989-996.
Cantarel et al., The Carbohydrate-Active Enzymes Database (CAZY): An Expert Resource for Glycogenomics, Nucleic Acids Research, vol. 37 (2009), Database Issue pp. D233-D238.
Konishi et al., Structure and Enzymatic Properties of Genetically Truncated Forms of the Water-Insoluable Glucan-Synthesizing Glucosyltransferase From *Streptococcus sobrinus*, J. Biochem., vol. 126 (1999), pp. 287-295.
Leemhuis et al., Glucansucrases: Three-Dimensional Structures, Reactions, Mechanism, α-Glucan Analysis and Their Implications in Biotechnology and Food Applications, Journal of Biotechnology, vol. 163 (2013), pp. 250-272.
Monchois et al., Cloning and Sequencing of a Gene Coding for a Novel Dextransucrase From Leuconostoc Mesenteroides NRRL B-1299 Synthesizing Only α(1-6) and α(1-3) Linkages, Gene, vol. 182 (1996), pp. 23-32.
Monchois et al., Isolation of an Active Catalytic Core of *Streptococcus downei* MFE28 GTF-I Glucosyltransferase, Journal of Bacteriology, vol. 181, No. 7 (1999), pp. 2290-2292.
Ogawa et al., Crystal Structure of (1→3)-α-D-Glucan, Fiber Differentiation Methods, vol. 47 (1980), pp. 353-362.
Simpson et al., Four Glucosyltransferases, GTFJ, GTFK, GTFL, and GTFM, From *Streptococcus salivarious* ATCC 25975, Microbiology, vol. 141 (1995), pp. 1451-1460.
Yoshimi et al., Functional Analysis of the α-1,3-Glucan Synthase Genes AGSA and AGSB in *Aspergillus nidulans*: AGSB is the Major α-1,3-Glucan Sytnase in This Fungus, PloS One, vol. 8, Issue 1 (2013), E54893, pp. 1-16.
Database UNIPROT, Retrieved From EBI Accession No. UNIPROT: Q0060, Database Accession No. Q00600 Sequence, Nov. 1, 1996 (XP002720581).
Giffard et al., Molecular Characterization of a Cluster of At Least Two Glucosyltransferase Genes in *Streptococcus salivarius* ATCC 25975, Journal of General Microbiology (1991), vol. 137, No. 11, pp. 2577-2593.
Kingston et al., Role of the C-Terminal YG Repeats of the Primer-Dependent Streptococcal Glucosyltransferase, GTFJ, In Binding to Dextran and Mutan, Microbiology (2002), vol. 148, No. Part 2, pp. 549-558.

*Primary Examiner* — Nashaat Nashed

(57) ABSTRACT

Reaction solutions are disclosed herein comprising water, sucrose and a glucosyltransferase enzyme that synthesizes poly alpha-1,3-glucan. The glucosyltransferase enzyme can synthesize insoluble glucan polymer having at least 50% alpha-1,3 glycosidic linkages and a number average degree of polymerization of at least 100. Further disclosed are methods of using such glucosyltransferase enzymes to produce insoluble poly alpha-1,3-glucan.

20 Claims, No Drawings

SEQUENCE LISTING

```
<160> NUMBER OF SEQ ID NOS: 64

<210> SEQ ID NO 1
<211> LENGTH: 4308
<212> TYPE: DNA
<213> ORGANISM: Streptococcus sobrinus

<400> SEQUENCE: 1
atggttgacg gcaaatacta ctattatgat caggacggta acgtaaagaa gaatttcgcg      60
gtgagcgttg gtgacaaaat ctactacttc gatgaaactg gtgcatataa ggataccagc     120
aaagtggacg ccgacaagag cagcagcgcg gttagccaaa acgcgaccat ctttgcggcg     180
aataaccgtg cgtacagcac ctctgcaaag aattttgaag cggtggataa ctacctgacc     240
gcagacagct ggtatcgtcc gaaatccatc ctgaaggacg gcaaaacctg gaccgagagc     300
ggtaaggatg atttccgtcc actgctgatg gcatggtggc ctgacaccga aactaagcgc     360
aactacgtga actatatgaa taaagtggtc ggtattgaca agacgtacac tgcggaaacg     420
tcgcaagcgg atttgaccgc agcggcggag ctggttcaag cgcgtatcga gcagaagatt     480
accagcgaaa acaacaccaa atggctgcgc gaagcaatct ccgcgttcgt taagacgcag     540
cctcagtgga acggcgagtc cgaaaagccg tatgacgatc acttgcagaa cggtgcgctg     600
ctgtttgata accaaaccga cctgacgcca gacacccaaa gcaattaccg tttgctgaac     660
cgtaccccga ccaatcagac tggtagcctg gatagccgtt ttacgtataa tccgaatgac     720
ccgttgggcg gctacgattt cttgctggcg aacgacgttg acaatagcaa tccggtcgtc     780
caggctgaac agttgaactg gctgcattat ctgctgaact ttggctctat ttacgctaac     840
gatgccgacg ccaattttga cagcattcgc gttgatgccg tcgataatgt cgatgctgat     900
ctgctgcaaa tcagcagcga ttacctgaaa gcagcgtatg gcatcgacaa gaataacaag     960
aatgcgaaca accatgttag catcgtcgaa gcgtggagcg acaatgatac cccgtatttg    1020
cacgacgatg gcgataatct gatgaacatg gacaacaaat ttcgcctgtc catgctgtgg    1080
agcctggcaa agccgctgga caaacgtagc ggtttgaacc cgctgattca caatagcctg    1140
gtggaccgcg aggtggacga tcgtgaagtg gaaaccgtgc cgtcctacag ctttgctcgt    1200
gcacatgata gcgaggtgca ggacatcatc cgtgacatta tcaaggctga gattaaccca    1260
aatagctttg gttatagctt cactcaagaa gagatcgagc aagcctttaa gatttacaac    1320
gaggatttga agaaaacgga caagaaatac acccactaca atgtgccgct gagctacacc    1380
ctgctgctga ccaacaaggg cagcatcccg cgtgtgtact atggtgatat gttcaccgat    1440
gatggccaat acatggcaaa caagaccgtc aactacgacg caatcgagag cctgctgaaa    1500
gcccgtatga aatatgtcag cggtggccaa gcaatgcaga actatcaaat tggtaatggc    1560
gagattttga ccagcgtgcg ctatggtaaa ggtgccctga gcagagcga taagggtgac    1620 gcgacgacgc gcactagcgg tgttggcgtg gttatgggta atcagccgaa cttctccctg    1680
gacggtaaag ttgtggccct gaatatgggt gcggcccatg cgaatcaaga ataccgtgca    1740
```

```
ctgatggtca gcactaaaga cggtgtggca acttacgcaa ccgatgctga cgcatccaaa      1800
gcgggcctgg tcaagcgtac cgacgagaac ggctacctgt acttcctgaa tgatgatctg      1860
aagggcgtcg cgaaccctca ggtttccggc ttcttgcaag tgtgggttcc agttggtgcc      1920
gccgatgacc aggacattcg cgtcgccgcc agcgacacgg cgagcacgga tggtaaaagc      1980
ctgcatcaag atgcggcgat ggacagccgc gtcatgtttg agggtttcag caattttcaa      2040
tccttcgcga ccaaagaaga agaatacacg aatgttgtta tcgcgaacaa tgtcgataag      2100
ttcgttagct ggggtatcac cgattttgaa atggctccgc agtatgttag cagcaccgac      2160
ggtcagttct tggacagcgt catccagaat ggctatgcgt ttactgatcg ctatgatctg      2220
ggtatgtcca aggcgaacaa gtatggcacg gcagaccaac tggttaaggc aatcaaagcc      2280
ctgcacgcta aaggcctgaa agttatggcg gactgggtcc cggatcaaat gtacaccttt      2340
ccaaaacagg aagttgtgac cgttacccgc accgacaaat tcggtaaacc gatcgccggc      2400
tctcaaatca atcacagctt gtatgtgacc gacaccaaat ccagcggcga cgactaccaa      2460
gcgaagtacg gcggtgcctt cctggatgaa ctgaaagaaa gtacccggga actgttcacg      2520
aaaaagcaaa ttagcacggg ccaagcgatt gatccgagcg tgaaaatcaa gcagtggagc      2580
gcaaaatact tcaatggttc gaatatcctg ggtcgcggtg cggactatgt gctgagcgac      2640
caggtcagca ataagtattt caacgtggcg agcgacacct tgttcctgcc gtccagcctg      2700
ctgggcaagg tcgtggagag cggcattcgt tacgacggca agggttacat ctacaacagc      2760
tccgcgaccg gcgatcaggt caaagcgtct ttcattacgg aagccggtaa cctgtattac      2820
ttcggcaaag acggttacat ggttactggt gcccagacga ttaatggcgc caactacttc      2880
ttcctggaaa acggtacggc actgcgtaat acgatttaca ccgatgctca aggtaatagc      2940
cactattacg cgaatgatgg caaacgctat gaaaatggct atcaacagtt cggtaacgat      3000
tggcgctact ttaaagatgg taacatggca gtcggcctga ccacggttga tggcaacgtg      3060
caatactttg acaagacgg cgtccaggca aggataaga ttatcgtcac ccgtgatggc      3120
aaggtccgtt acttcgatca gcacaacggt aacgcggcga ccaacacgtt cattgctgat      3180
aaaactggcc attggtatta cctgggtaaa gatggcgtcg cggtgactgg cgcccagacc      3240
gtcggcaaac aaaaactgta cttcgaggcc aacggtcaac aagttaaagg tgactttgtt      3300
acgtccgatg agggcaaact gtatttctat gacgttgatt ctggtgacat gtggacggac      3360
accttcatcg aggataaggc gggcaactgg ttctatttgg caaggatgg tgcggcagtt      3420
acgggtgccc aaacgattcg cggtcagaag ctgtacttca aggccaatgg tcaacaggtc      3480
aagggtgaca ttgttaaggg caccgacggt aaaatccgct actatgatgc aaaatccggt      3540
gaacaggtgt tcaacaaaac ggtgaaagct gcggatggca aaacgtatgt tatcggtaat      3600
gatggtgtcg cggtggaccc tagcgtggtt aaaggtcaaa cctttaagga cgcttcgggc      3660
gctctgcgtt tctacaactt gaagggtcaa ctggtcactg gcagcggctg gtatgaaacc      3720
gcgaaccatg actgggttta cattcagtcc ggcaaggcac tgaccggcga acagaccatt      3780
aacggtcaac acctgtattt caaagaagat ggtcaccaag tcaagggtca gttggtcacg      3840
ggcaccgatg gtaaagtgcg ttactatgac gccaacagcg gtgaccaagc attcaacaag      3900
agcgtcactg tgaatggtaa aacctattac tttggcaacg atggtacggc gcagactgct      3960
ggcaacccga agggtcagac gttcaaggat ggctccgaca tccgtttttta ctctatggaa      4020
ggccaactgg tgaccggctc gggttggtac gagaacgcgc aaggccagtg gctgtatgtg      4080
aaaaacggta aggtgctgac tggtctgcaa accgttggca gccagcgtgt ttacttcgac      4140
```

```
gagaatggta ttcaggccaa gggcaaagca gtgcgtacca gcgatggcaa aattcgttat   4200
ttcgacgaaa acagcggcag catgatcacg aatcaatgga agttcgtcta tggtcagtat   4260
tactactttg gtaacgacgg tgcacgtatt taccgtggtt ggaactaa               4308
```

<210> SEQ ID NO 2
<211> LENGTH: 1435
<212> TYPE: PRT
<213> ORGANISM: Streptococcus sobrinus

<400> SEQUENCE: 2

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
            20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
    50                  55                  60

Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Asn Asp Ala Asp Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
```

-continued

```
                340                 345                 350
Lys Phe Arg Leu Ser Met Leu Trp Ser Leu Ala Lys Pro Leu Asp Lys
                355                 360                 365

Arg Ser Gly Leu Asn Pro Leu Ile His Asn Ser Leu Val Asp Arg Glu
            370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Glu Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
        450                 455                 460

Asn Lys Gly Ser Ile Pro Arg Val Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gln Ala Met
            500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
        530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
        610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Met Asp Ser Arg Val Met
            660                 665                 670

Phe Glu Gly Phe Ser Asn Phe Gln Ser Phe Ala Thr Lys Glu Glu Glu
            675                 680                 685

Tyr Thr Asn Val Val Ile Ala Asn Asn Val Asp Lys Phe Val Ser Trp
        690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765
```

-continued

```
Met Ala Asp Trp Val Pro Asp Gln Met Tyr Thr Phe Pro Lys Gln Glu
            770                 775                 780
Val Val Thr Val Thr Arg Thr Asp Lys Phe Gly Lys Pro Ile Ala Gly
785                 790                 795                 800
Ser Gln Ile Asn His Ser Leu Tyr Val Thr Asp Thr Lys Ser Ser Gly
                805                 810                 815
Asp Asp Tyr Gln Ala Lys Tyr Gly Gly Ala Phe Leu Asp Glu Leu Lys
                820                 825                 830
Glu Lys Tyr Pro Glu Leu Phe Thr Lys Lys Gln Ile Ser Thr Gly Gln
            835                 840                 845
Ala Ile Asp Pro Ser Val Lys Ile Lys Gln Trp Ser Ala Lys Tyr Phe
            850                 855                 860
Asn Gly Ser Asn Ile Leu Gly Arg Gly Ala Asp Tyr Val Leu Ser Asp
865                 870                 875                 880
Gln Val Ser Asn Lys Tyr Phe Asn Val Ala Ser Asp Thr Leu Phe Leu
                885                 890                 895
Pro Ser Ser Leu Leu Gly Lys Val Val Glu Ser Gly Ile Arg Tyr Asp
            900                 905                 910
Gly Lys Gly Tyr Ile Tyr Asn Ser Ser Ala Thr Gly Asp Gln Val Lys
            915                 920                 925
Ala Ser Phe Ile Thr Glu Ala Gly Asn Leu Tyr Tyr Phe Gly Lys Asp
            930                 935                 940
Gly Tyr Met Val Thr Gly Ala Gln Thr Ile Asn Gly Ala Asn Tyr Phe
945                 950                 955                 960
Phe Leu Glu Asn Gly Thr Ala Leu Arg Asn Thr Ile Tyr Thr Asp Ala
                965                 970                 975
Gln Gly Asn Ser His Tyr Tyr Ala Asn Asp Gly Lys Arg Tyr Glu Asn
                980                 985                 990
Gly Tyr Gln Gln Phe Gly Asn Asp Trp Arg Tyr Phe Lys Asp Gly Asn
            995                 1000                1005
Met Ala Val Gly Leu Thr Thr Val Asp Gly Asn Val Gln Tyr Phe
            1010                1015                1020
Asp Lys Asp Gly Val Gln Ala Lys Asp Lys Ile Ile Val Thr Arg
    1025                1030                1035
Asp Gly Lys Val Arg Tyr Phe Asp Gln His Asn Gly Asn Ala Ala
    1040                1045                1050
Thr Asn Thr Phe Ile Ala Asp Lys Thr Gly His Trp Tyr Tyr Leu
    1055                1060                1065
Gly Lys Asp Gly Val Ala Val Thr Gly Ala Gln Thr Val Gly Lys
    1070                1075                1080
Gln Lys Leu Tyr Phe Glu Ala Asn Gly Gln Gln Val Lys Gly Asp
    1085                1090                1095
Phe Val Thr Ser Asp Glu Gly Lys Leu Tyr Phe Tyr Asp Val Asp
    1100                1105                1110
Ser Gly Asp Met Trp Thr Asp Thr Phe Ile Glu Asp Lys Ala Gly
    1115                1120                1125
Asn Trp Phe Tyr Leu Gly Lys Asp Gly Ala Ala Val Thr Gly Ala
    1130                1135                1140
Gln Thr Ile Arg Gly Gln Lys Leu Tyr Phe Lys Ala Asn Gly Gln
    1145                1150                1155
Gln Val Lys Gly Asp Ile Val Lys Gly Thr Asp Gly Lys Ile Arg
    1160                1165                1170
```

Tyr Tyr Asp Ala Lys Ser Gly Glu Gln Val Phe Asn Lys Thr Val
1175                1180                1185

Lys Ala Ala Asp Gly Lys Thr Tyr Val Ile Gly Asn Asp Gly Val
1190                1195                1200

Ala Val Asp Pro Ser Val Val Lys Gly Gln Thr Phe Lys Asp Ala
1205                1210                1215

Ser Gly Ala Leu Arg Phe Tyr Asn Leu Lys Gly Gln Leu Val Thr
1220                1225                1230

Gly Ser Gly Trp Tyr Glu Thr Ala Asn His Asp Trp Val Tyr Ile
1235                1240                1245

Gln Ser Gly Lys Ala Leu Thr Gly Glu Gln Thr Ile Asn Gly Gln
1250                1255                1260

His Leu Tyr Phe Lys Glu Asp Gly His Gln Val Lys Gly Gln Leu
1265                1270                1275

Val Thr Gly Thr Asp Gly Lys Val Arg Tyr Tyr Asp Ala Asn Ser
1280                1285                1290

Gly Asp Gln Ala Phe Asn Lys Ser Val Thr Val Asn Gly Lys Thr
1295                1300                1305

Tyr Tyr Phe Gly Asn Asp Gly Thr Ala Gln Thr Ala Gly Asn Pro
1310                1315                1320

Lys Gly Gln Thr Phe Lys Asp Gly Ser Asp Ile Arg Phe Tyr Ser
1325                1330                1335

Met Glu Gly Gln Leu Val Thr Gly Ser Gly Trp Tyr Glu Asn Ala
1340                1345                1350

Gln Gly Gln Trp Leu Tyr Val Lys Asn Gly Lys Val Leu Thr Gly
1355                1360                1365

Leu Gln Thr Val Gly Ser Gln Arg Val Tyr Phe Asp Glu Asn Gly
1370                1375                1380

Ile Gln Ala Lys Gly Lys Ala Val Arg Thr Ser Asp Gly Lys Ile
1385                1390                1395

Arg Tyr Phe Asp Glu Asn Ser Gly Ser Met Ile Thr Asn Gln Trp
1400                1405                1410

Lys Phe Val Tyr Gly Gln Tyr Tyr Phe Gly Asn Asp Gly Ala
1415                1420                1425

Arg Ile Tyr Arg Gly Trp Asn
1430                1435

<210> SEQ ID NO 3
<211> LENGTH: 4026
<212> TYPE: DNA
<213> ORGANISM: Streptococcus salivarius

<400> SEQUENCE: 3
atgatcgacg gcaaatacta ttatgttaat gaggacggta gccacaaaga aaactttgcg     60
attacggtta atggtcaact gctgtatttc ggtaaggacg cgcactgac ctctagcagc    120 acttacagct ttaccccagg tacgacgaac atcgtggatg ctttttctat caacaaccgc    180
gcgtatgact ccagcgaagc gtcctttgaa ctgattgatg gctacttgac tgccgactcc    240
tggtatcgtc cggcttccat catcaaggac ggtgtcacgt ggcaggccag caccgcagag    300
gactttcgcc cgctgctgat ggcgtggtgg ccaaacgtgg atacccaggt gaactatctg    360
aactacatgt ctaaagtgtt taacctggac gcaaagtata gcagcaccga taaacaagag    420
actctgaagt tgcagctaa ggatattcag attaagatcg agcagaaaat tcaggcggag    480
aaaagcaccc aatggctgcg cgaaacgatc agcgcttttg tgaaaaccca accacagtgg    540

| | | | |
|---|---|---|---|
| aacaaagaga ctgagaatta ctcgaaaggt ggtggtgagg atcatctgca aggcggtgca | 600 |
| ctgctgtacg tgaatgatag ccgtacccccg tgggcaaata gcgattatcg ccgcctgaac | 660 |
| cgcaccgcta ccaatcaaac gggtacgatt gacaagtcca ttctggacga gcagagcgac | 720 |
| ccaaatcaca tgggcggttt cgacttcctg ctggcgaatg atgttgacct gtccaacccg | 780 |
| gttgtgcagg cagagcagct gaaccagatt cactacttga tgaattgggg ctctatcgtg | 840 |
| atgggtgaca aagacgcaaa cttttgatggt atccgtgtcg atgcagttga caacgtcgat | 900 |
| gccgacatgc tgcaactgta taccaactac ttccgtgaat actacggtgt aacaaaagc | 960 |
| gaagcgaacg cactggcgca cattagcgtt ttggaagcgt ggagcttgaa tgataatcac | 1020 |
| tacaacgaca aaaccgatgg tgcagcattg gcgatggaga ataagcagcg tctggcgctg | 1080 |
| ctgtttagcc tggctaaacc gattaaagag cgcaccccgg cagtgagccc gctgtataac | 1140 |
| aacaccttca atacgaccca acgcgatgag aaaaccgact ggatcaataa agacggttct | 1200 |
| aaggcctata cgaggatgg tactgtgaag cagagccacca ttggtaagta caatgaaaaa | 1260 |
| tatggtgatg catcgggcaa ttatgtgttc atccgtgccc atgataacaa tgtccaagac | 1320 |
| atcattgcgg agatcattaa gaaagaaatc aacccgaaaa gcgatggttt caccatcact | 1380 |
| gacgccgaaa tgaaacaagc gttcgagatt tacaataagg acatgctgag cagcgacaag | 1440 |
| aagtacaccc tgaataacat cccggcagct tatgccgtga tgttgcagaa catggaaacg | 1500 |
| attacccgtg tctattatgg tgacctgtac accgacgacg gccactacat ggaaaccaag | 1560 |
| tccccgtatt acgacaccat cgttaacctg atgaaaagcc gtatcaagta cgtcagcggt | 1620 |
| ggccaggccc aacgtagcta ctggctgccg accgacggca gatggacaa tagcgacgtt | 1680 |
| gagctgtatc gcaccaacga agtgtatacc agcgtccgtt acggtaaaga cattatgacc | 1740 |
| gcgaacgata ccgagggtag caagtacagc cgcaccagcg gccaggtcac cctggttgca | 1800 |
| aacaacccga agctgaccct ggaccagagc gcgaagctga atgtggaaat gggtaagatt | 1860 |
| cacgcgaatc agaaataccg tgccctgatt gtgggcacgg ctgacggtat caagaatttc | 1920 |
| accagcgacg cagatgctat cgcggcaggc tacgtgaaag aaaccgactc caatggcgtt | 1980 |
| ctgactttttg gcgctaatga catcaaaggt tatgaaacct cgacatgtc cggctttgtt | 2040 |
| gctgtttggg tgccggtcgg cgcgagcgat gatcaggaca ttcgtgtcgc tcctagcact | 2100 |
| gaggccaaga aagagggtga attgaccctg aaagcgaccg aagcatacga ttcccagctg | 2160 |
| atctatgaag gttttagcaa ttttcaaacc atcccggatg gtagcgaccc gagcgtgtac | 2220 |
| accaatcgca gatcgcaga gaacgtggac ctgttcaagt cctggggtgt tacctcgttt | 2280 |
| gaaatggcac cgcagttcgt ttccgcagat gatggcactt ttctggactc tgtgatccaa | 2340 |
| aacggctatg cgtttgccga tcgttacgat ttggcgatga gcaagaacaa caaatacggc | 2400 |
| agcaaagagg acttgcgtga cgcgctgaaa gccctgcata agcaggcat ccaggcgatt | 2460 |
| gcagactggg tcccggacca gatttatcag ttgccgggca aagaagtggt cacggcgact | 2520 |
| cgcaccgacg gcgcaggccg taaaatcgcg gacgcgatca ttgatcatag cctgtacgtt | 2580 |
| gcgaacacta agagcagcgg caaagattac caggcgaagt acggtggtga gttcttggcg | 2640 |
| gagctgaagg ccaagtaccc ggagatgttc aaagtgaaca tgatttctac cggcaaaccg | 2700 |
| attgatgaca gcgtcaaact gaaacagtgg aaagcagaat actttaacgg caccaacgtc | 2760 |
| ttggagcgcg gtgtgggtta tgtcctgagc gatgaagcca cgggtaaata ctttaccgtc | 2820 |
| acgaaggatg gcaacttcat tccgttgcag ctgacgggta atgagaaagt cgtgaccggc | 2880 |

```
tttagcaatg atggcaaagg tatcacctac ttcggtacga gcggcactca agcgaaatct   2940
gcgttcgtta cgttcaatgg taatacttac tattttgacg ctcgtggtca catggttacg   3000
aacggcgagt attcgccgaa cggtaaggat gtttaccgtt tcctgccgaa tggtattatg   3060
ctgtctaacg cttttttacgt tgatgcaaat ggtaacacgt acctgtacaa cagcaagggc   3120
caaatgtaca aaggcggtta caccaaattt gacgttaccg aaacggacaa agatggtaag   3180
gaaagcaagg tggtgaagtt tcgttacttt acgaacgaag gtgtcatggc aaaaggcgtt   3240
accgtgattg acggcttcac gcaatacttt ggtgaagatg gtttccaagc gaaagacaag   3300
ctggtcacgt tcaagggcaa gacgtactac ttcgatgcac acaccggcaa tgcgatcaag   3360
gacacctggc gtaatatcaa tggcaagtgg tatcatttcg acgcgaacgg cgttgcagcg   3420
accggcgctc aggtcatcaa tggccaaaaa ctgtatttca cgaggacgg cagccaagtg   3480 aaaggcggtg ttgtcaaaaa cgcggacggt acgtattcta atacaaaga gggttctggt   3540 gaactggtta ccaacgagtt cttcacgacg gatggcaatg tttggtacta cgcaggcgcg   3600
aatggcaaga ccgttacggg tgcccaggtg attaacggcc aacacctgta cttcaatgcg   3660
gacggttcgc aagtgaaggg cggtgtggtc aagaacgcgg atggcaccta tagcaaatat   3720
gatgcgtcta ccgcgaacg cctgaccaat gagttttca ccacgggtga taacaactgg   3780
tactacattg gcgcaaacgg caagagcgtg acgggcgagg tcaagatcgg tgacgatacc   3840
tatttctttg ccaaagatgg caagcaagtt aagggtcaaa ctgtcagcgc gggtaacggt   3900
cgtattagct actactatgg tgatagcggt aagcgtgcgg tgagcacttg gatcgaaatc   3960
caaccgggtg tttatgtcta cttcgacaag aacggcattg cctatccgcc tcgtgtgctg   4020
aattaa                                                              4026
```

<210> SEQ ID NO 4
<211> LENGTH: 1341
<212> TYPE: PRT
<213> ORGANISM: Streptococcus salivarius

<400> SEQUENCE: 4

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
```

```
            165                 170                 175
Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
            195                 200                 205

Thr Pro Trp Ala Asn Ser Asp Tyr Arg Arg Leu Asn Arg Thr Ala Thr
            210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Gln Ala Glu Gln Leu Asn Gln Ile His Tyr
                260                 265                 270

Leu Met Asn Trp Gly Ser Ile Val Met Gly Asp Lys Asp Ala Asn Phe
                275                 280                 285

Asp Gly Ile Arg Val Asp Ala Val Asp Asn Val Asp Ala Asp Met Leu
            290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
            370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
                500                 505                 510

Asp Gly His Tyr Met Glu Thr Lys Ser Pro Tyr Tyr Asp Thr Ile Val
            515                 520                 525

Asn Leu Met Lys Ser Arg Ile Lys Tyr Val Ser Gly Gly Gln Ala Gln
            530                 535                 540

Arg Ser Tyr Trp Leu Pro Thr Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
                580                 585                 590
```

-continued

```
Ser Gly Gln Val Thr Leu Val Ala Asn Asn Pro Lys Leu Thr Leu Asp
            595                 600                 605

Gln Ser Ala Lys Leu Asn Val Glu Met Gly Lys Ile His Ala Asn Gln
        610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
        915                 920                 925

Leu Ser Asp Glu Ala Thr Gly Lys Tyr Phe Thr Val Thr Lys Asp Gly
    930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
            980                 985                 990

Asp Ala Arg Gly His Met Val Thr  Asn Gly Glu Tyr Ser  Pro Asn Gly
        995                 1000                1005
```

```
Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Ser
    1025                1030                1035

Lys Gly Gln Met Tyr Lys Gly Gly Tyr Thr Lys Phe Asp Val Thr
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Ala Ile Lys Asp Thr Trp Arg Asn Ile Asn Gly
    1115                1120                1125

Lys Trp Tyr His Phe Asp Ala Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ser Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
    1265                1270                1275

Asp Thr Tyr Phe Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Ile Glu Ile Gln Pro Gly
    1310                1315                1320

Val Tyr Val Tyr Phe Asp Lys Asn Gly Ile Ala Tyr Pro Pro Arg
    1325                1330                1335

Val Leu Asn
    1340

<210> SEQ ID NO 5
<211> LENGTH: 3744
<212> TYPE: DNA
<213> ORGANISM: Streptococcus salivarius

<400> SEQUENCE: 5
atgccaagcc acattaagac catcaacggc aaacaatact acgtggagga tgacggtacg      60
```

```
attcgcaaga attacgtcct ggagcgtatc ggtggcagcc aatactttaa tgcagaaacc    120
ggtgaactgt ctaatcagaa agagtatcgt ttcgacaaaa atggtggtac tggtagcagc    180
gcggacagca cgaacaccaa cgtgactgtg aacggtgaca aaaacgcatt ttacggtacc    240
acggacaaag acattgagct ggtcgacggc tatttcaccg cgaacacctg gtatcgcccg    300
aaagaaatcc tgaaagacgg caaagaatgg accgccagca cggagaacga taaacgcccg    360
ctgctgaccg tctggtggcc tagcaaagca atccaggcgt cttatctgaa ctacatgaaa    420
gagcaaggcc tgggtaccaa ccaaacgtac acgagcttct ccagccaaac ccaaatggat    480
caagcagccc tggaagtgca aaagcgtatt gaagagcgca tcgcacgcga gggcaatacc    540
gactggctgc gcacgaccat caagaacttc gtgaaaaccc aaccgggttg gaacagcacc    600
tctgaaaatc tggacaataa tgatcatctg caaggtggcg ccctgctgta caataacgac    660
tcccgcacga gccacgcgaa cagcgactat cgcctgctga atcgtacgcc gaccagccag    720
accggcaaac acaatccgaa atacaccaaa gataccagca atggtggttt cgaatttctg    780
ctggcgaacg acatcgataa ctctaatccg gcggttcaag cagagcaact gaactggctg    840
cattacatta tgaacatcgg taccatcacg ggcggttctg aggatgaaaa cttcgacggc    900
gttcgtgttg acgctgtgga taatgtgaat gcggatctgc tgcaaatcgc gagcgactat    960
ttcaaagcaa atacggtgc tgatcaaagc caagatcagg cgatcaaaca cttgagcatc   1020
ctggaagcgt ggtcccataa cgacgcctac tataacgaag ataccaaagg cgcgcagttg   1080
ccgatggatg atccgatgca cctggctctg gtctactcgc tgctgcgtcc gatcggcaat   1140
cgcagcggtg tggaaccgct gatttccaac agcctgaatg accgtagcga gtccggtaag   1200
aacagcaaac gtatggcgaa ctacgcgttc gtacgcgcgc atgatagcga ggtgcaatcg   1260
attattggcc agatcatcaa aaacgagatc aatccgcaaa gcaccggtaa tacgttcacc   1320
ctggatgaga tgaagaaagc gtttgagatt tacaacaagg atatgcgtag cgcgaataag   1380
cagtatacgc agtacaacat cccgagcgcg tatgcgttga tgctgaccca aaggatacc   1440 gttccgcgtg tgtattacgg tgatatgtat acggacgacg gtcagtacat ggcgcaaaag   1500
agcccatact atgatgcgat cgaaacgctg ctgaaaggtc gcatccgcta tgccgcaggt   1560
ggtcaggaca tgaaggtcaa ctatattggt tacggtaaca ctaacggctg ggatgctgcg   1620
ggcgtgctga ccagcgtacg ttatggcacg ggcgcaaata cgccagcga tacgggtacc   1680 gccgaaacgc gtaatcaagg tatggcagtg attgttagca accaaccggc gctgcgtctg   1740
actagcaatt tgaccattaa catgggtgcc gcacaccgta tcaggcttaa ccgtccgctg   1800
ctgctgacga ccaacgatgg cgtcgcgacc tatttgaacg atagcgatgc gaatggtatc   1860
gttaagtaca ccgacggtaa tggtaatctg acccttctccg caaacgagat tcgtggcatc   1920
cgtaacccgc aagttgatgg ctatctggcc gtctgggttc cggtaggtgc gtcggagaat   1980
caggatgttc gtgtggcgcc gagcaaagag aagaacagct ccggtctggt ttacgagagc   2040
aatgctgccc tggatagcca agttatctac gaaggcttca gcaacttcca ggacttcgtt   2100
cagaatccga gccagtatac caacaaaaag attgcagaga atgcaaattt gttcaaatcc   2160
tggggtatta ccagctttga atttgcgccg cagtacgtga gctcggatga tggtagcttc   2220
ctggacagcg ttattcagaa cggttatgcg tttacggacc gctacgacat tggtatgagc   2280
aaagacaaca aatatggttc gctggcggat ttgaaggcag cactgaagag cttgcatgcc   2340
gttggtatta gcgcaatcgc ggattggggtt cctgatcaga tctacaatct gccaggcgac   2400
gaggtcgtca ccgcaacccg cgttaacaac tacggcgaaa ccaaagatgg tgcaatcatt   2460
```

```
gatcactctt tgtacgcggc caaaacccgt acttttggta acgactacca gggtaagtat    2520
ggtggtgcgt tcctggacga gctgaaacgt ctgtatccgc agatctttga ccgcgttcag    2580
atttctaccg gtaagcgcat gaccacggac gagaagatca cccaatggtc tgcaaagtat    2640
atgaacggta cgaacatctt ggaccgtggc tctgaatacg ttttgaagaa tggtctgaat    2700
ggttactatg gcaccaatgg tggcaaagtt tcgctgccga agttgtggg tagcaatcaa    2760 agcacgaatg gcgacaatca aaacggcgac ggtagcggca agtttgaaaa gcgtctgttc    2820
agcgtgcgtt accgttataa caatggccag tacgcgaaaa atgcctttat caaagataac    2880
gacggcaatg tttactattt cgacaatagc ggtcgtatgg ctgtcggtga aaaacgatt    2940 gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga gcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg gtgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tggcaacctg cgctattacg acgttaacag cggtgagctg    3480
taccgtaatc gtttccacga aatcgacggc agctggtatt actttgatgg taacggtaat    3540
gcggtgaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag gttggtgggt ttactttgac    3720
ggtgaaggtc gtggtcagat ctaa                                          3744
```

<210> SEQ ID NO 6
<211> LENGTH: 1247
<212> TYPE: PRT
<213> ORGANISM: Streptococcus salivarius

<400> SEQUENCE: 6

```
Met Pro Ser His Ile Lys Thr Ile Asn Gly Lys Gln Tyr Tyr Val Glu
1               5                   10                  15

Asp Asp Gly Thr Ile Arg Lys Asn Tyr Val Leu Glu Arg Ile Gly Gly
            20                  25                  30

Ser Gln Tyr Phe Asn Ala Glu Thr Gly Glu Leu Ser Asn Gln Lys Glu
        35                  40                  45

Tyr Arg Phe Asp Lys Asn Gly Gly Thr Gly Ser Ser Ala Asp Ser Thr
    50                  55                  60

Asn Thr Asn Val Thr Val Asn Gly Asp Lys Asn Ala Phe Tyr Gly Thr
65                  70                  75                  80

Thr Asp Lys Asp Ile Glu Leu Val Asp Gly Tyr Phe Thr Ala Asn Thr
                85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
        115                 120                 125

Lys Ala Ile Gln Ala Ser Tyr Leu Asn Tyr Met Lys Glu Gln Gly Leu
    130                 135                 140
```

```
Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Arg Ile Ala Arg
            165                 170                 175

Glu Gly Asn Thr Asp Trp Leu Arg Thr Thr Ile Lys Asn Phe Val Lys
                180                 185                 190

Thr Gln Pro Gly Trp Asn Ser Thr Ser Glu Asn Leu Asp Asn Asn Asp
        195                 200                 205

His Leu Gln Gly Gly Ala Leu Leu Tyr Asn Asn Asp Ser Arg Thr Ser
    210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
                245                 250                 255

Phe Glu Phe Leu Leu Ala Asn Asp Ile Asp Asn Ser Asn Pro Ala Val
                260                 265                 270

Gln Ala Glu Gln Leu Asn Trp Leu His Tyr Ile Met Asn Ile Gly Thr
            275                 280                 285

Ile Thr Gly Gly Ser Glu Asp Glu Asn Phe Asp Gly Val Arg Val Asp
            290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
                340                 345                 350

Glu Asp Thr Lys Gly Ala Gln Leu Pro Met Asp Asp Pro Met His Leu
            355                 360                 365

Ala Leu Val Tyr Ser Leu Leu Arg Pro Ile Gly Asn Arg Ser Gly Val
        370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Ile Gly Gln Ile Ile Lys Asn Glu Ile Asn Pro
            420                 425                 430

Gln Ser Thr Gly Asn Thr Phe Thr Leu Asp Glu Met Lys Lys Ala Phe
        435                 440                 445

Glu Ile Tyr Asn Lys Asp Met Arg Ser Ala Asn Lys Gln Tyr Thr Gln
    450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
            500                 505                 510

Gly Arg Ile Arg Tyr Ala Ala Gly Gly Gln Asp Met Lys Val Asn Tyr
            515                 520                 525

Ile Gly Tyr Gly Asn Thr Asn Gly Trp Asp Ala Ala Gly Val Leu Thr
        530                 535                 540

Ser Val Arg Tyr Gly Thr Gly Ala Asn Ser Ala Ser Asp Thr Gly Thr
545                 550                 555                 560
```

```
Ala Glu Thr Arg Asn Gln Gly Met Ala Val Ile Val Ser Asn Gln Pro
            565                 570                 575
Ala Leu Arg Leu Thr Ser Asn Leu Thr Ile Asn Met Gly Ala Ala His
        580                 585                 590
Arg Asn Gln Ala Tyr Arg Pro Leu Leu Leu Thr Thr Asn Asp Gly Val
        595                 600                 605
Ala Thr Tyr Leu Asn Asp Ser Asp Ala Asn Gly Ile Val Lys Tyr Thr
610                 615                 620
Asp Gly Asn Gly Asn Leu Thr Phe Ser Ala Asn Glu Ile Arg Gly Ile
625                 630                 635                 640
Arg Asn Pro Gln Val Asp Gly Tyr Leu Ala Val Trp Val Pro Val Gly
                645                 650                 655
Ala Ser Glu Asn Gln Asp Val Arg Val Ala Pro Ser Lys Glu Lys Asn
            660                 665                 670
Ser Ser Gly Leu Val Tyr Glu Ser Asn Ala Ala Leu Asp Ser Gln Val
        675                 680                 685
Ile Tyr Glu Gly Phe Ser Asn Phe Gln Asp Phe Val Gln Asn Pro Ser
        690                 695                 700
Gln Tyr Thr Asn Lys Lys Ile Ala Glu Asn Ala Asn Leu Phe Lys Ser
705                 710                 715                 720
Trp Gly Ile Thr Ser Phe Glu Phe Ala Pro Gln Tyr Val Ser Ser Asp
                725                 730                 735
Asp Gly Ser Phe Leu Asp Ser Val Ile Gln Asn Gly Tyr Ala Phe Thr
            740                 745                 750
Asp Arg Tyr Asp Ile Gly Met Ser Lys Asp Asn Lys Tyr Gly Ser Leu
        755                 760                 765
Ala Asp Leu Lys Ala Ala Leu Lys Ser Leu His Ala Val Gly Ile Ser
        770                 775                 780
Ala Ile Ala Asp Trp Val Pro Asp Gln Ile Tyr Asn Leu Pro Gly Asp
785                 790                 795                 800
Glu Val Val Thr Ala Thr Arg Val Asn Asn Tyr Gly Glu Thr Lys Asp
                805                 810                 815
Gly Ala Ile Ile Asp His Ser Leu Tyr Ala Ala Lys Thr Arg Thr Phe
            820                 825                 830
Gly Asn Asp Tyr Gln Gly Lys Tyr Gly Gly Ala Phe Leu Asp Glu Leu
        835                 840                 845
Lys Arg Leu Tyr Pro Gln Ile Phe Asp Arg Val Gln Ile Ser Thr Gly
        850                 855                 860
Lys Arg Met Thr Thr Asp Glu Lys Ile Thr Gln Trp Ser Ala Lys Tyr
865                 870                 875                 880
Met Asn Gly Thr Asn Ile Leu Asp Arg Gly Ser Glu Tyr Val Leu Lys
                885                 890                 895
Asn Gly Leu Asn Gly Tyr Tyr Gly Thr Asn Gly Gly Lys Val Ser Leu
            900                 905                 910
Pro Lys Val Val Gly Ser Asn Gln Ser Thr Asn Gly Asp Asn Gln Asn
        915                 920                 925
Gly Asp Gly Ser Gly Lys Phe Glu Lys Arg Leu Phe Ser Val Arg Tyr
        930                 935                 940
Arg Tyr Asn Asn Gly Gln Tyr Ala Lys Asn Ala Phe Ile Lys Asp Asn
945                 950                 955                 960
Asp Gly Asn Val Tyr Tyr Phe Asp Asn Ser Gly Arg Met Ala Val Gly
                965                 970                 975
Glu Lys Thr Ile Asp Gly Lys Gln Tyr Phe Phe Leu Ala Asn Gly Val
```

| | | | | | | | | | | |
|---|---|---|---|---|---|---|---|---|---|---|
| | | 980 | | | 985 | | | 990 | | |
| Gln | Leu | Arg | Asp | Gly | Tyr | Arg | Gln | Asn | Arg | Arg | Gly | Gln | Val | Phe | Tyr |

Gln Leu Arg Asp Gly Tyr Arg Gln  Asn Arg Arg Gly Gln  Val Phe Tyr
            980                 985                990
    995                 1000               1005
Tyr Asp  Gln Asn Gly Val Leu  Asn Ala Asn Gly Lys   Gln Asp Pro
    1010              1015                1020
Lys Pro  Asp Asn Asn Asn Asn  Ala Ser Gly Arg Asn   Gln Phe Val
    1025              1030                1035
Gln Ile  Gly Asn Asn Val Trp  Ala Tyr Tyr Asp Gly   Asn Gly Lys
    1040              1045                1050
Arg Val  Thr Gly His Gln Asn  Ile Asn Gly Gln Glu   Leu Phe Phe
    1055              1060                1065
Asp Asn  Asn Gly Val Gln Val  Lys Gly Arg Thr Val   Asn Glu Asn
    1070              1075                1080
Gly Ala  Ile Arg Tyr Tyr Asp  Ala Asn Ser Gly Glu   Met Ala Arg
    1085              1090                1095
Asn Arg  Phe Ala Glu Ile Glu  Pro Gly Val Trp Ala   Tyr Phe Asn
    1100              1105                1110
Asn Asp  Gly Thr Ala Val Lys  Gly Ser Gln Asn Ile   Asn Gly Gln
    1115              1120                1125
Asp Leu  Tyr Phe Asp Gln Asn  Gly Arg Gln Val Lys   Gly Ala Leu
    1130              1135                1140
Ala Asn  Val Asp Gly Asn Leu  Arg Tyr Tyr Asp Val   Asn Ser Gly
    1145              1150                1155
Glu Leu  Tyr Arg Asn Arg Phe  His Glu Ile Asp Gly   Ser Trp Tyr
    1160              1165                1170
Tyr Phe  Asp Gly Asn Gly Asn  Ala Val Lys Gly Met   Val Asn Ile
    1175              1180                1185
Asn Gly  Gln Asn Leu Leu Phe  Asp Asn Asn Gly Lys   Gln Ile Lys
    1190              1195                1200
Gly His  Leu Val Arg Val Asn  Gly Val Val Arg Tyr   Phe Asp Pro
    1205              1210                1215
Asn Ser  Gly Glu Met Ala Val  Asn Arg Trp Val Glu   Val Ser Pro
    1220              1225                1230
Gly Trp  Trp Val Tyr Phe Asp  Gly Glu Gly Arg Gly   Gln Ile
    1235              1240                1245

<210> SEQ ID NO 7
<211> LENGTH: 4434
<212> TYPE: DNA
<213> ORGANISM: Streptococcus salivarius

<400> SEQUENCE: 7

```
atggacgaaa cgcaggataa gaccgtgacg cagagcaaca gcggcaccac cgcttccctg      60
gtcactagcc ctgaagccac gaaagaggcg acaaacgca cgaacactaa agaggccgac     120
gttctgacgc ctgcaaaaga aacgaacgca gtcgagactg cgaccaccac taacacccag    180
gcgacggcgg aggccgccac gaccgcgacc accgcggacg tcgcggtggc tgcggtgccg    240
aacaaagaag cggtcgttac cacggatgct ccggcggtca cgaccgagaa agcggaagaa    300
cagccggcta ccgttaaagc agaagtcgtc aatacgaaag tgaaagcgcc ggaagcggct    360
ctgaaagaca gcgaggttga ggcagcgctg agcctgaaga acatcaagaa cattgatggc    420
aagtattact atgttaatga ggatggcagc cacaaagaga tttcgctat taccgtgaat    480
ggccagctgc tgtactttgg taaagacggt gcgctgacgt cctctagcac gtattctttt    540
```

```
acccccaggca ctaccaatat cgtggacggt tttagcatta caaccgcgc ttacgacagc      600 agcgaggcga gctttgagct gatcgacggt tacttgaccg cagacagctg gtatcgtccg      660
gctagcatca tcaaagatgg tgttacgtgg caagcgtcca ccgccgagga ttttcgtccg      720
ctgctgatgg catggtggcc gaatgtggat acgcaggtga actatttgaa ttacatgtcc      780
aaagttttca acctggacgc gaaatactct agcaccgaca acaggaaac cctgaaagtg       840 gcagcaaaag acattcaaat caagattgaa caaaagattc aagcggagaa gagcacgcag      900
tggctgcgtg aaactatcag cgcctttgtg aaaacccagc cgcagtggaa caaagaaacc      960
gagaattaca gcaagggtgg tggtgaggac cacctgcaag gtggcgcact gctgtatgtt     1020
aacgacagcc gtaccccttg ggcgaatagc gattaccgtc gtctgaatcg caccgcaacc     1080
aatcagacgg gcacgatcga taagtctatt ctggacgagc agtctgaccc aaaccacatg     1140
ggcggtttcg actttctgct ggcgaacgac gtcgacctga gcaatccggt cgtgcaggct     1200
gagcagctga tcaaatcca ctatctgatg aattggggtt ccattgtgat gggtgacaag       1260
gatgcgaact ttgacggcat tcgtgtcgat gcagttgaca acgtggacgc ggacatgttg     1320
caactgtata ccaattactt ccgtgagtac tacggtgtga acaagagcga agctaacgca     1380
ctggctcaca tcagcgttct ggaggcgtgg agcctgaatg ataatcatta caatgacaag     1440
accgatggtg cggcactggc aatggagaat aagcaacgtc tggcgctgtt gttttcgttg     1500
gcgaaaccga tcaaagagcg tacccccggca gtgagcccgc tgtataacaa caccttcaat    1560
accacccagc gtgatgaaaa gaccgattgg attaacaaag acggtagcaa ggcttacaac     1620
gaagatggca cggtcaaaca atcgaccatc ggtaagtaca acgagaaata cggtgacgca     1680
tccggtaact acgttttcat ccgtgcccac gataacaacg tccaggacat catcgccgag     1740
atcatcaaga aagagatcaa cccgaaaagc gacggcttca ccatcaccga cgccgaaatg     1800
aagcaagcct ttgaaatcta taacaaagat atgctgtcga gcgacaaaaa gtataccctg     1860
aataacattc cggcagcgta tgccgtgatg ttgcagaata tggaaacgat acccgcgtc      1920 tattacggtg atctgtatac ggacgacggt cactacatgg aaaccaaatc tccgtattac     1980
gataccatcg tgaatttgat gaagagccgt atcaagtatg tttcgggtgg ccaggcgcaa     2040
cgtagctatt ggctgccgac cgacggtaag atggacaata gcgacgttga gctgtaccgc     2100
acgaatgagg tttacacgag cgtgcgctat ggtaaggata tcatgaccgc taatgatacc     2160
gaaggctcta agtattcccg caccagcggc caagtcacct tggtcgcgaa caatccgaag     2220
ctgaatctgg accaaagcgc caagttgaat gtggagatgg gcaaaatcca tgcgaatcag     2280
aagtatcgcg cactgattgt cggcactgcg gacggcatta agaactttac ttccgacgcg     2340
gacgccattg cagcgggtta tgtgaaagaa accgatagca acggcgtgct gaccttcggt     2400
gctaacgaca ttaagggcta cgaaacgttt gatatgagcg gtttcgtggc ggtgtgggtt     2460
ccggtgggtg catctgacaa tcaggacatt cgtgttgcgc cgagcaccga ggcaaagaaa     2520
gaaggtgagc tgaccttgaa ggcgacgaaa gcgtatgata ccagctgat ttacgaaggc      2580 tttagcaatt ccagacgat cccagatggc agcgatccgt ccgtgtatac gaaccgcaag      2640
attgcggaga acgtggatct gttcaaaagc tggggtgtca ccagctttga gatgcaccg      2700 caatttgtct cggcggatga tggcacctt ctggatagcg ttattcagaa tggctacgcc      2760
ttcgccgacc gttatgacct ggccatgtcc aagaacaaca gtatggtag caaagaggac      2820 ctgcgtgatg cactgaaagc actgcataag gcgggtattc aagctatcgc agactggtt      2880 ccagaccaga tctaccagct gccgggcaaa gaagttgtca ccgccacccg tacggatggt     2940
```

```
gctggccgta agatcgcaga cgcgattatc gaccattctc tgtatgttgc aaacagcaaa    3000
agcagcggca aagattatca agcaaagtac ggtggcgagt tcctggccga gctgaaagcc    3060
aaatacccgg aaatgttcaa agttaacatg attagcacgg taagccgat tgatgactcc    3120 gtgaaattga agcaatggaa agccgagtac ttcaatggca ccaacgtttt ggaacgtggt    3180
gtcggctatg ttctgagcga cgaggcgacc ggtaagtatt tcacggtgac caaagaaggc    3240
aatttcattc cgctgcaact gacgggtaaa gagaaagtta tcacgggttt ctccagcgat    3300
ggtaagggta tcacctattt cggtacgagc ggtacgcagg cgaagtctgc gtttgttacc    3360
ttcaatggta acacctacta tttcgacgcg cgtggccaca tggttaccaa tagcgaatac    3420
agcccgaatg gcaaggacgt ctaccgtttt ctgccgaacg gtatcatgct gagcaatgcg    3480
ttttacattg atgcgaacgg taatacctac ctgtacaact ctaagggtca aatgtacaaa    3540
ggcggttaca cgaaattcga tgtttctgaa acggataagg acggtaaaga gtccaaggtc    3600
gtcaagttcc gctactttac gaacgaaggc gtcatggcca agggtgttac cgtcattgat    3660
ggttttaccc aatacttcgg tgaggacggc tttcaagcga aggataagct ggtcaccttc    3720
aagggcaaga cgtattactt cgacgcacac actggtaatg gtatcaaaga tacctggcgc    3780
aatatcaatg gtaaatggta ctatttcgac gcgaatggcg ttgctgcgac cggtgcgcag    3840
gtgattaacg ccagaaaact gtacttcaac gaggatggct cccaagtcaa aggcggcgtg    3900
gttaagaacg cagacggcac ctatagcaaa tacaaagaag gttttggtga gctggttact    3960 aacgagttt tcacgactga tgcaatgtt tggtactacg ccggtgcaaa tggtaaaacc    4020
gttaccggtg cacaagtgat caacggccaa catttgtact tcaatgcgga cggttcccag    4080
gtgaagggtg gcgttgtcaa gaacgcggat ggcacctaca gcaagtacaa tgctagcact    4140
ggtgaacgtc tgacgaacga gttctttacg accggtgata acaattggta ttacattggc    4200
gcaaacggta agagcgtgac gggtgaggtc aagattggtg atgatactta cttttcgcg     4260 aaggatggca aacaagttaa aggtcaaacc gtcagcgccg gtaatggtcg cattagctac    4320
tactacggtg acagcggcaa gcgtgcggtt agcacctgga ttgagattca gccgggtgtt    4380
tatgtgtatt tcgacaaaaa cggtttggcg taccctccgc gtgttctgaa ttaa          4434
```

<210> SEQ ID NO 8
<211> LENGTH: 1477
<212> TYPE: PRT
<213> ORGANISM: Streptococcus salivarius

<400> SEQUENCE: 8

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
                20                  25                  30

Arg Thr Asn Thr Lys Glu Ala Asp Val Leu Thr Pro Ala Lys Glu Thr
            35                  40                  45

Asn Ala Val Glu Thr Ala Thr Thr Asn Thr Gln Ala Thr Ala Glu
        50                  55                  60

Ala Ala Thr Thr Ala Thr Thr Ala Asp Val Ala Val Ala Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
                100                 105                 110
```

```
Glu Val Lys Ala Pro Glu Ala Ala Leu Lys Asp Ser Glu Val Glu Ala
            115                 120                 125

Ala Leu Ser Leu Lys Asn Ile Lys Asn Ile Asp Gly Lys Tyr Tyr Tyr
    130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Asn Ile Val Asp Gly Phe Ser
            180                 185                 190

Ile Asn Asn Arg Ala Tyr Asp Ser Ser Glu Ala Ser Phe Glu Leu Ile
        195                 200                 205

Asp Gly Tyr Leu Thr Ala Asp Ser Trp Tyr Arg Pro Ala Ser Ile Ile
    210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
                245                 250                 255

Asn Tyr Met Ser Lys Val Phe Asn Leu Asp Ala Lys Tyr Ser Ser Thr
            260                 265                 270

Asp Lys Gln Glu Thr Leu Lys Val Ala Ala Lys Asp Ile Gln Ile Lys
        275                 280                 285

Ile Glu Gln Lys Ile Gln Ala Glu Lys Ser Thr Gln Trp Leu Arg Glu
    290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Glu Asp His Leu Gln Gly Gly Ala
                325                 330                 335

Leu Leu Tyr Val Asn Asp Ser Arg Thr Pro Trp Ala Asn Ser Asp Tyr
            340                 345                 350

Arg Arg Leu Asn Arg Thr Ala Thr Asn Gln Thr Gly Thr Ile Asp Lys
        355                 360                 365

Ser Ile Leu Asp Glu Gln Ser Asp Pro Asn His Met Gly Gly Phe Asp
    370                 375                 380

Phe Leu Leu Ala Asn Asp Val Asp Leu Ser Asn Pro Val Val Gln Ala
385                 390                 395                 400

Glu Gln Leu Asn Gln Ile His Tyr Leu Met Asn Trp Gly Ser Ile Val
                405                 410                 415

Met Gly Asp Lys Asp Ala Asn Phe Asp Gly Ile Arg Val Asp Ala Val
            420                 425                 430

Asp Asn Val Asp Ala Asp Met Leu Gln Leu Tyr Thr Asn Tyr Phe Arg
        435                 440                 445

Glu Tyr Tyr Gly Val Asn Lys Ser Glu Ala Asn Ala Leu Ala His Ile
    450                 455                 460

Ser Val Leu Glu Ala Trp Ser Leu Asn Asp Asn His Tyr Asn Asp Lys
465                 470                 475                 480

Thr Asp Gly Ala Ala Leu Ala Met Glu Asn Lys Gln Arg Leu Ala Leu
                485                 490                 495

Leu Phe Ser Leu Ala Lys Pro Ile Lys Glu Arg Thr Pro Ala Val Ser
            500                 505                 510

Pro Leu Tyr Asn Asn Thr Phe Asn Thr Thr Gln Arg Asp Glu Lys Thr
        515                 520                 525
```

-continued

```
Asp Trp Ile Asn Lys Asp Gly Ser Lys Ala Tyr Asn Glu Asp Gly Thr
    530                 535                 540
Val Lys Gln Ser Thr Ile Gly Lys Tyr Asn Glu Lys Tyr Gly Asp Ala
545                 550                 555                 560
Ser Gly Asn Tyr Val Phe Ile Arg Ala His Asp Asn Asn Val Gln Asp
                565                 570                 575
Ile Ile Ala Glu Ile Ile Lys Lys Glu Ile Asn Pro Lys Ser Asp Gly
            580                 585                 590
Phe Thr Ile Thr Asp Ala Glu Met Lys Gln Ala Phe Glu Ile Tyr Asn
        595                 600                 605
Lys Asp Met Leu Ser Ser Asp Lys Lys Tyr Thr Leu Asn Asn Ile Pro
    610                 615                 620
Ala Ala Tyr Ala Val Met Leu Gln Asn Met Glu Thr Ile Thr Arg Val
625                 630                 635                 640
Tyr Tyr Gly Asp Leu Tyr Thr Asp Asp Gly His Tyr Met Glu Thr Lys
                645                 650                 655
Ser Pro Tyr Tyr Asp Thr Ile Val Asn Leu Met Lys Ser Arg Ile Lys
            660                 665                 670
Tyr Val Ser Gly Gly Gln Ala Gln Arg Ser Tyr Trp Leu Pro Thr Asp
        675                 680                 685
Gly Lys Met Asp Asn Ser Asp Val Glu Leu Tyr Arg Thr Asn Glu Val
    690                 695                 700
Tyr Thr Ser Val Arg Tyr Gly Lys Asp Ile Met Thr Ala Asn Asp Thr
705                 710                 715                 720
Glu Gly Ser Lys Tyr Ser Arg Thr Ser Gly Gln Val Thr Leu Val Ala
                725                 730                 735
Asn Asn Pro Lys Leu Asn Leu Asp Gln Ser Ala Lys Leu Asn Val Glu
            740                 745                 750
Met Gly Lys Ile His Ala Asn Gln Lys Tyr Arg Ala Leu Ile Val Gly
        755                 760                 765
Thr Ala Asp Gly Ile Lys Asn Phe Thr Ser Asp Ala Asp Ala Ile Ala
    770                 775                 780
Ala Gly Tyr Val Lys Glu Thr Asp Ser Asn Gly Val Leu Thr Phe Gly
785                 790                 795                 800
Ala Asn Asp Ile Lys Gly Tyr Glu Thr Phe Asp Met Ser Gly Phe Val
                805                 810                 815
Ala Val Trp Val Pro Val Gly Ala Ser Asp Asn Gln Asp Ile Arg Val
            820                 825                 830
Ala Pro Ser Thr Glu Ala Lys Lys Glu Gly Leu Thr Leu Lys Ala
        835                 840                 845
Thr Glu Ala Tyr Asp Ser Gln Leu Ile Tyr Glu Gly Phe Ser Asn Phe
    850                 855                 860
Gln Thr Ile Pro Asp Gly Ser Asp Pro Ser Val Tyr Thr Asn Arg Lys
865                 870                 875                 880
Ile Ala Glu Asn Val Asp Leu Phe Lys Ser Trp Gly Val Thr Ser Phe
                885                 890                 895
Glu Met Ala Pro Gln Phe Val Ser Ala Asp Gly Thr Phe Leu Asp
            900                 905                 910
Ser Val Ile Gln Asn Gly Tyr Ala Phe Ala Asp Arg Tyr Asp Leu Ala
        915                 920                 925
Met Ser Lys Asn Asn Lys Tyr Gly Ser Lys Glu Asp Leu Arg Asp Ala
    930                 935                 940
Leu Lys Ala Leu His Lys Ala Gly Ile Gln Ala Ile Ala Asp Trp Val
```

-continued

```
945                 950                 955                 960
Pro Asp Gln Ile Tyr Gln Leu Pro Gly Lys Glu Val Val Thr Ala Thr
                965                 970                 975
Arg Thr Asp Gly Ala Gly Arg Lys Ile Ala Asp Ala Ile Ile Asp His
                980                 985                 990
Ser Leu Tyr Val Ala Asn Ser Lys Ser Ser Gly Lys Asp Tyr Gln Ala
                995                 1000                1005
Lys Tyr Gly Gly Glu Phe Leu Ala Glu Leu Lys Ala Lys Tyr Pro
    1010                1015                1020
Glu Met Phe Lys Val Asn Met Ile Ser Thr Gly Lys Pro Ile Asp
    1025                1030                1035
Asp Ser Val Lys Leu Lys Gln Trp Lys Ala Glu Tyr Phe Asn Gly
    1040                1045                1050
Thr Asn Val Leu Glu Arg Gly Val Gly Tyr Val Leu Ser Asp Glu
    1055                1060                1065
Ala Thr Gly Lys Tyr Phe Thr Val Thr Lys Glu Gly Asn Phe Ile
    1070                1075                1080
Pro Leu Gln Leu Thr Gly Lys Glu Lys Val Ile Thr Gly Phe Ser
    1085                1090                1095
Ser Asp Gly Lys Gly Ile Thr Tyr Phe Gly Thr Ser Gly Thr Gln
    1100                1105                1110
Ala Lys Ser Ala Phe Val Thr Phe Asn Gly Asn Thr Tyr Tyr Phe
    1115                1120                1125
Asp Ala Arg Gly His Met Val Thr Asn Ser Glu Tyr Ser Pro Asn
    1130                1135                1140
Gly Lys Asp Val Tyr Arg Phe Leu Pro Asn Gly Ile Met Leu Ser
    1145                1150                1155
Asn Ala Phe Tyr Ile Asp Ala Asn Gly Asn Thr Tyr Leu Tyr Asn
    1160                1165                1170
Ser Lys Gly Gln Met Tyr Lys Gly Gly Tyr Thr Lys Phe Asp Val
    1175                1180                1185
Ser Glu Thr Asp Lys Asp Gly Lys Glu Ser Lys Val Val Lys Phe
    1190                1195                1200
Arg Tyr Phe Thr Asn Glu Gly Val Met Ala Lys Gly Val Thr Val
    1205                1210                1215
Ile Asp Gly Phe Thr Gln Tyr Phe Gly Glu Asp Gly Phe Gln Ala
    1220                1225                1230
Lys Asp Lys Leu Val Thr Phe Lys Gly Lys Thr Tyr Tyr Phe Asp
    1235                1240                1245
Ala His Thr Gly Asn Gly Ile Lys Asp Thr Trp Arg Asn Ile Asn
    1250                1255                1260
Gly Lys Trp Tyr Tyr Phe Asp Ala Asn Gly Val Ala Ala Thr Gly
    1265                1270                1275
Ala Gln Val Ile Asn Gly Gln Lys Leu Tyr Phe Asn Glu Asp Gly
    1280                1285                1290
Ser Gln Val Lys Gly Gly Val Val Lys Asn Ala Asp Gly Thr Tyr
    1295                1300                1305
Ser Lys Tyr Lys Glu Gly Phe Gly Glu Leu Val Thr Asn Glu Phe
    1310                1315                1320
Phe Thr Thr Asp Gly Asn Val Trp Tyr Tyr Ala Gly Ala Asn Gly
    1325                1330                1335
Lys Thr Val Thr Gly Ala Gln Val Ile Asn Gly Gln His Leu Tyr
    1340                1345                1350
```

| | | | | | | | | | |
|---|---|---|---|---|---|---|---|---|---|
| Phe | Asn | Ala | Asp | Gly | Ser | Gln | Val | Lys | Gly | Val | Val | Lys | Asn |
| | 1355 | | | | 1360 | | | | 1365 | | | | |

Phe Asn Ala Asp Gly Ser Gln Val Lys Gly Val Val Lys Asn
    1355                1360                1365

Ala Asp Gly Thr Tyr Ser Lys Tyr Asn Ala Ser Thr Gly Glu Arg
    1370                1375                1380

Leu Thr Asn Glu Phe Phe Thr Thr Gly Asp Asn Asn Trp Tyr Tyr
    1385                1390                1395

Ile Gly Ala Asn Gly Lys Ser Val Thr Gly Glu Val Lys Ile Gly
    1400                1405                1410

Asp Asp Thr Tyr Phe Phe Ala Lys Asp Gly Lys Gln Val Lys Gly
    1415                1420                1425

Gln Thr Val Ser Ala Gly Asn Gly Arg Ile Ser Tyr Tyr Tyr Gly
    1430                1435                1440

Asp Ser Gly Lys Arg Ala Val Ser Thr Trp Ile Glu Ile Gln Pro
    1445                1450                1455

Gly Val Tyr Val Tyr Phe Asp Lys Asn Gly Leu Ala Tyr Pro Pro
    1460                1465                1470

Arg Val Leu Asn
    1475

<210> SEQ ID NO 9
<211> LENGTH: 4311
<212> TYPE: DNA
<213> ORGANISM: Streptococcus downei

<400> SEQUENCE: 9

```
atggttgacg gcaaatacta ctactacgat caggacggca acgtaaagaa aaacttcgcg     60
gttagcgtgg gcgagaaaat ctattacttt gacgaaactg gcgcctacaa agacaccagc    120
aaagttgagc ggacaaaag cggcagcgac attagcaagg aagagactac cttcgcggca    180
aacaaccgcg cctacagcac cagcgcggag aattttgagg cgatcgacaa ttatctgacc    240
gcggactcct ggtatcgtcc taaatccatc ctgaaggatg caaaacgtg acgaaaagc    300
agcaaagatg actttcgtcc gctgctgatg gcgtggtggc cggataccga acgaagcgc    360
aattacgtga actacatgaa caaagttgtt ggcatcgaca agacctatac cgcggaaacc    420
agccaggccg acttgaccgc tgcggcggaa ctggtgcaag cacgcattga gcagaagatc    480
acgaccgaac agaacacgaa atggctgcgt gaggcaatct cggcatttgt aaaaacgcaa    540
ccgcagtgga cggtgaaag cgagaagccg tacgacgatc acctgcaaaa cggtgctctg    600
aaatttgata tcagagcga cctgaccccg gatacgcaaa gcaactaccg tctgttgaac    660
cgtaccccga ctaatcagac gggtagcctg acagccgct tcacttataa cgcgaacgac    720
cctttgggcg ttatgagct gctgctggca aatgacgtcg ataacagcaa tccgatcgtg    780
caggcggagc agctgaactg gctgcattac ctgctgaatt ttggtacgat ctacgccaaa    840
gatgccgacg ctaacttcga tagcattcgt gtggacgcgg ttgataacgt cgatgcggat    900
ctgctgcaaa ttagcagcga ttacctgaaa gcagcctacg gcattgataa gaataacaaa    960
aacgcgaaca ccacgtgag cattgtcgaa gcctggagcg ataatgatac cccgtacctg    1020
catgacgatg tgacaacct gatgaatatg ataacaaat tcgcctgtc catgctgtgg    1080
tcgctggcca aaccgctgga caagcgtagc ggtctgaacc cgctgattca taacagcttg    1140
gtggatcgtg aagttgatga ccgcgaggtt gaaacggttc cgagctattc ttttgcacgt    1200
gcgcatgata gcgaggtcca ggacttgatc cgtgacatca tcaaggcaga gatcaatccg    1260
aacgcattcg gttatagctt tacccaagac gagattgacc aggcctttaa gatttacaat    1320
```

```
gaggatctga agaaaacgga taagaaatac acccactata atgtgccgtt gagctacacc    1380
ctgctgctga cgaataaggg tagcatccca cgtgtctact atggtgatat gtttaccgac    1440
gatggtcagt atatggcgaa caaaaccgtc aactatgacg ccattgaatc tctgctgaaa    1500
gcgcgtatga agtatgtcgc tggcggtcaa gcaatgcaga actaccaaat cggtaatggt    1560
gagatcctga ccagcgttcg ttatggtaag ggtgccctga acagagcga caaaggtgat    1620 gcgaccacgc gcaccagcgg tgtcggtgtc gttatgggca atcagccaaa ctttagcttg    1680
gacggcaaag tggtggctct gaacatgggc gcagctcatg cgaatcagga gtatcgtgcg    1740
ctgatggtta gcacgaaaga cggtgttgcc acgtatgcga ccgatgcaga tgcgagcaaa    1800
gccggtctgg tcaaacgtac cgacgaaaac ggctacctgt atttcctgaa tgacgacctg    1860
aagggtgtgg ccaatcctca ggtgagcggt tcttgcagg tgtgggttcc ggtgggtgcc    1920
gcggatgatc aagatatccg tgttgcagct agcgataccg catccaccga tggcaagagc    1980
ctgcaccaag acgccgcgat ggatagccgt gttatgtttg aaggcttctc taactttcag    2040
tcctttgcca cgaaagaaga ggaatatacc aacgtcgtta tcgccaacaa tgtggataag    2100
ttcgttagct ggggtatcac ggatttcgag atggccccac aatatgtttc cagcaccgac    2160
ggtcaattcc tggactctgt cattcagaac ggttatgctt ttacggaccg ttatgacttg    2220
ggcatgtcta aggcaaacaa atacggcacg gccgatcaac tggttaaggc cattaaggcc    2280
ctgcacgcga agggcctgaa ggttatggca gattgggtgc cggatcagat gtataccttc    2340
ccgaaacagg aagtcgtgac cgttacccgt accgacaaat ttggcaaacc gatcgcaggt    2400
tcccaaatca atcatagcct gtatgttacc gataccaagt ccagcggcga tgactatcag    2460
gccaaatatg gtggtgcgtt tctggacgag ctgaaggaga aatatccgga gctgttcacg    2520
aagaaacaaa tcagcacggg tcaagctatt gacccgagcg tgaaaatcaa acagtggtct    2580
gctaagtatt tcaatggctc caacatcctg ggtcgcggtg cggactacgt actgtcggat    2640
caggcgagca acaaatacct gaacgtgtct gacgataaac tgttcctgcc gaaaaccttg    2700
ctgggccaag ttgtcgagag cggtatccgc tttgacggca ctggttatgt gtacaactct    2760
agcactacgg gtgaaaaagt taccgattcc ttcattacgg aggcaggtaa tctgtactac    2820
ttcggtcaag acggctatat ggtgaccggc gcacagaaca ttaagggcag caactattac    2880
ttcctggcca atggtgcggc cctgcgtaac accgtttaca ccgatgcgca aggtcagaat    2940
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt tcgataaaga tggtgtccag gccaaggata agatcattgt cacccgcgat    3120
ggcaaagtcc gctatttcga ccagcacaac ggtaatgcgg ttactaacac gttcgttgcg    3180
gacaagacgg gtcactggta ctatctgggc aaagacggcg tcgcggttac cggtgcgcag    3240
actgtgggta acagcatttt gtactttgaa gcgaacggtc aacaagtcaa gggtgacttc    3300
gtgacggcta agacggtaa actgtacttc tatgatgtgg acagcggcga catgtggacc    3360
aataccttta tcgaggataa agcgggtaat tggttctacc tgggtaagga cggtgcggcc    3420
gtcaccggtg cacagacgat caaaggccag aaattgtatt tcaaagccaa cggtcagcaa    3480
gttaaaggtg acattgtcaa ggacgcggac ggtaagatcc gttattacga cgctcagacc    3540
ggtgaacagt ctttaacaa gtccgttagc gtcaacggta agacctacta tttcggtagc    3600
gacggcaccg cgcaaaccca ggcgaatccg aaaggccaaa cctttaagga tggtagcggc    3660
```

-continued

```
gttctgcgtt tctacaattt ggagggccag tatgtctcgg gcagcggctg gtacgaaacg    3720
gccgagcacg agtgggtata tgtgaaatcc ggtaaagttc tgaccggtgc ccagacgatt    3780
ggtaatcaac gtgtttactt caaggacaat ggtcaccagg tgaaaggcca gctggtcacg    3840
ggtaatgacg gtaaattgcg ttactacgac gcgaacagcg gtgatcaagc attcaacaaa    3900
tccgtcacgg ttaacggtaa aacctactac tttggcagcg atggtacggc gcagacgcag    3960
gctaatccta aggtcagac cttcaaagat ggtagcggcg tgctgcgttt ttacaacttg     4020
gaaggccaat acgtgtctgg cagcggttgg tacaagaatg cgcagggcca gtggctgtac    4080
gtgaaagatg gcaaggtcct gaccggtctg caaacggtcg gcaatcagaa ggtctacttc    4140
gacaaaaatg gcatccaagc aaagggtaag gccgttcgca cgtccgatgg taaagtgcgc    4200
tactttgatg agaatagcgg tagcatgatt acgaaccaat ggaagttcgt ttacggtcaa    4260
tactattact tcggttctga cggcgcagcg gtttaccgtg gttggaacta a             4311
```

<210> SEQ ID NO 10
<211> LENGTH: 1436
<212> TYPE: PRT
<213> ORGANISM: Streptococcus downei

<400> SEQUENCE: 10

```
Met Val Asp Gly Lys Tyr Tyr Tyr Asp Gln Asp Gly Asn Val Lys
1               5                   10                  15

Lys Asn Phe Ala Val Ser Val Gly Glu Lys Ile Tyr Tyr Phe Asp Glu
            20                  25                  30

Thr Gly Ala Tyr Lys Asp Thr Ser Lys Val Glu Ala Asp Lys Ser Gly
        35                  40                  45

Ser Asp Ile Ser Lys Glu Glu Thr Thr Phe Ala Ala Asn Asn Arg Ala
    50                  55                  60

Tyr Ser Thr Ser Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Leu Leu Ala Asn Asp Val Asp Asn Ser
                245                 250                 255

Asn Pro Ile Val Gln Ala Glu Gln Leu Asn Trp Leu His Tyr Leu Leu
```

-continued

```
                260                 265                 270
Asn Phe Gly Thr Ile Tyr Ala Lys Asp Ala Asp Ala Asn Phe Asp Ser
            275                 280                 285
Ile Arg Val Asp Ala Val Asp Asn Val Asp Ala Asp Leu Leu Gln Ile
290                 295                 300
Ser Ser Asp Tyr Leu Lys Ala Ala Tyr Gly Ile Asp Lys Asn Asn Lys
305                 310                 315                 320
Asn Ala Asn Asn His Val Ser Ile Val Glu Ala Trp Ser Asp Asn Asp
                325                 330                 335
Thr Pro Tyr Leu His Asp Asp Gly Asp Asn Leu Met Asn Met Asp Asn
            340                 345                 350
Lys Phe Arg Leu Ser Met Leu Trp Ser Leu Ala Lys Pro Leu Asp Lys
        355                 360                 365
Arg Ser Gly Leu Asn Pro Leu Ile His Asn Ser Leu Val Asp Arg Glu
    370                 375                 380
Val Asp Asp Arg Glu Val Glu Thr Val Pro Ser Tyr Ser Phe Ala Arg
385                 390                 395                 400
Ala His Asp Ser Glu Val Gln Asp Leu Ile Arg Asp Ile Lys Ala
            405                 410                 415
Glu Ile Asn Pro Asn Ala Phe Gly Tyr Ser Phe Thr Gln Asp Glu Ile
                420                 425                 430
Asp Gln Ala Phe Lys Ile Tyr Asn Glu Asp Leu Lys Lys Thr Asp Lys
            435                 440                 445
Lys Tyr Thr His Tyr Asn Val Pro Leu Ser Tyr Thr Leu Leu Leu Thr
        450                 455                 460
Asn Lys Gly Ser Ile Pro Arg Val Tyr Tyr Gly Asp Met Phe Thr Asp
465                 470                 475                 480
Asp Gly Gln Tyr Met Ala Asn Lys Thr Val Asn Tyr Asp Ala Ile Glu
                485                 490                 495
Ser Leu Leu Lys Ala Arg Met Lys Tyr Val Ala Gly Gly Gln Ala Met
            500                 505                 510
Gln Asn Tyr Gln Ile Gly Asn Gly Glu Ile Leu Thr Ser Val Arg Tyr
        515                 520                 525
Gly Lys Gly Ala Leu Lys Gln Ser Asp Lys Gly Asp Ala Thr Thr Arg
    530                 535                 540
Thr Ser Gly Val Gly Val Val Met Gly Asn Gln Pro Asn Phe Ser Leu
545                 550                 555                 560
Asp Gly Lys Val Val Ala Leu Asn Met Gly Ala Ala His Ala Asn Gln
                565                 570                 575
Glu Tyr Arg Ala Leu Met Val Ser Thr Lys Asp Gly Val Ala Thr Tyr
            580                 585                 590
Ala Thr Asp Ala Asp Ala Ser Lys Ala Gly Leu Val Lys Arg Thr Asp
        595                 600                 605
Glu Asn Gly Tyr Leu Tyr Phe Leu Asn Asp Asp Leu Lys Gly Val Ala
    610                 615                 620
Asn Pro Gln Val Ser Gly Phe Leu Gln Val Trp Val Pro Val Gly Ala
625                 630                 635                 640
Ala Asp Asp Gln Asp Ile Arg Val Ala Ala Ser Asp Thr Ala Ser Thr
                645                 650                 655
Asp Gly Lys Ser Leu His Gln Asp Ala Ala Met Asp Ser Arg Val Met
            660                 665                 670
Phe Glu Gly Phe Ser Asn Phe Gln Ser Phe Ala Thr Lys Glu Glu Glu
        675                 680                 685
```

```
Tyr Thr Asn Val Val Ile Ala Asn Asn Val Asp Lys Phe Val Ser Trp
690                 695                 700

Gly Ile Thr Asp Phe Glu Met Ala Pro Gln Tyr Val Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
                740                 745                 750

Gln Leu Val Lys Ala Ile Lys Ala Leu His Ala Lys Gly Leu Lys Val
                755                 760                 765

Met Ala Asp Trp Val Pro Asp Gln Met Tyr Thr Phe Pro Lys Gln Glu
770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Ala Ser Asn Lys Tyr Leu Asn Val Ser Asp Lys Leu Phe Leu
                885                 890                 895

Pro Lys Thr Leu Leu Gly Gln Val Val Glu Ser Gly Ile Arg Phe Asp
                900                 905                 910

Gly Thr Gly Tyr Val Tyr Asn Ser Ser Thr Thr Gly Glu Lys Val Thr
                915                 920                 925

Asp Ser Phe Ile Thr Glu Ala Gly Asn Leu Tyr Tyr Phe Gly Gln Asp
930                 935                 940

Gly Tyr Met Val Thr Gly Ala Gln Asn Ile Lys Gly Ser Asn Tyr Tyr
945                 950                 955                 960

Phe Leu Ala Asn Gly Ala Ala Leu Arg Asn Thr Val Tyr Thr Asp Ala
                965                 970                 975

Gln Gly Gln Asn His Tyr Tyr Gly Asn Asp Gly Lys Arg Tyr Glu Asn
                980                 985                 990

Gly Tyr Gln Gln Phe Gly Asn Asp Ser Trp Arg Tyr Phe Lys Asn Gly
                995                 1000                1005

Val Met Ala Leu Gly Leu Thr Thr Val Asp Gly His Val Gln Tyr
    1010                1015                1020

Phe Asp Lys Asp Gly Val Gln Ala Lys Asp Lys Ile Ile Val Thr
    1025                1030                1035

Arg Asp Gly Lys Val Arg Tyr Phe Asp Gln His Asn Gly Asn Ala
    1040                1045                1050

Val Thr Asn Thr Phe Val Ala Asp Lys Thr Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095
```

| | | | | | | | | | | |
|---|---|---|---|---|---|---|---|---|---|---|
|Asp|Phe|Val|Thr|Ala|Lys|Asp|Gly|Lys|Leu|Tyr|Phe|Tyr|Asp|Val|
| |1100| | | |1105| | | |1110| |

Asp Ser Gly Asp Met Trp Thr Asn Thr Phe Ile Glu Asp Lys Ala
    1115                1120                1125

Gly Asn Trp Phe Tyr Leu Gly Lys Asp Gly Ala Ala Val Thr Gly
    1130                1135                1140

Ala Gln Thr Ile Lys Gly Gln Lys Leu Tyr Phe Lys Ala Asn Gly
    1145                1150                1155

Gln Gln Val Lys Gly Asp Ile Val Lys Asp Ala Asp Gly Lys Ile
    1160                1165                1170

Arg Tyr Tyr Asp Ala Gln Thr Gly Glu Gln Val Phe Asn Lys Ser
    1175                1180                1185

Val Ser Val Asn Gly Lys Thr Tyr Tyr Phe Gly Ser Asp Gly Thr
    1190                1195                1200

Ala Gln Thr Gln Ala Asn Pro Lys Gly Gln Thr Phe Lys Asp Gly
    1205                1210                1215

Ser Gly Val Leu Arg Phe Tyr Asn Leu Glu Gly Gln Tyr Val Ser
    1220                1225                1230

Gly Ser Gly Trp Tyr Glu Thr Ala Glu His Glu Trp Val Tyr Val
    1235                1240                1245

Lys Ser Gly Lys Val Leu Thr Gly Ala Gln Thr Ile Gly Asn Gln
    1250                1255                1260

Arg Val Tyr Phe Lys Asp Asn Gly His Gln Val Lys Gly Gln Leu
    1265                1270                1275

Val Thr Gly Asn Asp Gly Lys Leu Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Ser Asp Gly Thr Ala Gln Thr Gln Ala Asn Pro
    1310                1315                1320

Lys Gly Gln Thr Phe Lys Asp Gly Ser Gly Val Leu Arg Phe Tyr
    1325                1330                1335

Asn Leu Glu Gly Gln Tyr Val Ser Gly Ser Gly Trp Tyr Lys Asn
    1340                1345                1350

Ala Gln Gly Gln Trp Leu Tyr Val Lys Asp Gly Lys Val Leu Thr
    1355                1360                1365

Gly Leu Gln Thr Val Gly Asn Gln Lys Val Tyr Phe Asp Lys Asn
    1370                1375                1380

Gly Ile Gln Ala Lys Gly Lys Ala Val Arg Thr Ser Asp Gly Lys
    1385                1390                1395

Val Arg Tyr Phe Asp Glu Asn Ser Gly Ser Met Ile Thr Asn Gln
    1400                1405                1410

Trp Lys Phe Val Tyr Gly Gln Tyr Tyr Phe Gly Ser Asp Gly
    1415                1420                1425

Ala Ala Val Tyr Arg Gly Trp Asn
    1430                1435

<210> SEQ ID NO 11
<211> LENGTH: 3942
<212> TYPE: DNA
<213> ORGANISM: Streptococcus mutans

<400> SEQUENCE: 11
atgattgacg gcaaatacta ctactatgac aacaacggca agtacgcac caatttcacg    60

```
ttgatcgcgg acggtaaaat cctgcatttt gatgaaactg gcgcgtacac cgacactagc    120
attgataccg tgaacaagga tattgtcacg acgcgtagca acctgtataa gaaatacaat    180
caagtgtatg atcgcagcgc gcagagcttc gagcatgttg atcactacct gacggcggaa    240
tcttggtacc gtccgaaata cattctgaaa gatggcaaga cctggaccca gagcaccgag    300
aaggacttcc gtcctctgct gatgacctgg tggccgagcc aggaaacgca gcgccagtat    360
gtcaacttca tgaacgccca gttgggtatc aacaaaacgt acgacgacac cagcaatcag    420
ctgcaattga acatcgctgc tgcaacgatc caagcaaaga tcgaagccaa aatcacgacg    480
ctgaagaaca ccgattggct gcgtcaaacg atcagcgcgt tcgtcaaaac ccaaagcgct    540
tggaatagcg acagcgaaaa gccgtttgat gaccatctgc aaaacggtgc ggttctgtat    600
gataacgaag gtaaattgac gccgtatgcc aatagcaact atcgtattct gaaccgcacg    660
ccgaccaacc agaccggtaa gaaggacccg cgttataccg ccgacaacac gatcggcggc    720
tacgagtttc tgctggccaa cgacgttgga aatagcaacc cggtggttca ggccgagcag    780
ctgaactggc tgcacttcct gatgaacttt ggtaatatct acgcaaacga ccctgacgct    840
aacttcgact ccatccgcgt tgacgctgtc gataatgtgg acgccgatct gttacagatc    900
gcgggtgact atctgaaagc ggcaaagggc atccataaga atgacaaagc ggcgaacgac    960
cacctgtcca ttctggaagc gtggagcgac aatgacactc cgtatctgca tgatgatggc   1020
gacaacatga ttaacatgga taacaaactg cgcctgagcc tgctgttctc cctggcgaaa   1080
ccgctgaatc agcgtagcgg tatgaacccg ttgattacga acagcctggt caaccgtact   1140
gatgataatg ccgaaacggc ggcagtgcca agctactctt ttatccgtgc ccacgatagc   1200
gaggtccagg atttgattcg tgatatcatt aaggctgaga ttaacccgaa cgtcgtcggt   1260
tacagcttca cgatggaaga gattaagaag gcatttgaga tctacaataa ggacctgttg   1320
gccacggaga agaagtatac ccactataac accgcattga gctacgcgtt gctgctgacg   1380
aacaagagca gcgtgccgcg tgtctactat ggtgatatgt ttacggacga tggtcaatac   1440
atggcccaca agaccattaa ctacgaggca atcgaaaccc tgctgaaagc acgtatcaag   1500
tacgtgtccg gtggtcaggc tatgcgcaac cagcaagtgg gtaattcgga gatcatcacc   1560
agcgtgcgtt acggtaaagg tgcgctgaag gcgatggata cgggtgaccg cactacccgt   1620
acctctggtg tggcggtcat tgagggcaac aacccgagct gcgcctgaa ggcttctgat   1680 cgtgtggttg tgaatatggg tgcggcccac aaaaatcaag cctatcgccc gctgctgttg   1740
acgaccgata acggcattaa ggcctatcac agcgaccaag aagcggcagg cctggtgcgt   1800
tacaccaacg accgtggcga actgatcttt accgcagccg acattaaggg ctacgcaaat   1860
ccgcaagtta gcggctacct gggcgtctgg gtccctgttg gcgcagcagc tgatcaggac   1920
gttcgtgttg cggcgagcac cgcgccaagc acggacggca agagcgttca ccagaacgcg   1980
gctctggaca gccgtgtgat gttcgagggt ttctcgaact ccaggcatt  tgctaccaag   2040 aaagaagagt ataccaatgt ggtcatcgct aagaatgtgg ataagttcgc ggagtggggt   2100
gtcaccgatt tcgagatggc tccgcaatac gtttctagca ccgacggtag cttttttggat   2160 agcgtgattc aaaacggtta tgcttttacc gaccgttacg acctgggcat cagcaagccg   2220
aacaaatatg gcaccgcgga cgatctggtt aaagcgatta aggcattgca cagcaaaggc   2280
atcaaagtta tggcggattg ggttccggac cagatgtatg ccctgccgga aaaagaggtt   2340
gtgacggcaa cccgtgttga caaatacggt acgccggtag ctggcagcca gatcaaaaac   2400
acgctgtacg tggtcgatgg taaatctagc ggtaaggacc agcaggcgaa gtacggtggt   2460
```

```
gccttcctgg aagagctgca agcgaagtat ccggaactgt tcgcgcgcaa acagattagc    2520
accggtgttc cgatggaccc gagcgtcaag attaagcaat ggagcgcaaa atacttcaac    2580
ggcacgaata tcctgggtcg tggtgctggt tacgtgctga agatcaggc aaccaacacc     2640 tactttaaca tcagcgacaa taaagagatc aatttcctgc aaagacgtt gctgaaccag     2700 gattctcaag ttggctttag ctacgacggt aagggctatg tgtactacag cacctcgggc    2760
taccaggcta aaaacacgtt catcagcgag ggtgacaagt ggtattactt cgacaataac    2820
ggttatatgg ttaccggcgc acagagcatt aatggtgtga actattactt cctgccgaat    2880
ggtttacagc tgcgtgatgc gattctgaaa atgaggacg tacgtacgc gtattatggc      2940 aatgatggtc gccgctacga gaatggctat tatcagttta tgagcggtgt ttggcgccat    3000
ttcaataatg gcgagatgtc cgttggtctg accgtcattg acggtcaagt tcaatacttt    3060
gacgagatgg gttaccaggc gaaaggcaaa ttcgttacca ccgcggatgg taagatccgt    3120
tacttcgata gcagagcgg caatatgtat cgtaatcgtt tcattgagaa cgaagagggc     3180
aaatggctgt acctgggtga ggacggcgcg gcagtcaccg tagccagac gatcaatggt     3240 cagcacctgt atttcgtgc taacggcgtt caggttaagg gtgagttcgt gaccgatcgt     3300
catggccgca tctcttatta cgacggcaac agcggtgatc agatccgcaa ccgtttcgtc    3360
cgcaatgcgc aaggccagtg gttttacttt gacaacaatg gctatgcagt aactggtgct    3420
cgtacgatca acggccagca cctgtatttc cgcgcgaacg tgttcaggt aaaaggtgag     3480 tttgttacgg accgccacgg ccgcattagc tattatgatg gtaatagcgg tgaccaaatt    3540
cgcaatcgtt tcgtgcgtaa tgcacagggt cagtggttct acttcgacaa taatggttat    3600
gcagtcacgg gtgcacgtac cattaacggc caacacctgt actttcgcgc caatggtgtg    3660
caagtgaaag gcgaatttgt tactgatcgt tatggtcgta tcagctacta tgatggcaat    3720
tctggcgacc aaattcgcaa tcgctttgtt cgtaacgccc aaggtcaatg gttctatttc    3780
gacaacaacg gttacgcggt gaccggtgcc cgcacgatta atggtcaaca cttgtacttc    3840
cgtgccaacg tgtccaggt gaagggtgaa tttgtgaccg accgctatgg tcgcatttct    3900
tactacgacg caaattccgg tgaacgcgtc cgtatcaatt aa                       3942
```

<210> SEQ ID NO 12
<211> LENGTH: 1313
<212> TYPE: PRT
<213> ORGANISM: Streptococcus mutans

<400> SEQUENCE: 12

Met Ile Asp Gly Lys Tyr Tyr Tyr Asp Asn Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
    50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110

```
Ser Gln Glu Thr Gln Arg Gln Tyr Val Asn Phe Met Asn Ala Gln Leu
            115                 120                 125

Gly Ile Asn Lys Thr Tyr Asp Asp Thr Ser Asn Gln Leu Gln Leu Asn
        130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
                180                 185                 190

Leu Gln Asn Gly Ala Val Leu Tyr Asp Asn Glu Gly Lys Leu Thr Pro
                195                 200                 205

Tyr Ala Asn Ser Asn Tyr Arg Ile Leu Asn Arg Thr Pro Thr Asn Gln
            210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
            260                 265                 270

Ile Tyr Ala Asn Asp Pro Asp Ala Asn Phe Asp Ser Ile Arg Val Asp
        275                 280                 285

Ala Val Asp Asn Val Asp Ala Asp Leu Leu Gln Ile Ala Gly Asp Tyr
        290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
                325                 330                 335

His Asp Asp Gly Asp Asn Met Ile Asn Met Asp Asn Lys Leu Arg Leu
                340                 345                 350

Ser Leu Leu Phe Ser Leu Ala Lys Pro Leu Asn Gln Arg Ser Gly Met
            355                 360                 365

Asn Pro Leu Ile Thr Asn Ser Leu Val Asn Arg Thr Asp Asp Asn Ala
        370                 375                 380

Glu Thr Ala Ala Val Pro Ser Tyr Ser Phe Ile Arg Ala His Asp Ser
385                 390                 395                 400

Glu Val Gln Asp Leu Ile Arg Asp Ile Ile Lys Ala Glu Ile Asn Pro
                405                 410                 415

Asn Val Val Gly Tyr Ser Phe Thr Met Glu Glu Ile Lys Lys Ala Phe
                420                 425                 430

Glu Ile Tyr Asn Lys Asp Leu Leu Ala Thr Glu Lys Lys Tyr Thr His
            435                 440                 445

Tyr Asn Thr Ala Leu Ser Tyr Ala Leu Leu Leu Thr Asn Lys Ser Ser
        450                 455                 460

Val Pro Arg Val Tyr Tyr Gly Asp Met Phe Thr Asp Asp Gly Gln Tyr
465                 470                 475                 480

Met Ala His Lys Thr Ile Asn Tyr Glu Ala Ile Glu Thr Leu Leu Lys
                485                 490                 495

Ala Arg Ile Lys Tyr Val Ser Gly Gly Gln Ala Met Arg Asn Gln Gln
            500                 505                 510

Val Gly Asn Ser Glu Ile Ile Thr Ser Val Arg Tyr Gly Lys Gly Ala
            515                 520                 525
```

```
Leu Lys Ala Met Asp Thr Gly Asp Arg Thr Thr Arg Thr Ser Gly Val
    530                 535                 540

Ala Val Ile Glu Gly Asn Asn Pro Ser Leu Arg Leu Lys Ala Ser Asp
545                 550                 555                 560

Arg Val Val Asn Met Gly Ala Ala His Lys Asn Gln Ala Tyr Arg
                565                 570                 575

Pro Leu Leu Leu Thr Thr Asp Asn Gly Ile Lys Ala Tyr His Ser Asp
            580                 585                 590

Gln Glu Ala Ala Gly Leu Val Arg Tyr Thr Asn Asp Arg Gly Glu Leu
        595                 600                 605

Ile Phe Thr Ala Ala Asp Ile Lys Gly Tyr Ala Asn Pro Gln Val Ser
610                 615                 620

Gly Tyr Leu Gly Val Trp Val Pro Val Gly Ala Ala Asp Gln Asp
625                 630                 635                 640

Val Arg Val Ala Ala Ser Thr Ala Pro Ser Thr Asp Gly Lys Ser Val
                645                 650                 655

His Gln Asn Ala Ala Leu Asp Ser Arg Val Met Phe Glu Gly Phe Ser
                660                 665                 670

Asn Phe Gln Ala Phe Ala Thr Lys Lys Glu Glu Tyr Thr Asn Val Val
            675                 680                 685

Ile Ala Lys Asn Val Asp Lys Phe Ala Glu Trp Gly Val Thr Asp Phe
690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                725                 730                 735

Ile Ser Lys Pro Asn Lys Tyr Gly Thr Ala Asp Asp Leu Val Lys Ala
            740                 745                 750

Ile Lys Ala Leu His Ser Lys Gly Ile Lys Val Met Ala Asp Trp Val
            755                 760                 765

Pro Asp Gln Met Tyr Ala Leu Pro Glu Lys Glu Val Val Thr Ala Thr
    770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
                805                 810                 815

Lys Tyr Gly Gly Ala Phe Leu Glu Glu Leu Gln Ala Lys Tyr Pro Glu
                820                 825                 830

Leu Phe Ala Arg Lys Gln Ile Ser Thr Gly Val Pro Met Asp Pro Ser
            835                 840                 845

Val Lys Ile Lys Gln Trp Ser Ala Lys Tyr Phe Asn Gly Thr Asn Ile
850                 855                 860

Leu Gly Arg Gly Ala Gly Tyr Val Leu Lys Asp Gln Ala Thr Asn Thr
865                 870                 875                 880

Tyr Phe Asn Ile Ser Asp Asn Lys Glu Ile Asn Phe Leu Pro Lys Thr
                885                 890                 895

Leu Leu Asn Gln Asp Ser Gln Val Gly Phe Ser Tyr Asp Gly Lys Gly
                900                 905                 910

Tyr Val Tyr Tyr Ser Thr Ser Gly Tyr Gln Ala Lys Asn Thr Phe Ile
            915                 920                 925

Ser Glu Gly Asp Lys Trp Tyr Tyr Phe Asp Asn Asn Gly Tyr Met Val
            930                 935                 940

Thr Gly Ala Gln Ser Ile Asn Gly Val Asn Tyr Tyr Phe Leu Pro Asn
```

```
                    945                 950                 955                 960
            Gly Leu Gln Leu Arg Asp Ala Ile Leu Lys Asn Glu Asp Gly Thr Tyr
                            965                 970                 975
            Ala Tyr Tyr Gly Asn Asp Gly Arg Arg Tyr Glu Asn Gly Tyr Tyr Gln
                            980                 985                 990
            Phe Met Ser Gly Val Trp Arg His Phe Asn Asn Gly Glu Met Ser Val
                            995                 1000                1005
            Gly Leu Thr Val Ile Asp Gly Gln Val Gln Tyr Phe Asp Glu Met
                1010                1015                1020
            Gly Tyr Gln Ala Lys Gly Lys Phe Val Thr Thr Ala Asp Gly Lys
                1025                1030                1035
            Ile Arg Tyr Phe Asp Lys Gln Ser Gly Asn Met Tyr Arg Asn Arg
                1040                1045                1050
            Phe Ile Glu Asn Glu Glu Gly Lys Trp Leu Tyr Leu Gly Glu Asp
                1055                1060                1065
            Gly Ala Ala Val Thr Gly Ser Gln Thr Ile Asn Gly Gln His Leu
                1070                1075                1080
            Tyr Phe Arg Ala Asn Gly Val Gln Val Lys Gly Glu Phe Val Thr
                1085                1090                1095
            Asp Arg His Gly Arg Ile Ser Tyr Tyr Asp Gly Asn Ser Gly Asp
                1100                1105                1110
            Gln Ile Arg Asn Arg Phe Val Arg Asn Ala Gln Gly Gln Trp Phe
                1115                1120                1125
            Tyr Phe Asp Asn Asn Gly Tyr Ala Val Thr Gly Ala Arg Thr Ile
                1130                1135                1140
            Asn Gly Gln His Leu Tyr Phe Arg Ala Asn Gly Val Gln Val Lys
                1145                1150                1155
            Gly Glu Phe Val Thr Asp Arg His Gly Arg Ile Ser Tyr Tyr Asp
                1160                1165                1170
            Gly Asn Ser Gly Asp Gln Ile Arg Asn Arg Phe Val Arg Asn Ala
                1175                1180                1185
            Gln Gly Gln Trp Phe Tyr Phe Asp Asn Asn Gly Tyr Ala Val Thr
                1190                1195                1200
            Gly Ala Arg Thr Ile Asn Gly Gln His Leu Tyr Phe Arg Ala Asn
                1205                1210                1215
            Gly Val Gln Val Lys Gly Glu Phe Val Thr Asp Arg Tyr Gly Arg
                1220                1225                1230
            Ile Ser Tyr Tyr Asp Gly Asn Ser Gly Asp Gln Ile Arg Asn Arg
                1235                1240                1245
            Phe Val Arg Asn Ala Gln Gly Gln Trp Phe Tyr Phe Asp Asn Asn
                1250                1255                1260
            Gly Tyr Ala Val Thr Gly Ala Arg Thr Ile Asn Gly Gln His Leu
                1265                1270                1275
            Tyr Phe Arg Ala Asn Gly Val Gln Val Lys Gly Glu Phe Val Thr
                1280                1285                1290
            Asp Arg Tyr Gly Arg Ile Ser Tyr Tyr Asp Ala Asn Ser Gly Glu
                1295                1300                1305
            Arg Val Arg Ile Asn
                1310

<210> SEQ ID NO 13
<211> LENGTH: 3972
<212> TYPE: DNA
<213> ORGANISM: Streptococcus dentirousetti
```

<400> SEQUENCE: 13

```
atggttgacg gcaaatacta ctactacgat gcagacggca acgtaaagaa aaacttcgcg      60
gttagcgttg gcgatgccat tttctatttt gatgaaacgg gtgcctacaa agataccagc     120
aaagttgatg cggataagac cagctctagc gtcaatcaga ccacggaaac gttcgcagcg     180
aataaccgtg cgtatagcac cgcagccgag aactttgaag cgattgataa ctacctgact     240
gcggatagct ggtatcgtcc gaagtctatc ttgaaagatg gtacgacgtg gaccgaaagc     300
accaaggatg attttcgccc gctgctgatg gcgtggtggc cggataccga aaccaaacgt     360
aactacgtga actatatgaa caaggtggtc ggtatcgaca aaacgtacac cgcggaaacg     420
tcccaagctg acctgacggc ggcagccgaa ctggtgcagg cgcgtatcga gcagaaaatc     480
actagcgaaa agaatacgaa gtggctgcgt gaggcgattt ccgcgttcgt taagactcaa     540
ccgcagtgga atggcgagag cgagaaacct tatgatgacc acctgcaaaa tggtgcgctg     600
aagttcgaca tgaaaccagc ctgaccccg gatacgcaga gcggctatcg catcctgaac     660
cgtaccccga cgaatcaaac cggtagcctg acccgcgct tcacctttaa tcagaatgac     720
ccgctgggtg ttatgagta tttgctggct aatgatgtcg ataacagcaa cccggtcgtt     780
caggccgaga gcctgaactg gctgcattac ctgctgaatt ttggtagcat ttacgcgaat     840
gatccggagg ccaatttcga cagcatccgt gtggacgcgg tggacaatgt tgacgcagac     900
ctgctgcaaa ttagctcgga ttacctgaaa tcggcgtaca aaattgacaa gaacaacaaa     960
aatgcgaacg accacgttag catcgtcgag gcgtggagcg acaatgatac cccgtacctg    1020
aatgatgatg cgacaatct gatgaacatg gataacaagt tcgtctgag catgctgtgg    1080
agcctggcga agccaaccaa tgtccgtagc ggcttgaatc cgctgatcca aacagcgtg    1140
gttgaccgtg aggtggacga ccgtgaagtt gaggctaccc cgaattacag ctttgcacgc    1200
gcacacgaca cgcaagttca agatttgatt cgcgacatca tcaaagctga gatcaaccca    1260
aacagcttcg gttatagctt tacccaagag gaaatcgacc aggccttcaa gatctacaat    1320
gaggatttga agaaaaccaa taagaagtat acccactaca acgtcccgct gagctacacc    1380
ctgctgctga cgaacaaggg cagcattcca cgcatttact acggtgacat gtttacggat    1440
gacggtcagt atatggccaa caaaaccgtt aactatgacg ccattgagag cctgctgaaa    1500
gcacgtatga agtatgttag cggtggccaa gcgatgcaga attacaacat cggcaacggc    1560
gagattctga ccagcgtccg ttacggtaag ggtgccctga acagagcga caaggcgat    1620
aagactactc gtaccagcgg tattggcgtt gtgatgggta accagagcaa tttcagcctg    1680
gagggcaagg tggtggccct gaatatgggt gcaacgcata ccaaacagaa gtatcgtgca    1740
ttgatggtgt ctacgaaac cggcgtggcg atttacaata gcgatgaaga agcagaggca    1800
gcaggcctga tcaaaacgac cgatgagaat ggttatttgt actttctgaa tgacgatctg    1860
aagggcgtgc ctaacccgca ggtcagcggc ttcctgcaag tgtgggttcc ggttggtgca    1920
ccggctgacc aggacattcg tgtggcggcg accgatgcgg cttctaccga cggtaagagc    1980
ctgcatcagg acgcagctct ggattctcgc gtcatgtttg aaggtttcag caacttccag    2040
agcttcgcaa ccaaggaaga ggaatacacc aacgttgtta ttgcaaagaa cgtggataag    2100
ttcgtgagct ggggtatcac cgacttcgag atggcaccgc agtacgttag ctctaccgat    2160
ggcacctttc tggatagcgt gattcaaaat ggctatgcct ttacggaccg ttacgacctg    2220
ggtatgagca aagcaaacaa gtatggtact gctgaccaac tggtggccgc gattaaagcg    2280
```

```
ctgcatgcga agggtctgcg tgtgatggcg gattgggtcc cagatcaaat gtacactttc    2340
cctaagaagg aagtggttac cgttacccgt acggacaaat ttggcaatcc agtggcaggc    2400
agccaaatca accacacctt gtacgtcact gatactaagg gtagcggtga cgactaccag    2460
gcgaagtacg gtggcgcatt cctggatgaa ctgaaagaaa agtacccgga gctgtttacc    2520
aagaagcaaa tcagcaccgg tcaggcaatc gacccgagcg tgaaaatcaa gcagtggagc    2580
gcgaagtact tcaacggtag caatatcttg gtcgcggtg cgaactacgt gctgtccgac    2640
caggcgtcta acaagtactt taacgtggcc gaaggtaaag tctttctgcc agcggcgatg    2700
ctgggtaagg tcgtcgagag cggtatccgt ttcgacggta aaggttatat ctataacagc    2760
agcaccactg gcgaacaagt gaaggacagc ttcattaccg aagcgggtaa cttgtactat    2820
tttggcaaag atggttatat ggtcatgggt gcacagaata tccagggtgc taactactac    2880
ttcttggcga atggtgcggc cctgcgcaat agcatcctga cggatcagga tggcaaaagc    2940
cactattatg caaatgacgg caagcgttat gagaacggct actatcaatt cggtaacgac    3000
tcctggcgct attttgaaaa cggcgttatg gccgttggtt tgacgcgcgt tgcgggccac    3060
gaccaatact ttgataagga tggtatccaa gcgaagaata agatcattgt tacgcgtgac    3120
ggtaaggtcc gctacttcga cgaacacaac ggcaatgctg ccacgaatac gtttatcagc    3180
gatcaagccg gccattggta ctacctgggt aaagatggtg tcgccgtgac gggtgcgcag    3240
accgttggca agcaacacct gtacttcgag gctaacggcc aacaagtaaa aggcgatttt    3300
gttaccgcca aggacggtaa gttgtatttt ctggacggtg actctggcga catgtggacc    3360
gataccttcg tccaggataa ggctggtcat tggttctatc tgggcaaaga cggtgcggcg    3420
gtaaccggtg cccagaccgt ccgtggtcag aagctgtact tcaaagcgaa tggccagcag    3480
gttaagggtc acattgtgaa aggcgcggat ggtaaaatcc gttactatga tgcaaattcc    3540
ggtgaccagg tttacaatcg cacggtgaaa ggctccgacg gcaagaccta tcattggt    3600 aatgacggcg tcgcaatcac gcaaaccatc gccaaaggcc agaccatcaa ggatggcagc    3660
gttctgcgct tctatagcat ggagggtcag ctggtgaccg gcagcggctg gtattccaac    3720
gcgaaaggtc aatggttgta tgtcaagaac ggtcaagtcc tgacgggttt gcagacggtg    3780
ggcagccagc gtgtgtactt tgacgcaaat ggtattcaag cgaaaggtaa agcagtgcgt    3840
acctccgatg gcaaactgcg ttacttcgat gcgaacagcg gcagcatgat caccaatcag    3900
tggaaagaag ttaatggtca gtactactat ttcgacaaca acggtgttgc gatctatcgc    3960
ggttggaact aa                                                       3972
```

<210> SEQ ID NO 14
<211> LENGTH: 1323
<212> TYPE: PRT
<213> ORGANISM: Streptococcus dentirousetti

<400> SEQUENCE: 14

Met Val Asp Gly Lys Tyr Tyr Tyr Asp Ala Asp Gly Asn Val Lys
1               5                   10                  15

Lys Asn Phe Ala Val Ser Val Gly Asp Ala Ile Phe Tyr Phe Asp Glu
                20                  25                  30

Thr Gly Ala Tyr Lys Asp Thr Ser Lys Val Asp Ala Lys Thr Ser
            35                  40                  45

Ser Ser Val Asn Gln Thr Thr Glu Thr Phe Ala Ala Asn Asn Arg Ala
        50                  55                  60

Tyr Ser Thr Ala Ala Glu Asn Phe Glu Ala Ile Asp Asn Tyr Leu Thr

-continued

```
             65                  70                  75                  80
Ala Asp Ser Trp Tyr Arg Pro Lys Ser Ile Leu Lys Asp Gly Thr Thr
                     85                  90                  95
Trp Thr Glu Ser Thr Lys Asp Asp Phe Arg Pro Leu Leu Met Ala Trp
                    100                 105                 110
Trp Pro Asp Thr Glu Thr Lys Arg Asn Tyr Val Asn Tyr Met Asn Lys
                    115                 120                 125
Val Val Gly Ile Asp Lys Thr Tyr Thr Ala Glu Thr Ser Gln Ala Asp
            130                 135                 140
Leu Thr Ala Ala Ala Glu Leu Val Gln Ala Arg Ile Glu Gln Lys Ile
145                 150                 155                 160
Thr Ser Glu Lys Asn Thr Lys Trp Leu Arg Glu Ala Ile Ser Ala Phe
                    165                 170                 175
Val Lys Thr Gln Pro Gln Trp Asn Gly Glu Ser Glu Lys Pro Tyr Asp
                180                 185                 190
Asp His Leu Gln Asn Gly Ala Leu Lys Phe Asp Asn Glu Thr Ser Leu
            195                 200                 205
Thr Pro Asp Thr Gln Ser Gly Tyr Arg Ile Leu Asn Arg Thr Pro Thr
        210                 215                 220
Asn Gln Thr Gly Ser Leu Asp Pro Arg Phe Thr Phe Asn Gln Asn Asp
225                 230                 235                 240
Pro Leu Gly Gly Tyr Glu Tyr Leu Leu Ala Asn Asp Val Asp Asn Ser
                245                 250                 255
Asn Pro Val Val Gln Ala Glu Ser Leu Asn Trp Leu His Tyr Leu Leu
            260                 265                 270
Asn Phe Gly Ser Ile Tyr Ala Asn Asp Pro Glu Ala Asn Phe Asp Ser
        275                 280                 285
Ile Arg Val Asp Ala Val Asp Asn Val Asp Ala Asp Leu Leu Gln Ile
        290                 295                 300
Ser Ser Asp Tyr Leu Lys Ser Ala Tyr Lys Ile Asp Lys Asn Asn Lys
305                 310                 315                 320
Asn Ala Asn Asp His Val Ser Ile Val Glu Ala Trp Ser Asp Asn Asp
                325                 330                 335
Thr Pro Tyr Leu Asn Asp Asp Gly Asp Asn Leu Met Asn Met Asp Asn
                340                 345                 350
Lys Phe Arg Leu Ser Met Leu Trp Ser Leu Ala Lys Pro Thr Asn Val
            355                 360                 365
Arg Ser Gly Leu Asn Pro Leu Ile His Asn Ser Val Val Asp Arg Glu
        370                 375                 380
Val Asp Asp Arg Glu Val Glu Ala Thr Pro Asn Tyr Ser Phe Ala Arg
385                 390                 395                 400
Ala His Asp Ser Glu Val Gln Asp Leu Ile Arg Asp Ile Ile Lys Ala
                405                 410                 415
Glu Ile Asn Pro Asn Ser Phe Gly Tyr Ser Phe Thr Gln Glu Glu Ile
                420                 425                 430
Asp Gln Ala Phe Lys Ile Tyr Asn Glu Asp Leu Lys Lys Thr Asn Lys
            435                 440                 445
Lys Tyr Thr His Tyr Asn Val Pro Leu Ser Tyr Thr Leu Leu Leu Thr
        450                 455                 460
Asn Lys Gly Ser Ile Pro Arg Ile Tyr Tyr Gly Asp Met Phe Thr Asp
465                 470                 475                 480
Asp Gly Gln Tyr Met Ala Asn Lys Thr Val Asn Tyr Asp Ala Ile Glu
                485                 490                 495
```

-continued

```
Ser Leu Leu Lys Ala Arg Met Lys Tyr Val Ser Gly Gln Ala Met
            500                 505                 510
Gln Asn Tyr Asn Ile Gly Asn Gly Glu Ile Leu Thr Ser Val Arg Tyr
        515                 520                 525
Gly Lys Gly Ala Leu Lys Gln Ser Asp Lys Gly Asp Lys Thr Thr Arg
    530                 535                 540
Thr Ser Gly Ile Gly Val Val Met Gly Asn Gln Ser Asn Phe Ser Leu
545                 550                 555                 560
Glu Gly Lys Val Val Ala Leu Asn Met Gly Ala Thr His Thr Lys Gln
                565                 570                 575
Lys Tyr Arg Ala Leu Met Val Ser Glu Thr Gly Val Ala Ile Tyr
            580                 585                 590
Asn Ser Asp Glu Glu Ala Glu Ala Gly Leu Ile Lys Thr Thr Asp
        595                 600                 605
Glu Asn Gly Tyr Leu Tyr Phe Leu Asn Asp Asp Leu Lys Gly Val Ala
    610                 615                 620
Asn Pro Gln Val Ser Gly Phe Leu Gln Val Trp Val Pro Val Gly Ala
625                 630                 635                 640
Pro Ala Asp Gln Asp Ile Arg Val Ala Ala Thr Asp Ala Ala Ser Thr
                645                 650                 655
Asp Gly Lys Ser Leu His Gln Asp Ala Ala Leu Asp Ser Arg Val Met
            660                 665                 670
Phe Glu Gly Phe Ser Asn Phe Gln Ser Phe Ala Thr Lys Glu Glu Glu
        675                 680                 685
Tyr Thr Asn Val Val Ile Ala Lys Asn Val Asp Lys Phe Val Ser Trp
    690                 695                 700
Gly Ile Thr Asp Phe Glu Met Ala Pro Gln Tyr Val Ser Ser Thr Asp
705                 710                 715                 720
Gly Thr Phe Leu Asp Ser Val Ile Gln Asn Gly Tyr Ala Phe Thr Asp
                725                 730                 735
Arg Tyr Asp Leu Gly Met Ser Lys Ala Asn Lys Tyr Gly Thr Ala Asp
            740                 745                 750
Gln Leu Val Ala Ala Ile Lys Ala Leu His Ala Lys Gly Leu Arg Val
        755                 760                 765
Met Ala Asp Trp Val Pro Asp Gln Met Tyr Thr Phe Pro Lys Lys Glu
    770                 775                 780
Val Val Thr Val Thr Arg Thr Asp Lys Phe Gly Asn Pro Val Ala Gly
785                 790                 795                 800
Ser Gln Ile Asn His Thr Leu Tyr Val Thr Asp Thr Lys Gly Ser Gly
                805                 810                 815
Asp Asp Tyr Gln Ala Lys Tyr Gly Gly Ala Phe Leu Asp Glu Leu Lys
            820                 825                 830
Glu Lys Tyr Pro Glu Leu Phe Thr Lys Lys Gln Ile Ser Thr Gly Gln
        835                 840                 845
Ala Ile Asp Pro Ser Val Lys Ile Lys Gln Trp Ser Ala Lys Tyr Phe
    850                 855                 860
Asn Gly Ser Asn Ile Leu Gly Arg Gly Ala Asn Tyr Val Leu Ser Asp
865                 870                 875                 880
Gln Ala Ser Asn Lys Tyr Phe Asn Val Ala Glu Gly Lys Val Phe Leu
                885                 890                 895
Pro Ala Ala Met Leu Gly Lys Val Glu Ser Gly Ile Arg Phe Asp
            900                 905                 910
```

Gly Lys Gly Tyr Ile Tyr Asn Ser Ser Thr Gly Glu Gln Val Lys
            915                 920                 925

Asp Ser Phe Ile Thr Glu Ala Gly Asn Leu Tyr Tyr Phe Gly Lys Asp
        930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
                965                 970                 975

Asp Gly Lys Ser His Tyr Tyr Ala Asn Asp Gly Lys Arg Tyr Glu Asn
            980                 985                 990

Gly Tyr Tyr Gln Phe Gly Asn Asp Ser Trp Arg Tyr Phe Glu Asn Gly
            995                 1000                1005

Val Met Ala Val Gly Leu Thr Arg Val Ala Gly His Asp Gln Tyr
    1010                1015                1020

Phe Asp Lys Asp Gly Ile Gln Ala Lys Asn Lys Ile Ile Val Thr
    1025                1030                1035

Arg Asp Gly Lys Val Arg Tyr Phe Asp Glu His Asn Gly Asn Ala
    1040                1045                1050

Ala Thr Asn Thr Phe Ile Ser Asp Gln Ala Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Leu Asp Gly
    1100                1105                1110

Asp Ser Gly Asp Met Trp Thr Asp Thr Phe Val Gln Asp Lys Ala
    1115                1120                1125

Gly His Trp Phe Tyr Leu Gly Lys Asp Gly Ala Ala Val Thr Gly
    1130                1135                1140

Ala Gln Thr Val Arg Gly Gln Lys Leu Tyr Phe Lys Ala Asn Gly
    1145                1150                1155

Gln Gln Val Lys Gly Asp Ile Val Lys Gly Ala Asp Gly Lys Ile
    1160                1165                1170

Arg Tyr Tyr Asp Ala Asn Ser Gly Asp Gln Val Tyr Asn Arg Thr
    1175                1180                1185

Val Lys Gly Ser Asp Gly Lys Thr Tyr Tyr Ile Ile Gly Asn Asp Gly
    1190                1195                1200

Val Ala Ile Thr Gln Thr Ile Ala Lys Gly Gln Thr Ile Lys Asp
    1205                1210                1215

Gly Ser Val Leu Arg Phe Tyr Ser Met Glu Gly Gln Leu Val Thr
    1220                1225                1230

Gly Ser Gly Trp Tyr Ser Asn Ala Lys Gly Gln Trp Leu Tyr Val
    1235                1240                1245

Lys Asn Gly Gln Val Leu Thr Gly Leu Gln Thr Val Gly Ser Gln
    1250                1255                1260

Arg Val Tyr Phe Asp Ala Asn Gly Ile Gln Ala Lys Gly Lys Ala
    1265                1270                1275

Val Arg Thr Ser Asp Gly Lys Leu Arg Tyr Phe Asp Ala Asn Ser
    1280                1285                1290

Gly Ser Met Ile Thr Asn Gln Trp Lys Glu Val Asn Gly Gln Tyr
    1295                1300                1305

Tyr Tyr Phe Asp Asn Asn Gly Val Ala Ile Tyr Arg Gly Trp Asn

<210> SEQ ID NO 15
<211> LENGTH: 4047
<212> TYPE: DNA
<213> ORGANISM: Streptococcus oralis

<400> SEQUENCE: 15

```
atgatcgacg gcaaaaacta ctacgtacag gatgatggca cggtaaagaa gaatttcgcg      60
gtagaactga atggtcgtat cctgtatttt gatgcagaaa ccggcgctct ggttgatagc     120
aacgagtatc agttccaaca gggtacgagc agcctgaaca atgaattttc tcagaagaac     180
gcattctatg gtacgaccga taaggatatt gagactgtgg atggctacct gaccgcagat     240
agctggtatc gcccgaaatt catcctgaag gatggcaaga cgtggaccgc gagcacggaa     300
acggatctgc gtccgctgtt gatggcatgg tggccggaca agcgtaccca aatcaactat     360
ctgaactaca tgaaccagca gggtctgggt gcgggtgcgt ttgagaacaa agtggagcag     420
gccctgctga cgggtgcaag ccaacaggta caacgcaaga tcgaagagaa gattggtaaa     480
gagggtgata ccaagtggct gcgcaccctg atgggtgcgt tcgtgaaaac gcaaccaaac     540
tggaatatca aaccgagtc tgaaacgacc ggcacgaaaa aggaccatct gcaaggcggt     600
gcactgctgt atacgaacaa cgagaaatcc ccgcacgcgg acagcaaatt tcgtctgctg     660
aatcgtaccc cgaccagcca aaccggcacg ccgaagtatt tcatcgacaa gtctaacggt     720
ggctacgaat ttctgctggc gaacgatttt gacaatagca atcctgcggt acaagctgag     780
cagctgaatt ggctgcacta catgatgaac tttggcagca ttgttgcgaa tgatccgacc     840
gcgaatttcg acggcgttcg tgtggatgct gttgataacg tcaatgcgga cttgttgcaa     900
attgcaagcg attactttaa gagccgttac aaagtcggtg agagcgaaga gaagcgatc     960
aagcacctgt ccatcctgga agcatggagc gataacgacc cggactacaa caaagatacc    1020
aagggtgcac agttggcgat tgataacaaa ctgcgcctga gcctgctgta ctctttcatg    1080
cgtaatctga gcatccgtag cggtgttgaa ccgacgatta ccaatagcct gaatgaccgt    1140
tccagcgaaa agaagaacgg cgagcgtatg gcaaattaca tcttcgtgcg tgcccacgat    1200
agcgaggtcc aaacggtgat cgccgacatc attcgcgaaa acatcaatcc gaacaccgac    1260
ggcctgacgt ttacgatgga cgagctgaag caggcattca agatttacaa cgaggacatg    1320
cgcaaggcgg acaaaaagta tacccagttt aacattccta ccgcacacgc gctgatgctg    1380
tctaataagg attctattac ccgcgtgtac tatggtgatc tgtatactga cgatggtcag    1440
tacatggaga agaaaagccc gtatcacgat gcgattgacg ctctgctgcg tgcacgtatt    1500
aaatacgtcg cgggtggcca ggatatgaaa gtgacctata tgggcgtgcc gcgtgaagcg    1560
gataagtgga gctataacgg cattctgacc agcgtgcgct atggcacggg cgctaacgaa    1620
gccacggatg agggcactgc ggaaacgcgc acgcaaggta tggcagtgat tgcgagcaat    1680
aatccaaatc tgaaactgaa tgaatgggac aagttgcaag tcaacatggg tgcggcgcat    1740
aagaatcaat attaccgtcc ggttctgctg accactaagg acggtatcag ccgttatctg    1800
accgatgaag aagtgcctca gagcctgtgg aaaaagacgg acgcaaacgg tattctgacc    1860
ttcgacatga atgatattgc tggctacagc aacgtgcaag ttagcggtta cctggccgtc    1920
tgggtcccgg tcggtgcgaa ggcggatcaa gatgcgcgca cgaccgcatc caagaagaaa    1980
aatgcgtcgg gtcaggtgta cgaaagcagc gcggctctgg atagccagct gatttacgaa    2040
ggtttcagca actttcaaga ctttgccact cgcgatgatc agtacacgaa caaggtcatt    2100
```

```
gcgaaaaacg tgaatctgtt caaagaatgg ggtgtgacca gcttcgagct gccgccgcag    2160
tacgtgagca gccaagatgg caccttctg gacagcatta tccaaaacgg ctatgcattt    2220
gaagaccgtt acgatatggc gatgagcaag aataacaagt atggtagcct gaaagacctg    2280
ttgaacgcgc tgcgcgcact gcacagcgtc aacattcaag caatcgccga ttgggtgccg    2340
gaccaaattt acaacttgcc gggcaaagag gtggtgaccg caactcgtgt caacaactac    2400
ggcacctacc gtgagggtgc tgaaatcaaa gaaaagctgt atgtcgccaa tagcaagacc    2460
aacgaaaccg atttccaagg taaatacggt ggtgcgttcc tggatgagct gaaggcgaag    2520
tacccggaga ttttcgagcg tgtccaaatc agcaacggcc aaaagatgac taccgatgaa    2580
aagatcacca atggagcgc gaaatacttt aatggcacca atattctggg tcgtggcgcg    2640
tactatgtcc tgaaagattg gccagcaat gattacctga cgaaccgtaa cggcgagatt    2700
gttttgccga agcaactggt taacaagaat agctataccg ctttgtcag cgacgcgaac    2760 ggcacgaagt tctattctac ctctggctac caggcgaaga acagcttcat tcaagacgaa    2820
aacggtaatt ggtattactt tgacaaacgt ggttatctgg ttacgggcgc acacgagatt    2880
gatggcaagc atgtctactt cctgaaaaac ggtatccaac tgcgtgacag catccgtgag    2940
gatgagaacg gtaatcaata ctattacgac cagaccggcg cacaagtgct gaaccgttac    3000
tacacgacgg acgtcagaa ttggcgctat ttcgatgcga aggtgttat ggcacgcggc    3060 ctggtaaaga ttggtgacgg ccaacagttt ttcgatgaaa acggttacca ggtcaagggc    3120
aagattgtta gcgcaaaaga cggcaagctg cgctactttg ataaagactc tggcaatgct    3180
gtcattaatc gtttcgcgca gggtgacaat ccgagcgact ggtactattt cggtgtggaa    3240
tttgctaaac tgacgggttt gcaaaagatc ggccagcaga cgctgtattt tgaccaagac    3300
ggtaagcaag tcaaaggtaa gatcgtaact ctgtcggaca aaagcattcg ttacttcgat    3360
gccaacagcg gtgaaatggc ggttggcaag ttcgcggaag gtgcaaagaa tgagtggtat    3420
tatttcgata aaaccggcaa agcggttact ggtttgcaga aaattggtaa gcagaccctg    3480
tactttgacc aggacggtaa acaggttaaa ggcaaggttg tcacgctggc tgataaaagc    3540
atccgctact tcgacgcaga ctccggcgag atggcggtcg gtaagtttgc agagggtgcg    3600
aagaacgagt ggtactattt tgatcagact ggcaaggccg tgactggttt gcaaaagatt    3660
gacaagcaaa ccttgtactt cgaccaggac ggtaaacaag tcaagggtaa gattgtgacg    3720
ttgagcgaca gtcgatccg ttactttgat gctaatagcg gtgagatggc tactaacaaa    3780
ttcgtcgagg gctcgcagaa tgaatggtac tacttcgatc aagcgggtaa ggctgttacg    3840
ggcttgcaac aggtcggtca gcaaactctg tacttcaccc aggatggtaa gcaagtgaag    3900
ggtaaggtcg tggacgtgaa cggtgtttct cgttatttcg acgcaaactc cggtgacatg    3960
gctcgttcta aatggattca actggaagat ggcagctgga tgtatttcga ccgtgacggt    4020
cgtggccaga attttggccg taactaa                                       4047
```

<210> SEQ ID NO 16
<211> LENGTH: 1348
<212> TYPE: PRT
<213> ORGANISM: Streptococcus oralis

<400> SEQUENCE: 16

Met Ile Asp Gly Lys Asn Tyr Tyr Val Gln Asp Asp Gly Thr Val Lys
1               5                   10                  15

Lys Asn Phe Ala Val Glu Leu Asn Gly Arg Ile Leu Tyr Phe Asp Ala

-continued

```
                20                  25                  30
Glu Thr Gly Ala Leu Val Asp Ser Asn Glu Tyr Gln Phe Gln Gln Gly
             35                  40                  45
Thr Ser Ser Leu Asn Asn Glu Phe Ser Gln Lys Asn Ala Phe Tyr Gly
         50                  55                  60
Thr Thr Asp Lys Asp Ile Glu Thr Val Asp Gly Tyr Leu Thr Ala Asp
 65                  70                  75                  80
Ser Trp Tyr Arg Pro Lys Phe Ile Leu Lys Asp Gly Lys Thr Trp Thr
                 85                  90                  95
Ala Ser Thr Glu Thr Asp Leu Arg Pro Leu Leu Met Ala Trp Trp Pro
            100                 105                 110
Asp Lys Arg Thr Gln Ile Asn Tyr Leu Asn Tyr Met Asn Gln Gln Gly
        115                 120                 125
Leu Gly Ala Gly Ala Phe Glu Asn Lys Val Glu Gln Ala Leu Leu Thr
    130                 135                 140
Gly Ala Ser Gln Gln Val Gln Arg Lys Ile Glu Glu Lys Ile Gly Lys
145                 150                 155                 160
Glu Gly Asp Thr Lys Trp Leu Arg Thr Leu Met Gly Ala Phe Val Lys
                165                 170                 175
Thr Gln Pro Asn Trp Asn Ile Lys Thr Glu Ser Glu Thr Thr Gly Thr
            180                 185                 190
Lys Lys Asp His Leu Gln Gly Gly Ala Leu Leu Tyr Thr Asn Asn Glu
        195                 200                 205
Lys Ser Pro His Ala Asp Ser Lys Phe Arg Leu Leu Asn Arg Thr Pro
    210                 215                 220
Thr Ser Gln Thr Gly Thr Pro Lys Tyr Phe Ile Asp Lys Ser Asn Gly
225                 230                 235                 240
Gly Tyr Glu Phe Leu Leu Ala Asn Asp Phe Asn Ser Asn Pro Ala
                245                 250                 255
Val Gln Ala Glu Gln Leu Asn Trp Leu His Tyr Met Met Asn Phe Gly
            260                 265                 270
Ser Ile Val Ala Asn Asp Pro Thr Ala Asn Phe Asp Gly Val Arg Val
        275                 280                 285
Asp Ala Val Asp Asn Val Asn Ala Asp Leu Leu Gln Ile Ala Ser Asp
    290                 295                 300
Tyr Phe Lys Ser Arg Tyr Lys Val Gly Glu Ser Glu Glu Ala Ile
305                 310                 315                 320
Lys His Leu Ser Ile Leu Glu Ala Trp Ser Asp Asn Asp Pro Asp Tyr
                325                 330                 335
Asn Lys Asp Thr Lys Gly Ala Gln Leu Ala Ile Asp Asn Lys Leu Arg
            340                 345                 350
Leu Ser Leu Leu Tyr Ser Phe Met Arg Asn Leu Ser Ile Arg Ser Gly
        355                 360                 365
Val Glu Pro Thr Ile Thr Asn Ser Leu Asn Asp Arg Ser Ser Glu Lys
    370                 375                 380
Lys Asn Gly Glu Arg Met Ala Asn Tyr Ile Phe Val Arg Ala His Asp
385                 390                 395                 400
Ser Glu Val Gln Thr Val Ile Ala Asp Ile Ile Arg Glu Asn Ile Asn
                405                 410                 415
Pro Asn Thr Asp Gly Leu Thr Phe Thr Met Asp Glu Leu Lys Gln Ala
            420                 425                 430
Phe Lys Ile Tyr Asn Glu Asp Met Arg Lys Ala Asp Lys Lys Tyr Thr
        435                 440                 445
```

```
Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
                500                 505                 510

Tyr Met Gly Val Pro Arg Glu Ala Asp Lys Trp Ser Tyr Asn Gly Ile
            515                 520                 525

Leu Thr Ser Val Arg Tyr Gly Thr Gly Ala Asn Glu Ala Thr Asp Glu
    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
                580                 585                 590

Lys Asp Gly Ile Ser Arg Tyr Leu Thr Asp Glu Glu Val Pro Gln Ser
            595                 600                 605

Leu Trp Lys Lys Thr Asp Ala Asn Gly Ile Leu Thr Phe Asp Met Asn
    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Thr Thr Ala
                645                 650                 655

Ser Lys Lys Lys Asn Ala Ser Gly Gln Val Tyr Glu Ser Ser Ala Ala
                660                 665                 670

Leu Asp Ser Gln Leu Ile Tyr Glu Gly Phe Ser Asn Phe Gln Asp Phe
            675                 680                 685

Ala Thr Arg Asp Asp Gln Tyr Thr Asn Lys Val Ile Ala Lys Asn Val
    690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
                740                 745                 750

Lys Tyr Gly Ser Leu Lys Asp Leu Leu Asn Ala Leu Arg Ala Leu His
            755                 760                 765

Ser Val Asn Ile Gln Ala Ile Ala Asp Trp Val Pro Asp Gln Ile Tyr
    770                 775                 780

Asn Leu Pro Gly Lys Glu Val Val Thr Ala Thr Arg Val Asn Asn Tyr
785                 790                 795                 800

Gly Thr Tyr Arg Glu Gly Ala Glu Ile Lys Glu Lys Leu Tyr Val Ala
                805                 810                 815

Asn Ser Lys Thr Asn Glu Thr Asp Phe Gln Gly Lys Tyr Gly Gly Ala
                820                 825                 830

Phe Leu Asp Glu Leu Lys Ala Lys Tyr Pro Glu Ile Phe Glu Arg Val
            835                 840                 845

Gln Ile Ser Asn Gly Gln Lys Met Thr Thr Asp Glu Lys Ile Thr Lys
    850                 855                 860
```

```
Trp Ser Ala Lys Tyr Phe Asn Gly Thr Asn Ile Leu Gly Arg Gly Ala
865                 870                 875                 880

Tyr Tyr Val Leu Lys Asp Trp Ala Ser Asn Asp Tyr Leu Thr Asn Arg
            885                 890                 895

Asn Gly Glu Ile Val Leu Pro Lys Gln Leu Val Asn Lys Asn Ser Tyr
                900                 905                 910

Thr Gly Phe Val Ser Asp Ala Asn Gly Thr Lys Phe Tyr Ser Thr Ser
        915                 920                 925

Gly Tyr Gln Ala Lys Asn Ser Phe Ile Gln Asp Glu Asn Gly Asn Trp
    930                 935                 940

Tyr Tyr Phe Asp Lys Arg Gly Tyr Leu Val Thr Gly Ala His Glu Ile
945                 950                 955                 960

Asp Gly Lys His Val Tyr Phe Leu Lys Asn Gly Ile Gln Leu Arg Asp
                965                 970                 975

Ser Ile Arg Glu Asp Glu Asn Gly Asn Gln Tyr Tyr Asp Gln Thr
        980                 985                 990

Gly Ala Gln Val Leu Asn Arg Tyr Tyr Thr Thr Asp Gly Gln Asn Trp
    995                 1000                1005

Arg Tyr Phe Asp Ala Lys Gly Val Met Ala Arg Gly Leu Val Lys
1010                1015                1020

Ile Gly Asp Gly Gln Gln Phe Phe Asp Glu Asn Gly Tyr Gln Val
1025                1030                1035

Lys Gly Lys Ile Val Ser Ala Lys Asp Gly Lys Leu Arg Tyr Phe
1040                1045                1050

Asp Lys Asp Ser Gly Asn Ala Val Ile Asn Arg Phe Ala Gln Gly
1055                1060                1065

Asp Asn Pro Ser Asp Trp Tyr Tyr Phe Gly Val Glu Phe Ala Lys
1070                1075                1080

Leu Thr Gly Leu Gln Lys Ile Gly Gln Gln Thr Leu Tyr Phe Asp
1085                1090                1095

Gln Asp Gly Lys Gln Val Lys Gly Lys Ile Val Thr Leu Ser Asp
1100                1105                1110

Lys Ser Ile Arg Tyr Phe Asp Ala Asn Ser Gly Glu Met Ala Val
1115                1120                1125

Gly Lys Phe Ala Glu Gly Ala Lys Asn Glu Trp Tyr Tyr Phe Asp
1130                1135                1140

Lys Thr Gly Lys Ala Val Thr Gly Leu Gln Lys Ile Gly Lys Gln
1145                1150                1155

Thr Leu Tyr Phe Asp Gln Asp Gly Lys Gln Val Lys Gly Lys Val
1160                1165                1170

Val Thr Leu Ala Asp Lys Ser Ile Arg Tyr Phe Asp Ala Asp Ser
1175                1180                1185

Gly Glu Met Ala Val Gly Lys Phe Ala Glu Gly Ala Lys Asn Glu
1190                1195                1200

Trp Tyr Tyr Phe Asp Gln Thr Gly Lys Ala Val Thr Gly Leu Gln
1205                1210                1215

Lys Ile Asp Lys Gln Thr Leu Tyr Phe Asp Gln Asp Gly Lys Gln
1220                1225                1230

Val Lys Gly Lys Ile Val Thr Leu Ser Asp Lys Ser Ile Arg Tyr
1235                1240                1245

Phe Asp Ala Asn Ser Gly Glu Met Ala Thr Asn Lys Phe Val Glu
1250                1255                1260

Gly Ser Gln Asn Glu Trp Tyr Tyr Phe Asp Gln Ala Gly Lys Ala
```

| | | | | | | | | | | |
|---|---|---|---|---|---|---|---|---|---|---|
| | | 1265 | | | 1270 | | | 1275 | | |
| Val | Thr | Gly | Leu | Gln | Gln | Val | Gly | Gln | Gln | Thr | Leu | Tyr | Phe | Thr |
| | | 1280 | | | | 1285 | | | | 1290 |

Val Thr Gly Leu Gln Gln Val Gly Gln Gln Thr Leu Tyr Phe Thr
                1280                1285                1290

Gln Asp Gly Lys Gln Val Lys Gly Lys Val Val Asp Val Asn Gly
    1295                1300                1305

Val Ser Arg Tyr Phe Asp Ala Asn Ser Gly Asp Met Ala Arg Ser
    1310                1315                1320

Lys Trp Ile Gln Leu Glu Asp Gly Ser Trp Met Tyr Phe Asp Arg
    1325                1330                1335

Asp Gly Arg Gly Gln Asn Phe Gly Arg Asn
    1340                1345

<210> SEQ ID NO 17
<211> LENGTH: 4047
<212> TYPE: DNA
<213> ORGANISM: Streptococcus sanguinis

<400> SEQUENCE: 17

```
atgattgatg gtaaaaagta ttacgtacag gacgacggca cggttaagaa gaatttcgcg      60
gttgagctga atggcaagat cctgtacttc gatgcagaga ctggtgcgtt gattgacagc     120
gcggagtatc aattccaaca aggcaccagc agcctgaata atgagttcac tcaaaagaac     180
gccttttacg gtacgaccga taaggatgtg gaaaccattg atggttactt gaccgccgat     240
tcctggtatc gtccgaagtt cattctgaaa gatggcaaaa cctggacggc gagcacggaa     300
attgacttgc gtccgttgtt gatggcgtgg tggccggaca acagacccca ggttagctac     360
ctgaattaca tgaaccagca aggcttgggt gcaggcgcct tcgaaaacaa agtagagcag     420
gcaattctga ccggtgcgtc caacaggta caacgtaaaa tcgaagaacg catcggtaaa     480
gagggtgata ccaagtggct gcgtaccctg atgggtgcat ttgtaaagac ccagccgaac     540
tggaacatta agaccgagtc cgaaaccact ggcacgaata agatcatctc gcaaggtggc     600
gcactgctgt atagcaattc cgacaagacg agccatgcca actctaagta ccgtatcctg     660
aaccgcaccc cgaccaacca aacgggcacg ccgaaatact ttattgacaa gagcaatggt     720
ggttatgaat ttctgctggc gaatgacttt gacaatagca atccggcagt gcaagcggaa     780
cagctgaact ggttgcactt tatgatgaat tttggctcca tcgttgcaaa tgatccgacg     840
gccaacttcg acggcgtccg cgttgacgct gtggataacg tgaatgcgga tctgttgcaa     900
attgcgagcg actatttcaa gagccgctat aaagtcggcg aaagcgaaga gaggccatt     960
aagcacctgt ccatcctgga agcgtggagc gacaacgacc cggactacaa caaggatact    1020
aaaggtgccc aactgccgat cgacaacaaa ctgcgtctga gcctgctgta ctccttcatg    1080
cgtaagctga gcatccgtag cggcgtcgag ccgaccatca ccaactctct gaatgatcgc    1140
agcacggaga agaagaatgg tgagcgtatg gcaaactata tcttcgttcg tgcacatgat    1200
agcgaggtgc aaacggtcat cgccgacatt atccgtgaga acatcaatcc gaataccgac    1260
ggcctgacgt tcacgatgga tgaactgaag caggccttta aaatttacaa tgaggatatg    1320
cgtaaagccg acaaaaagta cacgcagttc aatatcccga ccgcgcacgc gctgatgctg    1380
agcaacaaag attctatcac ccgcgtttac tacggtgacc tgtatacgga tgacggtcag    1440
tatatggaaa agaaaagccc gtatcacgac gccattgacg ctctgctgcg tgcgcgtatc    1500
aaatatgttg cgggtggtca ggacatgaag gtgacctata tgggcgtgcc gcgtgaggca    1560
gataaatgga gctataacgg catcctgacc agcgttcgtt atggtacggg tgccaacgag    1620
```

```
gcaaccgacg agggtacggc agaaacccgt acccagggca tggccgtcat tgccagcaac   1680
aatccgaacc tgaaactgaa cgagtgggac aagttgcagg tcaacatggg tgcagctcac   1740
aaaaaccaat actatcgtcc ggtgctgctg accaccaagg acggcatctc gcgctacctg   1800
accgacgaag aagtcccgca gagcctgtgg aaaaagaccg atgcgaacgg catcttgacg   1860
tttgacatga atgatattgc gggttacagc aacgtccaag tgagcggtta tctggccgtc   1920
tgggttcctg tgggtgcgaa ggcggaccag gacgctcgtg ttacggcatc taagaagaaa   1980
aatgcctctg gccaagttta cgaaagcagc gcagccctgg actcccagct gatctatgag   2040
ggcttcagca attttcagga cttt gccacc cgtgacgacc agtacactaa caaggttatc   2100
gcgaaaaacg tcaatctgtt taaagagtgg ggcgtcacca gcttcgaatt gccgccacag   2160
tatgtgagca gccaagacgg tacgttcctg gatagcatca tccagaatgg ttatgcattc   2220
gaagatcgct atgatatggc gatgagcaaa aacaataagt acggtagctt gaacgacctg   2280
ttgaacgcct gcgtgcact gcatagcgtg aatatccaag cgattgcgga ttgggtgccg   2340
gaccagattt acaatctgcc gggtaaagaa gttgtcactg caacccgtgt taacaattat   2400
ggcacgtatc gtgagggtag cgagattaaa gagaacctgt acgttgctaa caccaaaacc   2460
aatggtacgg actaccaagg taagtatggt ggtgcgttct tggacgagct gaaagccaaa   2520
taccctgaga tttttgagcg cgtccaaatc agcaacggcc agaagatgac caccgacgag   2580
aagattacga aatggtccgc caaacacttt aacggcacga acattctggg tcgtggtgcg   2640
tattatgtgc tgaaagactg ggcgagcaac gagtacctga ataacaaaaa tggcgagatg   2700
gttctgccga gcagctggt taataaaaat gcatataccg gcttcgtcag cgacgcgagc   2760
ggcaccaaat actattctac cagcggctat caggctcgta atagctttat tcaagatgaa   2820
aatggtaatt ggtactactt caataaccgt ggttatttgg tgacgggtgc acaggaaatc   2880
gacggtaagc aactgtattt cctgaaaaac ggcattcagc tgcgtgattc tctgcgtgag   2940
gacgaaaacg gcaaccagta ttactatgat aagacgggtg cgcaagttct gaatcgttat   3000
tacactacgg acggccaaaa ttggcgctac ttcgacgtta aaggcgtcat ggcccgtggt   3060
ctggtcacga tgggtggtaa ccaacaattc tttgaccaaa acggttacca ggttaaaggc   3120
aaaattgcgc gtgcaaaaga cggtaaactg cgttacttcg ataaagacag cggtaatgcg   3180
gcagctaacc gttcgcccca aggcgataac cctagcgact ggtactattt cggtgcagat   3240
ggtgttgcgg ttacgggcct gcaaaaggtt ggtcagcaaa ctctgtactt tgatcaggac   3300
ggcaagcagg tgaaaggtaa agttgttacc ttggcggaca aaagcattcg ttatttcgat   3360
gcaaacagcg gcgagatggc ggtgaacaag tttgtggaag gtgctaagaa cgtgtggtac   3420
tacttcgatc aagcaggcaa agcggtgacc ggcctgcaaa ccatcaataa acaagtgctg   3480
tatttcgacc aggatggtaa acaagtcaaa ggtaaggtgg tcacgctggc tgataagtct   3540
atccgctact tcgacgcgaa cagcggtgag atggcagtgg gcaaattcgc cgaaggcgca   3600
aagaatgagt ggtattactt tgaccaggcg ggcaaggctg ttaccggtct gcaaaagatc   3660
ggccaacaga cgctgtattt cgaccagaac ggtaaacagg ttaagggtaa agtggtcacc   3720
ctggcggata gagcatccg ctatttcgac gctaactctg gcgaaatggc aagcaataag   3780
ttcgttgagg gtgccaaaaa tgaatggtac tatttcgatc aggctggcaa ggcagtgacg   3840
ggtctgcaac aaattggcca gcagaccctg tattttgacc agaatggcaa acaggtgaag   3900
ggtaagattg tgtatgttaa tggtgcgaat cgctactttg atgccaatag cggtgaaatg   3960
gcgcgtaaca agtggattca gctggaagat ggcagctgga tgtatttga ccgcaatggt   4020
```
cgtggtcgtc gtttcggttg gaactaa                                                      4047

<210> SEQ ID NO 18
<211> LENGTH: 1348
<212> TYPE: PRT
<213> ORGANISM: Streptococcus sanguinis

<400> SEQUENCE: 18

Met Ile Asp Gly Lys Lys Tyr Tyr Val Gln Asp Gly Thr Val Lys
1               5                   10                  15

Lys Asn Phe Ala Val Glu Leu Asn Gly Lys Ile Leu Tyr Phe Asp Ala
            20                  25                  30

Glu Thr Gly Ala Leu Ile Asp Ser Ala Glu Tyr Gln Phe Gln Gln Gly
        35                  40                  45

Thr Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
        195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asn Ser Asn Pro Ala
                245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
        355                 360                 365

```
Val Glu Pro Thr Ile Thr Asn Ser Leu Asn Asp Arg Ser Thr Glu Lys
    370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
        435                 440                 445

Gln Phe Asn Ile Pro Thr Ala His Ala Leu Met Leu Ser Asn Lys Asp
450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
        595                 600                 605

Leu Trp Lys Lys Thr Asp Ala Asn Gly Ile Leu Thr Phe Asp Met Asn
610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                645                 650                 655

Ser Lys Lys Lys Asn Ala Ser Gly Gln Val Tyr Glu Ser Ser Ala Ala
            660                 665                 670

Leu Asp Ser Gln Leu Ile Tyr Glu Gly Phe Ser Asn Phe Gln Asp Phe
        675                 680                 685

Ala Thr Arg Asp Asp Gln Tyr Thr Asn Lys Val Ile Ala Lys Asn Val
690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
            740                 745                 750

Lys Tyr Gly Ser Leu Asn Asp Leu Leu Asn Ala Leu Arg Ala Leu His
        755                 760                 765

Ser Val Asn Ile Gln Ala Ile Ala Asp Trp Val Pro Asp Gln Ile Tyr
770                 775                 780
```

```
Asn Leu Pro Gly Lys Glu Val Val Thr Ala Thr Arg Val Asn Asn Tyr
785                 790                 795                 800

Gly Thr Tyr Arg Glu Gly Ser Glu Ile Lys Glu Asn Leu Tyr Val Ala
                805                 810                 815

Asn Thr Lys Thr Asn Gly Thr Asp Tyr Gln Gly Lys Tyr Gly Gly Ala
            820                 825                 830

Phe Leu Asp Glu Leu Lys Ala Lys Tyr Pro Glu Ile Phe Glu Arg Val
        835                 840                 845

Gln Ile Ser Asn Gly Gln Lys Met Thr Thr Asp Glu Lys Ile Thr Lys
    850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                885                 890                 895

Asn Gly Glu Met Val Leu Pro Lys Gln Leu Val Asn Lys Asn Ala Tyr
            900                 905                 910

Thr Gly Phe Val Ser Asp Ala Ser Gly Thr Lys Tyr Tyr Ser Thr Ser
        915                 920                 925

Gly Tyr Gln Ala Arg Asn Ser Phe Ile Gln Asp Glu Asn Gly Asn Trp
    930                 935                 940

Tyr Tyr Phe Asn Asn Arg Gly Tyr Leu Val Thr Gly Ala Gln Glu Ile
945                 950                 955                 960

Asp Gly Lys Gln Leu Tyr Phe Leu Lys Asn Gly Ile Gln Leu Arg Asp
                965                 970                 975

Ser Leu Arg Glu Asp Glu Asn Gly Asn Gln Tyr Tyr Tyr Asp Lys Thr
            980                 985                 990

Gly Ala Gln Val Leu Asn Arg Tyr Tyr Thr Thr Asp Gly Gln Asn Trp
        995                 1000                1005

Arg Tyr Phe Asp Val Lys Gly Val Met Ala Arg Gly Leu Val Thr
    1010                1015                1020

Met Gly Gly Asn Gln Gln Phe Phe Asp Gln Asn Gly Tyr Gln Val
    1025                1030                1035

Lys Gly Lys Ile Ala Arg Ala Lys Asp Gly Lys Leu Arg Tyr Phe
    1040                1045                1050

Asp Lys Asp Ser Gly Asn Ala Ala Ala Asn Arg Phe Ala Gln Gly
    1055                1060                1065

Asp Asn Pro Ser Asp Trp Tyr Tyr Phe Gly Ala Asp Gly Val Ala
    1070                1075                1080

Val Thr Gly Leu Gln Lys Val Gly Gln Gln Thr Leu Tyr Phe Asp
    1085                1090                1095

Gln Asp Gly Lys Gln Val Lys Gly Lys Val Val Thr Leu Ala Asp
    1100                1105                1110

Lys Ser Ile Arg Tyr Phe Asp Ala Asn Ser Gly Glu Met Ala Val
    1115                1120                1125

Asn Lys Phe Val Glu Gly Ala Lys Asn Val Trp Tyr Tyr Phe Asp
    1130                1135                1140

Gln Ala Gly Lys Ala Val Thr Gly Leu Gln Thr Ile Asn Lys Gln
    1145                1150                1155

Val Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asn Ser
    1175                1180                1185

Gly Glu Met Ala Val Gly Lys Phe Ala Glu Gly Ala Lys Asn Glu
```

| | | | | | | | | | | | |
|---|---|---|---|---|---|---|---|---|---|---|---|
| | | 1190 | | | 1195 | | | 1200 | | | |
| Trp | Tyr | Tyr | Phe | Asp | Gln | Ala | Gly | Lys | Ala | Val | Thr | Gly | Leu | Gln |
| | 1205 | | | | 1210 | | | | 1215 | | |

Trp Tyr Tyr Phe Asp Gln Ala Gly Lys Ala Val Thr Gly Leu Gln
        1205                  1210                1215

Lys Ile Gly Gln Gln Thr Leu Tyr Phe Asp Gln Asn Gly Lys Gln
    1220                1225                1230

Val Lys Gly Lys Val Val Thr Leu Ala Asp Lys Ser Ile Arg Tyr
    1235                1240                1245

Phe Asp Ala Asn Ser Gly Glu Met Ala Ser Asn Lys Phe Val Glu
    1250                1255                1260

Gly Ala Lys Asn Glu Trp Tyr Tyr Phe Asp Gln Ala Gly Lys Ala
    1265                1270                1275

Val Thr Gly Leu Gln Gln Ile Gly Gln Gln Thr Leu Tyr Phe Asp
    1280                1285                1290

Gln Asn Gly Lys Gln Val Lys Gly Lys Ile Val Tyr Val Asn Gly
    1295                1300                1305

Ala Asn Arg Tyr Phe Asp Ala Asn Ser Gly Glu Met Ala Arg Asn
    1310                1315                1320

Lys Trp Ile Gln Leu Glu Asp Gly Ser Trp Met Tyr Phe Asp Arg
    1325                1330                1335

Asn Gly Arg Gly Arg Arg Phe Gly Trp Asn
    1340                1345

```
<210> SEQ ID NO 19
<211> LENGTH: 4023
<212> TYPE: DNA
<213> ORGANISM: Unknown
<220> FEATURE:
<223> OTHER INFORMATION: unknown Streptococcus species

<400> SEQUENCE: 19
atgatcgacg gcaaatacta ctacgtaaac gaggacggca gccacaaaga gaatttcgcg      60
atcacggtta atggtcaact gctgtatttt ggtaaggatg cgcgcgctga cagcagcagc     120
acgtacagct tcacccaagg cactaccaat attgtggacg gttttagcat taacaaccgt     180
gcgtatgact ccagcgaggc ctctttcgag ctgattgacg ttatctgac tgcggactct     240 tggtaccgtc cggcgagcat tatcaaagac ggtgtgacgt ggcaagcatc caccgccgag     300
gacttccgcc cgttgctgat ggcgtggtgg ccgaacgttg atactcaggt gaactacctg     360
aactacatgt ccaaagtctt taatctggat gctaaataca gctcgactga taaacaggaa     420
accctgaagg tggcggcgaa agatatccag atcaaaattg aacaaagat tcaggcggaa     480 aagtccacgc aatggctgcg tgaaacgatc agcgcctttg taaaaaccca gccgcaatgg     540
aacaaagaga ctgagaacta cagcaagggc ggtggtgagg accatctgca aggtggtgcc     600
ctgctgtatg ttaatgactc tcgtacccg tgggcgaaca gcaactatcg tttgctgaac     660
cgcacggcga ccaaccagac cggtacgatc gacaagagca tcctggacga gcagagcgat     720
ccgaatcaca tgggtggttt tgatttcttg ctggctaatg acgttgactt gagcaatccg     780
gtcgtccagg cggaacaact gaatcagatc cactacctga tgaattgggg ttctattgtc     840
atgggtgata agacgcgcaa ttttgacggt attcgtgtag acgcggtgga taatgttgat     900
gcggacatgc tgcaattgta caccaactat ttccgcgaat actatggtgt caacaaaagc     960
gaggcaaacg cgctggcgca cattagcgtc ctggaagcct ggagcctgaa tgacaaccat    1020
tacaatgata gactgatgt tgcggcgctg gcaatggaga ataagcagcg cttggcactg    1080
ttgtttagcc tggcgaaacc gattaaagaa cgcacgcctg ccgtgtctcc gctgtacaac    1140
```

```
aatacgttta acaccactca gcgtgatgaa aagacggact ggatcaataa agatggttcg    1200
aaagcctaca atgaggatgg cactgtcaag aaaagcacca tcggcaagta taacgagaag    1260
tatggtgatg ctagcggcaa ctacgttttc atccgcgctc acgacaataa cgtgcaagac    1320
atcatcgcgg agatcattaa gaaagagatt aacgagaaat ctgacggttt taccattacg    1380
gattcggaga tgaagcgtgc atttgagatc tataacaaag acatgctgtc taatgacaaa    1440
aagtacacgc tgaataacat cccggcggcg tacgcggtta tgctgcaaaa catggaaacg    1500
attacccgcg tgtattacgg cgatctgtac acggacgacg gtaattacat ggaagcgaaa    1560
agcccgtact acgatacgat tgttaacttg atgaagtctc gcatcaaata cgtgagcggt    1620
ggccaggcgc agcgcagcta ctggctgccg accgatggta agatggataa gtcggatgtt    1680
gagctgtacc gtacgaacga agtgtacacg agcgtccgtt acggcaaaga cattatgacc    1740
gccgatgaca cgcaaggtag caaatacagc cgtaccagcg gtcaggtgac cctggtcgtc    1800
aacaacccaa aactgacctt ggaccaaagc gcaaagctga acgtggttat gggcaagatt    1860
catgctaatc agaagtaccg cgcactgatt gtcggtaccc cgaacggtat taagaatttc    1920
accagcgacg cagaggctat tgccgcaggc tatgtcaaag aaaccgatgg caatggcgtg    1980
ctgaccttcg gtgcaaacga catcaagggt tatgaaactt cgatatgag cggcttcgtc     2040 gctgtttggg ttccggtcgg tgcgagcgac gaccaagata ttcgtgtggc ggcgtctacg    2100
gcagcaaaga aagagggtga gctgacgctg aaagcgaccg aagcctatga ctcccaactg    2160
atctatgaag gctttagcaa tttccagacc atcccagatg gcagcgatcc ttctgtttat    2220
accaatcgta agatcgcgga aaatgttgat ttgttcaaga gctggggtgt cacgagcttc    2280
gaaatggctc cgcagttcgt ttctgcggac gatggcacgt ttctggacag cgtcattcaa    2340
aacggctatg cgttcgcaga ccgttatgat ctggccatga gcaaaaacaa taagtacggt    2400
agcaaagaag atctgcgtaa cgcgctgaag gcactgcaca aagcaggcat tcaggcgatt    2460
gcagattggg tgccagacca aatctaccag ctgcctggca agaagttgt tactgccacc     2520 cgcacggacg tgctggtcg caaaatcagc gatgcaatca tcgatcattc cctgtacgtt     2580
gcgaactcca agagctccgg taaggactac caagcgaagt acgtggcga gttcttggcg     2640 gaactgaagg cgaaataccc ggaaatgttc aaagtgaaca tgattagcac cggcaaaccg    2700
attgatgata gcgtgaaact gaagcagtgg aaagcagaat acttcaacgg caccaatgtg    2760
ctggatcgcg tgtcggtta tgttctgagc gatgaggcaa ccggtaagta tttcaccgtt     2820
accaaagagg gtaactttat cccgttgcag ctgaagggta caagaaggt gattaccggc     2880 ttttccagcg acggtaaggg cattacctat ttcggtacta gcggtaacca agctaaatcc    2940
gcgttcgtca cttttaacgg taacacgtac tacttcgacg cacgtggcca catggttacc    3000
aacggtgagt actcgccgaa tggtaaagat gtgtatcgtt ttctgccgaa cggcattatg    3060
ctgagcaacg cgttctatgt tgacggcaat ggcaacacct acctgtacaa ctccaaaggc    3120
caaatgtata aggtggcta tagcaaattt gacgtcacgg aaacgaagga cggtaaagag    3180
agcaaagttg tcaagttccg ctactttacg aacgagggcg tgatggcgaa aggtgtcacg    3240
gttgtggatg gcttcactca gtactttaac gaggatggca ttcaaagcaa agacgagctg    3300
gtcacttaca atggcaagac ctattacttc gaagcacaca cgggcaatgc cattaagaat    3360
acgtggcgta atatcaaggg caaatggtac cattttgatg ctaacggtgt cgcggctact    3420
ggcgcacagg ttatcaacgg tcagcacctg tacttcaatg aagatggctc tcaagtaaaa    3480
```

-continued

```
ggtagcatcg tcaaaaacgc tgatggtacg ttcagcaagt acaaggacag ctctggcgat    3540
ctggtggtga acgagttttt cacgacgggt gataacgtct ggtactatgc tggtgccaat    3600
ggcaaaacgg ttactggtgc acaggtgatt aatggccagc acttgttctt caaagaggat    3660
ggcagccagg tcaagggcga ctttgtgaag aatagcgacg gcacctactc caagtatgac    3720
gctgcgagcg gcgaacgtct gaccaacgag ttcttcacta cgggcgacaa tcattggtac    3780
tatattggcg ccaacggtaa gaccgttacc ggtgaagtta agattggtga cgacacgtat    3840
ttcttcgcaa agacggtaa gcaactgaaa ggtcaaatcg ttaccacccg tagcggtcgt    3900
atcagctact actttggtga tagcggtaag aaggctatta gcacgtgggt ggagatccag    3960
ccgggtgtgt ttgttttctt cgacaaaaac ggcctggctt acccaccgga gaatatgaac    4020
tga                                                                 4023
```

<210> SEQ ID NO 20
<211> LENGTH: 1340
<212> TYPE: PRT
<213> ORGANISM: Unknown
<220> FEATURE:
<223> OTHER INFORMATION: unknown Streptococcus species

<400> SEQUENCE: 20

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
```

-continued

```
                260                 265                 270
Leu Met Asn Trp Gly Ser Ile Val Met Gly Asp Lys Asp Ala Asn Phe
            275                 280                 285

Asp Gly Ile Arg Val Asp Ala Val Asp Asn Val Asp Ala Asp Met Leu
            290                 295                 300

Gln Leu Tyr Thr Asn Tyr Phe Arg Glu Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
            340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
            370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Val Gln Asp Ile Ile Ala Glu Ile Ile Lys Lys
                435                 440                 445

Glu Ile Asn Glu Lys Ser Asp Gly Phe Thr Ile Thr Asp Ser Glu Met
            450                 455                 460

Lys Arg Ala Phe Glu Ile Tyr Asn Lys Asp Met Leu Ser Asn Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
                500                 505                 510

Asp Gly Asn Tyr Met Glu Ala Lys Ser Pro Tyr Tyr Asp Thr Ile Val
            515                 520                 525

Asn Leu Met Lys Ser Arg Ile Lys Tyr Val Ser Gly Gly Gln Ala Gln
            530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
                580                 585                 590

Ser Gly Gln Val Thr Leu Val Val Asn Asn Pro Lys Leu Thr Leu Asp
            595                 600                 605

Gln Ser Ala Lys Leu Asn Val Val Met Gly Lys Ile His Ala Asn Gln
            610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
                675                 680                 685
```

```
Ser Asp Asp Gln Asp Ile Arg Val Ala Ala Ser Thr Ala Ala Lys Lys
    690             695                 700

Glu Gly Glu Leu Thr Leu Lys Ala Thr Glu Ala Tyr Asp Ser Gln Leu
705             710                 715                 720

Ile Tyr Glu Gly Phe Ser Asn Phe Gln Thr Ile Pro Asp Gly Ser Asp
            725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
            770                 775                 780

Phe Ala Asp Arg Tyr Asp Leu Ala Met Ser Lys Asn Asn Lys Tyr Gly
785             790                 795                 800

Ser Lys Glu Asp Leu Arg Asn Ala Leu Lys Ala Leu His Lys Ala Gly
            805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
            835                 840                 845

Ile Ser Asp Ala Ile Ile Asp His Ser Leu Tyr Val Ala Asn Ser Lys
            850                 855                 860

Ser Ser Gly Lys Asp Tyr Gln Ala Lys Tyr Gly Gly Glu Phe Leu Ala
865             870                 875                 880

Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
            915                 920                 925

Leu Ser Asp Glu Ala Thr Gly Lys Tyr Phe Thr Val Thr Lys Glu Gly
            930                 935                 940

Asn Phe Ile Pro Leu Gln Leu Lys Gly Asn Lys Lys Val Ile Thr Gly
945             950                 955                 960

Phe Ser Ser Asp Gly Lys Gly Ile Thr Tyr Phe Gly Thr Ser Gly Asn
            965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010            1015                1020

Ala Phe Tyr Val Asp Gly Asn Gly Asn Thr Tyr Leu Tyr Asn Ser
    1025            1030                1035

Lys Gly Gln Met Tyr Lys Gly Gly Tyr Ser Lys Phe Asp Val Thr
    1040            1045                1050

Glu Thr Lys Asp Gly Lys Glu Ser Lys Val Val Lys Phe Arg Tyr
    1055            1060                1065

Phe Thr Asn Glu Gly Val Met Ala Lys Gly Val Thr Val Val Asp
    1070            1075                1080

Gly Phe Thr Gln Tyr Phe Asn Glu Asp Gly Ile Gln Ser Lys Asp
    1085            1090                1095
```

```
Glu Leu Val Thr Tyr Asn Gly Lys Thr Tyr Tyr Phe Glu Ala His
1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
1130                1135                1140

Val Ile Asn Gly Gln His Leu Tyr Phe Asn Glu Asp Gly Ser Gln
1145                1150                1155

Val Lys Gly Ser Ile Val Lys Asn Ala Asp Gly Thr Phe Ser Lys
1160                1165                1170

Tyr Lys Asp Ser Ser Gly Asp Leu Val Val Asn Glu Phe Phe Thr
1175                1180                1185

Thr Gly Asp Asn Val Trp Tyr Tyr Ala Gly Ala Asn Gly Lys Thr
1190                1195                1200

Val Thr Gly Ala Gln Val Ile Asn Gly Gln His Leu Phe Phe Lys
1205                1210                1215

Glu Asp Gly Ser Gln Val Lys Gly Asp Phe Val Lys Asn Ser Asp
1220                1225                1230

Gly Thr Tyr Ser Lys Tyr Asp Ala Ala Ser Gly Glu Arg Leu Thr
1235                1240                1245

Asn Glu Phe Phe Thr Thr Gly Asp Asn His Trp Tyr Tyr Ile Gly
1250                1255                1260

Ala Asn Gly Lys Thr Val Thr Gly Glu Val Lys Ile Gly Asp Asp
1265                1270                1275

Thr Tyr Phe Phe Ala Lys Asp Gly Lys Gln Leu Lys Gly Gln Ile
1280                1285                1290

Val Thr Thr Arg Ser Gly Arg Ile Ser Tyr Tyr Phe Gly Asp Ser
1295                1300                1305

Gly Lys Lys Ala Ile Ser Thr Trp Val Glu Ile Gln Pro Gly Val
1310                1315                1320

Phe Val Phe Phe Asp Lys Asn Gly Leu Ala Tyr Pro Pro Glu Asn
1325                1330                1335

Met Asn
1340

<210> SEQ ID NO 21
<211> LENGTH: 4479
<212> TYPE: DNA
<213> ORGANISM: Leuconostoc mesenteroides

<400> SEQUENCE: 21 atgacccat ccgtattagg tgattcttcc gtcccagatg tatcggctaa caatgtgcaa      60
tccgcgagcg ataatacgac ggacacccag caaaatacca ccatcaccga ggaaaatgat     120
aaggtccaga gcgctgcgac caacgataac gtgaccacgg cagcgtccga cacgacgcag     180
agcgccgata caacgttac cgagaaacaa tctgatgatc acgcgctgga taatgaaaag     240
gttgacaata agcaggacga ggtcgcccag accaacgtga ctagcaaaaa cgaggagagc     300
gcggtggcct ctaccgacac cgatccggca gagactacca cggacgaaac gcaacaggtt     360
agcggcaagt atgtggaaaa ggatggttct tggtattact actttgacga cggtaagaac     420
gcgaagggtc tgagcacgat tgacaacaat atccaatact tgatgaaag cggtaagcag     480 gtcaaaggtc agtatgtgac gattgataac cagacctatt actttgataa agatagcggt     540
gatgaactga ccggcctgca atctattgac ggtaacattg ttgccttcaa tgacgagggc     600
```

```
cagcagatct ttaatcaata ctaccagagc gagaacggta cgacctacta ttttgatgat    660
aagggccacg ctgccaccgg tattaagaat attgagggca agaactacta ttttgacaat    720
ctgggtcaac tgaaaaaggg cttctccggc gtgatcgacg gtcagattat gacgtttgac    780
caggaaactg gtcaagaggt ttccaatacc acgtccgaga tcaaagaggg cctgacgact    840
cagaacactg attactctga acataatgcg gcgcacggta ccgacgccga agattttgag    900
aacatcgatg gctatctgac cgccagctcc tggtaccgtc cgacggacat tctgcgcaat    960
ggcactgact gggaaccgag caccgacacg gactttcgtc aatcttgag cgtttggtgg   1020 ccggataaga atacgcaggt caactatctg aactacatgg cggacctggg cttcattagc   1080
aacgcagaca gcttcgaaac gggtgactct cagagcctgc tgaacgaggc gtccaattac   1140
gtccagaaaa gcatcgagat gaaaatctcc gcgcaacaga gcaccgagtg gctgaaagac   1200
gccatggccg cgtttattgt tacgcagccg caatggaatg aaacttccga agatatgagc   1260
aacgaccact gcaaaacgg tgcgctgacc tacgttaaca gcccgctgac cccggacgca   1320
aacagcaact ttcgcctgct gaatcgtacc cctaccaacc agaccggcga acaggcgtac   1380
aacctggata attctaaagg tggctttgag ctgctgctgg caaatgatgt ggataacagc   1440
aacccggtgg ttcaagcgga acaactgaat tggctgtact acctgatgaa tttcggtacg   1500
attaccgcca atgacgcgga tgccaacttt gacggcattc gcgtcgatgc agtggataac   1560
gtggatgctg atctgttgca gattgcggca gactacttta aactggccta cggtgtggac   1620
cagaatgata gcaccgcaaa ccaacacctg tctatcctgg aagattggag ccacaacgac   1680
ccgctgtatg tcacggatca aggcagcgac cagctgacta tggacgacta cgtgcatacg   1740
caattgattt ggagcctgac caaaagcagc gatatccgtg gtaccatgca acgttttgtg   1800
gattactata tggtggaccg ttccaatgac tccacggaga tgaagcgat cccgaattac   1860 agctttgtcc gcgcacacga tagcgaagtt caaaccgtta tcgcgcaaat cgtgagcgat   1920
ctgtatccag atgttgagaa tagcctggct ccgaccaccg agcagctggc agcagcattc   1980
aaggtgtata atgaagatga gaaattggcc gacaaaaagt atacccaata caacatggcg   2040
agcgcctatg cgatgctgct gaccaataaa gacacggtgc cgcgtgtcta ctatggcgac   2100
ctgtataccg atgacggtca atacatggca acgaagagcc cgtattacga cgcgattaac   2160
accctgctga agctcgtgt tcaatatgtc gcgggtggcc aaagcatgag cgtggatagc   2220
aacgatgtgc tgaccagcgt tcgctatggc aaagacgcga tgacggcgag cgacacgggc   2280
accagcgaga ctcgtaccga gggcgtcggt gtcattgtgt ccaacaatgc ggagctgcaa   2340
ctggaagatg gtcatacggt tacccctgcac atgggtgccg cgcacaaaaa tcaggcatac   2400
cgtgcgttgt tgtccaccac ggccgacggt ctggcgtatt atgatacgga cgagaatgcc   2460
ccggtggcat atacggatgc gaacggtgac ttgattttca ccaatgagtc catctacggc   2520
gttcagaatc cgcaagtcag cggttacctg gcgtgtgggg tcccggttgg tgcacaacag   2580
gaccaggacg cgcgcacggc aagcgatacc accactaaca ccagcgataa agttttccac   2640
agcaacgcgg ctctggacag ccaagtgatc tacgagggct cagcaactt ccaagcgttt   2700 gcgactgatt ccagcgaata caccaatgtt gttattgctc agaacgctga tcaattcaaa   2760
caatggggcg tgacctcgtt tcagctggct ccgcagtacc gcagcagcac ggacacttcc   2820
ttcctggata gcatcatcca aaatggttac gcgtttacgg accgctatga tctgggttat   2880
ggcacgccga cgaagtacgg taccgcgac caactgcgtg atgcaatcaa agcactgcat   2940
gcgagcggca tccaagcgat tgcagattgg gttccggacc agatttacaa tctgccggag   3000
```

```
caagaactgg cgactgtcac gcgcacgaat agcttcggtg atgatgatac tgacagcgac    3060
attgataatg ctctgtatgt ggttcaaagc cgcggtggtg gtcagtacca agagatgtat    3120
ggcggtgcgt ttctggagga gttgcaagcg ctgtacccta gcctgtttaa ggtgaaccag    3180
atttctactg tgtcccgat cgatggtagc gtgaagatta ccgagtgggc tgcgaaatac     3240
ttcaacggca gcaatatcca gggtaagggt gcgggttacg tgttgaaaga catgggtagc    3300
aataagtact tcaaggtcgt gagcaatacc gaggacggcg actatctgcc gaaacagctg    3360
accaacgacc tgagcgaaac cggtttcacc cacgacgaca agggtatcat ctactacacc    3420
ctgagcggct atcgtgcaca gaacgccttc attcaagacg atgataacaa ttactattac    3480
tttgacaaga ccggtcacct ggtcacgggt ttgcagaaaa tcaacaacca tacgtacttc    3540
ttcctgccga atggcattga gctggtgaaa tccttcttgc agaacgagga tggcacgatc    3600
gtttacttcg ataagaaagg tcatcaagtc tttgatcaat acattacgga tcaaaatggc    3660
aacgcgtact atttcgacga tgccggtgtt atgctgaagt ctggtctggc aacgattgat    3720
ggtcatcagc agtacttcga tcagaatggc gttcaagtta aggacaagtt cgttatcggt    3780
acggatggct acaagtacta cttcgagccg ggttgcggca atttggcaat tttgcgttac    3840
gtgcaaaata gcaagaacca atggttctat ttcgatggca atggccacgc agtcacgggt    3900
ttccaaacca tcaacggcaa gaagcagtat ttctacaacg atggtcacca agcaagggc    3960
gaatttatca atgcggacgg tgacaccttc tacaccagcg ccaccgacgg tcgtttggtg    4020
acgggtgttc agaagatcaa cggtatcacc tacgcgtttg acaataccgg caacctgatc    4080
acgaaccagt attatcagct ggcggacggt aagtacatgc tgctggacga ctctggtcgc    4140
gcaaaaacgg gctttgtcct gcaagacggt gtcctgcgtt atttcgacca gaacggtgaa    4200
caagtgaagg acgccattat cgtcgacccg gacaccaacc tgtcttatta ctttaacgcg    4260
acccagggtg tcgcggtgaa aaacgattac ttcgagtacc aaggcaactg gtacctgacc    4320
gatgcaaact accagctgat taaaggcttc aaagcagttg acgactcgct gcaacacttc    4380
gacgaagtta cgggtgtgca gaccaaggaa agcgctctga ttagcgcaca gggcaaagtt    4440
taccagttcg acaacaatgg taacgcggtg agcgcataa                           4479
```

<210> SEQ ID NO 22
<211> LENGTH: 1492
<212> TYPE: PRT
<213> ORGANISM: Leuconostoc mesenteroides

<400> SEQUENCE: 22

```
Met Thr Pro Ser Val Leu Gly Asp Ser Ser Pro Asp Val Ser Ala
1               5                   10                  15

Asn Asn Val Gln Ser Ala Ser Asp Asn Thr Thr Asp Thr Gln Gln Asn
                20                  25                  30

Thr Thr Ile Thr Glu Glu Asn Asp Lys Val Gln Ser Ala Ala Thr Asn
            35                  40                  45

Asp Asn Val Thr Thr Ala Ala Ser Asp Thr Thr Gln Ser Ala Asp Asn
        50                  55                  60

Asn Val Thr Glu Lys Gln Ser Asp Asp His Ala Leu Asp Asn Glu Lys
    65                  70                  75                  80

Val Asp Asn Lys Gln Asp Glu Val Ala Gln Thr Asn Val Thr Ser Lys
                85                  90                  95

Asn Glu Glu Ser Ala Val Ala Ser Thr Asp Thr Asp Pro Ala Glu Thr
            100                 105                 110
```

```
Thr Thr Asp Glu Thr Gln Gln Val Ser Gly Lys Tyr Val Glu Lys Asp
        115                 120                 125
Gly Ser Trp Tyr Tyr Tyr Phe Asp Asp Gly Lys Asn Ala Lys Gly Leu
    130                 135                 140
Ser Thr Ile Asp Asn Asn Ile Gln Tyr Phe Asp Glu Ser Gly Lys Gln
145                 150                 155                 160
Val Lys Gly Gln Tyr Val Thr Ile Asp Asn Gln Thr Tyr Tyr Phe Asp
                165                 170                 175
Lys Asp Ser Gly Asp Glu Leu Thr Gly Leu Gln Ser Ile Asp Gly Asn
            180                 185                 190
Ile Val Ala Phe Asn Asp Glu Gly Gln Gln Ile Phe Asn Gln Tyr Tyr
        195                 200                 205
Gln Ser Glu Asn Gly Thr Thr Tyr Tyr Phe Asp Lys Gly His Ala
    210                 215                 220
Ala Thr Gly Ile Lys Asn Ile Glu Gly Lys Asn Tyr Tyr Phe Asp Asn
225                 230                 235                 240
Leu Gly Gln Leu Lys Lys Gly Phe Ser Gly Val Ile Asp Gly Gln Ile
                245                 250                 255
Met Thr Phe Asp Gln Glu Thr Gly Gln Glu Val Ser Asn Thr Thr Ser
            260                 265                 270
Glu Ile Lys Glu Gly Leu Thr Thr Gln Asn Thr Asp Tyr Ser Glu His
        275                 280                 285
Asn Ala Ala His Gly Thr Asp Ala Glu Asp Phe Glu Asn Ile Asp Gly
    290                 295                 300
Tyr Leu Thr Ala Ser Ser Trp Tyr Arg Pro Thr Asp Ile Leu Arg Asn
305                 310                 315                 320
Gly Thr Asp Trp Glu Pro Ser Thr Asp Thr Asp Phe Arg Pro Ile Leu
                325                 330                 335
Ser Val Trp Trp Pro Asp Lys Asn Thr Gln Val Asn Tyr Leu Asn Tyr
            340                 345                 350
Met Ala Asp Leu Gly Phe Ile Ser Asn Ala Asp Ser Phe Glu Thr Gly
        355                 360                 365
Asp Ser Gln Ser Leu Leu Asn Glu Ala Ser Asn Tyr Val Gln Lys Ser
    370                 375                 380
Ile Glu Met Lys Ile Ser Ala Gln Gln Ser Thr Glu Trp Leu Lys Asp
385                 390                 395                 400
Ala Met Ala Ala Phe Ile Val Thr Gln Pro Gln Trp Asn Glu Thr Ser
                405                 410                 415
Glu Asp Met Ser Asn Asp His Leu Gln Asn Gly Ala Leu Thr Tyr Val
            420                 425                 430
Asn Ser Pro Leu Thr Pro Asp Ala Asn Ser Asn Phe Arg Leu Leu Asn
        435                 440                 445
Arg Thr Pro Thr Asn Gln Thr Gly Glu Gln Ala Tyr Asn Leu Asp Asn
    450                 455                 460
Ser Lys Gly Gly Phe Glu Leu Leu Leu Ala Asn Asp Val Asp Asn Ser
465                 470                 475                 480
Asn Pro Val Val Gln Ala Glu Gln Leu Asn Trp Leu Tyr Tyr Leu Met
                485                 490                 495
Asn Phe Gly Thr Ile Thr Ala Asn Asp Ala Asp Ala Asn Phe Asp Gly
            500                 505                 510
Ile Arg Val Asp Ala Val Asp Asn Val Asp Ala Asp Leu Leu Gln Ile
        515                 520                 525
```

```
Ala Ala Asp Tyr Phe Lys Leu Ala Tyr Gly Val Asp Gln Asn Asp Ser
        530                 535                 540

Thr Ala Asn Gln His Leu Ser Ile Leu Glu Asp Trp Ser His Asn Asp
545                 550                 555                 560

Pro Leu Tyr Val Thr Asp Gln Gly Ser Asp Gln Leu Thr Met Asp Asp
                565                 570                 575

Tyr Val His Thr Gln Leu Ile Trp Ser Leu Thr Lys Ser Ser Asp Ile
            580                 585                 590

Arg Gly Thr Met Gln Arg Phe Val Asp Tyr Met Val Asp Arg Ser
        595                 600                 605

Asn Asp Ser Thr Glu Asn Glu Ala Ile Pro Asn Tyr Ser Phe Val Arg
610                 615                 620

Ala His Asp Ser Glu Val Gln Thr Val Ile Ala Gln Ile Val Ser Asp
625                 630                 635                 640

Leu Tyr Pro Asp Val Glu Asn Ser Leu Ala Pro Thr Thr Glu Gln Leu
                645                 650                 655

Ala Ala Ala Phe Lys Val Tyr Asn Glu Asp Glu Lys Leu Ala Asp Lys
            660                 665                 670

Lys Tyr Thr Gln Tyr Asn Met Ala Ser Ala Tyr Ala Met Leu Leu Thr
        675                 680                 685

Asn Lys Asp Thr Val Pro Arg Val Tyr Tyr Gly Asp Leu Tyr Thr Asp
690                 695                 700

Asp Gly Gln Tyr Met Ala Thr Lys Ser Pro Tyr Tyr Asp Ala Ile Asn
705                 710                 715                 720

Thr Leu Leu Lys Ala Arg Val Gln Tyr Val Ala Gly Gly Gln Ser Met
                725                 730                 735

Ser Val Asp Ser Asn Asp Val Leu Thr Ser Val Arg Tyr Gly Lys Asp
            740                 745                 750

Ala Met Thr Ala Ser Asp Thr Gly Thr Ser Glu Thr Arg Thr Glu Gly
        755                 760                 765

Val Gly Val Ile Val Ser Asn Asn Ala Glu Leu Gln Leu Glu Asp Gly
770                 775                 780

His Thr Val Thr Leu His Met Gly Ala Ala His Lys Asn Gln Ala Tyr
785                 790                 795                 800

Arg Ala Leu Leu Ser Thr Thr Ala Asp Gly Leu Ala Tyr Tyr Asp Thr
                805                 810                 815

Asp Glu Asn Ala Pro Val Ala Tyr Thr Asp Ala Asn Gly Asp Leu Ile
            820                 825                 830

Phe Thr Asn Glu Ser Ile Tyr Gly Val Gln Asn Pro Gln Val Ser Gly
        835                 840                 845

Tyr Leu Ala Val Trp Val Pro Val Gly Ala Gln Gln Asp Gln Asp Ala
850                 855                 860

Arg Thr Ala Ser Asp Thr Thr Asn Thr Ser Asp Lys Val Phe His
865                 870                 875                 880

Ser Asn Ala Ala Leu Asp Ser Gln Val Ile Tyr Glu Gly Phe Ser Asn
                885                 890                 895

Phe Gln Ala Phe Ala Thr Asp Ser Ser Glu Tyr Thr Asn Val Val Ile
            900                 905                 910

Ala Gln Asn Ala Asp Gln Phe Lys Gln Trp Gly Val Thr Ser Phe Gln
        915                 920                 925

Leu Ala Pro Gln Tyr Arg Ser Ser Thr Asp Thr Ser Phe Leu Asp Ser
930                 935                 940

Ile Ile Gln Asn Gly Tyr Ala Phe Thr Asp Arg Tyr Asp Leu Gly Tyr
```

-continued

```
945              950              955              960
Gly Thr Pro Thr Lys Tyr Gly Thr Ala Asp Gln Leu Arg Asp Ala Ile
                 965              970              975
Lys Ala Leu His Ala Ser Gly Ile Gln Ala Ile Ala Asp Trp Val Pro
                 980              985              990
Asp Gln Ile Tyr Asn Leu Pro Glu Gln Glu Leu Ala Thr Val Thr Arg
                 995              1000             1005
Thr Asn Ser Phe Gly Asp Asp Thr Asp Ser Asp Ile Asp Asn
        1010             1015             1020
Ala Leu Tyr Val Val Gln Ser Arg Gly Gly Gln Tyr Gln Glu
        1025             1030             1035
Met Tyr Gly Gly Ala Phe Leu Glu Glu Leu Gln Ala Leu Tyr Pro
        1040             1045             1050
Ser Leu Phe Lys Val Asn Gln Ile Ser Thr Gly Val Pro Ile Asp
        1055             1060             1065
Gly Ser Val Lys Ile Thr Glu Trp Ala Ala Lys Tyr Phe Asn Gly
        1070             1075             1080
Ser Asn Ile Gln Gly Lys Gly Ala Gly Tyr Val Leu Lys Asp Met
        1085             1090             1095
Gly Ser Asn Lys Tyr Phe Lys Val Val Ser Asn Thr Glu Asp Gly
        1100             1105             1110
Asp Tyr Leu Pro Lys Gln Leu Thr Asn Asp Leu Ser Glu Thr Gly
        1115             1120             1125
Phe Thr His Asp Asp Lys Gly Ile Ile Tyr Tyr Thr Leu Ser Gly
        1130             1135             1140
Tyr Arg Ala Gln Asn Ala Phe Ile Gln Asp Asp Asp Asn Asn Tyr
        1145             1150             1155
Tyr Tyr Phe Asp Lys Thr Gly His Leu Val Thr Gly Leu Gln Lys
        1160             1165             1170
Ile Asn Asn His Thr Tyr Phe Phe Leu Pro Asn Gly Ile Glu Leu
        1175             1180             1185
Val Lys Ser Phe Leu Gln Asn Glu Asp Gly Thr Ile Val Tyr Phe
        1190             1195             1200
Asp Lys Lys Gly His Gln Val Phe Asp Gln Tyr Ile Thr Asp Gln
        1205             1210             1215
Asn Gly Asn Ala Tyr Tyr Phe Asp Asp Ala Gly Val Met Leu Lys
        1220             1225             1230
Ser Gly Leu Ala Thr Ile Asp Gly His Gln Gln Tyr Phe Asp Gln
        1235             1240             1245
Asn Gly Val Gln Val Lys Asp Lys Phe Val Ile Gly Thr Asp Gly
        1250             1255             1260
Tyr Lys Tyr Tyr Phe Glu Pro Gly Cys Gly Asn Leu Ala Ile Leu
        1265             1270             1275
Arg Tyr Val Gln Asn Ser Lys Asn Gln Trp Phe Tyr Phe Asp Gly
        1280             1285             1290
Asn Gly His Ala Val Thr Gly Phe Gln Thr Ile Asn Gly Lys Lys
        1295             1300             1305
Gln Tyr Phe Tyr Asn Asp Gly His Gln Ser Lys Gly Glu Phe Ile
        1310             1315             1320
Asn Ala Asp Gly Asp Thr Tyr Thr Ser Ala Thr Asp Gly Arg
        1325             1330             1335
Leu Val Thr Gly Val Gln Lys Ile Asn Gly Ile Thr Tyr Ala Phe
        1340             1345             1350
```

| Asp | Asn | Thr | Gly | Asn | Leu | Ile | Thr | Asn | Gln | Tyr | Tyr | Gln | Leu | Ala |
| | 1355 | | | | 1360 | | | | 1365 | | | | | |

| Asp | Gly | Lys | Tyr | Met | Leu | Leu | Asp | Asp | Ser | Gly | Arg | Ala | Lys | Thr |
| 1370 | | | | | 1375 | | | | | 1380 | | | | |

| Gly | Phe | Val | Leu | Gln | Asp | Gly | Val | Leu | Arg | Tyr | Phe | Asp | Gln | Asn |
| 1385 | | | | | 1390 | | | | | 1395 | | | | |

| Gly | Glu | Gln | Val | Lys | Asp | Ala | Ile | Ile | Val | Asp | Pro | Asp | Thr | Asn |
| 1400 | | | | | 1405 | | | | | 1410 | | | | |

| Leu | Ser | Tyr | Tyr | Phe | Asn | Ala | Thr | Gln | Gly | Val | Ala | Val | Lys | Asn |
| 1415 | | | | | 1420 | | | | | 1425 | | | | |

| Asp | Tyr | Phe | Glu | Tyr | Gln | Gly | Asn | Trp | Tyr | Leu | Thr | Asp | Ala | Asn |
| 1430 | | | | | 1435 | | | | | 1440 | | | | |

| Tyr | Gln | Leu | Ile | Lys | Gly | Phe | Lys | Ala | Val | Asp | Asp | Ser | Leu | Gln |
| 1445 | | | | | 1450 | | | | | 1455 | | | | |

| His | Phe | Asp | Glu | Val | Thr | Gly | Val | Gln | Thr | Lys | Glu | Ser | Ala | Leu |
| 1460 | | | | | 1465 | | | | | 1470 | | | | |

| Ile | Ser | Ala | Gln | Gly | Lys | Val | Tyr | Gln | Phe | Asp | Asn | Asn | Gly | Asn |
| 1475 | | | | | 1480 | | | | | 1485 | | | | |

Ala Val Ser Ala
    1490

<210> SEQ ID NO 23
<211> LENGTH: 3972
<212> TYPE: DNA
<213> ORGANISM: Streptococcus criceti

<400> SEQUENCE: 23

```
atggttgatg caaatacta ctactacgac gcagatggca acgttaagaa gaatttcgcg    60
attagcgtcg gtgacgcaat cttctacttt gacgaaaccg gtgcttacaa ggacaccagc   120
aaagttggtg cggataaaac cagcagcagc gcgaatcaaa ccacggccac cttcgcggca   180
aacaaccgtg cctatagcac tgcggcggag aactttgagg caattgacaa ctatttgacc   240
gcagacagct ggtatcgtcc gaagagcatt ctgaaagatg gtaagacgtg gaccgaatcc   300
accaaagacg acttccgtcc gctgctgatg gcttggtggc cggataccga aactaaacgc   360
aactatgtca actatatgaa taaggtcgtc ggcattgata aaacctatac cgcggagact   420
agccaagccg acctgacggc agctgcggag ctggttcaag cgcgcattga gcaacgcatc   480
acgtctgaga agaacacgaa atggctgcgc gaggctatta gcgcgtttgt caagacccag   540
ccgcaatgga atggcgagtc cgaaaagccg tatgatgatc atttgcagaa cggtgcactg   600
aagttcgaca cgaaacctc tctgaccccg gacacccagt ctggttatcg tatcttgaat   660
cgcacgccga ccaatcaaac gggcagcctg gaccgcgtt tcacctttaa tcaaaatgat   720
ccgctgggtg gctatgaata tctgctggca acgacgtgg ataatagcaa cccggtggtg   780
caagcggaga gcttgaattg gctgcactac ctgctgaact tcggcagcat ctacgcgaat   840
gatccggaag cgaatttcga ttccattcgt gtagacgccg tggataacgt ggatgcggat   900
ctgttgcaga ttagcagcga ctacctgaaa tctgcgtaca aaatcgataa gaacaacaaa   960
aatgcgaatg accacgtgag catcgttgag gcgtggagcg ataacgacac cccgtacctg  1020
cacgatgaag cgataacttt gatgaatatg acaataagt ttcgcctgag catgttgcgc  1080
tccctggcga agcctctgga caaacgtagc ggcctgaacc ctctgatcca taatagcgtc  1140
gttgatcgcg aggtggatga ccgtgaggtt gagaaaattc cgagctactc ttttgcacgc  1200
```

-continued

```
gctcacgaca gcgaggttca ggatctgatt cgtgacatca ttaaggcaga aatcaatccg      1260
aacagcttcg gctacagctt tacccaagaa gaaatcgatc aagcgttcaa gatctacaac      1320
gaggacctga agaaaaccaa caagaagtac acccattaca atgtcccgct gtcttacacc      1380
ttgctgctga cgaataaggg tagcattccg cgtatttact acggcgacat gtttaccgac      1440
gatggccagt atatggcgaa caaaacggtg aattacaatg ctattgagag cctgctgaag      1500
gctcgtatga agtatgtgag cggtggtcag gcgatgcaaa actatcaaat tggtaatggt      1560
gaaattctga cgtcggtgcg ctacggtaaa ggtgcgctga agcaatcgga caagggcgac      1620
gcaacgacgc gtacctctgg tattggtatt gtcatgggca accagccgaa tttctcgctg      1680
gaaggtaaag tcgttgccct gaacatgggt gcagcgcatg ccaatcagga gtatcgtgcc      1740
ctgatggtga gcactaaaga cggcgtggcg acctatgcga cggatgcaga cgcgagcaaa      1800
gcgggtatga cgaaacgtac cgacgagaac ggctacttgt atttcctgaa tgacgacttg      1860
aagggtgttg caaatccaca gatctccggt tttctgcaag tatgggtgcc ggtcggtgct      1920
cctgccgacc aggatattcg cgttgccgcg acgaacgctg caagcacgga tggtaagtcc      1980
ctgcaccaag atgcggcgat ggatagccgt gttatgttcg agggttttc caactttcag      2040 gcgttcgcaa cgaaagaaga tgagtatgct aatgttgtta ttgcgaaaaa tgtggataag      2100
tttgttagct ggggcatcac tgactttgag atggcaccgc agtataccte tagcgatgac      2160 ggtcagttcc tggatagcgt tattcagaat ggttatgcat tcacggaccg ttatgatctg      2220
ggtatgagca aggcaaacaa atatggtacg gcggaacacc tggtcaaagc tatcaaagcg      2280
ttgcacaaag caggtctgaa agttatgcg gattgggtcc cggaccagat gtatacccttt      2340 ccgaagaaag aggttgtcac cgttacgcgt acggacaagt tcggtaaacc ggttgcgggc      2400
agccaaatca atcatacccct gtatgtgact gacaccaaag gtagcggtga tgactatcag      2460
gccaaatacg gtggtgcgtt tctggacgag ctgaaagaga aataccggga attgtttacg      2520
aaaaagcaga tttctacggg ccaagcaatc gacccaagcg tcaagattaa gcagtggagc      2580
gcgaaatact ttaacggcag caatatcttg ggtcgtggtg caaattacgt cctgagcgac      2640
caggccagca acaagtattt caatgtggcg gaaggtaagg tttttctgcc aggcgccatg      2700
ctgggcaagg tggtggaaag cggcatccgt tttgacggca agggctacat ctataacagc      2760
tcgaccaccg gcgaacaagt caaagatagc ttcatcacgg aagcaggtaa tttgtattac      2820
ttcggtaaag acggttacat ggtcatgggt gcgcagaaca ttcaaggcgc caattactac      2880
ttcctggcca acggtgcggc actgcgtaat agcatcctga ccgatcaaga cggcaagtcc      2940
cactactacg cgaacgacgg caaacgttat gaaaacggct attatcagtt tggtaacgat      3000
tcctggcgct acttcgagaa tggtgtaatg gccgtcggcg tgacccgtgt ggctggccat      3060
gaccagtact tcgataagga tggtattcaa gcgaagaaca agatcatcgt tacccgcgat      3120
ggtaaggttc gttacttcga tgagcacaat ggcaatgcag tcaccaacac gttcattagc      3180
gatcaggcag gtcactggta ctatctgggt aaggacggtg tggcggtgac gggtgcccaa      3240
acggtgggca acagcaccct gtatttcgag gccaacggcc agcaggtcaa aggcgatttt      3300
gtgaccgcga agacggtaa actgtatttc ttcgatggcg atagcggtga catgtggacc      3360
gacacgttcg tccaagacaa aactggccat tggttttacc tgggtaaaga tggtgcggcg      3420
gtcaccggtg cacagaccgt gcgcggtcag aaattgtact ttaaagccaa cggtcagcaa      3480
gttaagggcg acattgtcaa aggtgctgat ggtaaaatcc gttactatga tgcaaattcg      3540
ggcgatcagg tctacaaccg tactgtgaag ggttccgacg gtaaaaccta catcatcggc      3600
```

```
aaagacggtg ttgccattac gcagaccatc gcgaagggtc aaaccattaa ggacggcagc    3660
gttctgcgtt tctacagcat ggaaggccag ctggttaccg gtagcggctg gtattctaac    3720
gcgaaaggtc agtggctgta cgtgaagaat ggtcaggttc tgaccggtct gcaaaccgtt    3780
ggttcccaac gtgtgtactt cgacgctaac ggtatccaag cgaagggcaa ggccgtgcgc    3840
accagcgacg gtaagctgcg ttactttgat gcgaacagcg gtagcatgat cactaaccag    3900
tggaaagagg tgaacggtca atactattac tttgacaaca atggcgtcgc catctaccgc    3960
ggctggaact aa                                                        3972

<210> SEQ ID NO 24
<211> LENGTH: 1323
<212> TYPE: PRT
<213> ORGANISM: Streptococcus criceti

<400> SEQUENCE: 24
```

Met Val Asp Gly Lys Tyr Tyr Tyr Asp Ala Asp Gly Asn Val Lys
1               5                   10                  15

Lys Asn Phe Ala Ile Ser Val Gly Asp Ala Ile Phe Tyr Phe Asp Glu
                20                  25                  30

Thr Gly Ala Tyr Lys Asp Thr Ser Lys Val Gly Ala Asp Lys Thr Ser
            35                  40                  45

Ser Ser Ala Asn Gln Thr Thr Ala Thr Phe Ala Ala Asn Asn Arg Ala
        50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Arg Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
    210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
    290                 295                 300

```
Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu His Asp Glu Gly Asp Asn Leu Met Asn Met Asp Asn
                340                 345                 350

Lys Phe Arg Leu Ser Met Leu Arg Ser Leu Ala Lys Pro Leu Asp Lys
                355                 360                 365

Arg Ser Gly Leu Asn Pro Leu Ile His Asn Ser Val Asp Arg Glu
370                 375                 380

Val Asp Asp Arg Glu Val Glu Lys Ile Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
                420                 425                 430

Asp Gln Ala Phe Lys Ile Tyr Asn Glu Asp Leu Lys Lys Thr Asn Lys
                435                 440                 445

Lys Tyr Thr His Tyr Asn Val Pro Leu Ser Tyr Thr Leu Leu Leu Thr
                450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asn Ala Ile Glu
                485                 490                 495

Ser Leu Leu Lys Ala Arg Met Lys Tyr Val Ser Gly Gln Ala Met
                500                 505                 510

Gln Asn Tyr Gln Ile Gly Asn Gly Glu Ile Leu Thr Ser Val Arg Tyr
                515                 520                 525

Gly Lys Gly Ala Leu Lys Gln Ser Asp Lys Gly Asp Ala Thr Thr Arg
                530                 535                 540

Thr Ser Gly Ile Gly Ile Val Met Gly Asn Gln Pro Asn Phe Ser Leu
545                 550                 555                 560

Glu Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
                580                 585                 590

Ala Thr Asp Ala Asp Ala Ser Lys Ala Gly Met Thr Lys Arg Thr Asp
                595                 600                 605

Glu Asn Gly Tyr Leu Tyr Phe Leu Asn Asp Asp Leu Lys Gly Val Ala
                610                 615                 620

Asn Pro Gln Ile Ser Gly Phe Leu Gln Val Trp Val Pro Val Gly Ala
625                 630                 635                 640

Pro Ala Asp Gln Asp Ile Arg Val Ala Ala Thr Asn Ala Ala Ser Thr
                645                 650                 655

Asp Gly Lys Ser Leu His Gln Asp Ala Ala Met Asp Ser Arg Val Met
                660                 665                 670

Phe Glu Gly Phe Ser Asn Phe Gln Ala Phe Ala Thr Lys Glu Asp Glu
                675                 680                 685

Tyr Ala Asn Val Val Ile Ala Lys Asn Val Asp Lys Phe Val Ser Trp
                690                 695                 700

Gly Ile Thr Asp Phe Glu Met Ala Pro Gln Tyr Thr Ser Ser Asp Asp
705                 710                 715                 720
```

```
Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Glu
            740                 745                 750

His Leu Val Lys Ala Ile Lys Ala Leu His Lys Ala Gly Leu Lys Val
            755                 760                 765

Met Ala Asp Trp Val Pro Asp Gln Met Tyr Thr Phe Pro Lys Lys Glu
            770                 775                 780

Val Val Thr Val Thr Arg Thr Asp Lys Phe Lys Pro Val Ala Gly
785                 790                 795                 800

Ser Gln Ile Asn His Thr Leu Tyr Val Thr Asp Thr Lys Gly Ser Gly
                805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe
            850                 855                 860

Asn Gly Ser Asn Ile Leu Gly Arg Gly Ala Asn Tyr Val Leu Ser Asp
865                 870                 875                 880

Gln Ala Ser Asn Lys Tyr Phe Asn Val Ala Glu Gly Lys Val Phe Leu
                885                 890                 895

Pro Gly Ala Met Leu Gly Lys Val Val Glu Ser Gly Ile Arg Phe Asp
            900                 905                 910

Gly Lys Gly Tyr Ile Tyr Asn Ser Ser Thr Thr Gly Glu Gln Val Lys
            915                 920                 925

Asp Ser Phe Ile Thr Glu Ala Gly Asn Leu Tyr Tyr Phe Gly Lys Asp
            930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
                965                 970                 975

Asp Gly Lys Ser His Tyr Tyr Ala Asn Asp Gly Lys Arg Tyr Glu Asn
            980                 985                 990

Gly Tyr Tyr Gln Phe Gly Asn Asp Ser Trp Arg Tyr Phe Glu Asn Gly
            995                 1000                1005

Val Met Ala Val Gly Val Thr Arg Val Ala Gly His Asp Gln Tyr
1010                1015                1020

Phe Asp Lys Asp Gly Ile Gln Ala Lys Asn Lys Ile Ile Val Thr
    1025                1030                1035

Arg Asp Gly Lys Val Arg Tyr Phe Asp Glu His Asn Gly Asn Ala
    1040                1045                1050

Val Thr Asn Thr Phe Ile Ser Asp Gln Ala Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Phe Asp Gly
    1100                1105                1110

Asp Ser Gly Asp Met Trp Thr Asp Thr Phe Val Gln Asp Lys Thr
    1115                1120                1125

Gly His Trp Phe Tyr Leu Gly Lys Asp Gly Ala Ala Val Thr Gly
```

|   |   |   |   |   |   |   |   |   |   |
|---|---|---|---|---|---|---|---|---|---|
| | | 1130 | | | 1135 | | | 1140 | |
| Ala | Gln | Thr | Val | Arg | Gly | Gln | Lys | Leu | Tyr | Phe | Lys | Ala | Asn | Gly |

Ala Gln Thr Val Arg Gly Gln Lys Leu Tyr Phe Lys Ala Asn Gly
             1145                1150                1155

Gln Gln Val Lys Gly Asp Ile Val Lys Gly Ala Asp Gly Lys Ile
             1160                1165                1170

Arg Tyr Tyr Asp Ala Asn Ser Gly Asp Gln Val Tyr Asn Arg Thr
 1175                   1180                1185

Val Lys Gly Ser Asp Gly Lys Thr Tyr Ile Ile Gly Lys Asp Gly
 1190                   1195                1200

Val Ala Ile Thr Gln Thr Ile Ala Lys Gly Gln Thr Ile Lys Asp
 1205                   1210                1215

Gly Ser Val Leu Arg Phe Tyr Ser Met Glu Gly Gln Leu Val Thr
 1220                   1225                1230

Gly Ser Gly Trp Tyr Ser Asn Ala Lys Gly Gln Trp Leu Tyr Val
 1235                   1240                1245

Lys Asn Gly Gln Val Leu Thr Gly Leu Gln Thr Val Gly Ser Gln
 1250                   1255                1260

Arg Val Tyr Phe Asp Ala Asn Gly Ile Gln Ala Lys Gly Lys Ala
 1265                   1270                1275

Val Arg Thr Ser Asp Gly Lys Leu Arg Tyr Phe Asp Ala Asn Ser
 1280                   1285                1290

Gly Ser Met Ile Thr Asn Gln Trp Lys Glu Val Asn Gly Gln Tyr
 1295                   1300                1305

Tyr Tyr Phe Asp Asn Asn Gly Val Ala Ile Tyr Arg Gly Trp Asn
 1310                   1315                1320

<210> SEQ ID NO 25
<211> LENGTH: 4308
<212> TYPE: DNA
<213> ORGANISM: Streptococcus sobrinus

<400> SEQUENCE: 25

| | |
|---|---|
| atggttgacg gcaaatacta ctattatgat caggatggca acgttaagaa gaatttcgcg | 60 |
| gttagcgttg gtgacaagat ctactacttt gacgagactg gtgcctacaa agacaccctct | 120 |
| aaagtggacg cggacaagtc tagcagcgcc gttagccaaa atgcgacgat ctttgcggct | 180 |
| aacaatcgtg cgtatagcac ctctgctgag aactttgagg ccgttgataa ctatctgacg | 240 |
| gcagatagct ggtatcgtcc taaatctatt ctgaaagatg caagacgtg gaccgagtcg | 300 |
| ggtaaggacg acttccgtcc gctgctgatg gcgtggtggc cggacacgga gactaaacgc | 360 |
| aattacgtga attacatgaa cctggttgtc ggcatcgaca agacgtacac cgcggaaacc | 420 |
| tctcaagcag atttgaccgc agcggcggag ctggtccagg cgcgtattga acagaaaatc | 480 |
| accacggaac agaatacgaa atggctgcgc gaggcgatct ctgctttcgt caagacccag | 540 |
| ccgcagtgga atggtgaaag cgagaagccg tatgacgacc acctgcaaaa cggtgctctg | 600 |
| aaattcgata tcagagcga cctgaccccg gacacccaga gcaactatcg cctgctgaat | 660 |
| cgcacccga ctaaccagac tggcagcctg acagccgtt tcacctataa tgcgaacgat | 720 |
| ccgttgggtg gctacgaatt tctgctggct aacgacgtgg ataatagcaa ccctgtggtg | 780 |
| caggcagaac aactgaactg gttgcattac ctgttgaatt ttggtagcat ttacgcgaaa | 840 |
| gatgcggatg caaacttcga ttccatccgt gtggacgccg tggacaacgt cgatgcagat | 900 |
| ctgttgcaga ttagcagcga ttacctgaag gcagcctatg gcattgacaa gaacaataag | 960 |
| aacgcgaaca accatgttag cattgttgag gcttggagcg ataacgatac gccgtacctg | 1020 |

```
cacgatgacg gtgataacct gatgaacatg gacaataagt tccgcttgag catgctgtgg      1080
agcctggcca agccgctgga caagcgcagc ggtctgaatc ctctgattca taacagcctg      1140
gtggaccgtg aggttgatga ccgtgaagtg gaaacggttc cgagctactc ttttgcgcgt      1200
gcgcatgatt ccgaggtcca agacattatc cgcgacatta tcaaggccga aatcaacccg      1260
aatagctttg gttatagctt cacccaagaa gagattgacc aggcgtttaa gatctataat      1320
gaagatctga agaaaaccga caagaaatac acccactata atgtcccgtt gagctatact      1380
ttgctgctga cgaataaagg ttcgattccg cgtgtgtatt acggtgatat gttcaccgat      1440
gatggtcaat acatggcgaa caaaacggtt aactatgatg ccattgagtc gctgctgaaa      1500
gcgcgcatga agtacgttag cggcggtcaa gcgatgcaaa actatcaaat cggcaatggt      1560
gagattctga ccagcgttcg ttatggtaag ggtgcattga agcaatccga caagggtgac      1620
gcgaccacgc gtacgtccgg tgtgggcgtc gtgatgggca accagccgaa ctttagcctg      1680
gacggcaagg tggtggcatt gaacatgggt gccgctcatg caaatcagga gtatcgtgcg      1740
ctgatggtga gcaccaagga tggcgttgcc acgtatgcca ccgacgcgga cgcaagcaag      1800
gcaggtctgg tcaaacgcac cgatgaaaat ggttatttgt actttctgaa cgacgatctg      1860
aagggtgtgg caaacccaca agtcagcggt ttcttgcagg tgtgggtccc agtgggtgcg      1920
gctgacgatc aggacattcg tgttgcagcg agcgacacgg ctagcacgga cggtaagtcc      1980
ctgcatcaag atgcggcaat ggatagccgt gttatgtttg agggttttag caacttccag      2040
agctttgcaa ccaaagaaga agagtacacc aacgtagtta ttgcgaacaa cgtggacaaa      2100
ttcgttagct ggggtattac cgactttgag atggcaccgc aatatgtcag ctccaccgat      2160
ggccagtttc tggatagcgt tatccagaat ggttacgcgt tcaccgaccg ttatgatctg      2220
ggtatgagca agccaacaa atacggtacc gcggatcagc tggttaaagc aatcaaagcg      2280
ttgcacgcga agggtctgaa ggtgatggcg gactgggttc cagaccagat gtacacgttt      2340
ccgaagcagg aagttgtcac tgtcacgcgc accgacaaat ttggtaagcc gattgcgggc      2400
agccaaatca atcacagcct gtacgtgacg gacaccaaat ccagcggtga tgattaccag      2460
gccaaatatg gtggtgcgtt cctggatgag ctgaaagaga aatacccgga gctgttcacc      2520
aaaaagcaga tctcgaccgg tcaggcgatc gacccgagcg tgaagattaa gcagtggagc      2580
gcgaaatact ttaatggtag caacattctg ggtcgtggtg ccgactacgt cctgtccgat      2640
caagttagca caagtatt caatgtggcc agcgacacgc tgtttctgcc gtctagcctg      2700
ttgggtaagg ttgtcgaaag cggtattcgt tacgatggca aaggttatat ctataacagc      2760
agcgcgactg gcgaccaagt caaggcgtct tttatcacgg aagcaggcaa tctgtactac      2820
ttcggcaaag acggttacat ggttactggt gcgcagacca ttaacggtgc gaattacttc      2880
ttcttggaaa atggtacggc cctgcgtaat accatctaca ccgatgcaca gggcaactcc      2940
cactattatg ctaatgatgg caagcgttac gagaacggtt accagcagtt cggcaacgat      3000
tggcgttact tcaaagatgg taacatggcc gtcggtctga ccacggtgga tggtaacgtt      3060
cagtatttcg acaaggacgg tgtccaagct aaagacaaga ttattgtgac ccgcgatggt      3120
aaggtgcgct actttgatca acacaatggc aacgcggtca cgaataccct tatcgccgac      3180
aagaccggtc actggtacta cctgggcaaa gatggcgtcg cggtcaccgg cgctcaaacc      3240
gtcggtaagc aaaaactgta ttttgaggcg aacggtgagc aggtgaaagg cgactttgtg      3300
actagccatg aaggcaaact gtactttttat gatgttgaca gcggcgacat gtggaccgat      3360
```

-continued

```
accttcatcg aggataaggc cggcaactgg ttctacctgg gtaaagacgg cgcagcagtt    3420
agcggtgcac agaccattcg cggtcaaaag ctgtacttca aggcgtacgg tcaacaggtc    3480
aaaggtgaca tcgttaaagg caccgacggc aagatccgtt actacgatgc gaaatccggc    3540
gagcaggttt tcaataagac ggtcaaagcc gctgatggca aaacctatgt gatcggcaac    3600
aatggtgtgg cggtcgatcc gagcgttgtt aagggtcaga cgttcaaaga cgccagcggc    3660
gcactgcgtt tttacaatct gaaaggtcaa ctggttacgg ctccggttg gtatgaaacg    3720 gccaatcacg attgggtgta tattcagagc ggtaaagcac tgaccggtga gcaaaccatc    3780
aatggtcagc acctgtactt taaagaagat ggccaccaag ttaaaggtca gctggtcacc    3840
cgtacggacg gcaaagtgcg ttactatgac gcaaattctg gcgatcaagc gttcaacaag    3900
tccgtgacgg ttaacggcaa aacgtattac ttcggtaatg atggtaccgc gcaaaccgcg    3960
ggtaacccga aaggccaaat cttcaaggac ggcagcgttc tgcgtttcta tagcatggaa    4020
ggccagctgg taattggcag cggctggtat tccaacgcgc aaggccaatg gctgtatgtg    4080
aagaatggta aagtgttgac cggttttgcag accgtcggtt cccagcgcgt gtactttgat    4140
gagaatggca ttcaagcaaa aggcaaagcg gttcgcacga gcgacggcaa aattcgctac    4200
ttcgacgaga acagcggtag catgatcacc aatcaatgga gtttgtttta cggtcaatac    4260
tattactttg gtaatgacgg tgcggcaatc taccgtggtt ggaattaa                 4308
```

<210> SEQ ID NO 26
<211> LENGTH: 1435
<212> TYPE: PRT
<213> ORGANISM: Streptococcus sobrinus

<400> SEQUENCE: 26

```
Met Val Asp Gly Lys Tyr Tyr Tyr Asp Gln Asp Gly Asn Val Lys
 1               5                  10                  15

Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
                35                  40                  45

Ser Ala Val Ser Gln Asn Ala Thr Ile Phe Ala Ala Asn Asn Arg Ala
        50                  55                  60

Tyr Ser Thr Ser Ala Glu Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Phe Arg Pro Leu Leu Met Ala Trp
                100                 105                 110

Trp Pro Asp Thr Glu Thr Lys Arg Asn Tyr Val Asn Tyr Met Asn Leu
            115                 120                 125

Val Val Gly Ile Asp Lys Thr Tyr Thr Ala Glu Thr Ser Gln Ala Asp
        130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205
```

-continued

```
Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Lys Asp Ala Asp Ala Asn Phe Asp Ser
                275                 280                 285

Ile Arg Val Asp Ala Val Asp Asn Val Asp Ala Asp Leu Leu Gln Ile
290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
                340                 345                 350

Lys Phe Arg Leu Ser Met Leu Trp Ser Leu Ala Lys Pro Leu Asp Lys
                355                 360                 365

Arg Ser Gly Leu Asn Pro Leu Ile His Asn Ser Leu Val Asp Arg Glu
            370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
                420                 425                 430

Asp Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
    450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gln Ala Met
                500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
                595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
```

```
           625                 630                 635                 640
Ala Asp Asp Gln Asp Ile Arg Val Ala Ala Ser Asp Thr Ala Ser Thr
                    645                 650                 655

Asp Gly Lys Ser Leu His Gln Asp Ala Ala Met Asp Ser Arg Val Met
                    660                 665                 670

Phe Glu Gly Phe Ser Asn Phe Gln Ser Phe Ala Thr Lys Glu Glu Glu
                    675                 680                 685

Tyr Thr Asn Val Val Ile Ala Asn Asn Val Asp Lys Phe Val Ser Trp
                    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                    725                 730                 735

Arg Tyr Asp Leu Gly Met Ser Lys Ala Asn Lys Tyr Gly Thr Ala Asp
                    740                 745                 750

Gln Leu Val Lys Ala Ile Lys Ala Leu His Ala Lys Gly Leu Lys Val
                    755                 760                 765

Met Ala Asp Trp Val Pro Asp Gln Met Tyr Thr Phe Pro Lys Gln Glu
770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                    805                 810                 815

Asp Asp Tyr Gln Ala Lys Tyr Gly Gly Ala Phe Leu Asp Glu Leu Lys
                    820                 825                 830

Glu Lys Tyr Pro Glu Leu Phe Thr Lys Lys Gln Ile Ser Thr Gly Gln
                    835                 840                 845

Ala Ile Asp Pro Ser Val Lys Ile Lys Gln Trp Ser Ala Lys Tyr Phe
                    850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                    885                 890                 895

Pro Ser Ser Leu Leu Gly Lys Val Val Glu Ser Gly Ile Arg Tyr Asp
                    900                 905                 910

Gly Lys Gly Tyr Ile Tyr Asn Ser Ser Ala Thr Gly Asp Gln Val Lys
                    915                 920                 925

Ala Ser Phe Ile Thr Glu Ala Gly Asn Leu Tyr Tyr Phe Gly Lys Asp
930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                    965                 970                 975

Gln Gly Asn Ser His Tyr Tyr Ala Asn Asp Gly Lys Arg Tyr Glu Asn
                    980                 985                 990

Gly Tyr Gln Gln Phe Gly Asn Asp Trp Arg Tyr Phe Lys Asp Gly Asn
                    995                 1000                1005

Met Ala Val Gly Leu Thr Thr Val Asp Gly Asn Val Gln Tyr Phe
        1010                1015                1020

Asp Lys Asp Gly Val Gln Ala Lys Asp Lys Ile Ile Val Thr Arg
        1025                1030                1035

Asp Gly Lys Val Arg Tyr Phe Asp Gln His Asn Gly Asn Ala Val
        1040                1045                1050
```

```
Thr Asn Thr Phe Ile Ala Asp Lys Thr Gly His Trp Tyr Tyr Leu
    1055            1060                1065

Gly Lys Asp Gly Val Ala Val Thr Gly Ala Gln Thr Val Gly Lys
    1070            1075                1080

Gln Lys Leu Tyr Phe Glu Ala Asn Gly Glu Gln Val Lys Gly Asp
    1085            1090                1095

Phe Val Thr Ser His Glu Gly Lys Leu Tyr Phe Tyr Asp Val Asp
    1100            1105                1110

Ser Gly Asp Met Trp Thr Asp Thr Phe Ile Glu Asp Lys Ala Gly
    1115            1120                1125

Asn Trp Phe Tyr Leu Gly Lys Asp Gly Ala Ala Val Ser Gly Ala
    1130            1135                1140

Gln Thr Ile Arg Gly Gln Lys Leu Tyr Phe Lys Ala Tyr Gly Gln
    1145            1150                1155

Gln Val Lys Gly Asp Ile Val Lys Gly Thr Asp Gly Lys Ile Arg
    1160            1165                1170

Tyr Tyr Asp Ala Lys Ser Gly Glu Gln Val Phe Asn Lys Thr Val
    1175            1180                1185

Lys Ala Ala Asp Gly Lys Thr Tyr Val Ile Gly Asn Asn Gly Val
    1190            1195                1200

Ala Val Asp Pro Ser Val Val Lys Gly Gln Thr Phe Lys Asp Ala
    1205            1210                1215

Ser Gly Ala Leu Arg Phe Tyr Asn Leu Lys Gly Gln Leu Val Thr
    1220            1225                1230

Gly Ser Gly Trp Tyr Glu Thr Ala Asn His Asp Trp Val Tyr Ile
    1235            1240                1245

Gln Ser Gly Lys Ala Leu Thr Gly Glu Gln Thr Ile Asn Gly Gln
    1250            1255                1260

His Leu Tyr Phe Lys Glu Asp Gly His Gln Val Lys Gly Gln Leu
    1265            1270                1275

Val Thr Arg Thr Asp Gly Lys Val Arg Tyr Tyr Asp Ala Asn Ser
    1280            1285                1290

Gly Asp Gln Ala Phe Asn Lys Ser Val Thr Val Asn Gly Lys Thr
    1295            1300                1305

Tyr Tyr Phe Gly Asn Asp Gly Thr Ala Gln Thr Ala Gly Asn Pro
    1310            1315                1320

Lys Gly Gln Ile Phe Lys Asp Gly Ser Val Leu Arg Phe Tyr Ser
    1325            1330                1335

Met Glu Gly Gln Leu Val Ile Gly Ser Gly Trp Tyr Ser Asn Ala
    1340            1345                1350

Gln Gly Gln Trp Leu Tyr Val Lys Asn Gly Lys Val Leu Thr Gly
    1355            1360                1365

Leu Gln Thr Val Gly Ser Gln Arg Val Tyr Phe Asp Glu Asn Gly
    1370            1375                1380

Ile Gln Ala Lys Gly Lys Ala Val Arg Thr Ser Asp Gly Lys Ile
    1385            1390                1395

Arg Tyr Phe Asp Glu Asn Ser Gly Ser Met Ile Thr Asn Gln Trp
    1400            1405                1410

Lys Phe Val Tyr Gly Gln Tyr Tyr Tyr Phe Gly Asn Asp Gly Ala
    1415            1420                1425

Ala Ile Tyr Arg Gly Trp Asn
    1430            1435
```

<210> SEQ ID NO 27
<211> LENGTH: 4023
<212> TYPE: DNA
<213> ORGANISM: Streptococcus salivarius

<400> SEQUENCE: 27

| | | | | | |
|---|---|---|---|---|---|
| atgattgacg | gcaaatacta | ctacgtaaac | aaagatggct | cgcacaaaga | gaatttcgca | 60 |
| attaccgtga | atggtcagtt | gttgtatttc | ggtaaggacg | gtgcattgac | gtctagcagc | 120 |
| acctacagct | ttacgcaggg | caccaccaac | atcgttgatg | gctttagcaa | aaacaaccgt | 180 |
| gcgtacgatt | ccagcgaggc | gagctttgaa | ctgatcgacg | gttatctgac | cgcggactcc | 240 |
| tggtatcgtc | cggtgagcat | tatcaaggac | ggcgttacgt | ggcaagccag | caccaaagag | 300 |
| gactttcgcc | cgctgctgat | ggcctggtgg | ccgaatgttg | acacccaggt | caactacctg | 360 |
| aattacatgt | cgaaggtgtt | taacctggac | gcgaagtata | cgagcaccga | caaacaggtt | 420 |
| gacctgaatc | gcgcagccaa | ggacattcag | gttaagattg | agcaaaagat | tcaggccgag | 480 |
| aagagcactc | aatggctgcg | tgaagcgatt | tcggccttcg | tcaaaaccca | gccgcagtgg | 540 |
| aataaagaaa | cggagaactt | ctccaagggt | ggtggtgagg | atcatctgca | aggtggtgca | 600 |
| ctgctgtacg | ttaacgaccc | gcgtaccccg | tgggctaact | ccaactaccg | cctgctgaat | 660 |
| cgtactgcga | ccaaccagac | cggcacgatc | gacaagagcg | ttctggacga | acagagcgat | 720 |
| cctaaccaca | tgggcggctt | cgattttctg | ctggcgaatg | acgtcgatac | cagcaatccg | 780 |
| gtggtgcagg | cggaacaact | gaatcagatc | cactacctga | tgaattgggg | ttccattgtt | 840 |
| atgggcgaca | agatgcaaa | cttcgatggt | atccgcgtgg | acgcggtcga | taacgttgac | 900 |
| gcagatatgc | tgcaactgta | caccaactac | tttcgtgagt | attatggcgt | gaacaaaagc | 960 |
| gaggcaaacg | ctttggcgca | catctcggtg | ctggaagcgt | ggagcttgaa | tgataatcac | 1020 |
| tataatgaca | agactgacgg | tgcggccctg | gcgatggaga | caaacagcg | tttggccctg | 1080 |
| ctgtttagct | tggcgaaacc | gatcaaagaa | cgtaccctg | cggtgagccc | gctgtacaac | 1140 |
| aacactttca | cacgacgca | gcgtgacgaa | aagaccgatt | ggattaacaa | agacggtagc | 1200 |
| aaagcctata | tgaggacgg | caccgtcaag | cagtccacca | tcggcaagta | caacgagaaa | 1260 |
| tacggcgacg | cgtccggcaa | ttatgtgttc | attcgcgccc | acgataacaa | cgtccaagac | 1320 |
| attattgcag | agatcattaa | gaaagaaatc | aatccgaaaa | gcgacggttt | caccattacc | 1380 |
| gacgccgaaa | tgaaaaaggc | attcgaaatc | tacaacaaag | atatgctgtc | ctctgataag | 1440 |
| aaatacaccc | tgaacaacat | cccagcggcc | tacgcggtga | tgctgcaaaa | catggaaacc | 1500 |
| attactcgtg | tgtattacgg | cgatctgtat | accgacgatg | gccattacat | ggaaaccaag | 1560 |
| agcccgtact | acgacaccat | tgtgaacctg | atgaagaacc | gtatcaaata | cgtgtccggt | 1620 |
| ggtcaagcgc | aacgttccta | ttggctgccg | accgacggta | agatggataa | aagcgatgtc | 1680 |
| gaactgtatc | gcaccaacga | ggtgtacacc | agcgtccgtt | acggtaagga | catcatgact | 1740 |
| gccgatgaca | cccaaggtag | caagtacagc | cgtaccagcg | gtcaggtgac | cctggtggtg | 1800 |
| aacaacccga | agctgtcttt | ggataagagc | gcgaagctgg | acgtcgaaat | gggcaagatc | 1860 |
| catgcaaacc | agaaataccg | tgctctgatc | gtgggtacgc | cgaacggcat | caaaaacttc | 1920 |
| acgagcgacg | ccgaggcaat | cgcggctggc | tacgtgaaag | aaaccgacgg | caatggtgtg | 1980 |
| ctgaccttcg | gtgcaaatga | catcaaaggt | tacgaaacgt | ttgacatgag | cggtttcgtt | 2040 |
| gcagtttggg | ttccggtagg | tgcaagcgat | gatcaagaca | tccgtgtcgc | cgcaagcacc | 2100 |
| gcggcaaaga | aagaaggtga | gctgactttg | aaggcaactg | aggcgtatga | ctctcagctg | 2160 |

```
atttacgaag gtttttcgaa ttttcagacc attccggatg gtagcgatcc gagcgtttac    2220
accaatcgta agatcgcgga aaatgttgat ttgttcaaga gctggggtgt gacctctttc    2280
gaaatggcgc cacagtttgt gagcgcagac gacggtacgt ttctggacag cgttatccag    2340
aacggctatg cgtttgcgga ccgttatgat ctggcgatgc ccaaaaacaa taagtacggt    2400 tcgaagaag  atctgcgtaa cgcgttgaag gctttgcaca aggccggcat ccaagccatt    2460
gcggactggg ttccggatca gatctaccaa ctgccgggca agaagtagt  gaccgccact    2520 cgtaccgatg gtgccggtcg taagattagc gatgcaatta tcgatcacag cctgtacgtc    2580
gcaaacagca agtcgtctgg caaagactat caagctaaat acggtggtga gttcctggcc    2640
gagctgaaag caaagtaccc ggaaatgttt aaagtcaaca tgattagcac gggtaaaccg    2700
atcgacgact ctgtcaaact gaagcaatgg aaggcggagt actttaacgg tacgaatgtt    2760
ctggaccgtg gtgttggtta cgtcctgagc gatgaggcga cgggcaagta ctttaccgtt    2820
acgaaagagg gtaactttat cccactgcaa ttgaaaggta cgagaaagt  tatcacgggc    2880 ttcagctctg acggcaaggg cattacctat ttcggcacct cgggtaatca agcgaaaagc    2940
gcttttgtca cgttcaatgg taatacctac tattttgacg cgcgtggcca catggttacc    3000
aacggcgaat atagccctaa tggtaaggat gtgtatcgtt tcctgccgaa tggtattatg    3060
ttgagcaatg cattctacgt tgacggtaac ggcaatacct acctgtacaa ctccaagggc    3120
caaatgtaca aggtggtta  tagcaaattc gacgttacgg aaaccaaaga tggtaaagag    3180
agcaaagtgg tgaaatttcg ctactttacc aatgaaggtg tgatggcaaa aggtgttacc    3240
gtggtggacg gcttcactca atacttcaac gaagatggca ttcagagcaa ggacgaactg    3300
gtgacctaca atggtaaaac ctattacttc gaagcgcata ccggtaatgc gatcaaaaac    3360
acgtggcgca atatcaaggg taagtggtat cactttgatg cgaatggcgt ggcggcaacg    3420
ggtgcacagg ttatcaatgg tcagcacctg tactttaatg aggatggttc ccaggtgaag    3480
ggtggcgtcg tgaagaatgc ggatggtacc ttcagcaagt ataaagatgg ttccggtgac    3540
ctggtggtca atgagttctt cactactggt gataacgtgt ggtactacgc tggtgccaac    3600
ggcaaaactg tgacgggtgc ccaggtcatc aatggccaac acctgttttt caaagaggac    3660
ggtagccagg ttaagggtga tttcgttaag aacagcgacg gcacctactc taagtatgat    3720
gcggccagcg gcgaacgcct gacgaatgag ttttcacga  ccggtgacaa ccactggtac    3780
tatattggtg ccaatggcaa aaccgttacc ggcgaagtca agatcggtga tgatacgtac    3840
ttcttcgcaa agatggcaa  gcagctgaag ggccagatcg tgacgacccg cagcggtcgt    3900
atcagctact acttcggcga ctctggtaag aaggcgatta gcacctgggt ggagattcag    3960
ccgggtgttt tcgtgttttt cgacaaaaat ggcctggcat atccgccgga aacatgaat    4020 taa                                                                 4023
```

<210> SEQ ID NO 28
<211> LENGTH: 1340
<212> TYPE: PRT
<213> ORGANISM: Streptococcus salivarius

<400> SEQUENCE: 28

Met Ile Asp Gly Lys Tyr Tyr Tyr Val Asn Lys Asp Gly Ser His Lys
1               5                   10                  15

Glu Asn Phe Ala Ile Thr Val Asn Gly Gln Leu Leu Tyr Phe Gly Lys
            20                  25                  30

-continued

```
Asp Gly Ala Leu Thr Ser Ser Thr Tyr Ser Phe Thr Gln Gly Thr
         35                  40                  45
Thr Asn Ile Val Asp Gly Phe Ser Lys Asn Asn Arg Ala Tyr Asp Ser
 50                  55                  60
Ser Glu Ala Ser Phe Glu Leu Ile Asp Gly Tyr Leu Thr Ala Asp Ser
 65                  70                  75                  80
Trp Tyr Arg Pro Val Ser Ile Ile Lys Asp Gly Val Thr Trp Gln Ala
                 85                  90                  95
Ser Thr Lys Glu Asp Phe Arg Pro Leu Leu Met Ala Trp Trp Pro Asn
            100                 105                 110
Val Asp Thr Gln Val Asn Tyr Leu Asn Tyr Met Ser Lys Val Phe Asn
        115                 120                 125
Leu Asp Ala Lys Tyr Thr Ser Thr Asp Lys Gln Val Asp Leu Asn Arg
    130                 135                 140
Ala Ala Lys Asp Ile Gln Val Lys Ile Glu Gln Lys Ile Gln Ala Glu
145                 150                 155                 160
Lys Ser Thr Gln Trp Leu Arg Glu Ala Ile Ser Ala Phe Val Lys Thr
                165                 170                 175
Gln Pro Gln Trp Asn Lys Glu Thr Glu Asn Phe Ser Lys Gly Gly Gly
            180                 185                 190
Glu Asp His Leu Gln Gly Gly Ala Leu Leu Tyr Val Asn Asp Pro Arg
        195                 200                 205
Thr Pro Trp Ala Asn Ser Asn Tyr Arg Leu Leu Asn Arg Thr Ala Thr
    210                 215                 220
Asn Gln Thr Gly Thr Ile Asp Lys Ser Val Leu Asp Glu Gln Ser Asp
225                 230                 235                 240
Pro Asn His Met Gly Gly Phe Asp Phe Leu Leu Ala Asn Asp Val Asp
                245                 250                 255
Thr Ser Asn Pro Val Val Gln Ala Glu Gln Leu Asn Gln Ile His Tyr
            260                 265                 270
Leu Met Asn Trp Gly Ser Ile Val Met Gly Asp Lys Asp Ala Asn Phe
        275                 280                 285
Asp Gly Ile Arg Val Asp Ala Val Asp Asn Val Asp Ala Asp Met Leu
    290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
            340                 345                 350
Glu Asn Lys Gln Arg Leu Ala Leu Leu Phe Ser Leu Ala Lys Pro Ile
        355                 360                 365
Lys Glu Arg Thr Pro Ala Val Ser Pro Leu Tyr Asn Asn Thr Phe Asn
    370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                405                 410                 415
Tyr Asn Glu Lys Tyr Gly Asp Ala Ser Gly Asn Tyr Val Phe Ile Arg
            420                 425                 430
Ala His Asp Asn Asn Val Gln Asp Ile Ile Ala Glu Ile Ile Lys Lys
        435                 440                 445
Glu Ile Asn Pro Lys Ser Asp Gly Phe Thr Ile Thr Asp Ala Glu Met
```

```
                450             455             460
    Lys Lys Ala Phe Glu Ile Tyr Asn Lys Asp Met Leu Ser Ser Asp Lys
    465             470             475             480
    Lys Tyr Thr Leu Asn Asn Ile Pro Ala Ala Tyr Ala Val Met Leu Gln
                    485             490             495
    Asn Met Glu Thr Ile Thr Arg Val Tyr Tyr Gly Asp Leu Tyr Thr Asp
                500             505             510
    Asp Gly His Tyr Met Glu Thr Lys Ser Pro Tyr Tyr Asp Thr Ile Val
                515             520             525
    Asn Leu Met Lys Asn Arg Ile Lys Tyr Val Ser Gly Gly Gln Ala Gln
                530             535             540
    Arg Ser Tyr Trp Leu Pro Thr Asp Gly Lys Met Asp Lys Ser Asp Val
    545             550             555             560
    Glu Leu Tyr Arg Thr Asn Glu Val Tyr Thr Ser Val Arg Tyr Gly Lys
                    565             570             575
    Asp Ile Met Thr Ala Asp Asp Thr Gln Gly Ser Lys Tyr Ser Arg Thr
                    580             585             590
    Ser Gly Gln Val Thr Leu Val Val Asn Asn Pro Lys Leu Ser Leu Asp
                595             600             605
    Lys Ser Ala Lys Leu Asp Val Glu Met Gly Lys Ile His Ala Asn Gln
    610             615             620
    Lys Tyr Arg Ala Leu Ile Val Gly Thr Pro Asn Gly Ile Lys Asn Phe
    625             630             635             640
    Thr Ser Asp Ala Glu Ala Ile Ala Ala Gly Tyr Val Lys Glu Thr Asp
                    645             650             655
    Gly Asn Gly Val Leu Thr Phe Gly Ala Asn Asp Ile Lys Gly Tyr Glu
                    660             665             670
    Thr Phe Asp Met Ser Gly Phe Val Ala Val Trp Val Pro Val Gly Ala
                    675             680             685
    Ser Asp Asp Gln Asp Ile Arg Val Ala Ala Ser Thr Ala Ala Lys Lys
                690             695             700
    Glu Gly Glu Leu Thr Leu Lys Ala Thr Glu Ala Tyr Asp Ser Gln Leu
    705             710             715             720
    Ile Tyr Glu Gly Phe Ser Asn Phe Gln Thr Ile Pro Asp Gly Ser Asp
                    725             730             735
    Pro Ser Val Tyr Thr Asn Arg Lys Ile Ala Glu Asn Val Asp Leu Phe
                    740             745             750
    Lys Ser Trp Gly Val Thr Ser Phe Glu Met Ala Pro Gln Phe Val Ser
                    755             760             765
    Ala Asp Asp Gly Thr Phe Leu Asp Ser Val Ile Gln Asn Gly Tyr Ala
                770             775             780
    Phe Ala Asp Arg Tyr Asp Leu Ala Met Ser Lys Asn Asn Lys Tyr Gly
    785             790             795             800
    Ser Lys Glu Asp Leu Arg Asn Ala Leu Lys Ala Leu His Lys Ala Gly
                    805             810             815
    Ile Gln Ala Ile Ala Asp Trp Val Pro Asp Gln Ile Tyr Gln Leu Pro
                    820             825             830
    Gly Lys Glu Val Val Thr Ala Thr Arg Thr Asp Gly Ala Gly Arg Lys
                    835             840             845
    Ile Ser Asp Ala Ile Ile Asp His Ser Leu Tyr Val Ala Asn Ser Lys
                    850             855             860
    Ser Ser Gly Lys Asp Tyr Gln Ala Lys Tyr Gly Gly Glu Phe Leu Ala
    865             870             875             880
```

-continued

```
Glu Leu Lys Ala Lys Tyr Pro Glu Met Phe Lys Val Asn Met Ile Ser
            885                 890                 895
Thr Gly Lys Pro Ile Asp Asp Ser Val Lys Leu Lys Gln Trp Lys Ala
        900                 905                 910
Glu Tyr Phe Asn Gly Thr Asn Val Leu Asp Arg Gly Val Gly Tyr Val
        915                 920                 925
Leu Ser Asp Glu Ala Thr Gly Lys Tyr Phe Val Thr Lys Glu Gly
    930                 935                 940
Asn Phe Ile Pro Leu Gln Leu Lys Gly Asn Glu Lys Val Ile Thr Gly
945                 950                 955                 960
Phe Ser Ser Asp Gly Lys Gly Ile Thr Tyr Phe Gly Ser Gly Asn
                965                 970                 975
Gln Ala Lys Ser Ala Phe Val Thr Phe Asn Gly Asn Thr Tyr Tyr Phe
            980                 985                 990
Asp Ala Arg Gly His Met Val Thr Asn Gly Glu Tyr Ser Pro Asn Gly
            995                 1000                1005
Lys Asp Val Tyr Arg Phe Leu Pro Asn Gly Ile Met Leu Ser Asn
        1010                1015                1020
Ala Phe Tyr Val Asp Gly Asn Gly Asn Thr Tyr Leu Tyr Asn Ser
        1025                1030                1035
Lys Gly Gln Met Tyr Lys Gly Gly Tyr Ser Lys Phe Asp Val Thr
        1040                1045                1050
Glu Thr Lys Asp Gly Lys Glu Ser Lys Val Val Lys Phe Arg Tyr
        1055                1060                1065
Phe Thr Asn Glu Gly Val Met Ala Lys Gly Val Thr Val Val Asp
        1070                1075                1080
Gly Phe Thr Gln Tyr Phe Asn Glu Asp Gly Ile Gln Ser Lys Asp
        1085                1090                1095
Glu Leu Val Thr Tyr Asn Gly Lys Thr Tyr Tyr Phe Glu Ala His
        1100                1105                1110
Thr Gly Asn Ala Ile Lys Asn Thr Trp Arg Asn Ile Lys Gly Lys
        1115                1120                1125
Trp Tyr His Phe Asp Ala Asn Gly Val Ala Ala Thr Gly Ala Gln
        1130                1135                1140
Val Ile Asn Gly Gln His Leu Tyr Phe Asn Glu Asp Gly Ser Gln
        1145                1150                1155
Val Lys Gly Gly Val Val Lys Asn Ala Asp Gly Thr Phe Ser Lys
        1160                1165                1170
Tyr Lys Asp Gly Ser Gly Asp Leu Val Val Asn Glu Phe Phe Thr
        1175                1180                1185
Thr Gly Asp Asn Val Trp Tyr Tyr Ala Gly Ala Asn Gly Lys Thr
        1190                1195                1200
Val Thr Gly Ala Gln Val Ile Asn Gly Gln His Leu Phe Phe Lys
        1205                1210                1215
Glu Asp Gly Ser Gln Val Lys Gly Asp Phe Val Lys Asn Ser Asp
        1220                1225                1230
Gly Thr Tyr Ser Lys Tyr Asp Ala Ala Ser Gly Glu Arg Leu Thr
        1235                1240                1245
Asn Glu Phe Phe Thr Thr Gly Asp Asn His Trp Tyr Tyr Ile Gly
        1250                1255                1260
Ala Asn Gly Lys Thr Val Thr Gly Glu Val Lys Ile Gly Asp Asp
        1265                1270                1275
```

```
Thr Tyr Phe Phe Ala Lys Asp Gly Lys Gln Leu Lys Gly Gln Ile
    1280            1285                1290

Val Thr Thr Arg Ser Gly Arg Ile Ser Tyr Tyr Phe Gly Asp Ser
1295            1300                1305

Gly Lys Lys Ala Ile Ser Thr Trp Val Glu Ile Gln Pro Gly Val
    1310            1315               1320

Phe Val Phe Phe Asp Lys Asn Gly Leu Ala Tyr Pro Pro Glu Asn
    1325            1330               1335

Met Asn
    1340

<210> SEQ ID NO 29
<211> LENGTH: 4026
<212> TYPE: DNA
<213> ORGANISM: Streptococcus salivarius

<400> SEQUENCE: 29
atgacggacg gtaaatacta ttatgtaaat gaggacggca gccacaaaga gaatttcgca      60
attacggtaa acggtcaact gttgtacttt ggcaaggacg gcgctctgac gagcagcagc     120
acgcacagct tcacgccggg tactacgaat attgtggacg gtttctcgat caacaaccgt     180
gcgtacgata gcagcgaagc gagctttgag ctgatcaacg ttacctgacg gcggattcc      240 tggtatcgcc cggtttctat catcaaggat ggcgtcacgt ggcaggcaag cactgccgag     300
gattttcgtc cgctgttgat ggcctggtgg ccgaacgttg atcccaggt gaactatctg      360 aactatatgt ccaaggtctt taaccctgaa gccaagtaca ccagcaccga taaacaggct     420
gatctgaacc gtgctgcaaa ggatatccag gtcaagatcg aacagaagat ccaggcggaa     480
aagagcacgc agtggctgcg tgagactatc tccgcgtttg ttaaaaccca gccgcaatgg     540
aacaaagaga ctgagaatta ctccaagggt ggtggcgaag atcatctgca aggcggtgcg     600
ctgttgtacg tgaacgacag ccgtaccccg tgggcgaata gcaattaccg cctgctgaat     660
cgcacggcaa cgaaccagac cggtaccatt aacaagtcgg tgttggacga gcaatccgat     720
ccaaatcaca tgggtggctt cgacttcctg ctggcaaacg atgtggatct gagcaatcct     780
gttgtgcagg ccgagcagct gaatcaaatc cattatctga tgaactgggg cagcattgtt     840
atgggtgaca agacgcgaa ttttgatggt atccgtgtgg acgccgttga caacgtgaac      900
gctgacatgt tgcagctgta cacgaactac tttcgtgagt attacggcgt caacaaaagc     960
gaagcgcaag cgctggcgca cattagcgtt ctggaagcgt ggagcttgaa cgataaccac    1020
tataacgaca aaaccgatgg tgcggcactg gcgatggaga taagcaacg tctggccttg     1080 ctgttctctc tggccaagcc gatcaaagat cgtactccgg cagtgagccc actgtataac    1140
aatactttca ataccaccca acgtgacttc aagacggatt ggattaacaa ggacggtagc    1200
accgcctaca tgaggatgg caccgcgaaa caatctacca tcggtaagta caatgagaaa    1260
tatggtgatg caagcggtaa ctatgtgttt ttcgtgccc atgacaataa cgtccaagac    1320
attattgcgg agatcattaa gaaagaaatc aataagaaga gcgatggttt taccatcagc    1380
gatagcgaaa tgaaacaggc gttcgaaatc tacaacaaag atatgctgag cagcaataag    1440
aaatacactc tgaataacat tccggcagcg tacgccgtga tgctgcaaaa catggagact    1500
atcacccgtg tgtattatgg tgacctgtac accgacgacg tcactatat ggaaaccaag     1560 agcccgtatc atgacaccat tgtgaacctg atgaaaaaccc gtatcaagta cgtttctggt    1620
ggccaggccc aacgctccta ttggctgccg accgacggta aaatggacaa tagcgatgtc    1680
```

-continued

```
gaactgtacc gtactagcga ggtctatacc agcgttcgct acggtaagga cattatgacg    1740
gcggatgaca ccgagggtag caagtactcc cgcacgagcg gtcaggttac cctggttgtt    1800
aacaacccga agctgactct gcatgaaagc gccaaactga acgtcgagat gggtaagatc    1860
cacgcaaacc agaaataccg tgcgctgatt gtgggtaccg ccgatggcat caaaaacttt    1920
acgtctgatg ccgaagcgat cgcggcaggc tacgtaaaag aaacggacag caatggtgtt    1980
ctgaccttcg gcgcaaatga tatcaaaggt tacgagactt tcgatatgag cggtttcgtc    2040
gcagtttggg tgccggtggg tgcgagcgat gatcaggaca tccgcgtggc gccgtcgacg    2100
gaagcgaaga aagaaggtga actgacgctg aaagccacgg aagcgtatga tagccagttg    2160
atttatgaag gcttctccaa tttccagacc attccggatg gcagcgaccc gagcgtttat    2220
accaaccgca aaattgctga gaatgttgat ctgtttaagt cctggggtgt cactagcttc    2280
gaaatggctc gcagtttgt  ttcggcggac gacggcacct tcctggatag cgttatccag    2340
aacggttacg cctttgcgga ccgttatgat ttggccatga gcaagaacaa caagtacggt    2400
tctaaagagg atctgcgcga cgcactgaaa gcgctgcaca aagctggcat tcaggcaatc    2460
gcggactggg tcccagacca aatctaccaa ctgccaggca agaagtggt  tacggcgacg    2520
cgcacggacg gtgcgggtcg caagatcgcg gacgccatca ttgatcatag cctgtatgtt    2580
gctaactcca agagctccgg tcgcgattac caagcgcagt atggtggcga gtttctggca    2640
gagctgaaag cgaagtaccc gaaaatgttc acggaaaaca tgattagcac gggtaagccg    2700
atcgatgaca gcgtcaaact gaagcaatgg aaagccaagt atttcaatgg tacgaatgtg    2760
ctggaccgtg gtgtcggtta cgtcctgtcc gacgaggcga ccggcaaata cttcaccgtt    2820
accaaagagg gtaacttcat tccgctgcaa ctgaccggca atgaaaaagc ggtgaccggt    2880
ttcagcaacg acggcaaggg tatcacctac tttggtacga gcggtaatca ggccaagagc    2940
gcgttcgtca cctttaacgg caatacgtac tatttcgacg cgcgtggcca catggtcacg    3000
aacggcgagt atagcccgaa cggcaaagat gtctaccgtt ttctgccaaa tggtattatg    3060
ttgtcgaacg cgttttatgt cgacgcaaac ggtaatacgt acttgtacaa ctacaagggc    3120
cagatgtaca aagtgggtta tacgaaattt gatgtcaccg aaactgataa agatggtaat    3180
gagagcaagg tggtcaagtt tcgttatttc accaatgagg gcgtcatggc taagggtctg    3240
accgtcattg acggtagcac ccagtacttt ggtgaggatg gttttcaaac gaaggacaag    3300
ctggcgacct ataaaggtaa gacttattac ttcgaggcac acacgggcaa tgcgatcaaa    3360
aacacctggc gtaacatcga cggtaagtgg tatcacttcg atgagaatgg cgttgccgcg    3420
accggtgcac aagtgattaa cggtcaaaaa ctgtatttca acgaggatgg ctcgcaagtg    3480
aagggcggtg ttgttaagaa cgccgacggt acctacagca aatacaaaga gggcagcggt    3540
gagctggtta ccaacgagtt tttcacgacc gacggtaatg tgtggtacta tgctggtgcg    3600
gatggcaaga ctgtgaccgg tgctcaggtc attaatggtc agcacctgta ctttaaagaa    3660
gatggcagcc aggtgaaagg tggtgtggtg aaaaacgcgg acggtacgta cagcaagtat    3720
gacgccgcca ccggtgaacg cttgaccaat gagttcttta ccacgggcga taacaattgg    3780
tactatattg gttctaatgg taagaccgta accggtgaag tcaaaatcgg tgcggacacc    3840
tattactttg ccaaagatgg caaacaggtc aagggccaaa ccgtcaccgc aggcaatggc    3900
cgcatctcct attactacgg cgattctggt aagaaagcaa tcagcacgtg gatcgaaatt    3960
caaccgggta tctatgtcta ttttgataag acgggcatcg cgtacccacc gcgtgtgctg    4020
aattaa                                                               4026
```

<210> SEQ ID NO 30
<211> LENGTH: 1341
<212> TYPE: PRT
<213> ORGANISM: Streptococcus salivarius

<400> SEQUENCE: 30

```
Met Thr Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr His Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asn Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Glu Ala Lys Tyr Thr Ser Thr Asp Lys Gln Ala Asp Leu Asn Arg
130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asn Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asn Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Gln Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Asp Arg Thr Pro Ala Val Ser Pro Leu Tyr Asn Asn Thr Phe Asn
```

```
              370                 375                 380
Thr Thr Gln Arg Asp Phe Lys Thr Asp Trp Ile Asn Lys Asp Gly Ser
385                 390                 395                 400

Thr Ala Tyr Asn Glu Asp Gly Thr Ala Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Lys Lys Ser Asp Gly Phe Thr Ile Ser Asp Ser Glu Met
    450                 455                 460

Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr His Asp Thr Ile Val
        515                 520                 525

Asn Leu Met Lys Asn Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
        595                 600                 605

Glu Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Glu Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800
```

```
Ser Lys Glu Asp Leu Arg Asp Ala Leu Lys Ala Leu His Lys Ala Gly
            805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
            835                 840                 845

Ile Ala Asp Ala Ile Ile Asp His Ser Leu Tyr Val Ala Asn Ser Lys
            850                 855                 860

Ser Ser Gly Arg Asp Tyr Gln Ala Gln Tyr Gly Gly Glu Phe Leu Ala
865                 870                 875                 880

Glu Leu Lys Ala Lys Tyr Pro Lys Met Phe Thr Glu Asn Met Ile Ser
            885                 890                 895

Thr Gly Lys Pro Ile Asp Asp Ser Val Lys Leu Lys Gln Trp Lys Ala
            900                 905                 910

Lys Tyr Phe Asn Gly Thr Asn Val Leu Asp Arg Gly Val Gly Tyr Val
            915                 920                 925

Leu Ser Asp Glu Ala Thr Gly Lys Tyr Phe Thr Val Thr Lys Glu Gly
            930                 935                 940

Asn Phe Ile Pro Leu Gln Leu Thr Gly Asn Glu Lys Ala Val Thr Gly
945                 950                 955                 960

Phe Ser Asn Asp Gly Lys Gly Ile Thr Tyr Phe Gly Thr Ser Gly Asn
            965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
            1010                1015                1020

Ala Phe Tyr Val Asp Ala Asn Gly Asn Thr Tyr Leu Tyr Asn Tyr
            1025                1030                1035

Lys Gly Gln Met Tyr Lys Gly Gly Tyr Thr Lys Phe Asp Val Thr
            1040                1045                1050

Glu Thr Asp Lys Asp Gly Asn Glu Ser Lys Val Val Lys Phe Arg
            1055                1060                1065

Tyr Phe Thr Asn Glu Gly Val Met Ala Lys Gly Leu Thr Val Ile
            1070                1075                1080

Asp Gly Ser Thr Gln Tyr Phe Gly Glu Asp Gly Phe Gln Thr Lys
            1085                1090                1095

Asp Lys Leu Ala Thr Tyr Lys Gly Lys Thr Tyr Tyr Phe Glu Ala
            1100                1105                1110

His Thr Gly Asn Ala Ile Lys Asn Thr Trp Arg Asn Ile Asp Gly
            1115                1120                1125

Lys Trp Tyr His Phe Asp Glu Asn Gly Val Ala Ala Thr Gly Ala
            1130                1135                1140

Gln Val Ile Asn Gly Gln Lys Leu Tyr Phe Asn Glu Asp Gly Ser
            1145                1150                1155

Gln Val Lys Gly Gly Val Val Lys Asn Ala Asp Gly Thr Tyr Ser
            1160                1165                1170

Lys Tyr Lys Glu Gly Ser Gly Glu Leu Val Thr Asn Glu Phe Phe
            1175                1180                1185

Thr Thr Asp Gly Asn Val Trp Tyr Tyr Ala Gly Ala Asp Gly Lys
            1190                1195                1200
```

```
Thr Val Thr Gly Ala Gln Val Ile Asn Gly Gln His Leu Tyr Phe
    1205            1210                1215

Lys Glu Asp Gly Ser Gln Val Lys Gly Val Val Lys Asn Ala
    1220            1225                1230

Asp Gly Thr Tyr Ser Lys Tyr Asp Ala Ala Thr Gly Glu Arg Leu
    1235            1240                1245

Thr Asn Glu Phe Phe Thr Thr Gly Asp Asn Asn Trp Tyr Tyr Ile
    1250            1255                1260

Gly Ser Asn Gly Lys Thr Val Thr Gly Glu Val Lys Ile Gly Ala
    1265            1270                1275

Asp Thr Tyr Tyr Phe Ala Lys Asp Gly Lys Gln Val Lys Gly Gln
    1280            1285                1290

Thr Val Thr Ala Gly Asn Gly Arg Ile Ser Tyr Tyr Tyr Gly Asp
    1295            1300                1305

Ser Gly Lys Lys Ala Ile Ser Thr Trp Ile Glu Ile Gln Pro Gly
    1310            1315                1320

Ile Tyr Val Tyr Phe Asp Lys Thr Gly Ile Ala Tyr Pro Pro Arg
    1325            1330                1335

Val Leu Asn
    1340
```

<210> SEQ ID NO 31
<211> LENGTH: 3918
<212> TYPE: DNA
<213> ORGANISM: Streptococcus salivarius

<400> SEQUENCE: 31

```
atgatcgacg gcaaacagta ttatgtagag aacggtgtgg ttaagaaaaa tgcggcaatt      60
gaactggatg gccgcctgta ctactttgat gagactggcg caatggtcga tcagagcaaa     120
ccgttgtatc gtgcggacgc gattccgaac aactctatct acgccgtgta caaccaagcg     180
tatgatacca gcagcaaatc cttcgagcat ttggataact tcctgaccgc ggatagctgg     240
tatcgcccga acagattctc gaaggacggt aaaaactgga ccgcaagcac tgagaaagac     300
tatcgtcctc tgctgatgac ctggtggccg acaaggtga cccaggtgaa ttacctgaac     360
tatatgtctc aacagggttt tggtaacaaa acgtacacca cggatatgat gagctacgac     420
ctggcggctg cggcagaaac ggtgcagcgt ggcatcgaag agcgtatcgg tcgcgagggt     480
aacaccacgt ggctgcgcca gctgatgagc gatttcatca aacccagcc gggttggaat     540
agcgagagcg aggacaatct gctggttggt aaggaccatc tgcaaggtgg tgcgctgacc     600
tttctgaaca atagcgcaac gagccacgcg aatagcgact tcgtctgat gaccgtacc      660
ccgaccaatc agaccggtac ccgtaaatac cacatcgatc gtagcaatgg cggctatgag     720
ctgctgctgg ctaacgacat tgataatagc aatccggcag ttcaagcaga gcaactgaat     780
tggctgcact acattatgaa tattggcagc atcttgggta atgacccgag cgcgaatttt     840
gacggtgttc gtatcgatgc ggtggataat gtggacgcgg atttgctgca aatcgcgtct     900
gattacttca agagaagta ccgtgtcgcg gacaacgagg caaacgcgat tgcccacctg     960
agcattctgg aagcgtggag ctataatgat catcagtaca caaggacac gaagggcgca    1020
cagctgtcca tcgataaccc gctgcgcgaa accctgctga ctaccttcct gcgtaaaagc    1080
aattatcgtg gtagcttgga gcgcgttatt accaactccc tgaataaccg ctctagcgag    1140
caaaagcaca ctccgcgcga cgcgaactac atctttgtac gtgcgcatga cagcgaagtt    1200
caagacgtgc tggcgaatat cattagcaaa cagatcaacc caaagacgga tggcttcacg    1260
```

```
ttcaccatgg atgaactgaa gcaggcgttc gagatctaca atgcggatat tgcgaaggcg     1320
gacaagaagt atacccaata caacattccg gcagcttacg caaccatgct gacgaacaag     1380
gatagcatta cccgcgttta ctacggcgac ctgtttacgg atgacggtca gtatatggcc     1440
gagaaatccc cgtactataa cgcaattgac gctctgctgc gtgcgcgcat taagtacgtc     1500
gcgggtggtc aggacatgaa ggtgactaaa ctgaatggtt atgagattat gagcagcgtg     1560
cgttatggta aggtgcaga agaggctaac cagctgggta cggcagaaac ccgcaatcaa     1620
ggtatgctgg ttctgacggc taaccgtccg gacatgaaac tgggtgcaaa cgatcgcctg     1680
gtcgtgaata tgggcgctgc ccacaaaaac caggcctacc gcccgttgct gttgtccaaa     1740
tctactggcc tggcgacgta tctgaaagat agcgacgttc cggcaggcct ggtgcgttat     1800
accgataacc agggtaatct gacctttacg gcggacgata ttgcaggcca tagcacggtt     1860
gaagtgagcg gttacttggc ggtctgggtt ccggtcggcg cgagcgagaa ccaggacgcg     1920
cgcacgaagg ccagctctac caagaagggc gagcaagttt tcgaatctag cgccgctctg     1980
gacagccagg ttatctacga aggtttctcc aatttccaag attttgtcaa gaccccgagc     2040
cagtacacca accgcgtgat cgcgcaaaat gcgaagctgt ttaaagaatg ggcatcact     2100 agctttgagt tcgcgcctca gtatgtttct agccaagacg gcacctttt ggatagcatc     2160 attgaaaacg gctacgcgtt cgaggatcgt tacgatatcg caatgagcaa gaacaataag     2220
tatggcagcc tgaaagattt gatggacgca ctgcgtgcgt tgcatgcgga aggcatcagc     2280
gcaatcgccg attgggtccc ggaccaaatc tataatctgc cgggtaaaga agttgtcacg     2340
gcgagccgta ccaacagcta tggtaccccg cgtccgaatg cggaaatcta caatagcctg     2400
tacgctgcta aaacgcgcac gttcggtaat gacttccagg gtaagtatgg tggcgcattt     2460
ctggacgaac tgaaagcaaa gtaccccggcc atctttgagc gtgttcaaat cagcaacggt     2520
cgtaaattga ccacgaatga gaagattacc cagtggagcg ccaaatactt taatggtagc     2580
aatattcagg gcacgggtgc gcgttacgtt ttgcaggaca acgctaccaa tcagtacttt     2640
agcgttaagg cgggtcagac tttcctgccg aagcagatga ccgaaattac cggcagcggt     2700
ttccgtcgtg tcggtgacga tgtccaatat ctgagcattg gtggttatct ggcgaagaat     2760
acctttatcc aggtcggtgc gaatcagtgg tattattttg acaaaaacgg caatatggtt     2820
acgggtgaac aggtgatcga tggtaaaaag tacttcttct tggataacgg tctgcaactg     2880
cgtcatgttc tgcgccaggg ctccgatggt cacgtctatt actatgaccc taaaggtgtg     2940
caagcgttca atggttccta cgactttgca ggccctcgcc aagacgttcg ttacttcgat     3000
ggcaatggtc agatgtatcg cggcctgcac gatatgtacg gtacgacctt ttacttcgac     3060 gagaaaccg gcatccaagc aaaagacaag ttcattcgct tcgcagacgg tcgtacccgt     3120
tacttcattc cggacaccgg taatctggca gtgaatcgtt tcgcccaaaa cccggagaac     3180
aaagcctggt attacctgga tagcaacggt tacgctgtca ccggcttgca gacgattaat     3240
ggcaagcagt attactttga caacgaaggc cgtcaggtta aaggccactt tgtgaccatt     3300
aacaaccagc gttactttct ggatggtgac tcgggcgaga tcgcgccatc gcgtttcgtt     3360
accgagaaca acaagtggta ctacgtcgac ggtaatggta agctggtcaa gggtgcacag     3420
gtgattaacg gtaaccacta ctacttcaat aacgactata gccaggtgaa gggtgcatgg     3480
gcgaacggtc gttactacga tgcgacagc ggtcaagcgg tcagcaacca gtttattcaa     3540
attgcggcga accaatgggc atatctgaat caagatggcc acaaggtcac gggtctgcaa     3600
```

```
aacatcaaca ataaagtgta ctattttggc tctaatggcg cgcaagttaa gggtaaactg    3660
ctgaccgtgc aaggcaagaa atgctacttt gacgcccaca ccggtgagca agtcgttaat    3720
cgcttcgtgg aagctgcccg tggttgctgg tactatttca attccgctgg ccaggccgtt    3780
accggccaac aagtcatcaa cggtaagcag ttgtattttg atggttctgg tcgtcaagtc    3840
aaaggccgtt atgtgtacgt gggtggtaaa cgtttgttct gtgatgcgaa aacgggcgag    3900
ctgcgtcaac gccgttaa                                                  3918
```

```
<210> SEQ ID NO 32
<211> LENGTH: 1305
<212> TYPE: PRT
<213> ORGANISM: Streptococcus salivarius

<400> SEQUENCE: 32
```

```
Met Ile Asp Gly Lys Gln Tyr Tyr Val Glu Asn Gly Val Val Lys Lys
  1               5                  10                  15

Asn Ala Ala Ile Glu Leu Asp Gly Arg Leu Tyr Tyr Phe Asp Glu Thr
             20                  25                  30

Gly Ala Met Val Asp Gln Ser Lys Pro Leu Tyr Arg Ala Asp Ala Ile
         35                  40                  45

Pro Asn Asn Ser Ile Tyr Ala Val Tyr Asn Gln Ala Tyr Asp Thr Ser
     50                  55                  60

Ser Lys Ser Phe Glu His Leu Asp Asn Phe Leu Thr Ala Asp Ser Trp
 65                  70                  75                  80

Tyr Arg Pro Lys Gln Ile Leu Lys Asp Gly Lys Asn Trp Thr Ala Ser
                 85                  90                  95

Thr Glu Lys Asp Tyr Arg Pro Leu Leu Met Thr Trp Trp Pro Asp Lys
            100                 105                 110

Val Thr Gln Val Asn Tyr Leu Asn Tyr Met Ser Gln Gln Gly Phe Gly
        115                 120                 125

Asn Lys Thr Tyr Thr Thr Asp Met Met Ser Tyr Asp Leu Ala Ala Ala
    130                 135                 140

Ala Glu Thr Val Gln Arg Gly Ile Glu Glu Arg Ile Gly Arg Glu Gly
145                 150                 155                 160

Asn Thr Thr Trp Leu Arg Gln Leu Met Ser Asp Phe Ile Lys Thr Gln
                165                 170                 175

Pro Gly Trp Asn Ser Glu Ser Glu Asp Asn Leu Leu Val Gly Lys Asp
            180                 185                 190

His Leu Gln Gly Gly Ala Leu Thr Phe Leu Asn Asn Ser Ala Thr Ser
        195                 200                 205

His Ala Asn Ser Asp Phe Arg Leu Met Asn Arg Thr Pro Thr Asn Gln
    210                 215                 220

Thr Gly Thr Arg Lys Tyr His Ile Asp Arg Ser Asn Gly Gly Tyr Glu
225                 230                 235                 240

Leu Leu Leu Ala Asn Asp Ile Asp Asn Ser Asn Pro Ala Val Gln Ala
                245                 250                 255

Glu Gln Leu Asn Trp Leu His Tyr Ile Met Asn Ile Gly Ser Ile Leu
            260                 265                 270

Gly Asn Asp Pro Ser Ala Asn Phe Asp Gly Val Arg Ile Asp Ala Val
        275                 280                 285

Asp Asn Val Asp Ala Asp Leu Leu Gln Ile Ala Ser Asp Tyr Phe Lys
    290                 295                 300

Glu Lys Tyr Arg Val Ala Asp Asn Glu Ala Asn Ala Ile Ala His Leu
305                 310                 315                 320
```

```
Ser Ile Leu Glu Ala Trp Ser Tyr Asn Asp His Gln Tyr Asn Lys Asp
            325                 330                 335

Thr Lys Gly Ala Gln Leu Ser Ile Asp Asn Pro Leu Arg Glu Thr Leu
        340                 345                 350

Leu Thr Thr Phe Leu Arg Lys Ser Asn Tyr Arg Gly Ser Leu Glu Arg
            355                 360                 365

Val Ile Thr Asn Ser Leu Asn Asn Arg Ser Ser Glu Gln Lys His Thr
    370                 375                 380

Pro Arg Asp Ala Asn Tyr Ile Phe Val Arg Ala His Asp Ser Glu Val
385                 390                 395                 400

Gln Asp Val Leu Ala Asn Ile Ile Ser Lys Gln Ile Asn Pro Lys Thr
                405                 410                 415

Asp Gly Phe Thr Phe Thr Met Asp Glu Leu Lys Gln Ala Phe Glu Ile
            420                 425                 430

Tyr Asn Ala Asp Ile Ala Lys Ala Asp Lys Lys Tyr Thr Gln Tyr Asn
        435                 440                 445

Ile Pro Ala Ala Tyr Ala Thr Met Leu Thr Asn Lys Asp Ser Ile Thr
    450                 455                 460

Arg Val Tyr Tyr Gly Asp Leu Phe Thr Asp Asp Gly Gln Tyr Met Ala
465                 470                 475                 480

Glu Lys Ser Pro Tyr Tyr Asn Ala Ile Asp Ala Leu Leu Arg Ala Arg
                485                 490                 495

Ile Lys Tyr Val Ala Gly Gly Gln Asp Met Lys Val Thr Lys Leu Asn
            500                 505                 510

Gly Tyr Glu Ile Met Ser Ser Val Arg Tyr Gly Lys Gly Ala Glu Glu
        515                 520                 525

Ala Asn Gln Leu Gly Thr Ala Glu Thr Arg Asn Gln Gly Met Leu Val
    530                 535                 540

Leu Thr Ala Asn Arg Pro Asp Met Lys Leu Gly Ala Asn Asp Arg Leu
545                 550                 555                 560

Val Val Asn Met Gly Ala Ala His Lys Asn Gln Ala Tyr Arg Pro Leu
                565                 570                 575

Leu Leu Ser Lys Ser Thr Gly Leu Ala Thr Tyr Leu Lys Asp Ser Asp
            580                 585                 590

Val Pro Ala Gly Leu Val Arg Tyr Thr Asp Asn Gln Gly Asn Leu Thr
        595                 600                 605

Phe Thr Ala Asp Asp Ile Ala Gly His Ser Thr Val Glu Val Ser Gly
    610                 615                 620

Tyr Leu Ala Val Trp Val Pro Val Gly Ala Ser Glu Asn Gln Asp Ala
625                 630                 635                 640

Arg Thr Lys Ala Ser Ser Thr Lys Lys Gly Glu Gln Val Phe Glu Ser
                645                 650                 655

Ser Ala Ala Leu Asp Ser Gln Val Ile Tyr Glu Gly Phe Ser Asn Phe
            660                 665                 670

Gln Asp Phe Val Lys Thr Pro Ser Gln Tyr Thr Asn Arg Val Ile Ala
        675                 680                 685

Gln Asn Ala Lys Leu Phe Lys Glu Trp Gly Ile Thr Ser Phe Glu Phe
    690                 695                 700

Ala Pro Gln Tyr Val Ser Ser Gln Asp Gly Thr Phe Leu Asp Ser Ile
705                 710                 715                 720

Ile Glu Asn Gly Tyr Ala Phe Glu Asp Arg Tyr Asp Ile Ala Met Ser
                725                 730                 735
```

-continued

```
Lys Asn Asn Lys Tyr Gly Ser Leu Lys Asp Leu Met Asp Ala Leu Arg
                740                 745                 750

Ala Leu His Ala Glu Gly Ile Ser Ala Ile Ala Asp Trp Val Pro Asp
                755                 760                 765

Gln Ile Tyr Asn Leu Pro Gly Lys Glu Val Val Thr Ala Ser Arg Thr
            770                 775                 780

Asn Ser Tyr Gly Thr Pro Arg Pro Asn Ala Glu Ile Tyr Asn Ser Leu
785                 790                 795                 800

Tyr Ala Ala Lys Thr Arg Thr Phe Gly Asn Asp Phe Gln Gly Lys Tyr
                805                 810                 815

Gly Gly Ala Phe Leu Asp Glu Leu Lys Ala Lys Tyr Pro Ala Ile Phe
            820                 825                 830

Glu Arg Val Gln Ile Ser Asn Gly Arg Lys Leu Thr Thr Asn Glu Lys
            835                 840                 845

Ile Thr Gln Trp Ser Ala Lys Tyr Phe Asn Gly Ser Asn Ile Gln Gly
        850                 855                 860

Thr Gly Ala Arg Tyr Val Leu Gln Asp Asn Ala Thr Asn Gln Tyr Phe
865                 870                 875                 880

Ser Val Lys Ala Gly Gln Thr Phe Leu Pro Lys Gln Met Thr Glu Ile
                885                 890                 895

Thr Gly Ser Gly Phe Arg Arg Val Gly Asp Asp Val Gln Tyr Leu Ser
            900                 905                 910

Ile Gly Gly Tyr Leu Ala Lys Asn Thr Phe Ile Gln Val Gly Ala Asn
        915                 920                 925

Gln Trp Tyr Tyr Phe Asp Lys Asn Gly Asn Met Val Thr Gly Glu Gln
    930                 935                 940

Val Ile Asp Gly Lys Lys Tyr Phe Phe Leu Asp Asn Gly Leu Gln Leu
945                 950                 955                 960

Arg His Val Leu Arg Gln Gly Ser Asp Gly His Val Tyr Tyr Tyr Asp
            965                 970                 975

Pro Lys Gly Val Gln Ala Phe Asn Gly Phe Tyr Asp Phe Ala Gly Pro
        980                 985                 990

Arg Gln Asp Val Arg Tyr Phe Asp  Gly Asn Gly Gln Met  Tyr Arg Gly
    995                 1000                1005

Leu His  Asp Met Tyr Gly Thr  Thr Phe Tyr Phe Asp  Glu Lys Thr
    1010                1015                1020

Gly Ile  Gln Ala Lys Asp Lys  Phe Ile Arg Phe Ala  Asp Gly Arg
    1025                1030                1035

Thr Arg  Tyr Phe Ile Pro Asp  Thr Gly Asn Leu Ala  Val Asn Arg
    1040                1045                1050

Phe Ala  Gln Asn Pro Glu Asn  Lys Ala Trp Tyr Tyr  Leu Asp Ser
    1055                1060                1065

Asn Gly  Tyr Ala Val Thr Gly  Leu Gln Thr Ile Asn  Gly Lys Gln
    1070                1075                1080

Tyr Tyr  Phe Asp Asn Glu Gly  Arg Gln Val Lys Gly  His Phe Val
    1085                1090                1095

Thr Ile  Asn Asn Gln Arg Tyr  Phe Leu Asp Gly Asp  Ser Gly Glu
    1100                1105                1110

Ile Ala  Pro Ser Arg Phe Val  Thr Glu Asn Asn Lys  Trp Tyr Tyr
    1115                1120                1125

Val Asp  Gly Asn Gly Lys Leu  Val Lys Gly Ala Gln  Val Ile Asn
    1130                1135                1140

Gly Asn  His Tyr Tyr Phe Asn  Asn Asp Tyr Ser Gln  Val Lys Gly
```

```
              1145                1150                1155
Ala Trp Ala Asn Gly Arg Tyr  Tyr Asp Gly Asp Ser  Gly Gln Ala
            1160                1165                1170

Val Ser Asn Gln Phe Ile Gln  Ile Ala Ala Asn Gln  Trp Ala Tyr
            1175                1180                1185

Leu Asn Gln Asp Gly His Lys  Val Thr Gly Leu Gln  Asn Ile Asn
            1190                1195                1200

Asn Lys Val Tyr Tyr Phe Gly  Ser Asn Gly Ala Gln  Val Lys Gly
            1205                1210                1215

Lys Leu Leu Thr Val Gln Gly  Lys Lys Cys Tyr Phe  Asp Ala His
            1220                1225                1230

Thr Gly Glu Gln Val Val Asn  Arg Phe Val Glu Ala  Ala Arg Gly
            1235                1240                1245

Cys Trp Tyr Tyr Phe Asn Ser  Ala Gly Gln Ala Val  Thr Gly Gln
            1250                1255                1260

Gln Val Ile Asn Gly Lys Gln  Leu Tyr Phe Asp Gly  Ser Gly Arg
            1265                1270                1275

Gln Val Lys Gly Arg Tyr Val  Tyr Val Gly Gly Lys  Arg Leu Phe
            1280                1285                1290

Cys Asp Ala Lys Thr Gly Glu  Leu Arg Gln Arg Arg
            1295                1300                1305

<210> SEQ ID NO 33
<211> LENGTH: 4026
<212> TYPE: DNA
<213> ORGANISM: Streptococcus salivarius

<400> SEQUENCE: 33
atgatcgacg gcaaatacta ctatgtaaac gaggacggca gccacaaaga gaatttcgcg      60
attacggtaa acggtcagct gctgtacttt ggtaaggacg gtgctctgac gagcagctcc     120
acgtacagct ttaccccggg tacgaccaat attgtcgatg gcttcagcat taacaaccgt     180
gcgtatgaca gcagcgaggc atcctttgag ctgatcgatg ttatttgac cgcggatagc      240 tggtatcgtc cggcgagcat cattaaggac ggcgttacgt ggcaggcctc gaccgcagaa     300
gattttcgtc cgctgctgat ggcttggtgg ccgaatgttg acacccaggt gaattatctg     360
aattacatgt ccaaggtttt caacctggat gcaaagtaca ccagcaccga caagcaggaa     420
accctgaacg tggctgcgaa agatatccaa gtcaagattg agcaaaagat tcaggcagag     480
aaatctaccc agtggctgcg tgaaactgat tagcgcgtttg ttaaaactca gccgcaatgg    540
aataaagaaa cggaaaacta ttccaagggt ggtggcgagg accatctgca aggcggtgcc    600
ctgttgtacg ttaacgattc gcgcaccccg tgggcgaact cgaactatcg cttgctgaac    660
cataccgcta ccaatcaaaa aggcactatt gacaaatctg tcctggacga gcagagcgac    720
ccgaaccaca tggcggtttt cgattttctg ctggcgaacg acgtcgacct gagcaacccg    780
gtggtgcagg ccgaacaact gaccagatt cactacctga tgaattgggg tagcatcgtg     840
atgggtgata agatgcgaa ctttgacggc attcgtgtcg atgcggtcga taacgtggac     900
gccgacatgt tgcagctgta cacgaactac tttcgtgagt actacggcgt taacaagagc    960
gaagcaaatg ccctggcgca tatcagcgtt ctggaagcgt ggagcctgaa tgacaatcac   1020
tataacgata agacggacgg tgcggccctg gcaatggaga ataaacaacg tctggcgctg   1080
ctgttcagcc tggcgaaacc gatcaaagag cgtacgccgg ctgtgagccc actgtataac   1140
aacacccttc aatactacgc agcgtgacga aaaacggact ggattaacaa agacggtagc   1200
```

```
aaagcgtata acgaggatgg taccgtcaag caatcgacca ttggtaagta caatgagaag    1260
tatggcgacg caagcggtaa ttacgtgttc attcgtgccc acgacaacaa tgttcaagac    1320
atcatcgccg aaatcatcaa gaaagagatc aaccctaaga gcgacggttt caccatcacc    1380
gacgcagaga tgaagaaggc ctttgaaatc tacaacaagg acatgttgag cagcgataag    1440
aagtatactc tgaacaacat tccggctgcg tacgcggtga tgttgcagaa tatggaaacc    1500
atcacgcgtg tttactatgg tgatctgtat accgataatg caactacat ggaaacgaaa     1560 agcccgtact atgacaccat tgttaatctg atgaagaatc gcatcaagta tgtgtctggc    1620
ggtcaagcgc agcgttctta ctggctgccg accgatggta agatggacaa tagcgatgtg    1680
gaactgtacc gcaccaacga ggtatacgct tctgtgcgct atggtaaaga cattatgacc    1740
gccgatgata ccgagggttc caagtactcc cgtacgagcg ccaagttac cttggtggca     1800 aacaacccga aattgaccct ggaccaaagc gcgaaactga agtggagat gggtaagatc     1860 cacgcaaatc aaaagtaccg tgcactgatt gtcggtaccg ccgacggtat caagaatttc    1920
accagcgatg cggatgcgat tgcagcaggc tatgttaaag agactgatag caatggtgtg    1980
ctgacgtttg gtgcgaacga cattaaaggc tatgaaacgt ttgacatgag cggtttcgtt    2040
gcggtgtggg tgcctgtggg tgctagcgat gatcaggata tccgtgtcgc gccgagcacc    2100
gaggcaaaga aagaaggtga gctgacgttg aaagcgaccg aggcctatga cagccagttg    2160
atttacgaag gtttcagcaa tttccaaacc attccagacg gttccgatcc gagcgtctac    2220
accaatcgca aaatcgcgga aaacgttgat ctgttcaaaa gctggggtgt gaccagcttc    2280
gaaatggcac cgcaattcgt tagcgcggac gatggtacgt tcttggacag cgttatccaa    2340
aatggctatg cgttcgccga tcgttatgac ttggcgatga gcaaaaacaa caaatacggc    2400
agcaaagagg atctgcgcga cgccctgaaa gcgctgcata aagcgggtat tcaagccatc    2460
gctgactggg ttccggacca gatctaccag ctgccgggta agaagtcgt taccgcgacc     2520 cgcaccgatg gcgctggccg taagatcgcg gatgcaatta tcgatcatag cttgtatgtg    2580
gccaatacta aaagctccgg taaggattac caggcgaaat atggtggtga atttctggct    2640
gagctgaagg ccaaataccc ggagatgttc aaggtcaaca tgattagcac cggcaaacct    2700
attgatgact ctgtcaaatt gaaacaatgg aaggcagagt atttcaatgg cactaacgtc    2760
ctggaacgtg tgttggtta cgtgctgagc gacgaggcga ccgtaaata cttcaccgtt     2820 acgaaggacg gcaatttcat cccgctgcaa ctgaccggta tgagaaggt tgtgacgggt    2880 ttttctaatg acgtaagggg cattacctac ttcggtacct cgggtaccca ggcaaagagc    2940
gcattcgtga cgtttaacgg taacacctac tactttgatg cacgcggcca catggtgacg    3000 aacgcgagt acagcccgaa cggcaaggat gtttatcgct tcctgccgaa tggcatcatg     3060
ctgtccaatg cgttttacgt cgatgcaaat ggtaatactt acctgtacaa cagcaagggt    3120
cagatgtata agggcggtta taccaagttc gacgttactg aaacggacaa ggacggtaaa    3180
gagagcaaag tagtgaagtt tcgttatttc acgaacgaag gcgtcatggc gaaaggtgtc    3240
accgttattg atggctttac ccagtatttc ggtgaagatg gcttcaagc gaaggacaag     3300 ctggtgacct ttaagggcaa aacctactat tttgacgcgc acacgggcaa cgccatcaag    3360
aacacctggc gtaatatcga cggtaagtgg tatcattttg atgcgaacgg tgtggcggcg    3420
accggcgcac aggtcattaa tggtcaaaaa ctgtactta atgaggacgg tagccaagtc     3480
aaaggtggcg tcgtcaagaa tgcagatggc acctatagca aatacaaaga gggctccggt    3540
```

-continued

```
gagctggtta ccaacgagtt ctttaccacg gatggtaacg tctggtacta tgctggtgcg    3600
aatggcaaga ccgttaccgg tgcacaggtt atcaacggcc agcacctgta cttcaatgcg    3660
gatggctctc aagtgaaggg cggtgtcgtc aaaaacgcgg acggtacgta ctccaaatac    3720
gatgccgcga ccggtgaacg tctgaccaat gagtttttca cgactggtga caacaattgg    3780
tactacatcg gcgccaacgg taagacggtt acgggcgaag tgaaaattgg cgacgatacg    3840
tactacttcg caaagatgg taaacaggtg aaaggtcaga cggtttccgc tggtaatggc     3900
cgcatcagct actattacgg tgactctggt aaacgtgcgg ttagcacgtg ggttgaaatt    3960
caaccgggcg tgtatgtcta ttttgataag aatggcctgg catatccacc gcgcgttttg    4020
aattaa                                                                4026
```

<210> SEQ ID NO 34
<211> LENGTH: 1341
<212> TYPE: PRT
<213> ORGANISM: Streptococcus salivarius

<400> SEQUENCE: 34

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Glu Thr Leu Asn Val
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn His Thr Ala Thr
    210                 215                 220

Asn Gln Lys Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285
```

-continued

```
Asp Gly Ile Arg Val Asp Ala Val Asp Asn Val Asp Ala Asp Met Leu
        290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
                340                 345                 350
Glu Asn Lys Gln Arg Leu Ala Leu Leu Phe Ser Leu Ala Lys Pro Ile
                355                 360                 365
Lys Glu Arg Thr Pro Ala Val Ser Pro Leu Tyr Asn Asn Thr Phe Asn
        370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                405                 410                 415
Tyr Asn Glu Lys Tyr Gly Asp Ala Ser Gly Asn Tyr Val Phe Ile Arg
                420                 425                 430
Ala His Asp Asn Asn Val Gln Asp Ile Ile Ala Glu Ile Ile Lys Lys
                435                 440                 445
Glu Ile Asn Pro Lys Ser Asp Gly Phe Thr Ile Thr Asp Ala Glu Met
        450                 455                 460
Lys Lys Ala Phe Glu Ile Tyr Asn Lys Asp Met Leu Ser Ser Asp Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
                500                 505                 510
Asn Gly Asn Tyr Met Glu Thr Lys Ser Pro Tyr Tyr Asp Thr Ile Val
                515                 520                 525
Asn Leu Met Lys Asn Arg Ile Lys Tyr Val Ser Gly Gly Gln Ala Gln
        530                 535                 540
Arg Ser Tyr Trp Leu Pro Thr Asp Gly Lys Met Asp Asn Ser Asp Val
545                 550                 555                 560
Glu Leu Tyr Arg Thr Asn Glu Val Tyr Ala Ser Val Arg Tyr Gly Lys
                565                 570                 575
Asp Ile Met Thr Ala Asp Asp Thr Glu Gly Ser Lys Tyr Ser Arg Thr
                580                 585                 590
Ser Gly Gln Val Thr Leu Val Ala Asn Asn Pro Lys Leu Thr Leu Asp
                595                 600                 605
Gln Ser Ala Lys Leu Lys Val Glu Met Gly Lys Ile His Ala Asn Gln
        610                 615                 620
Lys Tyr Arg Ala Leu Ile Val Gly Thr Ala Asp Gly Ile Lys Asn Phe
625                 630                 635                 640
Thr Ser Asp Ala Asp Ala Ile Ala Ala Gly Tyr Val Lys Glu Thr Asp
                645                 650                 655
Ser Asn Gly Val Leu Thr Phe Gly Ala Asn Asp Ile Lys Gly Tyr Glu
                660                 665                 670
Thr Phe Asp Met Ser Gly Phe Val Ala Val Trp Val Pro Val Gly Ala
                675                 680                 685
Ser Asp Asp Gln Asp Ile Arg Val Ala Pro Ser Thr Glu Ala Lys Lys
        690                 695                 700
```

-continued

```
Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
                755                 760                 765

Ala Asp Asp Gly Thr Phe Leu Asp Ser Val Ile Gln Asn Gly Tyr Ala
                770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
                820                 825                 830

Gly Lys Glu Val Val Thr Ala Thr Arg Thr Asp Gly Ala Gly Arg Lys
                835                 840                 845

Ile Ala Asp Ala Ile Ile Asp His Ser Leu Tyr Val Ala Asn Thr Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
                900                 905                 910

Glu Tyr Phe Asn Gly Thr Asn Val Leu Glu Arg Gly Val Gly Tyr Val
                915                 920                 925

Leu Ser Asp Glu Ala Thr Gly Lys Tyr Phe Thr Val Thr Lys Asp Gly
930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
                980                 985                 990

Asp Ala Arg Gly His Met Val Thr Asn Gly Glu Tyr Ser Pro Asn Gly
                995                 1000                1005

Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Ser
    1025                1030                1035

Lys Gly Gln Met Tyr Lys Gly Gly Tyr Thr Lys Phe Asp Val Thr
    1040                1045                1050

Glu Thr Asp Lys Asp Gly Lys Glu Ser Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Ala Ile Lys Asn Thr Trp Arg Asn Ile Asp Gly
```

|  | 1115 |  |  |  | 1120 |  |  |  | 1125 |  |  |
|---|---|---|---|---|---|---|---|---|---|---|---|

Lys Trp Tyr His Phe Asp Ala Asn Gly Val Ala Ala Thr Gly Ala
    1130                        1135                      1140

Gln Val Ile Asn Gly Gln Lys Leu Tyr Phe Asn Glu Asp Gly Ser
    1145                      1150                        1155

Gln Val Lys Gly Gly Val Val Lys Asn Ala Asp Gly Thr Tyr Ser
    1160                      1165                        1170

Lys Tyr Lys Glu Gly Ser Gly Glu Leu Val Thr Asn Glu Phe Phe
    1175                      1180                        1185

Thr Thr Asp Gly Asn Val Trp Tyr Tyr Ala Gly Ala Asn Gly Lys
    1190                      1195                        1200

Thr Val Thr Gly Ala Gln Val Ile Asn Gly Gln His Leu Tyr Phe
    1205                      1210                        1215

Asn Ala Asp Gly Ser Gln Val Lys Gly Gly Val Val Lys Asn Ala
    1220                      1225                        1230

Asp Gly Thr Tyr Ser Lys Tyr Asp Ala Ala Thr Gly Glu Arg Leu
    1235                      1240                        1245

Thr Asn Glu Phe Phe Thr Thr Gly Asp Asn Asn Trp Tyr Tyr Ile
    1250                      1255                        1260

Gly Ala Asn Gly Lys Thr Val Thr Gly Glu Val Lys Ile Gly Asp
    1265                      1270                        1275

Asp Thr Tyr Tyr Phe Ala Lys Asp Gly Lys Gln Val Lys Gly Gln
    1280                      1285                        1290

Thr Val Ser Ala Gly Asn Gly Arg Ile Ser Tyr Tyr Gly Asp
    1295                      1300                        1305

Ser Gly Lys Arg Ala Val Ser Thr Trp Val Glu Ile Gln Pro Gly
    1310                      1315                        1320

Val Tyr Val Tyr Phe Asp Lys Asn Gly Leu Ala Tyr Pro Pro Arg
    1325                      1330                        1335

Val Leu Asn
    1340

```
<210> SEQ ID NO 35
<211> LENGTH: 3996
<212> TYPE: DNA
<213> ORGANISM: Streptococcus salivarius

<400> SEQUENCE: 35
atggtcgacg gcaaatacta ctacgtgaaa gaggatggca gctacaaaac gaacttcgca      60
gtttccgtca acggccaact gctgtatttc ggcaaggatg gcgcgctgac gtccaccagc     120
acccatagct ttacgccagg cactaccaat ctggttgatg cgttcagctc ccataaccgc     180
gcctacgact ccaaaaagga gagcttcgaa ctggtggatg ttatctgac gccgaactct      240 tggtatcgtc cggtcactat cctggaaaat ggtgaaaaat ggcgtgttag caccgagaag     300
gactttcgcc cgttgttgat ggcctggtgg ccggatgtcg acacgcaagt tgcctatctg     360
aacacctttt ctaaacactt caacctgaac gcgacgtact ctacttctca gagccaaagc     420
gagctgaatg cggcagctaa aaccatccaa atcaaaatcg aacaggagat tagcgcgaaa     480
aagagcacgg agtggctgcg ccaggcaatt gagtcctttg tcaaggagca ggatcagtgg     540
aacaccacga ccgagaacta caccctggcg gatcatttgc agggcggtgc gctgctgtat     600
gtgaacaatg acaagacgcc gtgggcgaac agcgactatc gtctgctgaa ccgtactccg     660
agcaaccagg acggcagcct gaacggtact ggccgttatc tgggtggtta cgagtttctg     720
```

```
ctggcgaatg acgtggacaa tagcaatccg gtggtccagg ctgagcagct gaatcaaatt    780
cactatctgg tcaactgggg cagcattgtc atgggtgaca aggacgcgaa tttcgacggc    840
attcgtgttg acgccgttga caatgtggac gccgatctgt tgcaggttta cacgaactac    900
ttccgtgcgg cgtttggtgt ggataaaagc gaagcgaacg cactggccca catcagcatt    960
ctggaggcgt gggatctgaa cgacaatgcg tacaaccaga acatgacgg tgcggccttg     1020
gcaatggata caaccctgcg ttacgcgatc atgggtgcac tgtatggtag cggtagctcg    1080
ctgaaagatc tgattaccag cagcctgacc gaccgtacga ataactccaa atatggtgat    1140
acccaagcaa actacatctt cgcccgtgct catgataatc tggtccagga cattattcgt    1200
gacatcgtgc agaaagagat caatccgaag agcgacggct acacgatgac cgatgcggag    1260
ctgaagcgtg cgtttgaaat ctacaacgag gatatgaaaa aggccgaaaa acgctacact    1320
atcaacaaca tcccggcagc gtatgcactg attttgcaga acatggaaca ggttactcgt    1380
gtgtactacg tgatctgta taccgacaat ggtcagtaca tggcgaccaa aagcccgtac    1440
tacgacgcga ttacgaccct gctgaaaaat cgtatgaagt atgtgagcgg cggtcagagc    1500
atgaaagttg acactttcaa cggtaaagaa attctgtcgt ctgttcgtta cggtaaggac    1560
atcatgaccg cggaccaaac gaccggtgtc gcagaaacca gcaagcacag cggcatgctg    1620
accctgatcg ccaataacca ggattttttct ctgggcgatg gcaccttgaa agtgaacatg    1680
ggcaagctgc acgcgaacca ggcgtatcgc ccgctgctgc tgggcacgga taagggcatc    1740
gttacctatg aaaatgacgc ggctgcggca ggcaaaatca gtacacgga cgcagagggt    1800
aatctgacct tcagcggtga cgagatcaag ggctatcgca ccgtggacat gcgcggctac    1860
ctgggtgtgt gggtcccggt cggcgcaccg gacaatcaag acattcgcgt taagggtagc    1920
gataagaaac tggacaagac tttcagcgca accgaagctc tggatagcca ggtgatttac    1980
gaaggtttta gcaactttca ggacttcgtg gaaaaagaca gccagtacac caacaagctg    2040
attgcggaaa acgcggaact gtttaagagc tgggggtatta ctagctttga aatggcccct    2100
cagtttgtca gcgcagacga tcgtaccttc ctggatagcg ttatccaaaa cggttatgcg    2160
tttaccgatc gttacgatct ggccatgtct aagaataaca agtatggcag caaagaagat    2220
ctgcgtgatg cgctgaaggc gctgcacaag cagggcattc aagcaattgc cgactgggtt    2280
ccggatcaac tgtaccaact gccgggtcaa gaggttgtca ccgctacccg tgcaaatagc    2340
tacggcaccc cgaaggccaa tgcctacatt aacaatacgc tgtatgttgc caatagcaag    2400
agcagcggta aagacttcca ggctcaatac ggtggcgagt tcctggatga attgcagaag    2460
aagtacccgc agttgttcga ggatgtgatg atcagcacgg gtaaaaagat tgacccgagc    2520
gtgaaaatca gcagtggag cgccaaatac atgaatggca ccaacattct gggtcgtggc    2580
aaccgttacg ttctgtcgaa tgacgccacc ggtcgctatt atcaagtgac cgacaacggc    2640
attttcttgc cgaagccgct gacggatcag ggtggtaaga ccggcttcta ttacgatggt    2700
aagggcatgg cctatttcga caattccggc tttcaagcga aaaatgcgtt catcaagtac    2760
gcgggtaact actactactt cgataaagag ggctatatgc tgacgggccg tcaagatatt    2820
gacagcaaga cgtatttctt tctgccgaat ggtatccaac tgcgtgatag catttaccaa    2880
caagatggca agtactacta ttttggtagc ttcggcgaac aatacaaaga cggttatttc    2940
gtctttgacg tgccaaaaga gggcaccagc gaaaccgagg ctaagttccg ctactttttct   3000
ccgacgggtg agatggcagt gggttttgacc tatgcgggtg gtggtctgca atactttgat    3060
gagaacggtt tccaggcgaa gggtacgaag tatgttacgc cggatggtaa gttgtatttc    3120
```

```
ttcgacaaga atagcggcaa cgcgtacacc aatcgttggg cggagatcga tggtatttgg    3180
tacgagttta atgaccaagg ttacgcgcag gcgaagaaag gtgagtttta caccacggat    3240
ggtagcacgt ggttttaccg cgacgcagca ggtaaaaacg ttaccggtgc cctgaccctg    3300
gacggtcacg agtattactt tcgtgcgaac ggtgcgcagg tgaaaggcga gttcgtcacc    3360
gaaaacggta agattagcta ttacaccgtt gataacggtt acaaggtaaa agacaagttc    3420
ttcgaagtca atggtaagtg gtatcacgct gataaggacg gtaatttggc gacgggtcgt    3480
cagaccatcg accatctgaa ttactacttc aacgcggacg gctcccaggt taagtccgat    3540
ttcttcactc tggatggtgg taaaacctgg tattatgcca agacaacgg tgagattgtg     3600 accggtgcgt actcggtgcg tggcaagaac tattacttca agaggacgg tagccaagtt     3660 aagggcgatt cgtcaaaaa tgcggacggt tccctgagct attatgacaa ggatagcggc     3720
gaacgtctga acaaccgttt cttgaccacg gtaacaatg tctggtatta ctttaaggat     3780
ggtaaagcgg tcacgggtcg ccagaacatc gacggtaagg agtactactt tgatcacctg     3840
ggtcgtcaag tcaaaggctc cccgattagc actccgaagg gcgttgagta ttatgagtct     3900
gtgctgggtg agcgtgtcac caacacctgg atcaccttcc aagacggcaa aaccgtgttc     3960
tttgatgaaa atggctacgc ggactttgat aagtaa                              3996
```

<210> SEQ ID NO 36
<211> LENGTH: 1331
<212> TYPE: PRT
<213> ORGANISM: Streptococcus salivarius

<400> SEQUENCE: 36

```
Met Val Asp Gly Lys Tyr Tyr Val Lys Glu Asp Gly Ser Tyr Lys
1               5                   10                  15

Thr Asn Phe Ala Val Ser Val Asn Gly Gln Leu Leu Tyr Phe Gly Lys
                20                  25                  30

Asp Gly Ala Leu Thr Ser Thr Ser Thr His Ser Phe Thr Pro Gly Thr
            35                  40                  45

Thr Asn Leu Val Asp Ala Phe Ser Ser His Asn Arg Ala Tyr Asp Ser
        50                  55                  60

Lys Lys Glu Ser Phe Glu Leu Val Asp Gly Tyr Leu Thr Pro Asn Ser
65                  70                  75                  80

Trp Tyr Arg Pro Val Thr Ile Leu Glu Asn Gly Glu Lys Trp Arg Val
                85                  90                  95

Ser Thr Glu Lys Asp Phe Arg Pro Leu Leu Met Ala Trp Trp Pro Asp
                100                 105                 110

Val Asp Thr Gln Val Ala Tyr Leu Asn Thr Phe Ser Lys His Phe Asn
            115                 120                 125

Leu Asn Ala Thr Tyr Ser Thr Ser Gln Ser Gln Ser Glu Leu Asn Ala
        130                 135                 140

Ala Ala Lys Thr Ile Gln Ile Lys Ile Glu Gln Glu Ile Ser Ala Lys
145                 150                 155                 160

Lys Ser Thr Glu Trp Leu Arg Gln Ala Ile Glu Ser Phe Val Lys Glu
                165                 170                 175

Gln Asp Gln Trp Asn Thr Thr Thr Glu Asn Tyr Thr Leu Ala Asp His
                180                 185                 190

Leu Gln Gly Gly Ala Leu Leu Tyr Val Asn Asn Asp Lys Thr Pro Trp
            195                 200                 205

Ala Asn Ser Asp Tyr Arg Leu Leu Asn Arg Thr Pro Ser Asn Gln Asp
```

-continued

```
            210             215             220
Gly Ser Leu Asn Gly Thr Gly Arg Tyr Leu Gly Gly Tyr Glu Phe Leu
225                 230                 235                 240
Leu Ala Asn Asp Val Asp Asn Ser Asn Pro Val Val Gln Ala Glu Gln
                245                 250                 255
Leu Asn Gln Ile His Tyr Leu Val Asn Trp Gly Ser Ile Val Met Gly
            260                 265                 270
Asp Lys Asp Ala Asn Phe Asp Gly Ile Arg Val Asp Ala Val Asp Asn
        275                 280                 285
Val Asp Ala Asp Leu Leu Gln Val Tyr Thr Asn Tyr Phe Arg Ala Ala
    290                 295                 300
Phe Gly Val Asp Lys Ser Glu Ala Asn Ala Leu Ala His Ile Ser Ile
305                 310                 315                 320
Leu Glu Ala Trp Asp Leu Asn Asp Asn Ala Tyr Asn Gln Lys His Asp
                325                 330                 335
Gly Ala Ala Leu Ala Met Asp Asn Asn Leu Arg Tyr Ala Ile Met Gly
            340                 345                 350
Ala Leu Tyr Gly Ser Gly Ser Ser Leu Lys Asp Leu Ile Thr Ser Ser
        355                 360                 365
Leu Thr Asp Arg Thr Asn Asn Ser Lys Tyr Gly Asp Thr Gln Ala Asn
    370                 375                 380
Tyr Ile Phe Ala Arg Ala His Asp Asn Leu Val Gln Asp Ile Ile Arg
385                 390                 395                 400
Asp Ile Val Gln Lys Glu Ile Asn Pro Lys Ser Asp Gly Tyr Thr Met
                405                 410                 415
Thr Asp Ala Glu Leu Lys Arg Ala Phe Glu Ile Tyr Asn Glu Asp Met
            420                 425                 430
Lys Lys Ala Glu Lys Arg Tyr Thr Ile Asn Asn Ile Pro Ala Ala Tyr
        435                 440                 445
Ala Leu Ile Leu Gln Asn Met Glu Gln Val Thr Arg Val Tyr Tyr Gly
    450                 455                 460
Asp Leu Tyr Thr Asp Asn Gly Gln Tyr Met Ala Thr Lys Ser Pro Tyr
465                 470                 475                 480
Tyr Asp Ala Ile Thr Thr Leu Leu Lys Asn Arg Met Lys Tyr Val Ser
                485                 490                 495
Gly Gly Gln Ser Met Lys Val Asp Thr Phe Asn Gly Lys Glu Ile Leu
            500                 505                 510
Ser Ser Val Arg Tyr Gly Lys Asp Ile Met Thr Ala Asp Gln Thr Thr
        515                 520                 525
Gly Val Ala Glu Thr Ser Lys His Ser Gly Met Leu Thr Leu Ile Ala
    530                 535                 540
Asn Asn Gln Asp Phe Ser Leu Gly Asp Gly Thr Leu Lys Val Asn Met
545                 550                 555                 560
Gly Lys Leu His Ala Asn Gln Ala Tyr Arg Pro Leu Leu Gly Thr
                565                 570                 575
Asp Lys Gly Ile Val Thr Tyr Glu Asn Asp Ala Ala Ala Gly Lys
            580                 585                 590
Ile Lys Tyr Thr Asp Ala Glu Gly Asn Leu Thr Phe Ser Gly Asp Glu
        595                 600                 605
Ile Lys Gly Tyr Arg Thr Val Asp Met Arg Gly Tyr Leu Gly Val Trp
    610                 615                 620
Val Pro Val Gly Ala Pro Asp Asn Gln Asp Ile Arg Val Lys Gly Ser
625                 630                 635                 640
```

-continued

```
Asp Lys Lys Leu Asp Lys Thr Phe Ser Ala Thr Glu Ala Leu Asp Ser
            645                 650                 655
Gln Val Ile Tyr Glu Gly Phe Ser Asn Phe Gln Asp Phe Val Glu Lys
                660                 665                 670
Asp Ser Gln Tyr Thr Asn Lys Leu Ile Ala Glu Asn Ala Glu Leu Phe
            675                 680                 685
Lys Ser Trp Gly Ile Thr Ser Phe Glu Met Ala Pro Gln Phe Val Ser
        690                 695                 700
Ala Asp Asp Arg Thr Phe Leu Asp Ser Val Ile Gln Asn Gly Tyr Ala
705                 710                 715                 720
Phe Thr Asp Arg Tyr Asp Leu Ala Met Ser Lys Asn Asn Lys Tyr Gly
                725                 730                 735
Ser Lys Glu Asp Leu Arg Asp Ala Leu Lys Ala Leu His Lys Gln Gly
                740                 745                 750
Ile Gln Ala Ile Ala Asp Trp Val Pro Asp Gln Leu Tyr Gln Leu Pro
            755                 760                 765
Gly Gln Glu Val Val Thr Ala Thr Arg Ala Asn Ser Tyr Gly Thr Pro
770                 775                 780
Lys Ala Asn Ala Tyr Ile Asn Asn Thr Leu Tyr Val Ala Asn Ser Lys
785                 790                 795                 800
Ser Ser Gly Lys Asp Phe Gln Ala Gln Tyr Gly Gly Glu Phe Leu Asp
                805                 810                 815
Glu Leu Gln Lys Lys Tyr Pro Gln Leu Phe Glu Asp Val Met Ile Ser
                820                 825                 830
Thr Gly Lys Lys Ile Asp Pro Ser Val Lys Ile Lys Gln Trp Ser Ala
            835                 840                 845
Lys Tyr Met Asn Gly Thr Asn Ile Leu Gly Arg Gly Asn Arg Tyr Val
        850                 855                 860
Leu Ser Asn Asp Ala Thr Gly Arg Tyr Gln Val Thr Asp Asn Gly
865                 870                 875                 880
Ile Phe Leu Pro Lys Pro Leu Thr Asp Gln Gly Lys Thr Gly Phe
                885                 890                 895
Tyr Tyr Asp Gly Lys Gly Met Ala Tyr Phe Asp Asn Ser Gly Phe Gln
            900                 905                 910
Ala Lys Asn Ala Phe Ile Lys Tyr Ala Gly Asn Tyr Tyr Phe Asp
        915                 920                 925
Lys Glu Gly Tyr Met Leu Thr Gly Arg Gln Asp Ile Asp Ser Lys Thr
    930                 935                 940
Tyr Phe Phe Leu Pro Asn Gly Ile Gln Leu Arg Asp Ser Ile Tyr Gln
945                 950                 955                 960
Gln Asp Gly Lys Tyr Tyr Phe Gly Ser Phe Gly Glu Gln Tyr Lys
                965                 970                 975
Asp Gly Tyr Phe Val Phe Asp Val Pro Lys Glu Gly Thr Ser Glu Thr
            980                 985                 990
Glu Ala Lys Phe Arg Tyr Phe Ser Pro Thr Gly Glu Met Ala Val Gly
        995                 1000                1005
Leu Thr Tyr Ala Gly Gly Gly Leu Gln Tyr Phe Asp Glu Asn Gly
    1010                1015                1020
Phe Gln Ala Lys Gly Thr Lys Tyr Val Thr Pro Asp Gly Lys Leu
    1025                1030                1035
Tyr Phe Phe Asp Lys Asn Ser Gly Asn Ala Tyr Thr Asn Arg Trp
    1040                1045                1050
```

Ala Glu Ile Asp Gly Ile Trp Tyr Glu Phe Asn Asp Gln Gly Tyr
1055                1060                1065

Ala Gln Ala Lys Lys Gly Glu Phe Tyr Thr Thr Asp Gly Ser Thr
1070                1075                1080

Trp Phe Tyr Arg Asp Ala Ala Gly Lys Asn Val Thr Gly Ala Leu
1085                1090                1095

Thr Leu Asp Gly His Glu Tyr Tyr Phe Arg Ala Asn Gly Ala Gln
1100                1105                1110

Val Lys Gly Glu Phe Val Thr Glu Asn Gly Lys Ile Ser Tyr Tyr
1115                1120                1125

Thr Val Asp Asn Gly Tyr Lys Val Lys Asp Lys Phe Phe Glu Val
1130                1135                1140

Asn Gly Lys Trp Tyr His Ala Asp Lys Asp Gly Asn Leu Ala Thr
1145                1150                1155

Gly Arg Gln Thr Ile Asp His Leu Asn Tyr Tyr Phe Asn Ala Asp
1160                1165                1170

Gly Ser Gln Val Lys Ser Asp Phe Phe Thr Leu Asp Gly Gly Lys
1175                1180                1185

Thr Trp Tyr Tyr Ala Lys Asp Asn Gly Glu Ile Val Thr Gly Ala
1190                1195                1200

Tyr Ser Val Arg Gly Lys Asn Tyr Tyr Phe Lys Glu Asp Gly Ser
1205                1210                1215

Gln Val Lys Gly Asp Phe Val Lys Asn Ala Asp Gly Ser Leu Ser
1220                1225                1230

Tyr Tyr Asp Lys Asp Ser Gly Glu Arg Leu Asn Asn Arg Phe Leu
1235                1240                1245

Thr Thr Gly Asn Asn Val Trp Tyr Tyr Phe Lys Asp Gly Lys Ala
1250                1255                1260

Val Thr Gly Arg Gln Asn Ile Asp Gly Lys Glu Tyr Tyr Phe Asp
1265                1270                1275

His Leu Gly Arg Gln Val Lys Gly Ser Pro Ile Ser Thr Pro Lys
1280                1285                1290

Gly Val Glu Tyr Tyr Glu Ser Val Leu Gly Glu Arg Val Thr Asn
1295                1300                1305

Thr Trp Ile Thr Phe Gln Asp Gly Lys Thr Val Phe Phe Asp Glu
1310                1315                1320

Asn Gly Tyr Ala Asp Phe Asp Lys
1325                1330

<210> SEQ ID NO 37
<211> LENGTH: 3918
<212> TYPE: DNA
<213> ORGANISM: Streptococcus salivarius

<400> SEQUENCE: 37

| | | | | | |
|---|---|---|---|---|---|
| atgattgacg | gcaaacagta | ttatgtagag | aacggtgtgg | ttaagaagaa | tacggcgatt | 60 |
| gaactggatg | gccgtctgta | ttactttgac | gaaaccggtg | caatggttga | tcaatctaag | 120 |
| ccgctgtatc | gcgcggatgc | aatcccgaac | aactctatct | acgcagttta | caaccaggct | 180 |
| tacgacacca | gcagcaagag | ctttgaacac | ctggacaact | tctgacggc | cgatagctgg | 240 |
| taccgtccga | agcagatttt | gaaagacggc | aagaattgga | ccgcctcgac | ggagaaggac | 300 |
| tatcgtcctt | tgctgatgac | gtggtggccg | ataaagtca | cgcaagtcaa | ctacctgaac | 360 |
| tatatgtccc | aacagggctt | tggtaacaag | acctacacca | cggatatgat | gagctacgac | 420 |

```
ctggcggcag cggcggaaac ggttcagcgt ggcatcgaag agcgtattgg tcgtgagggt    480
aatacgacgt ggctgcgtca gttgatgagc gacttcatca aaacccagcc gggctggaat    540
agcgagagcg aagataatct gctggtcggt aaggatcatc tgcaaggtgg tgcactgacg    600
tttctgaaca atagcaccac gagccatgcg aacagcgatt ccgcctgat gaatcgtacc    660 ccgacgaacc agaccggcac ccgcaaatac cacatcgatc gtagcaatgg tggctacgaa    720
ctgctgctgg cgaacgacat cgacaatagc aatccggccg tccaagcgga acagctgaac    780
tggctgcatt acatcatgaa catcggctct atcctgggca atgacccaag cgcgaatttt    840
gatggcgtcc gtatcgatgc agttgacaat gtggatgcgg acttgttgca aattgcgtct    900
gactacttta aggaaaagta ccgtgttgcc gataacgagg caaacgctat tgcgcacctg    960
tcgattctgg aggcatggtc ctacaatgat catcaataca caaagacac gaagggcgct   1020 caactgagca ttgataatcc gctgcgtgag actttgctga cgaccttcct gcgcaagtct   1080
aactaccgtg gttccctgga gcgtgtgatc accaactcgt tgaacaaccg tagcagcgaa   1140
cagaagcaca cgccgcgtga cgccaactac atttttgtgc gtgctcacga cagcgaagtt   1200
caagcggtgc tggcaaacat catctctaaa cagatcaacc gaaaaccga cggttttacc   1260 tttacgatgg atgagctgaa gcaggcgttt gagatttaca cgcagacat gcgtaaggcg   1320 gataagaagt acacgcagta caacattccg gcagcttacg ccaccatgct gaccaataag   1380
gatagcatca cccgtgtgta ctatggtgat ttgtttaccg acgacggtca atacatggcg   1440
gagaaaagcc cgtactataa cgcaattgac gccctgctgc gtgctcgcat caaatacgtc   1500
gcgggtggtc aggacatgaa ggtgaccaaa ttgaacggct atgagatcat gtcctccgtt   1560
cgctacggta aggcgcaga ggaagctaat cagctgggca ccgcagaaac ccgcaatcaa   1620
ggcatgctgg tcctgaccgc gaatcgccca gacatgaagc tgggtacgaa tgatcgcctg   1680
gtcgtcaata tgggtgcagc ccacaagaat caggcgtatc gtccgctgct gctgtccaag   1740
tccaccggct tggcaaccta cctgaaagac agcgacgtcc ctgcgggcct ggtgcgttac   1800
acggacaatc aaggtaatct gaccttcacg gcggacgaca tcaccggcca tagcaccgta   1860
gaggtgagcg gttacctggc ggtttgggtg ccggtgggtg cgagcgagaa ccaagatgcg   1920
cgcacgaaag cgagcacgac gaaaaagggc gaacaagttt ttgaaagctc cgcagcgctg   1980
gatagccagg tcatctatga gggtttctcc aacttccagg attttgttaa gaccccttcc   2040
cagtacacga atcgcgttat cgcacagaac gcgaagcgct ttaaggagtg gggtatcacc   2100
agctttgagt tcgcgcctca atatgttagc agccaagacg gtaccttcct ggatagcatt   2160
attgagaacg gctacgcgtt cgaggaccgt tacgatatcg cgatgagcaa aaacaacaag   2220
tacggcagcc tgaaggatct gatggacgcg ctgcgtgcac tgcacgcgga gggtatcagc   2280
gccattgctg actgggttcc ggaccaaatc tataacctgc cgggtaagga agttgtaacc   2340
gcaagccgca cgaatagcta cggtacgccg cgtccgaacg cggaaatcta taacagcctg   2400
tatgcggcga aaacgcgtac gtttggcaat gatttttcagg gtaaatacgg tggcgcgttt   2460
ctggatgaac tgaaagcaaa gtacccggcg atcttcgagc gtgtgcaaat ttcgaatggt   2520
cgtaagctga ctaccaatga gaaaatcacg caatggagcg cgaagtactt taatggcagc   2580
aacattcaag gtaccggtgc gcgttacgtt ctgcaagata atgccacgaa ccagtatttc   2640
aacctgaagg ccggtcaaac cttctctgcca aagcagatga ccgagattac cgcaacgggc   2700
ttccgtcgtg tcggtgacaa agtgcaatac ctgtccacgt ccggctacct ggcgaagaat   2760
acctttatcc agattggtgc gaaccagtgg tattacttcg acaagaatgg caacatggtg   2820
```

```
accggtgagc aagtgattga tggtaaaaag tatttcttcc tggataacgg tctgcaactg    2880
cgtcatgtct tgcgtcaagg ttctgacggt cacgtgtatt actacgatcc gaaaggcgtc    2940
caggcgttta atggtttcta tgactttgcg ggtccgcgcc aagatgtccg ttatttcgac    3000
ggtaatggtc agatgtaccg tggtctgcat gatatgtatg gtaccacgtt ctactttgat    3060
gaaaagacgg gtatccaggc taaggataag tttatccgtt tcgccgacgg ccgtacccgt    3120
tactttattc cggacaccgg caatttggct gtgaatcgct tcgctcagaa tccggaaaac    3180
aaggcgtggt actacctgga cagcaacggt tatgcagtga cgggtttgca gaccattaat    3240
ggcaaacaat actatttcga caacgagggc cgtcaggtca agggccactt cgttactatc    3300
aacaatcagc gctacttctt ggacggtgac tcgggtgaga tcgcacgtag ccgcttcgtg    3360
acggagaaca caaatggta ctatgtggat ggtaacggta aattggtcaa gggtgcacaa    3420
gtcatcaacg gtaaccacta ttacttcaat aatgattatt ctcaggtgaa aggtgcttgg    3480
gccaatggcc gctactacga cggcgatagc ggccaggcgg tcacgaatcg tttcgtgcag    3540
gtcggtgcaa accagtgggc ctatctgaat cagaacggtc agaaggttgt gggcttgcaa    3600
cacatcaatg gcaagctgta ctactttgaa ggcaacggtg tccaagcaaa aggcaagctg    3660
ctgacctata agggtaagaa atactacttc gatgctaaca gcggtgaggc agtcaccaac    3720
cgctttattc aaatctctcg cggtgtttgg tactatttca atgcgagcgg tcaagcagtg    3780
accggcgagc aagttatcaa tggtcaacac ctgtacttcg acgaagcgg tcgccaggtt    3840 aaaggccgct atgtctggat taaaggccag cgccgttatt acgacgcgaa cactggtgcc    3900
tgggtacgta atcgttaa                                                  3918

<210> SEQ ID NO 38
<211> LENGTH: 1305
<212> TYPE: PRT
<213> ORGANISM: Streptococcus salivarius

<400> SEQUENCE: 38

Met Ile Asp Gly Lys Gln Tyr Tyr Val Glu Asn Gly Val Val Lys Lys
1               5                   10                  15

Asn Thr Ala Ile Glu Leu Asp Gly Arg Leu Tyr Tyr Phe Asp Glu Thr
            20                  25                  30

Gly Ala Met Val Asp Gln Ser Lys Pro Leu Tyr Arg Ala Asp Ala Ile
        35                  40                  45

Pro Asn Asn Ser Ile Tyr Ala Val Tyr Asn Gln Ala Tyr Asp Thr Ser
    50                  55                  60

Ser Lys Ser Phe Glu His Leu Asp Asn Phe Leu Thr Ala Asp Ser Trp
65                  70                  75                  80

Tyr Arg Pro Lys Gln Ile Leu Lys Asp Gly Lys Asn Trp Thr Ala Ser
                85                  90                  95

Thr Glu Lys Asp Tyr Arg Pro Leu Leu Met Thr Trp Trp Pro Asp Lys
            100                 105                 110

Val Thr Gln Val Asn Tyr Leu Asn Tyr Met Ser Gln Gln Gly Phe Gly
        115                 120                 125

Asn Lys Thr Tyr Thr Thr Asp Met Met Ser Tyr Asp Leu Ala Ala Ala
    130                 135                 140

Ala Glu Thr Val Gln Arg Gly Ile Glu Glu Arg Ile Gly Arg Glu Gly
145                 150                 155                 160

Asn Thr Thr Trp Leu Arg Gln Leu Met Ser Asp Phe Ile Lys Thr Gln
                165                 170                 175
```

```
Pro Gly Trp Asn Ser Glu Ser Glu Asp Asn Leu Leu Val Gly Lys Asp
            180                 185                 190

His Leu Gln Gly Gly Ala Leu Thr Phe Leu Asn Asn Ser Thr Thr Ser
            195                 200                 205

His Ala Asn Ser Asp Phe Arg Leu Met Asn Arg Thr Pro Thr Asn Gln
            210                 215                 220

Thr Gly Thr Arg Lys Tyr His Ile Asp Arg Ser Asn Gly Gly Tyr Glu
225                 230                 235                 240

Leu Leu Leu Ala Asn Asp Ile Asp Asn Ser Asn Pro Ala Val Gln Ala
                245                 250                 255

Glu Gln Leu Asn Trp Leu His Tyr Ile Met Asn Ile Gly Ser Ile Leu
            260                 265                 270

Gly Asn Asp Pro Ser Ala Asn Phe Asp Gly Val Arg Ile Asp Ala Val
            275                 280                 285

Asp Asn Val Asp Ala Asp Leu Leu Gln Ile Ala Ser Asp Tyr Phe Lys
            290                 295                 300

Glu Lys Tyr Arg Val Ala Asp Asn Glu Ala Asn Ala Ile Ala His Leu
305                 310                 315                 320

Ser Ile Leu Glu Ala Trp Ser Tyr Asn Asp His Gln Tyr Asn Lys Asp
                325                 330                 335

Thr Lys Gly Ala Gln Leu Ser Ile Asp Asn Pro Leu Arg Glu Thr Leu
            340                 345                 350

Leu Thr Thr Phe Leu Arg Lys Ser Asn Tyr Arg Gly Ser Leu Glu Arg
            355                 360                 365

Val Ile Thr Asn Ser Leu Asn Asn Arg Ser Ser Glu Gln Lys His Thr
            370                 375                 380

Pro Arg Asp Ala Asn Tyr Ile Phe Val Arg Ala His Asp Ser Glu Val
385                 390                 395                 400

Gln Ala Val Leu Ala Asn Ile Ile Ser Lys Gln Ile Asn Pro Lys Thr
            405                 410                 415

Asp Gly Phe Thr Phe Thr Met Asp Glu Leu Lys Gln Ala Phe Glu Ile
            420                 425                 430

Tyr Asn Ala Asp Met Arg Lys Ala Asp Lys Lys Tyr Thr Gln Tyr Asn
            435                 440                 445

Ile Pro Ala Ala Tyr Ala Thr Met Leu Thr Asn Lys Asp Ser Ile Thr
            450                 455                 460

Arg Val Tyr Tyr Gly Asp Leu Phe Thr Asp Asp Gly Gln Tyr Met Ala
465                 470                 475                 480

Glu Lys Ser Pro Tyr Tyr Asn Ala Ile Asp Ala Leu Leu Arg Ala Arg
            485                 490                 495

Ile Lys Tyr Val Ala Gly Gly Gln Asp Met Lys Val Thr Lys Leu Asn
            500                 505                 510

Gly Tyr Glu Ile Met Ser Ser Val Arg Tyr Gly Lys Gly Ala Glu Glu
            515                 520                 525

Ala Asn Gln Leu Gly Thr Ala Glu Thr Arg Asn Gln Gly Met Leu Val
            530                 535                 540

Leu Thr Ala Asn Arg Pro Asp Met Lys Leu Gly Thr Asn Asp Arg Leu
545                 550                 555                 560

Val Val Asn Met Gly Ala Ala His Lys Asn Gln Ala Tyr Arg Pro Leu
            565                 570                 575

Leu Leu Ser Lys Ser Thr Gly Leu Ala Thr Tyr Leu Lys Asp Ser Asp
            580                 585                 590
```

```
Val Pro Ala Gly Leu Val Arg Tyr Thr Asp Asn Gln Gly Asn Leu Thr
            595                 600                 605

Phe Thr Ala Asp Asp Ile Thr Gly His Ser Thr Val Glu Val Ser Gly
610                 615                 620

Tyr Leu Ala Val Trp Val Pro Val Gly Ala Ser Glu Asn Gln Asp Ala
625                 630                 635                 640

Arg Thr Lys Ala Ser Thr Thr Lys Lys Gly Glu Gln Val Phe Glu Ser
                645                 650                 655

Ser Ala Ala Leu Asp Ser Gln Val Ile Tyr Glu Gly Phe Ser Asn Phe
                660                 665                 670

Gln Asp Phe Val Lys Thr Pro Ser Gln Tyr Thr Asn Arg Val Ile Ala
            675                 680                 685

Gln Asn Ala Lys Arg Phe Lys Glu Trp Gly Ile Thr Ser Phe Glu Phe
        690                 695                 700

Ala Pro Gln Tyr Val Ser Ser Gln Asp Gly Thr Phe Leu Asp Ser Ile
705                 710                 715                 720

Ile Glu Asn Gly Tyr Ala Phe Glu Asp Arg Tyr Asp Ile Ala Met Ser
                    725                 730                 735

Lys Asn Asn Lys Tyr Gly Ser Leu Lys Asp Leu Met Asp Ala Leu Arg
                740                 745                 750

Ala Leu His Ala Glu Gly Ile Ser Ala Ile Ala Asp Trp Val Pro Asp
            755                 760                 765

Gln Ile Tyr Asn Leu Pro Gly Lys Glu Val Val Thr Ala Ser Arg Thr
        770                 775                 780

Asn Ser Tyr Gly Thr Pro Arg Pro Asn Ala Glu Ile Tyr Asn Ser Leu
785                 790                 795                 800

Tyr Ala Ala Lys Thr Arg Thr Phe Gly Asn Asp Phe Gln Gly Lys Tyr
                    805                 810                 815

Gly Gly Ala Phe Leu Asp Glu Leu Lys Ala Lys Tyr Pro Ala Ile Phe
                820                 825                 830

Glu Arg Val Gln Ile Ser Asn Gly Arg Lys Leu Thr Thr Asn Glu Lys
            835                 840                 845

Ile Thr Gln Trp Ser Ala Lys Tyr Phe Asn Gly Ser Asn Ile Gln Gly
        850                 855                 860

Thr Gly Ala Arg Tyr Val Leu Gln Asp Asn Ala Thr Asn Gln Tyr Phe
865                 870                 875                 880

Asn Leu Lys Ala Gly Gln Thr Phe Leu Pro Lys Gln Met Thr Glu Ile
                    885                 890                 895

Thr Ala Thr Gly Phe Arg Arg Val Gly Asp Lys Val Gln Tyr Leu Ser
                900                 905                 910

Thr Ser Gly Tyr Leu Ala Lys Asn Thr Phe Ile Gln Ile Gly Ala Asn
            915                 920                 925

Gln Trp Tyr Tyr Phe Asp Lys Asn Gly Asn Met Val Thr Gly Glu Gln
        930                 935                 940

Val Ile Asp Gly Lys Lys Tyr Phe Phe Leu Asp Asn Gly Leu Gln Leu
945                 950                 955                 960

Arg His Val Leu Arg Gln Gly Ser Asp Gly His Val Tyr Tyr Tyr Asp
                    965                 970                 975

Pro Lys Gly Val Gln Ala Phe Asn Gly Phe Tyr Asp Phe Ala Gly Pro
                980                 985                 990

Arg Gln Asp Val Arg Tyr Phe Asp Gly Asn Gly Gln Met Tyr Arg Gly
            995                 1000                1005

Leu His Asp Met Tyr Gly Thr Thr Phe Tyr Phe Asp Glu Lys Thr
```

|  | 1010 |  |  | 1015 |  |  |  | 1020 |  |
|---|---|---|---|---|---|---|---|---|---|

Gly Ile Gln Ala Lys Asp Lys Phe Ile Arg Phe Ala Asp Gly Arg
    1025                1030                1035

Thr Arg Tyr Phe Ile Pro Asp Thr Gly Asn Leu Ala Val Asn Arg
    1040                1045                1050

Phe Ala Gln Asn Pro Glu Asn Lys Ala Trp Tyr Tyr Leu Asp Ser
    1055                1060                1065

Asn Gly Tyr Ala Val Thr Gly Leu Gln Thr Ile Asn Gly Lys Gln
    1070                1075                1080

Tyr Tyr Phe Asp Asn Glu Gly Arg Gln Val Lys Gly His Phe Val
    1085                1090                1095

Thr Ile Asn Asn Gln Arg Tyr Phe Leu Asp Gly Asp Ser Gly Glu
    1100                1105                1110

Ile Ala Arg Ser Arg Phe Val Thr Glu Asn Asn Lys Trp Tyr Tyr
    1115                1120                1125

Val Asp Gly Asn Gly Lys Leu Val Lys Gly Ala Gln Val Ile Asn
    1130                1135                1140

Gly Asn His Tyr Tyr Phe Asn Asn Asp Tyr Ser Gln Val Lys Gly
    1145                1150                1155

Ala Trp Ala Asn Gly Arg Tyr Tyr Asp Gly Asp Ser Gly Gln Ala
    1160                1165                1170

Val Thr Asn Arg Phe Val Gln Val Gly Ala Asn Gln Trp Ala Tyr
    1175                1180                1185

Leu Asn Gln Asn Gly Gln Lys Val Val Gly Leu Gln His Ile Asn
    1190                1195                1200

Gly Lys Leu Tyr Tyr Phe Glu Gly Asn Gly Val Gln Ala Lys Gly
    1205                1210                1215

Lys Leu Leu Thr Tyr Lys Gly Lys Lys Tyr Tyr Phe Asp Ala Asn
    1220                1225                1230

Ser Gly Glu Ala Val Thr Asn Arg Phe Ile Gln Ile Ser Arg Gly
    1235                1240                1245

Val Trp Tyr Tyr Phe Asn Ala Ser Gly Gln Ala Val Thr Gly Glu
    1250                1255                1260

Gln Val Ile Asn Gly Gln His Leu Tyr Phe Asp Ala Ser Gly Arg
    1265                1270                1275

Gln Val Lys Gly Arg Tyr Val Trp Ile Lys Gly Gln Arg Arg Tyr
    1280                1285                1290

Tyr Asp Ala Asn Thr Gly Ala Trp Val Arg Asn Arg
    1295                1300                1305

<210> SEQ ID NO 39
<211> LENGTH: 3933
<212> TYPE: DNA
<213> ORGANISM: Streptococcus gallolyticus

<400> SEQUENCE: 39
atgatcgacg gcaaatacta ctatgttcag gcagatggca gcgttaagaa gaatttcgcg     60
attacggtca acggtcagct gctgtacttt gatgctgaga ctggcgctct gacgagcacg    120
agcacttata gctttaccga aggcctgacc aatctggtgg ataactttag caagaacaat    180
caagcgtatg acagcacgga gaaatccttt gagctggttg atggctacct gacggcgaac    240
agctggtatc gtccgactaa agttttggag aatggcgaaa cctgggttga cagcaccgaa    300
gagagcttcc gtccactggt gatggcttgg tggcctgacg tcgataccca gattaactac    360

-continued

| | |
|---|---|
| ctgaacagca tgagcgaata ctttggtttg aataagaagt attctgcatc ggatagccaa | 420 |
| gcatctctga atgtggcggc tgaagcgatc caggtgaaaa ttgagcagga gattgcgcgt | 480 |
| cgtggttcga ccgagtggtt gcgtgaggtc attagctctt ttgttacgac ccaagataag | 540 |
| tggaatatga acagcgaaga tcgcgacact gaccacctgc aaggtggcgc actgctgtat | 600 |
| gtcaacagcg atctgactga gtgggccaat agcgattacc gcctgctgaa ccgcgctccg | 660 |
| acctatcaaa ctggtgaaac taagtaccac aaagccgacc gcacgggtgg ctacgacttc | 720 |
| ctgctggcga atgatgttga caatagcaat ccggttgttc aggccgaaca actgaatcag | 780 |
| ctgtactacc tgatgaactg gggtaagatt gtgttcggtg acgcagatgc aaacttcgat | 840 |
| ggcgtccgtg ttgacgcggt ggacaacgtg gatgctgatc tgttgcaaat ctacacgaat | 900 |
| ctgtttgaag cggcctacgg cgtcgataag accgaagcac aagcgctggc gcatattagc | 960 |
| atcttggaag cgtggagctt caacgacccg gactataatc acgacaccaa cggtgcagca | 1020 |
| ctggccatcg acaacggtct gcgtatggcc ttcctggatg ctctgactcg tcctctggac | 1080 |
| tcccgcacta atttggagag cctgattcac aacgatctgg gcatgactga ccgtaccgtc | 1140 |
| gatagcgcgt atggtgatgc tatgccgagc tatgccttcg tccgtgccca cgactctgaa | 1200 |
| gttcagggca tcattgcatc tatcatcgcc ggtcagatca atccgaaaac ggacggtttt | 1260 |
| acctttacct tggatgagct gcaaaaggca ttcgaaatct acaacgccga catgaactcc | 1320 |
| gtgcacaaga agtatacccca tttcaatatc ccagcagcat acgctttgct gctgaccaac | 1380 |
| atggagagcg ttccgcgtgt atactatggc gatttgttca ccgataacgg tcagtacatg | 1440 |
| gccgttaaaa gcccgtacta cgaccagatc accgcgctgc tgaagtctcg tatcaagtac | 1500 |
| gcggcaggcg gtcaagccat gaatgtgcaa tacccggatg gtgcgggtgc gggtatcctg | 1560 |
| acttctgtgc gcttcggcta tggcattatg acggcggatc aaaaagcgac cgacgacagc | 1620 |
| gttactacca gcggcattgt caccattgtt ccaacaacc cgaacctgaa actgaatagc | 1680 |
| agcgacaaaa ttgcggtgca agttggtctg cacacgcag gccaatacta ccgtccgctg | 1740 |
| ctgtctccga cggagaatgg tctgcaagtg ttcctgaatg attccgacac cgacatcacc | 1800 |
| aagctggtcg atgataacgg ttacatctat ttcacgggtg atgagatcaa aggttttcgag | 1860 |
| actgtggaca tgaatggctt cctgaccgtt tgggttccgg tgggtgcggc agccgatcag | 1920 |
| gatattcgcg tcaaggcgag cacggaagcg aagaaggatg tgagctgac ctatgaaacc | 1980 |
| tctgcggcgc tggattctca ggtcattttt gaaggcttta gcaactttca agactttgtt | 2040 |
| caggacccaa gccagtacac caataaggtg attgcggaga atgcggatct gttcgcgagc | 2100 |
| tggggcatca cgtctttcga gctggcaccg cagtatgtta gcagcacgga cggtacgttc | 2160 |
| ctggacagca ttattcagaa cggttatgct tttacggatc gttatgactt ggcgatgtct | 2220 |
| aagaacaata agtatggtag cgcagaagat ttgcgcaatg cgattaaagc gctgcacgca | 2280 |
| cgcggtattc aagtgattgc tgattgggtc cctgaccaga tttatgcgct gcctggtgaa | 2340 |
| gagattgtga cggcgacccg tgttaatgac tacggcgaag aacgtgaagg cgcgcaaatc | 2400 |
| aagaacaaac cgtatgcggc gaatacgaaa agctccggtg aggattacca agcccaatac | 2460 |
| ggtggcgagt tcttggaata tctgcaagag aattacccgg agttgtttga aaaggtcatg | 2520 |
| attagcacgg gtaagaccat tgacccatcg acgaagatca aggtctggaa agcggagtat | 2580 |
| ttcaacggca cgaatattct gggtaagggt gccgattacg tcctgaacga tgcggccacc | 2640 |
| ggcacctact tcaccgtaac ggagaacggc gccttcctgc cgaaacaaat gacgagcgat | 2700 |
| accgcccaaa cgggtttcta ttatgatggc accggcatga cgtactattc tacctcgggt | 2760 |

-continued

```
taccaagcta agtctagctt cgtgctgtac aacggcaacc gttactattt cgatgaaaac   2820
ggtcacatgg ttacgggtat gcgcgatatt gatggtcaga cgtactactt tctgccgaat   2880
ggtatcgaac tgcgtgacgc gatctatgag gacgcgaacg gtaatcagta ttactttggc   2940
aaatcgggta accgctacgc gggtcattac tacgcctttg aaaccacgag caccgttgac   3000
ggtgtcacca agaccactac taactggcgc tattttgatg aaaacggcgt tatggcacgc   3060
ggcctggtga aaatcggtaa tgattatcaa tactacgacg ataacggcaa tcagatcaag   3120
ggtcaactgg tgacggacaa ggacggcaac acccgttact ttaaagctga cagcggtgca   3180
atggttacgg gtgagtttgc actggtgaat ggtggttggt actacttcga tgacaatggt   3240
gttgcagtca aggtgctcga gaccattaac ggtcaacagt tgtacttcga cgagaatggt   3300
gtccaagcaa aaggtgtgtt cgtgaccaat gaggatggca cccgtagcta ttacgacgcc   3360
aagtccggtg agaagtttgt tggcgacttc tttacgaccg cgacaaccca ttggtactat   3420
gccgacgaga acggcaattt ggcaacgggt agccaggtta ccgtggtca gaagttgtat   3480 tttgcagccg atggtttgca ggcgaaaggt atctttacca ccgacgccga aggtaaccgc   3540
cacttctacg acccggactc cggcgatctg gcggaaaaca gtttatcgc ggatggtgac   3600 gactggtact attttgacga aacgggtcat gttgttaccg gcgagcaagt gatcaacggc   3660
caacagctgt atttcgacga aaatggcgtt caggcgaagg tgttttcgt gaccgatgat   3720 aatggtaata gcgttacta tgatgcacag acgggtgaga tggtggtgaa ccagacgctg   3780
acggtggatg tgtggaata tacctttggt gcggatggcg tcgcggtggt taatgcacaa   3840
gatagcgacg aacaaagcga aagcacggat gaaacgcaag tgaccagcga tgacgcgacg   3900
gttgcaaaga cggaaaccag ctctgctgaa taa                                3933
```

<210> SEQ ID NO 40
<211> LENGTH: 1310
<212> TYPE: PRT
<213> ORGANISM: Streptococcus gallolyticus

<400> SEQUENCE: 40

```
Met Ile Asp Gly Lys Tyr Tyr Tyr Val Gln Ala Asp Gly Ser Val Lys
1               5                   10                  15

Lys Asn Phe Ala Ile Thr Val Asn Gly Gln Leu Leu Tyr Phe Asp Ala
            20                  25                  30

Glu Thr Gly Ala Leu Thr Ser Thr Ser Thr Tyr Ser Phe Thr Glu Gly
        35                  40                  45

Leu Thr Asn Leu Val Asp Asn Phe Ser Lys Asn Asn Gln Ala Tyr Asp
    50                  55                  60

Ser Thr Glu Lys Ser Phe Glu Leu Val Asp Gly Tyr Leu Thr Ala Asn
65                  70                  75                  80

Ser Trp Tyr Arg Pro Thr Lys Val Leu Glu Asn Gly Glu Thr Trp Val
                85                  90                  95

Asp Ser Thr Glu Glu Ser Phe Arg Pro Leu Val Met Ala Trp Trp Pro
            100                 105                 110

Asp Val Asp Thr Gln Ile Asn Tyr Leu Asn Ser Met Ser Glu Tyr Phe
        115                 120                 125

Gly Leu Asn Lys Lys Tyr Ser Ala Ser Asp Ser Gln Ala Ser Leu Asn
    130                 135                 140

Val Ala Ala Glu Ala Ile Gln Val Lys Ile Glu Gln Glu Ile Ala Arg
145                 150                 155                 160
```

```
Arg Gly Ser Thr Glu Trp Leu Arg Glu Val Ile Ser Ser Phe Val Thr
            165                 170                 175

Thr Gln Asp Lys Trp Asn Met Asn Ser Glu Asp Arg Thr Asp His
        180                 185                 190

Leu Gln Gly Gly Ala Leu Leu Tyr Val Asn Ser Asp Leu Thr Glu Trp
            195                 200                 205

Ala Asn Ser Asp Tyr Arg Leu Leu Asn Arg Ala Pro Thr Tyr Gln Thr
        210                 215                 220

Gly Glu Thr Lys Tyr His Lys Ala Asp Arg Thr Gly Tyr Asp Phe
225                 230                 235                 240

Leu Leu Ala Asn Asp Val Asp Asn Ser Asn Pro Val Val Gln Ala Glu
            245                 250                 255

Gln Leu Asn Gln Leu Tyr Tyr Leu Met Asn Trp Gly Lys Ile Val Phe
        260                 265                 270

Gly Asp Ala Asp Ala Asn Phe Asp Gly Val Arg Val Asp Ala Val Asp
            275                 280                 285

Asn Val Asp Ala Asp Leu Leu Gln Ile Tyr Thr Asn Leu Phe Glu Ala
        290                 295                 300

Ala Tyr Gly Val Asp Lys Thr Glu Ala Gln Ala Leu Ala His Ile Ser
305                 310                 315                 320

Ile Leu Glu Ala Trp Ser Phe Asn Asp Pro Asp Tyr Asn His Asp Thr
            325                 330                 335

Asn Gly Ala Ala Leu Ala Ile Asp Asn Gly Leu Arg Met Ala Phe Leu
        340                 345                 350

Asp Ala Leu Thr Arg Pro Leu Asp Ser Arg Thr Asn Leu Glu Ser Leu
            355                 360                 365

Ile His Asn Asp Leu Gly Met Thr Asp Arg Thr Val Asp Ser Ala Tyr
        370                 375                 380

Gly Asp Ala Met Pro Ser Tyr Ala Phe Val Arg Ala His Asp Ser Glu
385                 390                 395                 400

Val Gln Gly Ile Ile Ala Ser Ile Ile Ala Gly Gln Ile Asn Pro Lys
            405                 410                 415

Thr Asp Gly Phe Thr Phe Thr Leu Asp Glu Leu Gln Lys Ala Phe Glu
        420                 425                 430

Ile Tyr Asn Ala Asp Met Asn Ser Val His Lys Lys Tyr Thr His Phe
            435                 440                 445

Asn Ile Pro Ala Ala Tyr Ala Leu Leu Leu Thr Asn Met Glu Ser Val
        450                 455                 460

Pro Arg Val Tyr Tyr Gly Asp Leu Phe Thr Asp Asn Gly Gln Tyr Met
465                 470                 475                 480

Ala Val Lys Ser Pro Tyr Tyr Asp Gln Ile Thr Ala Leu Leu Lys Ser
            485                 490                 495

Arg Ile Lys Tyr Ala Ala Gly Gly Gln Ala Met Asn Val Gln Tyr Pro
        500                 505                 510

Asp Gly Ala Gly Ala Gly Ile Leu Thr Ser Val Arg Phe Gly Tyr Gly
            515                 520                 525

Ile Met Thr Ala Asp Gln Lys Ala Thr Asp Asp Ser Val Thr Thr Ser
        530                 535                 540

Gly Ile Val Thr Ile Val Ser Asn Asn Pro Asn Leu Lys Leu Asn Ser
545                 550                 555                 560

Ser Asp Lys Ile Ala Val Gln Val Gly Leu Ala His Ala Gly Gln Tyr
            565                 570                 575

Tyr Arg Pro Leu Leu Ser Pro Thr Glu Asn Gly Leu Gln Val Phe Leu
```

-continued

```
                580             585             590
Asn Asp Ser Asp Thr Asp Ile Thr Lys Leu Val Asp Asp Asn Gly Tyr
            595             600             605

Ile Tyr Phe Thr Gly Asp Glu Ile Lys Gly Phe Glu Thr Val Asp Met
            610             615             620

Asn Gly Phe Leu Thr Val Trp Val Pro Val Gly Ala Ala Ala Asp Gln
625             630             635             640

Asp Ile Arg Val Lys Ala Ser Thr Glu Ala Lys Lys Asp Gly Glu Leu
            645             650             655

Thr Tyr Glu Thr Ser Ala Ala Leu Asp Ser Gln Val Ile Phe Glu Gly
            660             665             670

Phe Ser Asn Phe Gln Asp Phe Val Gln Asp Pro Ser Gln Tyr Thr Asn
            675             680             685

Lys Val Ile Ala Glu Asn Ala Asp Leu Phe Ala Ser Trp Gly Ile Thr
            690             695             700

Ser Phe Glu Leu Ala Pro Gln Tyr Val Ser Ser Thr Asp Gly Thr Phe
705             710             715             720

Leu Asp Ser Ile Ile Gln Asn Gly Tyr Ala Phe Thr Asp Arg Tyr Asp
            725             730             735

Leu Ala Met Ser Lys Asn Asn Lys Tyr Gly Ser Ala Glu Asp Leu Arg
            740             745             750

Asn Ala Ile Lys Ala Leu His Ala Arg Gly Ile Gln Val Ile Ala Asp
            755             760             765

Trp Val Pro Asp Gln Ile Tyr Ala Leu Pro Gly Glu Glu Ile Val Thr
            770             775             780

Ala Thr Arg Val Asn Asp Tyr Gly Glu Glu Arg Glu Gly Ala Gln Ile
785             790             795             800

Lys Asn Lys Pro Tyr Ala Ala Asn Thr Lys Ser Ser Gly Glu Asp Tyr
            805             810             815

Gln Ala Gln Tyr Gly Gly Glu Phe Leu Glu Tyr Leu Gly Glu Asn Tyr
            820             825             830

Pro Glu Leu Phe Glu Lys Val Met Ile Ser Thr Gly Lys Thr Ile Asp
            835             840             845

Pro Ser Thr Lys Ile Lys Val Trp Lys Ala Glu Tyr Phe Asn Gly Thr
            850             855             860

Asn Ile Leu Gly Lys Gly Ala Asp Tyr Val Leu Asn Asp Ala Ala Thr
865             870             875             880

Gly Thr Tyr Phe Thr Val Thr Glu Asn Gly Ala Phe Leu Pro Lys Gln
            885             890             895

Met Thr Ser Asp Thr Ala Gln Thr Gly Phe Tyr Tyr Asp Gly Thr Gly
            900             905             910

Met Thr Tyr Tyr Ser Thr Ser Gly Tyr Gln Ala Lys Ser Ser Phe Val
            915             920             925

Leu Tyr Asn Gly Asn Arg Tyr Tyr Phe Asp Glu Asn Gly His Met Val
            930             935             940

Thr Gly Met Arg Asp Ile Asp Gly Gln Thr Tyr Tyr Phe Leu Pro Asn
945             950             955             960

Gly Ile Glu Leu Arg Asp Ala Ile Tyr Glu Asp Ala Asn Gly Asn Gln
            965             970             975

Tyr Tyr Phe Gly Lys Ser Gly Asn Arg Tyr Ala Gly His Tyr Tyr Ala
            980             985             990

Phe Glu Thr Thr Ser Thr Val Asp  Gly Val Thr Lys Thr  Thr Thr Asn
            995             1000             1005
```

Trp Arg Tyr Phe Asp Glu Asn Gly Val Met Ala Arg Gly Leu Val
    1010                1015                1020

Lys Ile Gly Asn Asp Tyr Gln Tyr Tyr Asp Asp Asn Gly Asn Gln
    1025                1030                1035

Ile Lys Gly Gln Leu Val Thr Asp Lys Asp Gly Asn Thr Arg Tyr
    1040                1045                1050

Phe Lys Ala Asp Ser Gly Ala Met Val Thr Gly Glu Phe Ala Leu
    1055                1060                1065

Val Asn Gly Gly Trp Tyr Tyr Phe Asp Asp Asn Gly Val Ala Val
    1070                1075                1080

Lys Gly Ala Gln Thr Ile Asn Gly Gln Gln Leu Tyr Phe Asp Glu
    1085                1090                1095

Asn Gly Val Gln Ala Lys Gly Val Phe Val Thr Asn Glu Asp Gly
    1100                1105                1110

Thr Arg Ser Tyr Tyr Asp Ala Lys Ser Gly Glu Lys Phe Val Gly
    1115                1120                1125

Asp Phe Phe Thr Thr Gly Asp Asn His Trp Tyr Tyr Ala Asp Glu
    1130                1135                1140

Asn Gly Asn Leu Ala Thr Gly Ser Gln Val Ile Arg Gly Gln Lys
    1145                1150                1155

Leu Tyr Phe Ala Ala Asp Gly Leu Gln Ala Lys Gly Ile Phe Thr
    1160                1165                1170

Thr Asp Ala Glu Gly Asn Arg His Phe Tyr Asp Pro Asp Ser Gly
    1175                1180                1185

Asp Leu Ala Glu Asn Lys Phe Ile Ala Asp Gly Asp Asp Trp Tyr
    1190                1195                1200

Tyr Phe Asp Glu Thr Gly His Val Val Thr Gly Glu Gln Val Ile
    1205                1210                1215

Asn Gly Gln Gln Leu Tyr Phe Asp Glu Asn Gly Val Gln Ala Lys
    1220                1225                1230

Gly Val Phe Val Thr Asp Asp Asn Gly Asn Lys Arg Tyr Tyr Asp
    1235                1240                1245

Ala Gln Thr Gly Glu Met Val Val Asn Gln Thr Leu Thr Val Asp
    1250                1255                1260

Gly Val Glu Tyr Thr Phe Gly Ala Asp Gly Val Ala Val Val Asn
    1265                1270                1275

Ala Gln Asp Ser Asp Glu Gln Ser Glu Ser Thr Asp Glu Thr Gln
    1280                1285                1290

Val Thr Ser Asp Asp Ala Thr Val Ala Lys Thr Glu Thr Ser Ser
    1295                1300                1305

Ala Glu
    1310

<210> SEQ ID NO 41
<211> LENGTH: 3804
<212> TYPE: DNA
<213> ORGANISM: Streptococcus mutans

<400> SEQUENCE: 41
atggtcaatg gcaaatacta ctactacaaa gaggacggta cgttgcagaa gaactacgca      60
ctgaacatta cggcaagac cttttctctt gacgagactg gcgccctgag caataacacc      120
ctgccgagca agaaaggtaa catcaccaat aacgacaata ccaatagctt cgcgcaaatac      180 aatcaggtgt attcgacgga tgcagcgaac ttcgaacatg tcgatcacta cctgacggcg      240

```
gagtcctggt atcgcccgaa gtatattctg aaagatggca agacgtggac tcagtccacg    300
gagaaagatt ttcgcccgtt gttgatgacc tggtggccgg atcaggaaac ccagcgtcag    360
tatgtaaact atatgaatgc ccagctgggt attcaccaga cctacaacac ggcgaccagc    420
ccgttgcaac tgaatctggc ggcacagacg atccagacca agattgaaga aagatcacg     480
gcggagaaga acactaattg gctgcgtcaa acgatttcgg cctttgtcaa aacccagagc    540
gcgtggaact cggacagcga aaaaccgttt gacgatcatc tgcaaaaggg tgcactgctg    600
tactctaaca atagcaagtt gacctctcaa gctaatagca actaccgtat tctgaaccgt    660
accccaacca accaaaccgg caagaaagat ccgcgttata ccgctgaccg taccatcggt    720
ggttatgagt tcttgctggc gaacgatgtg gataatagca atcctgttgt tcaagcggaa    780
cagctgaact ggctgcactt cctgatgaac tttggcaata tctatgcaaa cgaccctgac    840
gccaactttg acagcatccg tgtagacgcc gtggacaacg tggatgcaga tttgttgcaa    900
atcgctggtg actatctgaa ggctgcaaag ggcatccata agaacgacaa agcagcgaac    960
gaccacctgt cgatcctgga agcatggagc tataatgaca ccccgtatct gcacgacgac    1020
ggtgacaaca tgatcaatat ggacaaccgt ctgcgtctga gcctgctgta tagcctggcg    1080
aagccgttga accagcgttc gggcatgaac ccgctgatca cgaacagcct ggttaaccgt    1140
accgatgaca acgcagaaac cgcagcggtc ccgagctaca gctttatccg tgcacacgat    1200
agcgaggttc aagacctgat tcgtaacatt attcgtgctg agattaatcc gaacgtcgtc    1260
ggttatagct tcacgatgga agagatcaag aaggcctttg agatttacaa caaggatctg    1320
ctggcgacgg aaaagaaata cacccactat aacaccgcgc tgagctacgc gctgctgctg    1380
accaataaga gcagcgttcc gcgtgtgtat acggtgata tgtttactga cgacggtcag    1440
tacatggcac ataaaacgat caactacgag gctatcgaaa cgctgttgaa ggcgcgcatt    1500
aagtacgtgt ctggtggcca agcgatgcgt aatcaacagg tgggtaatag cgaaatcatt    1560
acgagcgtcc gctatggcaa gggcgcactg aaagcgacgg ataccggcga tcgtaccacg    1620
cgcaccagcg gcgttgcggt tattgaaggc aataacccga gcctgcgctt gaaggcgagc    1680
gaccgcgtcg ttgttaacat gggtgcagca cacaagaacc aggcatatcg tccgctgttg    1740
ctgaccactg ataatggcat caaagcgtat cacagcgatc aggaagctgc gggcctggtg    1800
cgctatacca atgatcgtgg tgaattgatc ttcacggcag ctgacattaa aggttatgca    1860
aatccgcaag tcagcggtta tctgggcgtc tgggtgccgg tcggcgcagc ggctgatcaa    1920
gacgtgcgtg tggccgcgag caccgcgcca tcgaccgacg gtaaaagcgt gcaccagaat    1980
gcggcgctgg acagccgtgt catgtttgag ggttttagca actttcaagc ctttgcaacg    2040
aagaaagaag agtacaccaa cgtcgtcatc gcgaagaacg tcgataagtt cgcggaatgg    2100
ggcgttaccg atttcgaaat ggcaccgcag tatgtgtcta gcaccgatgg ctcgtttctg    2160
gattccgtga tccaaaatgg ttatgcattt accgaccgct atgacctggg cattagcaag    2220
ccgaataagt atggtacggc ggatgatctg gttaaagcga tcaaggcgct gcattctaaa    2280
ggtattaagg ttatggccga ctgggttcca gatcagatgt atgctttccc ggaaaaagaa    2340
gtggtgacgg ccaccgcgt ggacaaatat ggtacgccgg tcgcgggcag ccagatcaaa    2400
aacactctgt atgtcgtgga tgcaaaagc tccggtaaag atcagcaagc gaaatatggc    2460
ggtgccttcc tggaagagtt gcaggcgaaa tacccggaac tgttcgcgcg taagcagatc    2520
agcactggtg ttccgatgga cccgagcgtg aagattaaac aatggtccgc gaaatacttt    2580
```

```
aacggcacga acatcctggg tcgtggtgcc ggctacgtgc tgaaagacca ggcaacgaat    2640
acgtacttta gcttggtgtc cgacaatacg tttctgccga agtctctggt caacccgaac    2700
cacggtacga gcagctctgt gaccggcctg gtgttcgatg gtaagggcta cgtgtactac    2760
tctaccagcg gttaccaggc caagaatacg ttcatcagcc tgggtaacaa ctggtattac    2820
ttcgacaata acggttacat ggtcacgggt gcgcagagca tcaacggtgc caactactat    2880
tttctgagca acggcattca gctgcgtaat gcgatttacg acaatggcaa taaggttctg    2940
agctactacg gtaatgacgg tcgtcgttat gagaatggct attacctgtt tggccaacag    3000
tggcgctact ttcaaaatgg tattatggcc gtcggtctga cccgtgtcca cggtgcggtg    3060
cagtattttg acgccagcgg cttccaagcc aagggccagt tcatcaccac tgcggacggt    3120
aaactgcgtt actttgaccg tgacagcggc aaccaaatca gcaatcgttt tgttcgtaac    3180
agcaagggtg aatggttttt gttcgatcat aacgcgtgg cggttaccgg caccgttact    3240
ttcaatggtc aacgtctgta ctttaagccg aacggtgttc aggcaaaggg tgagttcatt    3300
cgcgacgcgg atggtcactt gcgttactac gaccctaatt ccggtaatga ggttcgtaac    3360
cgtttcgtcc gcaactctaa gggcgaatgg ttcctgtttg accacaatgg catcgcagtc    3420
accggcgctc gtgtggtcaa cggccaacgc ttgtacttca aaagcaatgg cgtccaagct    3480
aagggtgagc tgattaccga acgtaagggc cgtattaagt attatgatcc taacagcggt    3540
aacgaagtgc gtaaccgcta cgtccgcacc agcagcggta attggtacta ttttggtaac    3600
gatggttacg cgctgatcgg ctggcatgtt gttgagggtc gtcgtgtgta ctttgatgag    3660
aacggtgtct atcgttacgc gagccacgac cagcgtaatc attggaacta cgactatcgt    3720
cgcgatttcg gtcgtggtag cagctccgct atccgttttc gccatagccg taacggcttt    3780
ttcgacaact tcttccgctt ctaa                                            3804

<210> SEQ ID NO 42
<211> LENGTH: 1267
<212> TYPE: PRT
<213> ORGANISM: Streptococcus mutans

<400> SEQUENCE: 42

Met Val Asn Gly Lys Tyr Tyr Tyr Lys Glu Asp Gly Thr Leu Gln
1               5                   10                  15

Lys Asn Tyr Ala Leu Asn Ile Asn Gly Lys Thr Phe Phe Phe Asp Glu
            20                  25                  30

Thr Gly Ala Leu Ser Asn Asn Thr Leu Pro Ser Lys Lys Gly Asn Ile
        35                  40                  45

Thr Asn Asn Asp Asn Thr Asn Ser Phe Ala Gln Tyr Asn Gln Val Tyr
    50                  55                  60

Ser Thr Asp Ala Ala Asn Phe Glu His Val Asp His Tyr Leu Thr Ala
65                  70                  75                  80

Glu Ser Trp Tyr Arg Pro Lys Tyr Ile Leu Lys Asp Gly Lys Thr Trp
                85                  90                  95

Thr Gln Ser Thr Glu Lys Asp Phe Arg Pro Leu Leu Met Thr Trp Trp
            100                 105                 110

Pro Asp Gln Glu Thr Gln Arg Gln Tyr Val Asn Tyr Met Asn Ala Gln
        115                 120                 125

Leu Gly Ile His Gln Thr Tyr Asn Thr Ala Thr Ser Pro Leu Gln Leu
    130                 135                 140

Asn Leu Ala Ala Gln Thr Ile Gln Thr Lys Ile Glu Glu Lys Ile Thr
145                 150                 155                 160
```

-continued

```
Ala Glu Lys Asn Thr Asn Trp Leu Arg Gln Thr Ile Ser Ala Phe Val
                165                 170                 175
Lys Thr Gln Ser Ala Trp Asn Ser Asp Ser Glu Lys Pro Phe Asp Asp
            180                 185                 190
His Leu Gln Lys Gly Ala Leu Leu Tyr Ser Asn Asn Ser Lys Leu Thr
        195                 200                 205
Ser Gln Ala Asn Ser Asn Tyr Arg Ile Leu Asn Arg Thr Pro Thr Asn
    210                 215                 220
Gln Thr Gly Lys Lys Asp Pro Arg Tyr Thr Ala Asp Arg Thr Ile Gly
225                 230                 235                 240
Gly Tyr Glu Phe Leu Leu Ala Asn Asp Val Asp Asn Ser Asn Pro Val
                245                 250                 255
Val Gln Ala Glu Gln Leu Asn Trp Leu His Phe Leu Met Asn Phe Gly
            260                 265                 270
Asn Ile Tyr Ala Asn Asp Pro Asp Ala Asn Phe Asp Ser Ile Arg Val
        275                 280                 285
Asp Ala Val Asp Asn Val Asp Ala Asp Leu Leu Gln Ile Ala Gly Asp
    290                 295                 300
Tyr Leu Lys Ala Ala Lys Gly Ile His Lys Asn Asp Lys Ala Ala Asn
305                 310                 315                 320
Asp His Leu Ser Ile Leu Glu Ala Trp Ser Tyr Asn Asp Thr Pro Tyr
                325                 330                 335
Leu His Asp Asp Gly Asp Asn Met Ile Asn Met Asp Asn Arg Leu Arg
            340                 345                 350
Leu Ser Leu Leu Tyr Ser Leu Ala Lys Pro Leu Asn Gln Arg Ser Gly
        355                 360                 365
Met Asn Pro Leu Ile Thr Asn Ser Leu Val Asn Arg Thr Asp Asp Asn
    370                 375                 380
Ala Glu Thr Ala Ala Val Pro Ser Tyr Ser Phe Ile Arg Ala His Asp
385                 390                 395                 400
Ser Glu Val Gln Asp Leu Ile Arg Asn Ile Ile Arg Ala Glu Ile Asn
                405                 410                 415
Pro Asn Val Val Gly Tyr Ser Phe Thr Met Glu Glu Ile Lys Lys Ala
            420                 425                 430
Phe Glu Ile Tyr Asn Lys Asp Leu Leu Ala Thr Glu Lys Lys Tyr Thr
        435                 440                 445
His Tyr Asn Thr Ala Leu Ser Tyr Ala Leu Leu Leu Thr Asn Lys Ser
    450                 455                 460
Ser Val Pro Arg Val Tyr Tyr Gly Asp Met Phe Thr Asp Asp Gly Gln
465                 470                 475                 480
Tyr Met Ala His Lys Thr Ile Asn Tyr Glu Ala Ile Glu Thr Leu Leu
                485                 490                 495
Lys Ala Arg Ile Lys Tyr Val Ser Gly Gly Gln Ala Met Arg Asn Gln
            500                 505                 510
Gln Val Gly Asn Ser Glu Ile Ile Thr Ser Val Arg Tyr Gly Lys Gly
        515                 520                 525
Ala Leu Lys Ala Thr Asp Thr Gly Asp Arg Thr Thr Arg Thr Ser Gly
    530                 535                 540
Val Ala Val Ile Glu Gly Asn Asn Pro Ser Leu Arg Leu Lys Ala Ser
545                 550                 555                 560
Asp Arg Val Val Val Asn Met Gly Ala Ala His Lys Asn Gln Ala Tyr
                565                 570                 575
```

```
Arg Pro Leu Leu Leu Thr Thr Asp Asn Gly Ile Lys Ala Tyr His Ser
            580                 585                 590

Asp Gln Glu Ala Ala Gly Leu Val Arg Tyr Thr Asn Asp Arg Gly Glu
        595                 600                 605

Leu Ile Phe Thr Ala Ala Asp Ile Lys Gly Tyr Ala Asn Pro Gln Val
        610                 615                 620

Ser Gly Tyr Leu Gly Val Trp Val Pro Val Gly Ala Ala Asp Gln
625                 630                 635                 640

Asp Val Arg Val Ala Ala Ser Thr Ala Pro Ser Thr Asp Gly Lys Ser
            645                 650                 655

Val His Gln Asn Ala Ala Leu Asp Ser Arg Val Met Phe Glu Gly Phe
            660                 665                 670

Ser Asn Phe Gln Ala Phe Ala Thr Lys Lys Glu Glu Tyr Thr Asn Val
        675                 680                 685

Val Ile Ala Lys Asn Val Asp Lys Phe Ala Glu Trp Gly Val Thr Asp
        690                 695                 700

Phe Glu Met Ala Pro Gln Tyr Val Ser Ser Thr Asp Gly Ser Phe Leu
705                 710                 715                 720

Asp Ser Val Ile Gln Asn Gly Tyr Ala Phe Thr Asp Arg Tyr Asp Leu
            725                 730                 735

Gly Ile Ser Lys Pro Asn Lys Tyr Gly Thr Ala Asp Asp Leu Val Lys
            740                 745                 750

Ala Ile Lys Ala Leu His Ser Lys Gly Ile Lys Val Met Ala Asp Trp
            755                 760                 765

Val Pro Asp Gln Met Tyr Ala Phe Pro Glu Lys Glu Val Val Thr Ala
        770                 775                 780

Thr Arg Val Asp Lys Tyr Gly Thr Pro Val Ala Gly Ser Gln Ile Lys
785                 790                 795                 800

Asn Thr Leu Tyr Val Val Asp Gly Lys Ser Ser Gly Lys Asp Gln Gln
            805                 810                 815

Ala Lys Tyr Gly Gly Ala Phe Leu Glu Glu Leu Gln Ala Lys Tyr Pro
        820                 825                 830

Glu Leu Phe Ala Arg Lys Gln Ile Ser Thr Gly Val Pro Met Asp Pro
    835                 840                 845

Ser Val Lys Ile Lys Gln Trp Ser Ala Lys Tyr Phe Asn Gly Thr Asn
850                 855                 860

Ile Leu Gly Arg Gly Ala Gly Tyr Val Leu Lys Asp Gln Ala Thr Asn
865                 870                 875                 880

Thr Tyr Phe Ser Leu Val Ser Asp Asn Thr Phe Leu Pro Lys Ser Leu
            885                 890                 895

Val Asn Pro Asn His Gly Thr Ser Ser Ser Val Thr Gly Leu Val Phe
        900                 905                 910

Asp Gly Lys Gly Tyr Val Tyr Tyr Ser Thr Ser Gly Tyr Gln Ala Lys
        915                 920                 925

Asn Thr Phe Ile Ser Leu Gly Asn Asn Trp Tyr Tyr Phe Asp Asn Asn
        930                 935                 940

Gly Tyr Met Val Thr Gly Ala Gln Ser Ile Asn Gly Ala Asn Tyr Tyr
945                 950                 955                 960

Phe Leu Ser Asn Gly Ile Gln Leu Arg Asn Ala Ile Tyr Asp Asn Gly
            965                 970                 975

Asn Lys Val Leu Ser Tyr Tyr Gly Asn Asp Gly Arg Arg Tyr Glu Asn
            980                 985                 990

Gly Tyr Tyr Leu Phe Gly Gln Gln  Trp Arg Tyr Phe Gln  Asn Gly Ile
```

```
                 995              1000              1005
Met Ala Val Gly Leu Thr Arg Val His Gly Ala Val Gln Tyr Phe
   1010             1015             1020

Asp Ala Ser Gly Phe Gln Ala Lys Gly Gln Phe Ile Thr Thr Ala
   1025             1030             1035

Asp Gly Lys Leu Arg Tyr Phe Asp Arg Asp Ser Gly Asn Gln Ile
   1040             1045             1050

Ser Asn Arg Phe Val Arg Asn Ser Lys Gly Glu Trp Phe Leu Phe
   1055             1060             1065

Asp His Asn Gly Val Ala Val Thr Gly Thr Val Thr Phe Asn Gly
   1070             1075             1080

Gln Arg Leu Tyr Phe Lys Pro Asn Gly Val Gln Ala Lys Gly Glu
   1085             1090             1095

Phe Ile Arg Asp Ala Asp Gly His Leu Arg Tyr Tyr Asp Pro Asn
   1100             1105             1110

Ser Gly Asn Glu Val Arg Asn Arg Phe Val Arg Asn Ser Lys Gly
   1115             1120             1125

Glu Trp Phe Leu Phe Asp His Asn Gly Ile Ala Val Thr Gly Ala
   1130             1135             1140

Arg Val Val Asn Gly Gln Arg Leu Tyr Phe Lys Ser Asn Gly Val
   1145             1150             1155

Gln Ala Lys Gly Glu Leu Ile Thr Glu Arg Lys Gly Arg Ile Lys
   1160             1165             1170

Tyr Tyr Asp Pro Asn Ser Gly Asn Glu Val Arg Asn Arg Tyr Val
   1175             1180             1185

Arg Thr Ser Ser Gly Asn Trp Tyr Tyr Phe Gly Asn Asp Gly Tyr
   1190             1195             1200

Ala Leu Ile Gly Trp His Val Val Glu Gly Arg Arg Val Tyr Phe
   1205             1210             1215

Asp Glu Asn Gly Val Tyr Arg Tyr Ala Ser His Asp Gln Arg Asn
   1220             1225             1230

His Trp Asn Tyr Asp Tyr Arg Arg Asp Phe Gly Arg Gly Ser Ser
   1235             1240             1245

Ser Ala Ile Arg Phe Arg His Ser Arg Asn Gly Phe Phe Asp Asn
   1250             1255             1260

Phe Phe Arg Phe
   1265

<210> SEQ ID NO 43
<211> LENGTH: 3864
<212> TYPE: DNA
<213> ORGANISM: Streptococcus mutans

<400> SEQUENCE: 43
atgattgacg gcaaatacta ctacatcggc agcgacggtc agccaaagaa gaattttgcg      60
ttgacggtta acaataaagt cctgtatttt gacaagaaca cgggtgcgct gaccgacacc     120
agccaatatc agttcaaaca aggtctgacg aagctgaaca acgactacac ccctcacaat     180
cagattgtca actttgaaaa tactagcctg gaaactattg ataactatgt tactgccgac     240
tcttggtatc gtccgaaaga cattctgaag aacggtaaga cgtggaccgc gtcctctgag     300
agcgatctgc gtccgctgct gatgtcctgg tggcctgata gcagaccca gatcgcatac     360 ctgaactaca tgaaccaaca aggcttgggc actggcgaga actataccgc tgatagctct     420
caagagagcc tgaacctggc ggcacaaacc gttcaagtca aaatcgaaac caagatcagc     480
```

```
caaacgcaac agactcagtg gctgcgtgac atcattaact ctttcgttaa gacgcaaccg      540
aactggaata gccaaaccga gtctgacacg agcgctggtg aaaaagatca tttgcagggc      600
ggtgccctgc tgtatagcaa ttcggacaaa accgcatacg caaatagcga ctatcgtctg      660
ctgaaccgta ccccgaccag ccagactggt aagccgaaat acttcgagga caatagcagc      720
ggtggttacg acttcctgtt ggcaaacgat attgataatt ccaatccggt ggtgcaggct      780
gagcagctga attggctgca ttacctgatg aattacggta gcattgtcgc aaatgacccg      840
gaagcgaatt tcgatggtgt ccgtgttgac gcggtggata acgtgaacgc agacctgttg      900
cagatcgcaa gcgattatct gaaagcccat tatggtgttg ataagagcga gaagaatgcg      960
atcaaccacc tgagcatcct ggaagcgtgg tctgacaacg acccacagta taacaaagac     1020
accaaaggtg cccagctgcc gatcgacaac aaactgcgtc tgtcgttgct gtacgcactg     1080
acccgtccgc tggagaagga tgcaagcaac aaaaatgaga ttcgtagcgg tctggagccg     1140
gttattacca attccctgaa taatcgttcc gctgagggca agaactctga acgcatggcg     1200
aattacatct tcatccgtgc tcacgattct gaagttcaaa cggtgatcgc aaagatcatc     1260
aaagcgcaga ttaacccgaa aacggatggc ctgaccttca ccctggatga gctgaaacag     1320
gcgttcaaaa tctataacga ggatatgcgc caggcgaaga agaagtatac ccagagcaat     1380
atcccgacgg catacgccct gatgctgagc aataaggact ccatcacgcg cctgtattac     1440
ggtgatatgt acagcgatga tggccaatac atggcgacca atccccgta ctacgatgcg     1500 attgacaccc tgctgaaggc gcgcattaag tatgccgctg gcggtcagga tatgaagatc     1560
acctacgttg agggtgacaa aagccacatg gactgggact atacgggtgt cctgacgagc     1620
gttcgctacg gcacgggcgc aaacgaagcg accgaccagg gcagcgaagc taccaagacg     1680
caaggtatgg ccgtcatcac ttctaacaac ccgtccctga gctgaatca gaacgacaag     1740 gtcattgtca atatgggcac cgctcacaaa aatcaggaat accgtccgtt gctgctgacc     1800
accaaagacg gtctgaccag ctacaccagc gacgccgctg ccaagagcct gtaccgtaaa     1860
acgaacgata agggcgagtt ggtgttcgat gcaagcgaca ttcagggcta tctgaatccg     1920
caagtgagcg gttacctggc tgtttgggtg cctgtgggtg cgagcgacaa ccaggatgtg     1980
cgtgtcgcgg ccagcaataa agccaatgcg accggccaag tctatgaaag cagcagcgca     2040
ctggatagcc aactgattta tgagggtttt tccaactttc aggacttcgt caccaaggat     2100
tctgattaca ccaataaaaa gatcgcgcaa aatgtccagc tgtttaagag ctggggcgtc     2160
accagctttg agatggctcc gcaatacgtc agcagcgagg acggcagctt tttggacagc     2220
attatccaga acggctatgc gttcgaggat cgttacgacc tggcgatgag caaaaacaac     2280
aaatacggct cccagcagga catgatcaac gcggttaagg cgctgcataa gagcggtatc     2340
caagtgatcg cggactgggt cccggatcaa atctacaatt gccgggtaa agaggtcgtc     2400 accgcgaccc gtgtgaacga ctacggcgag tatcgcaagg actccgaaat caaaaacacc     2460
ctgtacgccg ccaacaccaa agcaacggt aaagattatc aagcaaagta cggtggcgcc     2520
tttttgagcg agctgccgc caaatatccg agcatcttta accgcactca gattagcaat     2580
ggcaagaaga tcgacccgtc tgaaaagatc accgcctgga aggccaaata cttcaatggt     2640
acgaacattt gggtcgcgg cgttggttac gtcttgaaag acaatgccag cgacaagtat     2700
tttgagctga agggcaatca gacttatctg ccgaagcaaa tgacgaataa agaagcctcg     2760
actggtttcg ttaatgacgg caatggtatg accttttaca gcacgagcgg ttatcaagcg     2820
```

-continued

```
aagaacagct tcgttcagga cgcaaaaggc aactggtact actttgacaa caatggccac    2880
atggtttacg gtctgcaaca tctgaacggg aggtgcaat acttcctgag caatggcgtg     2940
caactgcgtg aatccttctt ggaaaatgcc gacggcagca aaaactattt cggtcacctg    3000
ggcaaccgtt atagcaatgg ttactacagc ttcgataatg atagcaaatg gcgctatttc    3060
gatgcgagcg gtgttatggc agtgggtctg aaaactatta acggtaacac ccagtatttc    3120
gatcaagacg gctaccaagt gaagggtgca tggattaccg gcagcgatgg taagaagcgt    3180
tacttcgacg acggtagcgg caatatggca gttaatcgct ttgctaacga caagaatggc    3240
gattggtatt acctgaatag cgacggtatt gcactggtgg gtgttcagac catcaacggc    3300
aaaacgtatt actttggcca agatggtaaa caaatcaaag gcaaaatcat taccgataat    3360
ggtaaactga atactttct ggcgaacagc ggtgagctgg cgcgtaacat ttttgcgacc     3420
gacagccaga acaactggta ttacttcggc tcggatggtg ttgcggttac gggttcgcag    3480
acgattgcgg gtaaaaagtt gtactttgcg tccgacggta acaggtgaa gggtagcttt     3540 gttacttaca atggtaaagt gcactattac catgcggaca cgggcgaact gcaagtcaac    3600
cgtttcgagg cggataaaga cggtaattgg tactatctgg acagcaacgg tgaggcactg    3660
acgggtagcc agcgtatcaa tggtcaacgt gtgtttttca cccgcgaggg caaacaggtt    3720
aagggtgatg tcgcgtatga tgaacgcggc ttgctgcgct attacgacaa aaacagcggt    3780
aatatggtgt acaacaaggt ggtcacgctg gcgaacggtc gtcgtattgg tattgaccgc    3840
tggggtattg ctcgctatta ctaa                                          3864
```

<210> SEQ ID NO 44
<211> LENGTH: 1287
<212> TYPE: PRT
<213> ORGANISM: Streptococcus mutans

<400> SEQUENCE: 44

```
Met Ile Asp Gly Lys Tyr Tyr Ile Gly Ser Asp Gly Gln Pro Lys
1               5                   10                  15

Lys Asn Phe Ala Leu Thr Val Asn Asn Lys Val Leu Tyr Phe Asp Lys
            20                  25                  30

Asn Thr Gly Ala Leu Thr Asp Thr Ser Gln Tyr Gln Phe Lys Gln Gly
        35                  40                  45

Leu Thr Lys Leu Asn Asn Asp Tyr Thr Pro His Asn Gln Ile Val Asn
    50                  55                  60

Phe Glu Asn Thr Ser Leu Glu Thr Ile Asp Asn Tyr Val Thr Ala Asp
65                  70                  75                  80

Ser Trp Tyr Arg Pro Lys Asp Ile Leu Lys Asn Gly Lys Thr Trp Thr
                85                  90                  95

Ala Ser Ser Glu Ser Asp Leu Arg Pro Leu Leu Met Ser Trp Trp Pro
            100                 105                 110

Asp Lys Gln Thr Gln Ile Ala Tyr Leu Asn Tyr Met Asn Gln Gln Gly
        115                 120                 125

Leu Gly Thr Gly Glu Asn Tyr Thr Ala Asp Ser Ser Gln Glu Ser Leu
    130                 135                 140

Asn Leu Ala Ala Gln Thr Val Gln Val Lys Ile Glu Thr Lys Ile Ser
145                 150                 155                 160

Gln Thr Gln Gln Thr Gln Trp Leu Arg Asp Ile Ile Asn Ser Phe Val
                165                 170                 175

Lys Thr Gln Pro Asn Trp Asn Ser Gln Thr Glu Ser Asp Thr Ser Ala
            180                 185                 190
```

```
Gly Glu Lys Asp His Leu Gln Gly Gly Ala Leu Leu Tyr Ser Asn Ser
            195                 200                 205

Asp Lys Thr Ala Tyr Ala Asn Ser Asp Tyr Arg Leu Leu Asn Arg Thr
210                 215                 220

Pro Thr Ser Gln Thr Gly Lys Pro Lys Tyr Phe Glu Asp Asn Ser Ser
225                 230                 235                 240

Gly Gly Tyr Asp Phe Leu Leu Ala Asn Asp Ile Asp Asn Ser Asn Pro
            245                 250                 255

Val Val Gln Ala Glu Gln Leu Asn Trp Leu His Tyr Leu Met Asn Tyr
            260                 265                 270

Gly Ser Ile Val Ala Asn Asp Pro Glu Ala Asn Phe Asp Gly Val Arg
            275                 280                 285

Val Asp Ala Val Asp Asn Val Asn Ala Asp Leu Leu Gln Ile Ala Ser
            290                 295                 300

Asp Tyr Leu Lys Ala His Tyr Gly Val Asp Lys Ser Glu Lys Asn Ala
305                 310                 315                 320

Ile Asn His Leu Ser Ile Leu Glu Ala Trp Ser Asn Asp Pro Gln
                    325                 330                 335

Tyr Asn Lys Asp Thr Lys Gly Ala Gln Leu Pro Ile Asp Asn Lys Leu
            340                 345                 350

Arg Leu Ser Leu Leu Tyr Ala Leu Thr Arg Pro Leu Glu Lys Asp Ala
            355                 360                 365

Ser Asn Lys Asn Glu Ile Arg Ser Gly Leu Glu Pro Val Ile Thr Asn
370                 375                 380

Ser Leu Asn Asn Arg Ser Ala Glu Gly Lys Asn Ser Glu Arg Met Ala
385                 390                 395                 400

Asn Tyr Ile Phe Ile Arg Ala His Asp Ser Glu Val Gln Thr Val Ile
            405                 410                 415

Ala Lys Ile Ile Lys Ala Gln Ile Asn Pro Lys Thr Asp Gly Leu Thr
            420                 425                 430

Phe Thr Leu Asp Glu Leu Lys Gln Ala Phe Lys Ile Tyr Asn Glu Asp
            435                 440                 445

Met Arg Gln Ala Lys Lys Lys Tyr Thr Gln Ser Asn Ile Pro Thr Ala
450                 455                 460

Tyr Ala Leu Met Leu Ser Asn Lys Asp Ser Ile Thr Arg Leu Tyr Tyr
465                 470                 475                 480

Gly Asp Met Tyr Ser Asp Asp Gly Gln Tyr Met Ala Thr Lys Ser Pro
            485                 490                 495

Tyr Tyr Asp Ala Ile Asp Thr Leu Leu Lys Ala Arg Ile Lys Tyr Ala
            500                 505                 510

Ala Gly Gly Gln Asp Met Lys Ile Thr Tyr Val Glu Gly Asp Lys Ser
            515                 520                 525

His Met Asp Trp Asp Tyr Thr Gly Val Leu Thr Ser Val Arg Tyr Gly
530                 535                 540

Thr Gly Ala Asn Glu Ala Thr Asp Gln Gly Ser Glu Ala Thr Lys Thr
545                 550                 555                 560

Gln Gly Met Ala Val Ile Thr Ser Asn Asn Pro Ser Leu Lys Leu Asn
            565                 570                 575

Gln Asn Asp Lys Val Ile Val Asn Met Gly Thr Ala His Lys Asn Gln
            580                 585                 590

Glu Tyr Arg Pro Leu Leu Leu Thr Thr Lys Asp Gly Leu Thr Ser Tyr
            595                 600                 605
```

-continued

```
Thr Ser Asp Ala Ala Lys Ser Leu Tyr Arg Lys Thr Asn Asp Lys
610             615                 620

Gly Glu Leu Val Phe Asp Ala Ser Asp Ile Gln Gly Tyr Leu Asn Pro
625                 630                 635                 640

Gln Val Ser Gly Tyr Leu Ala Val Trp Val Pro Val Gly Ala Ser Asp
                645                 650                 655

Asn Gln Asp Val Arg Val Ala Ala Ser Asn Lys Ala Asn Ala Thr Gly
            660                 665                 670

Gln Val Tyr Glu Ser Ser Ala Leu Asp Ser Gln Leu Ile Tyr Glu
            675                 680                 685

Gly Phe Ser Asn Phe Gln Asp Phe Val Thr Lys Asp Ser Asp Tyr Thr
690                 695                 700

Asn Lys Lys Ile Ala Gln Asn Val Gln Leu Phe Lys Ser Trp Gly Val
705                 710                 715                 720

Thr Ser Phe Glu Met Ala Pro Gln Tyr Val Ser Ser Glu Asp Gly Ser
                725                 730                 735

Phe Leu Asp Ser Ile Ile Gln Asn Gly Tyr Ala Phe Glu Asp Arg Tyr
                740                 745                 750

Asp Leu Ala Met Ser Lys Asn Asn Lys Tyr Gly Ser Gln Gln Asp Met
            755                 760                 765

Ile Asn Ala Val Lys Ala Leu His Lys Ser Gly Ile Gln Val Ile Ala
770                 775                 780

Asp Trp Val Pro Asp Gln Ile Tyr Asn Leu Pro Gly Lys Glu Val Val
785                 790                 795                 800

Thr Ala Thr Arg Val Asn Asp Tyr Gly Glu Tyr Arg Lys Asp Ser Glu
                805                 810                 815

Ile Lys Asn Thr Leu Tyr Ala Ala Asn Thr Lys Ser Asn Gly Lys Asp
            820                 825                 830

Tyr Gln Ala Lys Tyr Gly Gly Ala Phe Leu Ser Glu Leu Ala Ala Lys
            835                 840                 845

Tyr Pro Ser Ile Phe Asn Arg Thr Gln Ile Ser Asn Gly Lys Lys Ile
850                 855                 860

Asp Pro Ser Glu Lys Ile Thr Ala Trp Lys Ala Lys Tyr Phe Asn Gly
865                 870                 875                 880

Thr Asn Ile Leu Gly Arg Gly Val Gly Tyr Val Leu Lys Asp Asn Ala
                885                 890                 895

Ser Asp Lys Tyr Phe Glu Leu Lys Gly Asn Gln Thr Tyr Leu Pro Lys
            900                 905                 910

Gln Met Thr Asn Lys Glu Ala Ser Thr Gly Phe Val Asn Asp Gly Asn
            915                 920                 925

Gly Met Thr Phe Tyr Ser Thr Ser Gly Tyr Gln Ala Lys Asn Ser Phe
930                 935                 940

Val Gln Asp Ala Lys Gly Asn Trp Tyr Tyr Phe Asp Asn Asn Gly His
945                 950                 955                 960

Met Val Tyr Gly Leu Gln His Leu Asn Gly Glu Val Gly Tyr Phe Leu
                965                 970                 975

Ser Asn Gly Val Gln Leu Arg Glu Ser Phe Leu Glu Asn Ala Asp Gly
            980                 985                 990

Ser Lys Asn Tyr Phe Gly His Leu  Gly Asn Arg Tyr Ser  Asn Gly Tyr
            995                 1000                1005

Tyr Ser  Phe Asp Asn Asp Ser  Lys Trp Arg Tyr Phe  Asp Ala Ser
    1010                1015                    1020

Gly Val  Met Ala Val Gly Leu  Lys Thr Ile Asn Gly  Asn Thr Gln
```

-continued

```
              1025                1030                1035
Tyr Phe Asp Gln Asp Gly Tyr Gln Val Lys Gly Ala Trp Ile Thr
      1040                1045                1050
Gly Ser Asp Gly Lys Lys Arg Tyr Phe Asp Asp Gly Ser Gly Asn
      1055                1060                1065
Met Ala Val Asn Arg Phe Ala Asn Asp Lys Asn Gly Asp Trp Tyr
      1070                1075                1080
Tyr Leu Asn Ser Asp Gly Ile Ala Leu Val Gly Val Gln Thr Ile
      1085                1090                1095
Asn Gly Lys Thr Tyr Tyr Phe Gly Gln Asp Gly Lys Gln Ile Lys
      1100                1105                1110
Gly Lys Ile Ile Thr Asp Asn Gly Lys Leu Lys Tyr Phe Leu Ala
      1115                1120                1125
Asn Ser Gly Glu Leu Ala Arg Asn Ile Phe Ala Thr Asp Ser Gln
      1130                1135                1140
Asn Asn Trp Tyr Tyr Phe Gly Ser Asp Gly Val Ala Val Thr Gly
      1145                1150                1155
Ser Gln Thr Ile Ala Gly Lys Lys Leu Tyr Phe Ala Ser Asp Gly
      1160                1165                1170
Lys Gln Val Lys Gly Ser Phe Val Thr Tyr Asn Gly Lys Val His
      1175                1180                1185
Tyr Tyr His Ala Asp Ser Gly Glu Leu Gln Val Asn Arg Phe Glu
      1190                1195                1200
Ala Asp Lys Asp Gly Asn Trp Tyr Tyr Leu Asp Ser Asn Gly Glu
      1205                1210                1215
Ala Leu Thr Gly Ser Gln Arg Ile Asn Gly Gln Arg Val Phe Phe
      1220                1225                1230
Thr Arg Glu Gly Lys Gln Val Lys Gly Asp Val Ala Tyr Asp Glu
      1235                1240                1245
Arg Gly Leu Leu Arg Tyr Tyr Asp Lys Asn Ser Gly Asn Met Val
      1250                1255                1260
Tyr Asn Lys Val Val Thr Leu Ala Asn Gly Arg Arg Ile Gly Ile
      1265                1270                1275
Asp Arg Trp Gly Ile Ala Arg Tyr Tyr
      1280                1285
```

<210> SEQ ID NO 45
<211> LENGTH: 4068
<212> TYPE: DNA
<213> ORGANISM: Streptococcus gallolyticus

<400> SEQUENCE: 45

| | | |
|---|---|---|
| atgatcgacg gcaaatacta ctatattgac gaggacggta acgtaaagaa gaatttcgcg | 60 |
| attacggtgg atggtcagtt gctgtacttc gacgctgaaa cgggtgctct gaccagcacg | 120 |
| tccacctata gcttctccga gggcctgact aatctggtcg ataacttcag cattaacaac | 180 |
| cagtcctacg acagcaccga agagtcgttt gagctgatcg acggttacct gaccgtcaat | 240 |
| acttggtacc gtccgaccaa aattctggaa aacggtgaaa cctgggtcga tagcaccgaa | 300 |
| acggatttcc gtccgctgct gatggcctgg tggccggatg ttgacaccca aattgactac | 360 |
| ttgaactaca tgagcgatta cttcgatctg gtacgaccct atagcgctga cgattcccaa | 420 |
| gcgagcctga atctggcagc tgaggcggtt caggtgaaaa ttgaacaaga aattacccgt | 480 |
| caagagaaca ccgcctggct gcgcgagatc atctctagct tgttaccac ccaggataaa | 540 |

```
tggaatatca ataccgagaa tgagggcacc gaccatctgc aaggtggtgc cctgctgtac    600
gttaacagcg acttgactcc gtgggcaaac agcgattatc gcctgctgaa ccgcaccccg    660
acgtaccaga cgggtgagac taattacttt aaagcagatc gtactggtgg ctacgaattt    720
ctgctggcaa atgacgtgga taattctaac ccggtcgttc aagccgaaca gttgaaccag    780
ctgtactact tgatgaattg gggctctatt gtattcggtg atgacgacgc caattttgat    840
ggcgtgcgtg ttgacgcggt ggacaatgtg aacgctgacc tgttgcagat ttacacgaac    900
ctgttcgaag cggcgtatgg tgttaacgag tctgaggcgc aggccctggc tcacattagc    960
atcctggaag cgtggtctta taacgacccg gactacaacc acgacacgaa tggcgctgcc   1020
ctggcaatcg acaatggtct gcgtctgagc tttctgtact ctttgacgcg ccctacggac   1080
gagcgcagcg gtttggagcc actgatcacc tctgagattg gcctgaccga tcgttccgag   1140
gactctgcat acggtgacac catgccgagc tatgttttcg tccgtgcaca tgacagcgag   1200
gttcagacca ttattgcgag cattatcgca gaacagatca cccggaaaac cgatggctat   1260
accttcaccc tggacgagct gaaccaggcg tttgagattt acaacgcgga tatgaacagc   1320
gtggataaag agtatacgca ttacaatatc ccggctgcgt atagcctgct gctgaccaac   1380
atggaaagcg tcccgcgtgt ttactacggt gacctgtata cggataacgg tcagtacatg   1440
gcgactaaga gcccgtatta tgaccagatc accaccctgc tgcaagcgcg cattcgttac   1500
gcggcgggtg gccaatctat ggctgttacg tactacaccc ctgcgtcgag catgtctacc   1560
gacaatgcgg atagcgtcct gaatgagact ggtgtgctga cttctgtgcg ttacggctat   1620
ggcatcatga ccgccgacca agaggccacg gacgactccg ttctgacctc tggtattgtt   1680
actattatca gcaacaaccc taatttgcag ctggatgatt ccgaagtgat tgcagtccag   1740
gttggtgtgg cgcacgctgg tcagtattat cgtccgctgt tgtacccgac ggcggatggt   1800
ctgcaaagct acctgaacga tagcgatacc gacattacta agctggtcga tgataatggt   1860
tatatctact ttacggcaga tgagattaaa ggctacgaaa cggttgacat gaatggctac   1920
ctgagcgttt gggtcccggt tggtgcagac gagaatcagg acatccgtgt cagcgcagac   1980
accagcgcgt acaccgaggg tgaattgatc tatcaagcaa ccgcagcgct ggatagccaa   2040
gtgatctacg agggtttcag caacttccaa gatttcgtta cctctaacag cgagtacact   2100
aacaagctga tcgcggagaa cgtcgatctg tttaccagct ggggcattac gagctttgag   2160
atggcgccac agtatgtgag caccgatgac ggtacttttc tggatagcat cattcaaaac   2220
ggttatgcat ttgacgatcg ctacgacctg gcaatgagcc agaataacaa gtatggtagc   2280
gctgaagatt tgcgtaatgc catcaaggcc ctgcacgctg ctggcattca ggtcattgct   2340
gactgggtgc cggatcaaat ctattcgctg ccaggcgaag aagtcgttac ggcgactcgc   2400
gtgaatgact atggcgaaga aaccgaaggc gcgtacatta acaatacgtt gtatgtggcg   2460
aacagcaaaa gcagcggcga ggactaccag gcacagtatg tggtgagtt cctggattac   2520 ttgcaagaaa cctacccgga aatgttcgaa gttgcgatga ttagcacggg tgagccgatt   2580
gatccgagca ccaagatcaa gatttggaaa gcagaatact ttaatggtac gaacattctg   2640
ggtaagggcg ctggttacgt gctgagcgat gccgcgactg gcacgtactt taccgtgact   2700
gagaatggca cgtttctgcc gaagcagctg accaccgact ccgccattac gggtttctat   2760
tacgacggta cgggtatgtc ttactttagc acctcgggtt atcgcgctaa agcgagcttc   2820 attgttaca cggctacta ctactatttt gatgataacg gctacatggt cactggcacg   2880
gtggaaatca acggtaagac ctactatttc ctgccgaatg gtattcagct gcgtgatgcg   2940
```

```
atttacgaag acgagaacgg taatcagtac tatttcggtc cgttgggcaa ccagtatttc      3000
aacaactatt acagctttga cgttgaagag gtggtggacg gtgtaacgac tacggtaacg      3060
aagtggcgtc attttgacga gaacggcgtg atggcgcgtg gtttggtcga gattgatggt      3120
gtctaccagt attacgatga aaacggctac caggtcaaag gtgagctgat caccgatgct      3180
gatggtaatt tgcgttattt caaagaagat agcggtgaaa tggttgttag cgattttgtg      3240
aagatcggcg ataacaactg gtactacttt gacgaaaacg gtattgcagt cacgggtgcc      3300
caaaccattg ccggccagaa cttgtatttc gatgacaacg gtgtgcaggc gaaaggtgcc      3360
tttgtcacga acgccgatgg cacgcgcagc tattatgacg cggacagcgg tgagaagatc      3420
gtggcagatt tcttcactac gggcgataat gactggtatt atgcagatga aaatggcaat      3480
ctggtgactg gtagccaaac tatcaatggt caaaacctgt actttgctga ggacggtttg      3540
caggccaagg gtgtgtttgt taccgatacg gctggtaaca ttcactatta tgatgcgaac      3600
tctggcgagt tggcggttaa taccttcgtt ggtgatggcg acgactggta ttactttgat      3660
gagaatggca tcgcagttac cggcgcacaa gtcattaacg gtcaacacct gtatttcgca      3720
gacaacggca tccaagtgaa aggtgaaatc gtcaccgacg caaacggcaa ccgctattac      3780
tacgatgcag attccggcga aatggcagtt aacacctttg tggagattga cggtgtttgg      3840
tactattttg gtgccgatgg tatcgcggtg acgggtgcac aagtaattga tggtcagaat      3900
ttgtacttta acgcagacgg tagccaagtc aagggtgacg ttgtccgtat caacggtttg      3960
cgttactact acgacgctaa tagcggcgaa caggtgcgca atcagtgggt cacgctgccg      4020
gatggtactg ttgttttctt taatgcgcgt ggctatactt ggggctaa                   4068
```

<210> SEQ ID NO 46
<211> LENGTH: 1355
<212> TYPE: PRT
<213> ORGANISM: Streptococcus gallolyticus

<400> SEQUENCE: 46

```
Met Ile Asp Gly Lys Tyr Tyr Ile Asp Glu Asp Gly Asn Val Lys
1               5                   10                  15

Lys Asn Phe Ala Ile Thr Val Asp Gly Gln Leu Leu Tyr Phe Asp Ala
            20                  25                  30

Glu Thr Gly Ala Leu Thr Ser Thr Ser Thr Tyr Ser Phe Ser Glu Gly
        35                  40                  45

Leu Thr Asn Leu Val Asp Asn Phe Ser Ile Asn Asn Gln Ser Tyr Asp
    50                  55                  60

Ser Thr Glu Glu Ser Phe Glu Leu Ile Asp Gly Tyr Leu Thr Val Asn
65                  70                  75                  80

Thr Trp Tyr Arg Pro Thr Lys Ile Leu Glu Asn Gly Glu Thr Trp Val
                85                  90                  95

Asp Ser Thr Glu Thr Asp Phe Arg Pro Leu Leu Met Ala Trp Trp Pro
            100                 105                 110

Asp Val Asp Thr Gln Ile Asp Tyr Leu Asn Tyr Met Ser Asp Tyr Phe
        115                 120                 125

Asp Leu Gly Thr Thr Tyr Ser Ala Asp Asp Ser Gln Ala Ser Leu Asn
    130                 135                 140

Leu Ala Ala Glu Ala Val Gln Val Lys Ile Glu Gln Glu Ile Thr Arg
145                 150                 155                 160

Gln Glu Asn Thr Ala Trp Leu Arg Glu Ile Ile Ser Ser Phe Val Thr
                165                 170                 175
```

```
Thr Gln Asp Lys Trp Asn Ile Asn Thr Glu Asn Glu Gly Thr Asp His
            180                 185                 190

Leu Gln Gly Gly Ala Leu Leu Tyr Val Asn Ser Asp Leu Thr Pro Trp
            195                 200                 205

Ala Asn Ser Asp Tyr Arg Leu Leu Asn Arg Thr Pro Thr Tyr Gln Thr
        210                 215                 220

Gly Glu Thr Asn Tyr Phe Lys Ala Asp Arg Thr Gly Gly Tyr Glu Phe
225                 230                 235                 240

Leu Leu Ala Asn Asp Val Asp Asn Ser Asn Pro Val Val Gln Ala Glu
                245                 250                 255

Gln Leu Asn Gln Leu Tyr Tyr Leu Met Asn Trp Gly Ser Ile Val Phe
            260                 265                 270

Gly Asp Asp Asp Ala Asn Phe Asp Gly Val Arg Val Asp Ala Val Asp
        275                 280                 285

Asn Val Asn Ala Asp Leu Leu Gln Ile Tyr Thr Asn Leu Phe Glu Ala
        290                 295                 300

Ala Tyr Gly Val Asn Glu Ser Glu Ala Gln Ala Leu Ala His Ile Ser
305                 310                 315                 320

Ile Leu Glu Ala Trp Ser Tyr Asn Asp Pro Asp Tyr Asn His Asp Thr
                325                 330                 335

Asn Gly Ala Ala Leu Ala Ile Asp Asn Gly Leu Arg Leu Ser Phe Leu
            340                 345                 350

Tyr Ser Leu Thr Arg Pro Thr Asp Glu Arg Ser Gly Leu Glu Pro Leu
            355                 360                 365

Ile Thr Ser Glu Ile Gly Leu Thr Asp Arg Ser Glu Asp Ser Ala Tyr
            370                 375                 380

Gly Asp Thr Met Pro Ser Tyr Val Phe Val Arg Ala His Asp Ser Glu
385                 390                 395                 400

Val Gln Thr Ile Ile Ala Ser Ile Ile Ala Glu Gln Ile Asn Pro Glu
                405                 410                 415

Thr Asp Gly Tyr Thr Phe Thr Leu Asp Glu Leu Asn Gln Ala Phe Glu
            420                 425                 430

Ile Tyr Asn Ala Asp Met Asn Ser Val Asp Lys Glu Tyr Thr His Tyr
        435                 440                 445

Asn Ile Pro Ala Ala Tyr Ser Leu Leu Leu Thr Asn Met Glu Ser Val
        450                 455                 460

Pro Arg Val Tyr Tyr Gly Asp Leu Tyr Thr Asp Asn Gly Gln Tyr Met
465                 470                 475                 480

Ala Thr Lys Ser Pro Tyr Tyr Asp Gln Ile Thr Thr Leu Leu Gln Ala
                485                 490                 495

Arg Ile Arg Tyr Ala Ala Gly Gly Gln Ser Met Ala Val Thr Tyr Tyr
            500                 505                 510

Thr Pro Ala Ser Ser Met Ser Thr Asp Asn Ala Asp Ser Val Leu Asn
            515                 520                 525

Glu Thr Gly Val Leu Thr Ser Val Arg Tyr Gly Tyr Gly Ile Met Thr
            530                 535                 540

Ala Asp Gln Glu Ala Thr Asp Ser Val Leu Thr Ser Gly Ile Val
545                 550                 555                 560

Thr Ile Ile Ser Asn Asn Pro Asn Leu Gln Leu Asp Asp Ser Glu Val
                565                 570                 575

Ile Ala Val Gln Val Gly Val Ala His Ala Gly Gln Tyr Tyr Arg Pro
            580                 585                 590
```

```
Leu Leu Tyr Pro Thr Ala Asp Gly Leu Gln Ser Tyr Leu Asn Asp Ser
        595                 600                 605

Asp Thr Asp Ile Thr Lys Leu Val Asp Asn Gly Tyr Ile Tyr Phe
610                 615                 620

Thr Ala Asp Glu Ile Lys Gly Tyr Glu Thr Val Asp Met Asn Gly Tyr
625                 630                 635                 640

Leu Ser Val Trp Val Pro Val Ala Asp Glu Asn Gln Asp Ile Arg
                645                 650                 655

Val Ser Ala Asp Thr Ser Ala Tyr Thr Glu Gly Glu Leu Ile Tyr Gln
                660                 665                 670

Ala Thr Ala Ala Leu Asp Ser Gln Val Ile Tyr Glu Gly Phe Ser Asn
        675                 680                 685

Phe Gln Asp Phe Val Thr Ser Asn Ser Glu Tyr Thr Asn Lys Leu Ile
690                 695                 700

Ala Glu Asn Val Asp Leu Phe Thr Ser Trp Gly Ile Thr Ser Phe Glu
705                 710                 715                 720

Met Ala Pro Gln Tyr Val Ser Asp Asp Gly Thr Phe Leu Asp Ser
                725                 730                 735

Ile Ile Gln Asn Gly Tyr Ala Phe Asp Asp Arg Tyr Asp Leu Ala Met
        740                 745                 750

Ser Gln Asn Asn Lys Tyr Gly Ser Ala Glu Asp Leu Arg Asn Ala Ile
        755                 760                 765

Lys Ala Leu His Ala Ala Gly Ile Gln Val Ile Ala Asp Trp Val Pro
        770                 775                 780

Asp Gln Ile Tyr Ser Leu Pro Gly Glu Glu Val Val Thr Ala Thr Arg
785                 790                 795                 800

Val Asn Asp Tyr Gly Glu Glu Thr Glu Gly Ala Tyr Ile Asn Asn Thr
                805                 810                 815

Leu Tyr Val Ala Asn Ser Lys Ser Ser Gly Glu Asp Tyr Gln Ala Gln
                820                 825                 830

Tyr Gly Gly Glu Phe Leu Asp Tyr Leu Gln Glu Thr Tyr Pro Glu Met
        835                 840                 845

Phe Glu Val Ala Met Ile Ser Thr Gly Glu Pro Ile Asp Pro Ser Thr
850                 855                 860

Lys Ile Lys Ile Trp Lys Ala Glu Tyr Phe Asn Gly Thr Asn Ile Leu
865                 870                 875                 880

Gly Lys Gly Ala Gly Tyr Val Leu Ser Asp Ala Ala Thr Gly Thr Tyr
                885                 890                 895

Phe Thr Val Thr Glu Asn Gly Thr Phe Leu Pro Lys Gln Leu Thr Thr
                900                 905                 910

Asp Ser Ala Ile Thr Gly Phe Tyr Tyr Asp Gly Thr Gly Met Ser Tyr
        915                 920                 925

Phe Ser Thr Ser Gly Tyr Arg Ala Lys Ala Ser Phe Ile Val Tyr Asn
930                 935                 940

Gly Tyr Tyr Tyr Tyr Phe Asp Asp Asn Gly Tyr Met Val Thr Gly Thr
945                 950                 955                 960

Val Glu Ile Asn Gly Lys Thr Tyr Tyr Phe Leu Pro Asn Gly Ile Gln
                965                 970                 975

Leu Arg Asp Ala Ile Tyr Glu Asp Glu Asn Gly Asn Gln Tyr Tyr Phe
        980                 985                 990

Gly Pro Leu Gly Asn Gln Tyr Phe  Asn Asn Tyr Tyr Ser  Phe Asp Val
        995                 1000                 1005

Glu Glu  Val Val Asp Gly Val  Thr Thr Thr Val Thr  Lys Trp Arg
```

```
                 1010                1015                1020

His Phe Asp Glu Asn Gly Val Met Ala Arg Gly Leu Val Glu Ile
    1025                1030                1035

Asp Gly Val Tyr Gln Tyr Tyr Asp Glu Asn Gly Tyr Gln Val Lys
    1040                1045                1050

Gly Glu Leu Ile Thr Asp Ala Asp Gly Asn Leu Arg Tyr Phe Lys
    1055                1060                1065

Glu Asp Ser Gly Glu Met Val Val Ser Asp Phe Val Lys Ile Gly
    1070                1075                1080

Asp Asn Asn Trp Tyr Tyr Phe Asp Glu Asn Gly Ile Ala Val Thr
    1085                1090                1095

Gly Ala Gln Thr Ile Ala Gly Gln Asn Leu Tyr Phe Asp Asp Asn
    1100                1105                1110

Gly Val Gln Ala Lys Gly Ala Phe Val Thr Asn Ala Asp Gly Thr
    1115                1120                1125

Arg Ser Tyr Tyr Asp Ala Asp Ser Gly Glu Lys Ile Val Ala Asp
    1130                1135                1140

Phe Phe Thr Thr Gly Asp Asn Asp Trp Tyr Tyr Ala Asp Glu Asn
    1145                1150                1155

Gly Asn Leu Val Thr Gly Ser Gln Thr Ile Asn Gly Gln Asn Leu
    1160                1165                1170

Tyr Phe Ala Glu Asp Gly Leu Gln Ala Lys Gly Val Phe Val Thr
    1175                1180                1185

Asp Thr Ala Gly Asn Ile His Tyr Tyr Asp Ala Asn Ser Gly Glu
    1190                1195                1200

Leu Ala Val Asn Thr Phe Val Gly Asp Gly Asp Trp Tyr Tyr
    1205                1210                1215

Phe Asp Glu Asn Gly Ile Ala Val Thr Gly Ala Gln Val Ile Asn
    1220                1225                1230

Gly Gln His Leu Tyr Phe Ala Asp Asn Gly Ile Gln Val Lys Gly
    1235                1240                1245

Glu Ile Val Thr Asp Ala Asn Gly Asn Arg Tyr Tyr Tyr Asp Ala
    1250                1255                1260

Asp Ser Gly Glu Met Ala Val Asn Thr Phe Val Glu Ile Asp Gly
    1265                1270                1275

Val Trp Tyr Tyr Phe Gly Ala Asp Gly Ile Ala Val Thr Gly Ala
    1280                1285                1290

Gln Val Ile Asp Gly Gln Asn Leu Tyr Phe Asn Ala Asp Gly Ser
    1295                1300                1305

Gln Val Lys Gly Asp Val Val Arg Ile Asn Gly Leu Arg Tyr Tyr
    1310                1315                1320

Tyr Asp Ala Asn Ser Gly Glu Gln Val Arg Asn Gln Trp Val Thr
    1325                1330                1335

Leu Pro Asp Gly Thr Val Val Phe Phe Asn Ala Arg Gly Tyr Thr
    1340                1345                1350

Trp Gly
    1355

<210> SEQ ID NO 47
<211> LENGTH: 4047
<212> TYPE: DNA
<213> ORGANISM: Streptococcus sanguinis

<400> SEQUENCE: 47
```

```
atgatcgatg gcaagaaata ctatgttcag gacgacggta cggtaaagaa gaatttcgcg      60
gttgaactga acggcaaggt cctgtatttc gatgcagaaa ccggtgccct ggtcgacagc     120
gcggagtacc agtttcaaca gggtacgagc tccctgaata acgagttcag ccgcatgaat     180
gcgttccatg gcacgacgga gaaagatatt gaaaccgtcg atggctatct gaccgcagat     240
acgtggtacc gcccgaaggc catcctgaaa gatggcaaaa cctggactca gagcaccgaa     300
accgatctgc gtccgctgct gatggcatgg tggccggaca acaaacgca ggtaagctac      360 ttgaactata tgaaccagca gggtctgggt gcgggtgcgt ttgagaacaa agttgagcag     420
gcaatcttga cgggcgcaag ccagcaggtg cagcgcaaga tcgaagaacg tattggcaaa     480
gacggcgata ccaaatggct gcgtaccctg atgggtgcat ttgtgaaaac ccagccgaat     540
tggaatatca agacggagag cgaaaccacg ggtactaata aggatcatct gcaaggtggt     600
gcgctgctgt acaccaactc tgaaaagacg agccacgcga acagcaaata ccgtattctg     660
aatcgtaccc cgaccaatca gaccggtacg ccgaagtatt tcatcgacaa atcgaatggt     720
ggttacgagt tcttgctggc aaatgatttt gataatagca cccagcagt ccaagcggaa      780 cagctgaatt ggctgcactt tatgatgaat tcggcagca ttgttgcaaa tgacccgacc      840
gcaaacttcg atggcgtgcg tgtggatgcg gtggacaatg ttaatgccga tttgctgcaa     900
attgccagcg actatttcaa atctcgttac aaagtgggcg agagcgaaga caagcgatt      960 aaacatctga gcatcctgga agccggagc gacaacgatc cggactataa caaagacacc     1020
aaaggcgccc aactgccgat cgacaataag ctgcgtctga gcctgttgta cagctttatg     1080
cgtaagctga gcattcgcag cggtgtcgaa ccgacgatta ccaacagcct gaacgaccgt     1140
tctgcggaga agaagaacgg tgagcgcatg gcaaactata tctttgttcg tgccgcatgat    1200 tccgaagtgc agacggtcat tgccgacatt attcgcgaga atatcaatcc gaacacggat     1260
ggtctgacct ttaccatgga cgagctgaaa caggcgttca agatctacaa tgaagatatg     1320
cgcaaggcga taagaagta cccaaattc aatattccga ccgctcacgc gttgatgttg       1380
agcaacaagg attccattac gcgtgtgtac tacggtgacc tgtatacgga tgatggtcag     1440
tatatggaaa agaaaagccc ttattacgac gcgatcgacg cgctgctgcg cgcacgcatt     1500
aagtacgttg cgggtggcca ggacatgaaa gttacctaca tgggtgtgcc gcgtgaaacc     1560
gacaaatgga gctacaacgg catcctgacc agcgtccgct acggcaccgg cgcaaatgag     1620
gctacggacg agggtactgc cgagactcgc acccagggta tggccgtcat cgcaagcaac     1680
aatccgaatt tgaaactgaa cgagtgggat aagttgcagg tcaacatggg tgcggcacac     1740
aagaaccaat actatcgtcc ggtgctgctg accaccaagg acggtattag ccgttacctg     1800
accgacgaag aagttccgca aagcctgtgg aagaaaaccg atgcaaacgg catcttgacg     1860
ttcgacatga acgatatcgc aggttacagc aatgtccaag tatctggcta cttggctgtg     1920
tgggtgccgg ttggtgccaa agcggatcaa gacgcgcgtg ttactgcgtc gaagaagaaa     1980
aacgccagcg gtcaggtgta tgagtccagc gctgcactgg acagccaact gatttatgaa     2040
ggcttctcta acttccaaga cttcgcgacc cgcgacgatc aatacaccaa caaagttatt     2100
gccaaaaatg ttaatctgtt taaagagtgg ggtgtgacca gctttgagct gccacctcag     2160
tatgtttcca gccaggatgg cacgttttg gatagcatca tccagaatgg ctacgcattt      2220
gaagatcgtt atgacatggc gatgagcaaa acaataagt acggtagcct ggacgacctg      2280
ctgaacgcgc tgcgtgcctt gcacagcgtc aacatccaag cgatcgcgga ctgggtcccg     2340
gatcagattt acaacctgcc gggcaaagaa gtggttacgg ctacgcgtgt caacaattat     2400
```

```
ggtacctatc gtgagggtgc ggaaatcaaa gaaaatctgt acgtggcaaa cacgaaaacc    2460
aacggcaccg actatcaagg caaatacggt ggtgcgttcc tggacgaact gaaagcgaaa    2520
tatcctgaga tcttcgaacg tgttcaaatt ccaatggtc aaaagatgac caccgatgag     2580
aagattacga aatggagcgc gaaacacttc aatggtacca acattctggg ccgtggtgca    2640
tactacgtgc tgaaagattg gccagcaat gagtatctga acaataagaa tggtgagatg     2700
gtgttgccga agcaactggt taacaaaaac gcgtacaccg ctttgttaa ggacaccacc     2760
ggttttaagt actatagcac ctcgggctat caagcgcgta atagcttcat ccaagatgag    2820
aacggtaatt ggtactactt tgacaaacgt ggttacctgg cgactggtgc acacgaaatc    2880
gacggcaagc aggtctattt cctgaaaaac ggcattcaac tgcgcgactc tctgcgtgag    2940
gacgagaacg gcaatcagta ctattacgac aagaccggtg cgcaggtgct gaaccgctac    3000
tacaccaccg acggccagaa ctggcgttac ttcgacgcca aggtgttat ggcgcgtggc     3060
ctggttacca tggtggtaa ccaacaattc ttcgaccaga acggttatca ggtgaaaggc     3120
aagatcgcgc gtgccaagga tggtaaactg cgctacttcg acaaagacag cggtaacgca   3180
gcggcgaatc gctttgcaca gggcgataat ccgagcgatt ggtattactt tggtgccgat   3240
ggcgtcgctg ttaccggttt gcaaaaactg ggtcaacaaa ctctgtactt tgatcaagaa   3300
ggtaaacaag tgaagggcaa gattgtcacg ctggctgata agtccatccg ttacttcgat   3360
gcgaacagcg gcgagatggc tgtcggtaag tttgctgagg gtagcaagaa cgaatggtac   3420
tatttcgatc agacgggcaa agcggttacg ggtctgcaaa agattggcca gcagaccctg   3480
tattttgacc aagatggtaa gcaggtaaag ggtaaagtgg taaccctggc agataagtcg   3540
attcgctact tgatgcaaa ctccggcgaa atggcggtgg gtaagttcgc cgagggtgct    3600
aagaatgagt ggtactactt tgaccaggcg ggcaaggcgg tgaccggctt gcagaaaatt   3660
ggtcagcaaa cgctgtattt tgatcaggac ggcaaacaag tcaaaggcca actggtgacg   3720
ctggcggaca agagcattcg ttatttcgac gcaaacagcg gtgagatggc ctctaacaag   3780
ttcgttgagg gtgccaaaaa cgaatggtac tatttcgacc aagccggtaa agcagtgacc   3840
ggtctgcaac aaatcggtca gcagaccttg tacttcgacc aaaacggtaa acaggtcaaa   3900
ggtaaaatcg tgtatgttaa cggtgccaat cgttactttg acgccaattc gggtgaaatg   3960
gcgcgcaata gtggatcca actggaagat ggtagctgga tgtacttcga tcgtaacggt   4020
cgtggtcgtc gtttcggctg aattaa                                        4047
```

<210> SEQ ID NO 48
<211> LENGTH: 1348
<212> TYPE: PRT
<213> ORGANISM: Streptococcus sanguinis

<400> SEQUENCE: 48

```
Met Ile Asp Gly Lys Lys Tyr Tyr Val Gln Asp Gly Thr Val Lys
1               5                   10                  15

Lys Asn Phe Ala Val Glu Leu Asn Gly Lys Val Leu Tyr Phe Asp Ala
                20                  25                  30

Glu Thr Gly Ala Leu Val Asp Ser Ala Glu Tyr Gln Phe Gln Gln Gly
            35                  40                  45

Thr Ser Ser Leu Asn Asn Glu Phe Ser Arg Met Asn Ala Phe His Gly
        50                  55                  60

Thr Thr Glu Lys Asp Ile Glu Thr Val Asp Gly Tyr Leu Thr Ala Asp
65                  70                  75                  80
```

```
Thr Trp Tyr Arg Pro Lys Ala Ile Leu Lys Asp Gly Lys Thr Trp Thr
                85                  90                  95
Gln Ser Thr Glu Thr Asp Leu Arg Pro Leu Leu Met Ala Trp Trp Pro
            100                 105                 110
Asp Lys Gln Thr Gln Val Ser Tyr Leu Asn Tyr Met Asn Gln Gln Gly
        115                 120                 125
Leu Gly Ala Gly Ala Phe Glu Asn Lys Val Glu Gln Ala Ile Leu Thr
    130                 135                 140
Gly Ala Ser Gln Gln Val Gln Arg Lys Ile Glu Arg Ile Gly Lys
145                 150                 155                 160
Asp Gly Asp Thr Lys Trp Leu Arg Thr Leu Met Gly Ala Phe Val Lys
                165                 170                 175
Thr Gln Pro Asn Trp Asn Ile Lys Thr Glu Ser Glu Thr Thr Gly Thr
            180                 185                 190
Asn Lys Asp His Leu Gln Gly Gly Ala Leu Leu Tyr Thr Asn Ser Glu
        195                 200                 205
Lys Thr Ser His Ala Asn Ser Lys Tyr Arg Ile Leu Asn Arg Thr Pro
    210                 215                 220
Thr Asn Gln Thr Gly Thr Pro Lys Tyr Phe Ile Asp Lys Ser Asn Gly
225                 230                 235                 240
Gly Tyr Glu Phe Leu Leu Ala Asn Asp Phe Asp Asn Ser Asn Pro Ala
                245                 250                 255
Val Gln Ala Glu Gln Leu Asn Trp Leu His Phe Met Met Asn Phe Gly
            260                 265                 270
Ser Ile Val Ala Asn Asp Pro Thr Ala Asn Phe Asp Gly Val Arg Val
        275                 280                 285
Asp Ala Val Asp Asn Val Asn Ala Asp Leu Leu Gln Ile Ala Ser Asp
    290                 295                 300
Tyr Phe Lys Ser Arg Tyr Lys Val Gly Glu Ser Glu Gln Ala Ile
305                 310                 315                 320
Lys His Leu Ser Ile Leu Glu Ala Trp Ser Asp Asn Asp Pro Asp Tyr
                325                 330                 335
Asn Lys Asp Thr Lys Gly Ala Gln Leu Pro Ile Asp Asn Lys Leu Arg
            340                 345                 350
Leu Ser Leu Leu Tyr Ser Phe Met Arg Lys Leu Ser Ile Arg Ser Gly
        355                 360                 365
Val Glu Pro Thr Ile Thr Asn Ser Leu Asn Asp Arg Ser Ala Glu Lys
    370                 375                 380
Lys Asn Gly Glu Arg Met Ala Asn Tyr Ile Phe Val Arg Ala His Asp
385                 390                 395                 400
Ser Glu Val Gln Thr Val Ile Ala Asp Ile Ile Arg Glu Asn Ile Asn
                405                 410                 415
Pro Asn Thr Asp Gly Leu Thr Phe Thr Met Asp Glu Leu Lys Gln Ala
            420                 425                 430
Phe Lys Ile Tyr Asn Glu Asp Met Arg Lys Ala Asp Lys Lys Tyr Thr
        435                 440                 445
Gln Phe Asn Ile Pro Thr Ala His Ala Leu Met Leu Ser Asn Lys Asp
    450                 455                 460
Ser Ile Thr Arg Val Tyr Tyr Gly Asp Leu Tyr Thr Asp Asp Gly Gln
465                 470                 475                 480
Tyr Met Glu Lys Lys Ser Pro Tyr Tyr Asp Ala Ile Asp Ala Leu Leu
                485                 490                 495
```

```
Arg Ala Arg Ile Lys Tyr Val Ala Gly Gln Asp Met Lys Val Thr
                500                 505                 510
Tyr Met Gly Val Pro Arg Glu Thr Asp Lys Trp Ser Tyr Asn Gly Ile
        515                 520                 525
Leu Thr Ser Val Arg Tyr Gly Thr Gly Ala Asn Glu Ala Thr Asp Glu
        530                 535                 540
Gly Thr Ala Glu Thr Arg Thr Gln Gly Met Ala Val Ile Ala Ser Asn
545                 550                 555                 560
Asn Pro Asn Leu Lys Leu Asn Glu Trp Asp Lys Leu Gln Val Asn Met
                565                 570                 575
Gly Ala Ala His Lys Asn Gln Tyr Tyr Arg Pro Val Leu Leu Thr Thr
                580                 585                 590
Lys Asp Gly Ile Ser Arg Tyr Leu Thr Asp Glu Glu Val Pro Gln Ser
                595                 600                 605
Leu Trp Lys Lys Thr Asp Ala Asn Gly Ile Leu Thr Phe Asp Met Asn
                610                 615                 620
Asp Ile Ala Gly Tyr Ser Asn Val Gln Val Ser Gly Tyr Leu Ala Val
625                 630                 635                 640
Trp Val Pro Val Gly Ala Lys Ala Asp Gln Asp Ala Arg Val Thr Ala
                645                 650                 655
Ser Lys Lys Lys Asn Ala Ser Gly Gln Val Tyr Glu Ser Ser Ala Ala
                660                 665                 670
Leu Asp Ser Gln Leu Ile Tyr Glu Gly Phe Ser Asn Phe Gln Asp Phe
                675                 680                 685
Ala Thr Arg Asp Asp Gln Tyr Thr Asn Lys Val Ile Ala Lys Asn Val
                690                 695                 700
Asn Leu Phe Lys Glu Trp Gly Val Thr Ser Phe Glu Leu Pro Pro Gln
705                 710                 715                 720
Tyr Val Ser Ser Gln Asp Gly Thr Phe Leu Asp Ser Ile Ile Gln Asn
                725                 730                 735
Gly Tyr Ala Phe Glu Asp Arg Tyr Asp Met Ala Met Ser Lys Asn Asn
                740                 745                 750
Lys Tyr Gly Ser Leu Asp Asp Leu Leu Asn Ala Leu Arg Ala Leu His
                755                 760                 765
Ser Val Asn Ile Gln Ala Ile Ala Asp Trp Val Pro Asp Gln Ile Tyr
                770                 775                 780
Asn Leu Pro Gly Lys Glu Val Val Thr Ala Thr Arg Val Asn Asn Tyr
785                 790                 795                 800
Gly Thr Tyr Arg Glu Gly Ala Glu Ile Lys Glu Asn Leu Tyr Val Ala
                805                 810                 815
Asn Thr Lys Thr Asn Gly Thr Asp Tyr Gln Gly Lys Tyr Gly Gly Ala
                820                 825                 830
Phe Leu Asp Glu Leu Lys Ala Lys Tyr Pro Glu Ile Phe Glu Arg Val
                835                 840                 845
Gln Ile Ser Asn Gly Gln Lys Met Thr Thr Asp Glu Lys Ile Thr Lys
                850                 855                 860
Trp Ser Ala Lys His Phe Asn Gly Thr Asn Ile Leu Gly Arg Gly Ala
865                 870                 875                 880
Tyr Tyr Val Leu Lys Asp Trp Ala Ser Asn Glu Tyr Leu Asn Asn Lys
                885                 890                 895
Asn Gly Glu Met Val Leu Pro Lys Gln Leu Val Asn Lys Asn Ala Tyr
                900                 905                 910
Thr Gly Phe Val Lys Asp Thr Thr Gly Phe Lys Tyr Tyr Ser Thr Ser
```

```
              915                 920                 925
    Gly Tyr Gln Ala Arg Asn Ser Phe Ile Gln Asp Glu Asn Gly Asn Trp
        930                 935                 940

Tyr Tyr Phe Asp Lys Arg Gly Tyr Leu Ala Thr Gly Ala His Glu Ile
    945                 950                 955                 960

Asp Gly Lys Gln Val Tyr Phe Leu Lys Asn Gly Ile Gln Leu Arg Asp
                    965                 970                 975

Ser Leu Arg Glu Asp Glu Asn Gly Asn Gln Tyr Tyr Asp Lys Thr
            980                 985                 990

Gly Ala Gln Val Leu Asn Arg Tyr  Tyr Thr Thr Asp Gly  Gln Asn Trp
                995                 1000                1005

Arg Tyr  Phe Asp Ala Lys Gly  Val Met Ala Arg Gly  Leu Val Thr
        1010                1015                1020

Met Gly  Gly Asn Gln Gln Phe  Phe Asp Gln Asn Gly  Tyr Gln Val
        1025                1030                1035

Lys Gly  Lys Ile Ala Arg Ala  Lys Asp Gly Lys Leu  Arg Tyr Phe
        1040                1045                1050

Asp Lys  Asp Ser Gly Asn Ala  Ala Ala Asn Arg Phe  Ala Gln Gly
        1055                1060                1065

Asp Asn  Pro Ser Asp Trp Tyr  Tyr Phe Gly Ala Asp  Gly Val Ala
        1070                1075                1080

Val Thr  Gly Leu Gln Lys Leu  Gly Gln Gln Thr Leu  Tyr Phe Asp
        1085                1090                1095

Gln Glu  Gly Lys Gln Val Lys  Gly Lys Ile Val Thr  Leu Ala Asp
        1100                1105                1110

Lys Ser  Ile Arg Tyr Phe Asp  Ala Asn Ser Gly Glu  Met Ala Val
        1115                1120                1125

Gly Lys  Phe Ala Glu Gly Ser  Lys Asn Glu Trp Tyr  Tyr Phe Asp
        1130                1135                1140

Gln Thr  Gly Lys Ala Val Thr  Gly Leu Gln Lys Ile  Gly Gln Gln
        1145                1150                1155

Thr Leu  Tyr Phe Asp Gln Asp  Gly Lys Gln Val Lys  Gly Lys Val
        1160                1165                1170

Val Thr  Leu Ala Asp Lys Ser  Ile Arg Tyr Phe Asp  Ala Asn Ser
        1175                1180                1185

Gly Glu  Met Ala Val Gly Lys  Phe Ala Glu Gly Ala  Lys Asn Glu
        1190                1195                1200

Trp Tyr  Tyr Phe Asp Gln Ala  Gly Lys Ala Val Thr  Gly Leu Gln
        1205                1210                1215

Lys Ile  Gly Gln Gln Thr Leu  Tyr Phe Asp Gln Asp  Gly Lys Gln
        1220                1225                1230

Val Lys  Gly Gln Leu Val Thr  Leu Ala Asp Lys Ser  Ile Arg Tyr
        1235                1240                1245

Phe Asp  Ala Asn Ser Gly Glu  Met Ala Ser Asn Lys  Phe Val Glu
        1250                1255                1260

Gly Ala  Lys Asn Glu Trp Tyr  Tyr Phe Asp Gln Ala  Gly Lys Ala
        1265                1270                1275

Val Thr  Gly Leu Gln Gln Ile  Gly Gln Gln Thr Leu  Tyr Phe Asp
        1280                1285                1290

Gln Asn  Gly Lys Gln Val Lys  Gly Lys Ile Val Tyr  Val Asn Gly
        1295                1300                1305

Ala Asn  Arg Tyr Phe Asp Ala  Asn Ser Gly Glu Met  Ala Arg Asn
        1310                1315                1320
```

Lys Trp Ile Gln Leu Glu Asp Gly Ser Trp Met Tyr Phe Asp Arg
    1325                1330                1335

Asn Gly Arg Gly Arg Arg Phe Gly Trp Asn
    1340                1345

<210> SEQ ID NO 49
<211> LENGTH: 4284
<212> TYPE: DNA
<213> ORGANISM: Streptococcus salivarius

<400> SEQUENCE: 49

| | | | | |
|---|---|---|---|---|
| atgaaggatg | gcaaatacta | ctacttgttg | gaagatggct | cgcacaaaaa gaatttcgca | 60 |
| atcaccgtca | atggtcaagt | gctgtatttt | gacgagaacg | gtgcgctgag cagcaccagc | 120 |
| acgtacagct | tcacgcagga | aaccaccaat | ctggttacgg | actttacgaa gaataatgcg | 180 |
| gcgtatgact | ccacgaaagc | gtctttcgaa | ttggtggacg | gctatctgac cgcagacagc | 240 |
| tggtatcgcc | cgaaagagat | tctggaagcc | ggcaccacct | ggaaggcgag caccgaaaag | 300 |
| gacttccgtc | cgctgctgat | gtcctggtgg | ccggataagg | acacgcaagt tgcttatctg | 360 |
| aattacatga | cgaaagcact | gtcgaacggc | gaagaaacca | aggatgtctt tacgatcgaa | 420 |
| aacagccaag | cgagcctgaa | tgcggcagcg | caaatcctgc | aacgtaagat tgaggtcaag | 480 |
| attgcggcca | acaagagcac | cgactggctg | cgccaaagca | tcgaggcgtt tgtcaaagac | 540 |
| caagataagt | ggaatatcaa | tagcgaaagc | cctggcaaag | agcatttcca aagggtgcg | 600 |
| ctgctgtttg | ttaatagcga | cagcaccaag | tgggcgaact | ccgattatcg taaactgaat | 660 |
| cagaccgcga | cgtcttacat | caagaatcat | aagatcgtga | acggtagcga tggtggttac | 720 |
| gagttcttgc | tgagcaacga | catcgacaac | agcaacccgg | tggtccaggc agagatgctg | 780 |
| aatcaactgt | actactttat | gaactggggt | cagattgtgt | tcggcgataa agataaagac | 840 |
| gcacatttcg | atggcatccg | tgtgacgcg | gtggacaatg | ttagcgttga catgctgcaa | 900 |
| ctggtcagca | gctacatgaa | ggcggcatac | aaggtcaatg | aatctgaagc ccgtgcgctg | 960 |
| gcgaatatca | gcattttgga | agcgtggagc | cataatgacc | cgtattatgt gaacgagcac | 1020 |
| aatacggcag | cactgagcat | ggataacggt | ctgcgtctgt | ctattgtgca tggtctgacg | 1080 |
| cgtccggtga | ctaacaaagg | cacgggtgct | cgtaacgcca | gcatgaagga cctgatcaac | 1140 |
| ggcggttact | ttggcttgag | caaccgtgcg | gaagttacta | gctacgacca gctgggcttt | 1200 |
| gccacttacc | tgtttgtgcg | tgcgcatgac | agcgaggttc | agacggttat cgctgatatt | 1260 |
| atttctaaaa | agattgaccc | gaccaccgac | ggttttacct | ttaccctgga ccagctgaag | 1320 |
| caggcttttg | atatttataa | cgcggacatg | ttgaaggttg | ataaagagta tacgcatagc | 1380 |
| aacatcccgg | ctgcgtatgc | gctgatgctg | caaacgatgg | gtgcagcgac cgcgtgtat | 1440 |
| tacggcgatc | tgtacactga | taacggccaa | tacatggcga | aaaagagccc gtattttgat | 1500 |
| cagattacca | cgctgttgaa | ggcccgtccg | aagtacgtgg | cgggtggcca gacgagctac | 1560 |
| atccacaacc | tggcaggcga | tggtgtcagc | tcggccaaag | ataacaaaga ggttctggtt | 1620 |
| agcgtgcgct | acggtcagga | tctgatgagc | aaaacggata | ctgagggcgg taaatacggt | 1680 |
| cgtaacagcg | gtatgctgac | tctgatcgcg | aacaacccgg | acctgaagct ggccgatggt | 1740 |
| gagactatca | cggttaacat | gggtgctgcc | cacaaaaatc | aggcgtatcg tccgttgctg | 1800 |
| ctgggcacgg | aaaagggtat | tgtcagcagc | ctgaacgata | gcgacaccaa atcgtgaag | 1860 |
| tatacggacg | cccaaggtaa | cctggttttc | accgccgacg | agatcaaggg cttcaaaacc | 1920 |

-continued

```
gtggacatgt ctggctacct gtctgtttgg gttccggttg gtgccacgga tgaccagaac   1980
gtcctggcga aaccgagcac caaagcatac aaagaaggtg ataaggttta cagcagcagc   2040
gcggctctgg aagctcaggt tatctatgaa ggttttagca atttccagga tttcgtgaaa   2100
gaagatagcc agtataccaa taagctgatt gcggctaatg cggacctgtt taagagctgg   2160
ggtatcacga gctttgagat cgcaccgcaa tatgtgagca gcaaagatgg tacttttctg   2220
gacagcatca ttgaaaatgg ttacgcgttc accgatcgtt atgacttcgc gatgagcaag   2280
aacaataagt atggtagcaa agaggatctg cgcgacgcgc tgaaggcact gcacaaacaa   2340
ggcatccaag tcatcgcgga ttgggtgccg gatcagctgt atccctgccc gggcaaagag   2400
gtggttacgg caacccgtac cgatacgcac ggtaaagtgc tggatgacac gagcctggtg   2460
aataaactgt atgtgaccaa tacgaagtct agcggtaacg atttccaggc acagtatggt   2520
ggtgcgttcc tggataaact gcaaaagctg tacccagaga ttttcaaaga agttatggaa   2580
gcgtccggca agaccatcga cccaagcgtc aagattaaac aatgggaagc taaatacttt   2640
aatggcacga atattcaaaa gcgtggttcc gattatgttc tgagcgatgg caaactgtac   2700
tttacggtta acgataaggg caccttcctg cctgctgccc tgacgggtga caccaaggct   2760
aaaacgggtt ttgcctacga tggtacgggt gtcacgtatt acactaccag cggtactcaa   2820
gctaagagcc agtttgtgac gtataatggt aagcaatact acttcaacga caagggttac   2880
ttggttaccg cgagcagac gattgatggc tccaactatt cttcctgcc gaatggtgtt   2940
atgtttaccg atggtgtgcg taaaaacgcg aagggtcaga gcctggttta tggcaagtct   3000
ggtaagctga ccacgcaaac gggctggaaa gaagtgaccg ttaaagatga tagcggcaaa   3060
gaagaaaagt tttaccagta tttcttcaag ggtggcatca tggcgaccgg cctgacggaa   3120
gttgaaggta aagagaagta tttctatgac aatggctacc aggctaaagg cgtcttttgtc   3180
ccgaccaaag acggccacct gatgttcttt tgcggcgaca gcggtgagcg taaatacagc   3240
ggtttctttg aacaagacgg taactggtac tatgcgaatg acaagggcta cgtcgcgacc   3300
ggctttacca aggtgggtaa acaaaatctg tatttcaatg agaaaggcgt ccaggtcaaa   3360
aaccgctttt tccaagtggg tgacgccacc tattacgcga taacgagggg cgacgtgctg   3420
cgtggtgcgc aaaccatcaa tggtgatgag ctgtacttcg acgaaagcgg caaacaagtt   3480
aagggtgagt cgtgaataa cccagacggc acgacctctt actatgatgc gatcacgggc   3540
gttaagctgg tcgataccct gctggttgtt gatggtcaga cgttcaacgt ggatgcgaag   3600
ggtgtcgtaa ccaaggcgca cacgccgggt ttctacacca cgggcgacaa caactggttc   3660
tacgcagata gctatggtcg taatgttacc ggtgcgcaag taatcaacgg ccaacacctg   3720
tatttcgatg caaatggtcg tcaagtgaaa ggcggctttg tcacgaacac ggacggtagc   3780
cgtagctttt accactggaa taccggcgac aaactggtgt ccacgttctt tgcgacgggt   3840
cacgatcgct ggtactacgc tgatgatcgt ggcaacgtcg tcacgggtgc acaggtcatc   3900
aacggtcaga agctgttctt tgacaccgat ggtaaacaag tcaaaggtgc tttcgcgacc   3960
aacgcgaatg gttcccgtag ctattatcat tggaatacgg caacaagct ggtgagcacc   4020
ttcttcacct cgggtgacaa taactggtat tacgcggacg ccaaaggtga ggttgtggtc   4080
ggtgaacaga cgattaatgg ccagcacctg tactttgacc agactggcaa gcaagtgaag   4140
ggcgcgactg caacgaaccc ggacggctcg atcagctatt atgatgtgca cacgggtgaa   4200
aaggctatca atcgttgggt gaagattccg agcggtcaat gggtgtactt caatgcgcag   4260
ggcaaaggtt acgtcagcaa ctaa                                         4284
```

<210> SEQ ID NO 50
<211> LENGTH: 1427
<212> TYPE: PRT
<213> ORGANISM: Streptococcus salivarius

<400> SEQUENCE: 50

```
Met Lys Asp Gly Lys Tyr Tyr Leu Leu Glu Asp Gly Ser His Lys
1               5                   10                  15

Lys Asn Phe Ala Ile Thr Val Asn Gly Gln Val Leu Tyr Phe Asp Glu
            20                  25                  30

Asn Gly Ala Leu Ser Ser Thr Ser Tyr Ser Phe Thr Gln Glu Thr
        35                  40                  45

Thr Asn Leu Val Thr Asp Phe Thr Lys Asn Asn Ala Ala Tyr Asp Ser
    50                  55                  60

Thr Lys Ala Ser Phe Glu Leu Val Asp Gly Tyr Leu Thr Ala Asp Ser
65                  70                  75                  80

Trp Tyr Arg Pro Lys Glu Ile Leu Glu Ala Gly Thr Thr Trp Lys Ala
                85                  90                  95

Ser Thr Glu Lys Asp Phe Arg Pro Leu Leu Met Ser Trp Trp Pro Asp
            100                 105                 110

Lys Asp Thr Gln Val Ala Tyr Leu Asn Tyr Met Thr Lys Ala Leu Ser
        115                 120                 125

Asn Gly Glu Glu Thr Lys Asp Val Phe Thr Ile Glu Asn Ser Gln Ala
    130                 135                 140

Ser Leu Asn Ala Ala Ala Gln Ile Leu Gln Arg Lys Ile Glu Val Lys
145                 150                 155                 160

Ile Ala Ala Asn Lys Ser Thr Asp Trp Leu Arg Gln Ser Ile Glu Ala
                165                 170                 175

Phe Val Lys Asp Gln Asp Lys Trp Asn Ile Asn Ser Glu Ser Pro Gly
            180                 185                 190

Lys Glu His Phe Gln Lys Gly Ala Leu Leu Phe Val Asn Ser Asp Ser
        195                 200                 205

Thr Lys Trp Ala Asn Ser Asp Tyr Arg Lys Leu Asn Gln Thr Ala Thr
    210                 215                 220

Ser Tyr Ile Lys Asn His Lys Ile Val Asn Gly Ser Asp Gly Gly Tyr
225                 230                 235                 240

Glu Phe Leu Leu Ser Asn Asp Ile Asp Asn Ser Asn Pro Val Val Gln
                245                 250                 255

Ala Glu Met Leu Asn Gln Leu Tyr Tyr Phe Met Asn Trp Gly Gln Ile
            260                 265                 270

Val Phe Gly Asp Lys Asp Lys Asp Ala His Phe Asp Gly Ile Arg Val
        275                 280                 285

Asp Ala Val Asp Asn Val Ser Val Asp Met Leu Gln Leu Val Ser Ser
    290                 295                 300

Tyr Met Lys Ala Ala Tyr Lys Val Asn Glu Ser Glu Ala Arg Ala Leu
305                 310                 315                 320

Ala Asn Ile Ser Ile Leu Glu Ala Trp Ser His Asn Asp Pro Tyr Tyr
                325                 330                 335

Val Asn Glu His Asn Thr Ala Ala Leu Ser Met Asp Asn Gly Leu Arg
            340                 345                 350

Leu Ser Ile Val His Gly Leu Thr Arg Pro Val Thr Asn Lys Gly Thr
        355                 360                 365

Gly Ala Arg Asn Ala Ser Met Lys Asp Leu Ile Asn Gly Gly Tyr Phe
```

```
            370                 375                 380
Gly Leu Ser Asn Arg Ala Glu Val Thr Ser Tyr Asp Gln Leu Gly Phe
385                 390                 395                 400

Ala Thr Tyr Leu Phe Val Arg Ala His Asp Ser Glu Val Gln Thr Val
                405                 410                 415

Ile Ala Asp Ile Ile Ser Lys Lys Ile Asp Pro Thr Thr Asp Gly Phe
                420                 425                 430

Thr Phe Thr Leu Asp Gln Leu Lys Gln Ala Phe Asp Ile Tyr Asn Ala
            435                 440                 445

Asp Met Leu Lys Val Asp Lys Glu Tyr Thr His Ser Asn Ile Pro Ala
        450                 455                 460

Ala Tyr Ala Leu Met Leu Gln Thr Met Gly Ala Ala Thr Arg Val Tyr
465                 470                 475                 480

Tyr Gly Asp Leu Tyr Thr Asp Asn Gly Gln Tyr Met Ala Lys Lys Ser
                485                 490                 495

Pro Tyr Phe Asp Gln Ile Thr Thr Leu Leu Lys Ala Arg Pro Lys Tyr
                500                 505                 510

Val Ala Gly Gly Gln Thr Ser Tyr Ile His Asn Leu Ala Gly Asp Gly
                515                 520                 525

Val Ser Ser Ala Lys Asp Asn Lys Glu Val Leu Val Ser Val Arg Tyr
        530                 535                 540

Gly Gln Asp Leu Met Ser Lys Thr Asp Thr Glu Gly Gly Lys Tyr Gly
545                 550                 555                 560

Arg Asn Ser Gly Met Leu Thr Leu Ile Ala Asn Asn Pro Asp Leu Lys
                565                 570                 575

Leu Ala Asp Gly Glu Thr Ile Thr Val Asn Met Gly Ala Ala His Lys
                580                 585                 590

Asn Gln Ala Tyr Arg Pro Leu Leu Leu Gly Thr Glu Lys Gly Ile Val
        595                 600                 605

Ser Ser Leu Asn Asp Ser Asp Thr Lys Ile Val Lys Tyr Thr Asp Ala
610                 615                 620

Gln Gly Asn Leu Val Phe Thr Ala Asp Glu Ile Lys Gly Phe Lys Thr
625                 630                 635                 640

Val Asp Met Ser Gly Tyr Leu Ser Val Trp Val Pro Val Gly Ala Thr
                645                 650                 655

Asp Asp Gln Asn Val Leu Ala Lys Pro Ser Thr Lys Ala Tyr Lys Glu
                660                 665                 670

Gly Asp Lys Val Tyr Ser Ser Ala Ala Leu Glu Ala Gln Val Ile
            675                 680                 685

Tyr Glu Gly Phe Ser Asn Phe Gln Asp Phe Val Lys Glu Asp Ser Gln
690                 695                 700

Tyr Thr Asn Lys Leu Ile Ala Ala Asn Ala Asp Leu Phe Lys Ser Trp
705                 710                 715                 720

Gly Ile Thr Ser Phe Glu Ile Ala Pro Gln Tyr Val Ser Ser Lys Asp
                725                 730                 735

Gly Thr Phe Leu Asp Ser Ile Ile Glu Asn Gly Tyr Ala Phe Thr Asp
                740                 745                 750

Arg Tyr Asp Phe Ala Met Ser Lys Asn Lys Tyr Gly Ser Lys Glu
            755                 760                 765

Asp Leu Arg Asp Ala Leu Lys Ala Leu His Lys Gln Gly Ile Gln Val
        770                 775                 780

Ile Ala Asp Trp Val Pro Asp Gln Leu Tyr Thr Leu Pro Gly Lys Glu
785                 790                 795                 800
```

```
-continued

Val Val Thr Ala Thr Arg Thr Asp Thr His Gly Lys Val Leu Asp Asp
            805                 810                 815

Thr Ser Leu Val Asn Lys Leu Tyr Val Thr Asn Thr Lys Ser Ser Gly
            820                 825                 830

Asn Asp Phe Gln Ala Gln Tyr Gly Gly Ala Phe Leu Asp Lys Leu Gln
            835                 840                 845

Lys Leu Tyr Pro Glu Ile Phe Lys Glu Val Met Glu Ala Ser Gly Lys
            850                 855                 860

Thr Ile Asp Pro Ser Val Lys Ile Lys Gln Trp Glu Ala Lys Tyr Phe
865                 870                 875                 880

Asn Gly Thr Asn Ile Gln Lys Arg Gly Ser Asp Tyr Val Leu Ser Asp
            885                 890                 895

Gly Lys Leu Tyr Phe Thr Val Asn Asp Lys Gly Thr Phe Leu Pro Ala
            900                 905                 910

Ala Leu Thr Gly Asp Thr Lys Ala Lys Thr Gly Phe Ala Tyr Asp Gly
            915                 920                 925

Thr Gly Val Thr Tyr Tyr Thr Thr Ser Gly Thr Gln Ala Lys Ser Gln
            930                 935                 940

Phe Val Thr Tyr Asn Gly Lys Gln Tyr Tyr Phe Asn Asp Lys Gly Tyr
945                 950                 955                 960

Leu Val Thr Gly Glu Gln Thr Ile Asp Gly Ser Asn Tyr Phe Phe Leu
            965                 970                 975

Pro Asn Gly Val Met Phe Thr Asp Gly Val Arg Lys Asn Ala Lys Gly
            980                 985                 990

Gln Ser Leu Val Tyr Gly Lys Ser Gly Lys Leu Thr Thr Gln Thr Gly
            995                 1000                1005

Trp Lys Glu Val Thr Val Lys Asp Asp Ser Gly Lys Glu Glu Lys
            1010                1015                1020

Phe Tyr Gln Tyr Phe Phe Lys Gly Gly Ile Met Ala Thr Gly Leu
            1025                1030                1035

Thr Glu Val Glu Gly Lys Glu Lys Tyr Phe Tyr Asp Asn Gly Tyr
            1040                1045                1050

Gln Ala Lys Gly Val Phe Val Pro Thr Lys Asp Gly His Leu Met
            1055                1060                1065

Phe Phe Cys Gly Asp Ser Gly Glu Arg Lys Tyr Ser Gly Phe Phe
            1070                1075                1080

Glu Gln Asp Gly Asn Trp Tyr Tyr Ala Asn Asp Lys Gly Tyr Val
            1085                1090                1095

Ala Thr Gly Phe Thr Lys Val Gly Lys Gln Asn Leu Tyr Phe Asn
            1100                1105                1110

Glu Lys Gly Val Gln Val Lys Asn Arg Phe Phe Gln Val Gly Asp
            1115                1120                1125

Ala Thr Tyr Tyr Ala Asn Asn Glu Gly Asp Val Leu Arg Gly Ala
            1130                1135                1140

Gln Thr Ile Asn Gly Asp Glu Leu Tyr Phe Asp Glu Ser Gly Lys
            1145                1150                1155

Gln Val Lys Gly Glu Phe Val Asn Asn Pro Asp Gly Thr Thr Ser
            1160                1165                1170

Tyr Tyr Asp Ala Ile Thr Gly Val Lys Leu Val Asp Thr Ser Leu
            1175                1180                1185

Val Val Asp Gly Gln Thr Phe Asn Val Asp Ala Lys Gly Val Val
            1190                1195                1200
```

| | | | | | | | | | | | |
|---|---|---|---|---|---|---|---|---|---|---|---|
|Thr|Lys|Ala|His|Thr|Pro|Gly|Phe|Tyr|Thr|Gly|Asp Asn Asn|
| |1205| | | |1210| | | |1215| | |
|Trp|Phe|Tyr|Ala|Asp|Ser|Tyr|Gly|Arg|Asn|Val|Thr Gly Ala Gln|
| |1220| | | |1225| | | |1230| | |
|Val|Ile|Asn|Gly|Gln|His|Leu|Tyr|Phe|Asp|Ala|Asn Gly Arg Gln|
| |1235| | | |1240| | | |1245| | |
|Val|Lys|Gly|Gly|Phe|Val|Thr|Asn|Thr|Asp|Gly|Ser Arg Ser Phe|
| |1250| | | |1255| | | |1260| | |
|Tyr|His|Trp|Asn|Thr|Gly|Asp|Lys|Leu|Val|Ser|Thr Phe Phe Ala|
| |1265| | | |1270| | | |1275| | |
|Thr|Gly|His|Asp|Arg|Trp|Tyr|Tyr|Ala|Asp|Asp|Arg Gly Asn Val|
| |1280| | | |1285| | | |1290| | |
|Val|Thr|Gly|Ala|Gln|Val|Ile|Asn|Gly|Gln|Lys|Leu Phe Phe Asp|
| |1295| | | |1300| | | |1305| | |
|Thr|Asp|Gly|Lys|Gln|Val|Lys|Gly|Ala|Phe|Ala|Thr Asn Ala Asn|
| |1310| | | |1315| | | |1320| | |
|Gly|Ser|Arg|Ser|Tyr|Tyr|His|Trp|Asn|Thr|Gly|Asn Lys Leu Val|
| |1325| | | |1330| | | |1335| | |
|Ser|Thr|Phe|Phe|Thr|Ser|Gly|Asp|Asn|Asn|Trp|Tyr Tyr Ala Asp|
| |1340| | | |1345| | | |1350| | |
|Ala|Lys|Gly|Glu|Val|Val|Val|Gly|Glu|Gln|Thr|Ile Asn Gly Gln|
| |1355| | | |1360| | | |1365| | |
|His|Leu|Tyr|Phe|Asp|Gln|Thr|Gly|Lys|Gln|Val|Lys Gly Ala Thr|
| |1370| | | |1375| | | |1380| | |
|Ala|Thr|Asn|Pro|Asp|Gly|Ser|Ile|Ser|Tyr|Tyr|Asp Val His Thr|
| |1385| | | |1390| | | |1395| | |
|Gly|Glu|Lys|Ala|Ile|Asn|Arg|Trp|Val|Lys|Ile|Pro Ser Gly Gln|
| |1400| | | |1405| | | |1410| | |
|Trp|Val|Tyr|Phe|Asn|Ala|Gln|Gly|Lys|Gly|Tyr|Val Ser Asn|
| |1415| | | |1420| | | |1425| | |

<210> SEQ ID NO 51
<211> LENGTH: 4182
<212> TYPE: DNA
<213> ORGANISM: Unknown
<220> FEATURE:
<223> OTHER INFORMATION: unknown Streptococcus species

<400> SEQUENCE: 51

```
atgatcaatg gcaaacagta ctatgtaaat tcggacggta gcgtgcgtaa gaatttcgtt      60
tttgaacagg atggtaagag ctactacttt gacgcgcgaaa ctggcgcgct ggccactaaa    120
agccaagatg aatttagcac ggagccgatt aaagcagcag tggacttctc tagcggcaac    180
cagctgtaca aaaatgacaa caaatcgctg atcagctgg atacgtttat caccgctgac    240
gcatggtacc gccctaagtc tattctgaag gatggcaaaa cctggaccgc gtctaccgaa    300
gctgataagc gtccgttgct gatggtgtgg tggccggaca gtccacccca gttaactac    360
ctgaactaca tgcagaacca gggtttgggt gcgggtagct tcagcaccaa tagcagccaa    420
gaatccctga atctggctgc gaaagcagtt cagaccaaga tcgaagaacg catcgcacgt    480
gagggtaaca ccaattggct gcgtaccagc attgaccaat tcattaagac gcagccaggc    540
tggaacagca gcactgagaa tagcagctat gatcacttgc agggtggtca actgctgttc    600
aataacagca aaggtgatac gggtaaccgc accagctatg cgaatagcga ctatcgtctg    660
ctgaaccgta ccccaactaa tcaaagcggc acccgtaagt actttaagga taattccatc    720
```

-continued

```
ggtggtctgg aatttctgct ggcaaacgac atcgacaaca gcaaccctgc cgttcaggcg    780
gagcagctga actggctgca cttcatgatg aacattggtt ctatcatggc gaatgacccg    840
acggcgaact ttgatggttt gcgtgtggac gcgttggata acgtggatgc ggacctgttg    900
cagatcgcga gcgattactt caaggcagtc tacggtgttg ataaatccga ggcgaatgcg    960
atcaagcacc tgagctatct ggaggcgtgg agcgccaatg acccgtatta caacaaggat   1020
accaaaggcg cgcaactgcc gattgacaac gcgctgcgca acgcactgac caacctgttg   1080
atgcgtgaca agaatacgcg catgcagctg ggtgacatga cggcgtttat gaatagctct   1140
ctgaacccac gtggtgcgaa tgacaaaaac ggcgagcgta tggcgaatta cattttcacc   1200
cgcgcacacg ataccgaggc gcagaccatc attcagcgta ttatccgcga tcgtatcaat   1260
ccgaacctgt ttggctacaa tttcacccgc gatgaaatca aaaaggcgtt tgagatctac   1320
aacgcggaca ttaacacggc gcataagacg tacgcgagct acaatctgcc gtccgtctac   1380
gcactgatgc tgacgaataa ggacagcgtg acccgtgtgt attacggtga cctgtatcgt   1440
gaggacggtc actacatggc caagaaaacg ccttatttcg atgcaatcga tacccctgctg   1500 cgtgcgcgca tcaaatacgt ggcgggtggt caagacatgg aggtgaagaa agttggtaat   1560
gacggcttgc tgacgagcgt ccgctatggc aagggtgcga acaatagcac cgactggggc   1620
acgactgaaa cccgtaccca aggtatgggc gttatcctga cgaacaacta tgatttccgc   1680
ctgggcagca acgaaccgt cacgatgaac atggccgtg cgcatcgcaa tcagctgtat    1740
cgtccgctgc tgctgacgac caaggatggt ctggccacgt acctgaatga tagcgacgtg   1800
ccttcgaatt tgctgaaacg cacggactgg aatggtaact tgacctttaa tgccaacgat   1860
gtgtttggtg tagagaacgt ccaggtcagc ggttacctgg tgtttgggt accggttggt    1920 gctaaagcta accaggatgc gcgtacccaa ccgagcaacc gtgcgaacag cgatggtcag   1980
gtctataagt cgtctgcggc attggacagc caggtcatgt atgaggcgtt tagcaatttt   2040
caggcatttg cggacgatca accggaactg tacatgaacc gcgttctggc gaagaacacc   2100
gatctgctga agcgtggggg cgttactagc gttggcttgc cgccacaata cgttagcagc   2160
aaagacggca ccttcctgga tagcactatt gataacggct atgcgttcga tgatcgttac   2220
gacatggcgc tgagccagaa caacaaatac ggttctctgg aggacttgct gaacgttctg   2280
cgcgctctgc acaaagacgg tattcaggcg attgcggact gggtcccgga tcaaatctac   2340
aatttgccgg gtaaagaggt tgttaatgcg acgcgtgtta acggttacgg ttaccatcag   2400
cagggctacc agattgttga ccaggcgtac gttgcaaaca cccgtacgga tggtaccgat   2460
tatcagggtc gttacggtgg tgcttttctg gacgaactga aggcgaagta cccgagcatt   2520
ttcaatcgtg tccagattag caacggtaaa cagctgccaa ccaatgagaa aatcacgaaa   2580
tggtccgcga aatacttcaa tggcacgaac atcctgggcc gtggtattaa ctatgtgctg   2640
cgcgacgaca agaccaatca gtatttcaac accagcgcaa acggccaact gctgccgacg   2700
ccactgcgcg acaccggtgc catcaccagc acgcaagttt ccagcgtcg tggccaagac    2760 gtctattttc tgcgtgataa ccaggttatc aaaaacgagt tgtgcaaga tggtaacggt    2820 aattggtact acttcggtgc cgacggtaaa atgacgaagg gtgcacaaaa catcaatagc   2880
aaggattact atttcttcga taatggcgtc cagctgcgta atgcgctgcg tcgcgcgtcc   2940
aatggttaca cctactatta tggcctggac ggtgccatga tcaagaacgc tttcgtcgat   3000
tttgatgata agcaccaaca ggtgcgtgcg tttactacgc agggcacgat ggtggtcggt   3060
aatttgcact ggagcggtca ccacttctat tttgaccgcg aaacgggtat ccaagccaaa   3120
```

```
gaccgcattg tgcgtaccga tgatggcaag ctgcactatt atgtcgcaca aaccggcgat   3180
atgggccgca atgtgtttgc gaccgacagc cgcacgggca agcgctatta ctttgatgcg   3240
gacggcaaca ccgttacggg ctcccgtgtc atcgacggca agacctacta cttcaaccag   3300
gacggttcgg tcgtaccgc gtacagcaat cgtgcggata gcattatctt tgagaatggc    3360
aaggctcgct atatcactcc ggctggcgag attggccgtt ccattttgt ctacaacccg    3420 gcgaccaaag cgtggaatta cttcgacaag gaaggtaacc gtgtcaccgg tcgtcagtat   3480
attgacggca atctgtacta ctttaaagag gacggctccc aagtgaaagg tgcgattgtt   3540
gaagagaacg gtatcaagta ctactacgaa ccgggcagcg gtatcctggc gagcggtcgt   3600
tatctgcaag tcggtgacga ccaatggatc tacttcaaac acgacggtag cctggcgatc   3660
ggtcaggttc gtgcagacgg tggttacttg aaatactttg ataagaatgg catccaggtc   3720
aagggccaaa ccattgtgga ggatggtcat acctattact acgatgccga ctccggtgct   3780
ctggtgacct ctagcttcgc ggagattgct ccgaaccagt gggcctactt caataccgag   3840
ggccaagccc tgaagggcaa atggaccatc aatggtaaag agtactattt tgatcagaac   3900
ggcattcagt ataaaggcaa ggcagttaag gtcggcagcc gttacaaata ctatgacgag   3960
aatgacggtc aaccggtcac taaccgtttt gcccagattg agccgaacgt ctgggcgtac   4020
tttggtgccg atggctacgc agttactggc gaacaggtga ttaatggcca gcacctgtac   4080
ttcgatcagt cgggtcgtca ggttaaaggt gcgtacgtca ccgtgaatgg tcaacgtcgt   4140
tactacgacg caaacacggg tgaatacatt ccgggtcgtt aa                      4182
```

<210> SEQ ID NO 52
<211> LENGTH: 1393
<212> TYPE: PRT
<213> ORGANISM: Unknown
<220> FEATURE:
<223> OTHER INFORMATION: unknown Streptococcus species

<400> SEQUENCE: 52

```
Met Ile Asn Gly Lys Gln Tyr Tyr Val Asn Ser Asp Gly Ser Val Arg
1               5                  10                  15

Lys Asn Phe Val Phe Glu Gln Asp Gly Lys Ser Tyr Tyr Phe Asp Ala
            20                  25                  30

Glu Thr Gly Ala Leu Ala Thr Lys Ser Gln Asp Glu Phe Ser Thr Glu
        35                  40                  45

Pro Ile Lys Ala Ala Val Asp Phe Ser Ser Gly Asn Gln Leu Tyr Lys
    50                  55                  60

Asn Asp Asn Lys Ser Leu Asp Gln Leu Asp Thr Phe Ile Thr Ala Asp
65                  70                  75                  80

Ala Trp Tyr Arg Pro Lys Ser Ile Leu Lys Asp Gly Lys Thr Trp Thr
                85                  90                  95

Ala Ser Thr Glu Ala Asp Lys Arg Pro Leu Leu Met Val Trp Trp Pro
            100                 105                 110

Asp Lys Ser Thr Gln Val Asn Tyr Leu Asn Tyr Met Gln Asn Gln Gly
        115                 120                 125

Leu Gly Ala Gly Ser Phe Ser Thr Asn Ser Ser Gln Glu Ser Leu Asn
    130                 135                 140

Leu Ala Ala Lys Ala Val Gln Thr Lys Ile Glu Glu Arg Ile Ala Arg
145                 150                 155                 160

Glu Gly Asn Thr Asn Trp Leu Arg Thr Ser Ile Asp Gln Phe Ile Lys
                165                 170                 175
```

```
Thr Gln Pro Gly Trp Asn Ser Ser Thr Glu Asn Ser Ser Tyr Asp His
            180                 185                 190

Leu Gln Gly Gly Gln Leu Leu Phe Asn Asn Ser Lys Gly Asp Thr Gly
            195                 200                 205

Asn Arg Thr Ser Tyr Ala Asn Ser Asp Tyr Arg Leu Leu Asn Arg Thr
            210                 215                 220

Pro Thr Asn Gln Ser Gly Thr Arg Lys Tyr Phe Lys Asp Asn Ser Ile
225                 230                 235                 240

Gly Gly Leu Glu Phe Leu Leu Ala Asn Asp Ile Asp Asn Ser Asn Pro
                245                 250                 255

Ala Val Gln Ala Glu Gln Leu Asn Trp Leu His Phe Met Met Asn Ile
            260                 265                 270

Gly Ser Ile Met Ala Asn Asp Pro Thr Ala Asn Phe Asp Gly Leu Arg
            275                 280                 285

Val Asp Ala Leu Asp Asn Val Asp Ala Asp Leu Leu Gln Ile Ala Ser
            290                 295                 300

Asp Tyr Phe Lys Ala Val Tyr Gly Val Asp Lys Ser Glu Ala Asn Ala
305                 310                 315                 320

Ile Lys His Leu Ser Tyr Leu Glu Ala Trp Ser Ala Asn Asp Pro Tyr
                325                 330                 335

Tyr Asn Lys Asp Thr Lys Gly Ala Gln Leu Pro Ile Asp Asn Ala Leu
            340                 345                 350

Arg Asn Ala Leu Thr Asn Leu Leu Met Arg Asp Lys Asn Thr Arg Met
            355                 360                 365

Gln Leu Gly Asp Met Thr Ala Phe Met Asn Ser Ser Leu Asn Pro Arg
            370                 375                 380

Gly Ala Asn Asp Lys Asn Gly Glu Arg Met Ala Asn Tyr Ile Phe Thr
385                 390                 395                 400

Arg Ala His Asp Thr Glu Ala Gln Thr Ile Ile Gln Arg Ile Ile Arg
                405                 410                 415

Asp Arg Ile Asn Pro Asn Leu Phe Gly Tyr Asn Phe Thr Arg Asp Glu
            420                 425                 430

Ile Lys Lys Ala Phe Glu Ile Tyr Asn Ala Asp Ile Asn Thr Ala His
            435                 440                 445

Lys Thr Tyr Ala Ser Tyr Asn Leu Pro Ser Val Tyr Ala Leu Met Leu
450                 455                 460

Thr Asn Lys Asp Ser Val Thr Arg Val Tyr Tyr Gly Asp Leu Tyr Arg
465                 470                 475                 480

Glu Asp Gly His Tyr Met Ala Lys Lys Thr Pro Tyr Phe Asp Ala Ile
                485                 490                 495

Asp Thr Leu Leu Arg Ala Arg Ile Lys Tyr Val Ala Gly Gly Gln Asp
            500                 505                 510

Met Glu Val Lys Lys Val Gly Asn Asp Gly Leu Leu Thr Ser Val Arg
            515                 520                 525

Tyr Gly Lys Gly Ala Asn Asn Ser Thr Asp Trp Gly Thr Thr Glu Thr
            530                 535                 540

Arg Thr Gln Gly Met Gly Val Ile Leu Thr Asn Asn Tyr Asp Phe Arg
545                 550                 555                 560

Leu Gly Ser Asn Glu Thr Val Thr Met Asn Met Gly Arg Ala His Arg
                565                 570                 575

Asn Gln Leu Tyr Arg Pro Leu Leu Leu Thr Thr Lys Asp Gly Leu Ala
            580                 585                 590
```

```
Thr Tyr Leu Asn Asp Ser Asp Val Pro Ser Asn Leu Leu Lys Arg Thr
            595                 600                 605

Asp Trp Asn Gly Asn Leu Thr Phe Asn Ala Asn Asp Val Phe Gly Val
610                 615                 620

Glu Asn Val Gln Val Ser Gly Tyr Leu Gly Val Trp Val Pro Val Gly
625                 630                 635                 640

Ala Lys Ala Asn Gln Asp Ala Arg Thr Gln Pro Ser Asn Arg Ala Asn
                645                 650                 655

Ser Asp Gly Gln Val Tyr Lys Ser Ser Ala Ala Leu Asp Ser Gln Val
                660                 665                 670

Met Tyr Glu Ala Phe Ser Asn Phe Gln Ala Phe Ala Asp Asp Gln Pro
                675                 680                 685

Glu Leu Tyr Met Asn Arg Val Leu Ala Lys Asn Thr Asp Leu Leu Lys
                690                 695                 700

Ala Trp Gly Val Thr Ser Val Gly Leu Pro Pro Gln Tyr Val Ser Ser
705                 710                 715                 720

Lys Asp Gly Thr Phe Leu Asp Ser Thr Ile Asp Asn Gly Tyr Ala Phe
                725                 730                 735

Asp Asp Arg Tyr Asp Met Ala Leu Ser Gln Asn Asn Lys Tyr Gly Ser
                740                 745                 750

Leu Glu Asp Leu Leu Asn Val Leu Arg Ala Leu His Lys Asp Gly Ile
                755                 760                 765

Gln Ala Ile Ala Asp Trp Val Pro Asp Gln Ile Tyr Asn Leu Pro Gly
                770                 775                 780

Lys Glu Val Val Asn Ala Thr Arg Val Asn Gly Tyr Gly Tyr His Gln
785                 790                 795                 800

Gln Gly Tyr Gln Ile Val Asp Gln Ala Tyr Val Ala Asn Thr Arg Thr
                805                 810                 815

Asp Gly Thr Asp Tyr Gln Gly Arg Tyr Gly Gly Ala Phe Leu Asp Glu
                820                 825                 830

Leu Lys Ala Lys Tyr Pro Ser Ile Phe Asn Arg Val Gln Ile Ser Asn
                835                 840                 845

Gly Lys Gln Leu Pro Thr Asn Glu Lys Ile Thr Lys Trp Ser Ala Lys
850                 855                 860

Tyr Phe Asn Gly Thr Asn Ile Leu Gly Arg Gly Ile Asn Tyr Val Leu
865                 870                 875                 880

Arg Asp Asp Lys Thr Asn Gln Tyr Phe Asn Thr Ser Ala Asn Gly Gln
                885                 890                 895

Leu Leu Pro Thr Pro Leu Arg Asp Thr Gly Ala Ile Thr Ser Thr Gln
                900                 905                 910

Val Phe Gln Arg Arg Gly Gln Asp Val Tyr Phe Leu Arg Asp Asn Gln
                915                 920                 925

Val Ile Lys Asn Glu Phe Val Gln Asp Gly Asn Gly Asn Trp Tyr Tyr
930                 935                 940

Phe Gly Ala Asp Gly Lys Met Thr Lys Gly Ala Gln Asn Ile Asn Ser
945                 950                 955                 960

Lys Asp Tyr Tyr Phe Phe Asp Asn Gly Val Gln Leu Arg Asn Ala Leu
                965                 970                 975

Arg Arg Ala Ser Asn Gly Tyr Thr Tyr Tyr Tyr Gly Leu Asp Gly Ala
                980                 985                 990

Met Ile Lys Asn Ala Phe Val Asp  Phe Asp Asp Lys His Gln Gln Val
                995                 1000                1005

Arg Ala  Phe Thr Thr Gln Gly  Thr Met Val Val Gly  Asn Leu His
```

```
            1010                1015                1020
Trp Ser Gly His His Phe Tyr Phe Asp Arg Glu Thr Gly Ile Gln
        1025                1030                1035

Ala Lys Asp Arg Ile Val Arg Thr Asp Asp Gly Lys Leu His Tyr
        1040                1045                1050

Tyr Val Ala Gln Thr Gly Asp Met Gly Arg Asn Val Phe Ala Thr
        1055                1060                1065

Asp Ser Arg Thr Gly Lys Arg Tyr Tyr Phe Asp Ala Asp Gly Asn
        1070                1075                1080

Thr Val Thr Gly Ser Arg Val Ile Asp Gly Lys Thr Tyr Tyr Phe
        1085                1090                1095

Asn Gln Asp Gly Ser Val Gly Thr Ala Tyr Ser Asn Arg Ala Asp
        1100                1105                1110

Ser Ile Ile Phe Glu Asn Gly Lys Ala Arg Tyr Ile Thr Pro Ala
        1115                1120                1125

Gly Glu Ile Gly Arg Ser Ile Phe Val Tyr Asn Pro Ala Thr Lys
        1130                1135                1140

Ala Trp Asn Tyr Phe Asp Lys Glu Gly Asn Arg Val Thr Gly Arg
        1145                1150                1155

Gln Tyr Ile Asp Gly Asn Leu Tyr Tyr Phe Lys Glu Asp Gly Ser
        1160                1165                1170

Gln Val Lys Gly Ala Ile Val Glu Glu Asn Gly Ile Lys Tyr Tyr
        1175                1180                1185

Tyr Glu Pro Gly Ser Gly Ile Leu Ala Ser Gly Arg Tyr Leu Gln
        1190                1195                1200

Val Gly Asp Asp Gln Trp Ile Tyr Phe Lys His Asp Gly Ser Leu
        1205                1210                1215

Ala Ile Gly Gln Val Arg Ala Asp Gly Gly Tyr Leu Lys Tyr Phe
        1220                1225                1230

Asp Lys Asn Gly Ile Gln Val Lys Gly Gln Thr Ile Val Glu Asp
        1235                1240                1245

Gly His Thr Tyr Tyr Tyr Asp Ala Asp Ser Gly Ala Leu Val Thr
        1250                1255                1260

Ser Ser Phe Ala Glu Ile Ala Pro Asn Gln Trp Ala Tyr Phe Asn
        1265                1270                1275

Thr Glu Gly Gln Ala Leu Lys Gly Lys Trp Thr Ile Asn Gly Lys
        1280                1285                1290

Glu Tyr Tyr Phe Asp Gln Asn Gly Ile Gln Tyr Lys Gly Lys Ala
        1295                1300                1305

Val Lys Val Gly Ser Arg Tyr Lys Tyr Tyr Asp Glu Asn Asp Gly
        1310                1315                1320

Gln Pro Val Thr Asn Arg Phe Ala Gln Ile Glu Pro Asn Val Trp
        1325                1330                1335

Ala Tyr Phe Gly Ala Asp Gly Tyr Ala Val Thr Gly Glu Gln Val
        1340                1345                1350

Ile Asn Gly Gln His Leu Tyr Phe Asp Gln Ser Gly Arg Gln Val
        1355                1360                1365

Lys Gly Ala Tyr Val Thr Val Asn Gly Gln Arg Arg Tyr Tyr Asp
        1370                1375                1380

Ala Asn Thr Gly Glu Tyr Ile Pro Gly Arg
        1385                1390

<210> SEQ ID NO 53
```

<211> LENGTH: 3789
<212> TYPE: DNA
<213> ORGANISM: Leuconostoc citreum

<400> SEQUENCE: 53

| | | | | | |
|---|---|---|---|---|---|
| atgattaacg | gccacaatta | ctatttcgac | agcttgggtc | aactgaagaa | aggtttcacg | 60 |
| ggcgtgatcg | acggtcaggt | ccgttacttc | gaccaggagt | ccggtcagga | agttagcacc | 120 |
| accgacagcc | aaatcaaaga | gggcttgacg | agcaaaacga | ccgactacac | cgcccataac | 180 |
| gcggtccaca | gcacggactc | cgcagatttt | gacaacttca | atggttacct | gaccgcgagc | 240 |
| agctggtatc | gtcctaagga | cgttctgcgt | aacggccaac | attgggaagc | caccaccgcg | 300 |
| aatgacttcc | gtcctatcgt | cagcgtgtgg | tggccgagca | agcaaacgca | ggtcaactac | 360 |
| ctgaactata | tgagccagat | gggtttgatc | gataaccgtc | aaatgttctc | gttgaaagat | 420 |
| aaccaagcga | tgctgaacat | cgcgtgcacg | accgtgcaac | aagcaatcga | actaaaatc | 480 |
| ggtgtggcga | atagcaccgc | gtggctgaaa | accgcgatcg | atgactttat | ccgtacccag | 540 |
| ccgcagtgga | acatgagcag | cgaagatccg | aagaatgacc | atctgcaaaa | tggcgccctg | 600 |
| acgtttgtta | cagcccgct | gaccccggat | acgaatagca | atttccgcct | gctgaatcgt | 660 |
| accccgacca | atcaaaccgg | tgttccgaaa | tacaccatcg | accaaagcaa | aggtggtttt | 720 |
| gaactgctgc | tggcgaatga | cgtggataat | tcgaacccgg | ttgtgcaggc | cgagcagttg | 780 |
| aactggctgc | actacctgat | gaactttggt | agcattactg | cgaatgacag | cgcagcaaac | 840 |
| ttcgacggta | ttcgcgttga | cgcagtggat | aacgtggatg | cggacctgct | gcaaattgcg | 900 |
| gcagattact | tcaaagcagc | atacggtgtg | acaagaacg | acgcaacggc | aaatcagcat | 960 |
| ctgtcgatcc | tggaagattg | gagccacaac | gacccggagt | acgttaaaga | cttcggcaat | 1020 |
| aaccaactga | ccatggacga | ttacatgcac | acgcagctga | tctggagcct | gacgaaagac | 1080 |
| atgcgtatgc | gtggtacgat | gcagcgctt | atggactact | atctggttaa | ccgcaatcac | 1140 |
| gacagcaccg | agaatactgc | cattccgaat | tacagctttg | tccgtgccca | tgacagcgaa | 1200 |
| gttcaaacgg | ttattgcgca | gatcatttct | gagctgcatc | cagacgtgaa | gaatagcctg | 1260 |
| gcgccgaccg | cggatcaact | ggctgaggcg | ttcaaaatct | acaacaacga | cgagaagcaa | 1320 |
| gctgataaga | agtatacccca | atacaatatg | ccaagcgcgt | acgcaatgct | gttgaccaat | 1380 |
| aaagataccg | ttccgcgtgt | ttactacggt | gacctgtata | ccgatgacgg | tcagtatatg | 1440 |
| gctaacaaat | ccccgtattt | tgacgctatc | aacggtctgc | tgaagagccg | tatcaaatat | 1500 |
| gtggcaggcg | gtcaaagcat | ggcggtggat | cagaatgata | tcctgacgaa | tgtgcgctat | 1560 |
| ggcaaaggtg | ccatgagcgt | gacggatagc | ggcaacgcgg | atacgcgtac | ccagggcatc | 1620 |
| ggcgttattg | ttagcaacaa | agaaaaacctg | gctctgaaat | ccggcgacac | cgttaccctg | 1680 |
| cacatgggcg | cagcgcacaa | gaaccaggcg | tttcgcctgc | tgttgggtac | gacggcggac | 1740 |
| aacctgagct | actacgacaa | tgacaatgcg | ccggtgaagt | acaccaatga | tcaaggtgat | 1800 |
| ctgatttttcg | ataataccga | gatttatggt | gttcgcaatc | cgcaagtctc | tggttttctg | 1860 |
| gcggtgtggg | tcccggttgg | tgccgatagc | catcaagatg | ctcgcacttt | gagcgacgat | 1920 |
| acggcacacc | acgacggcaa | gaccttccac | tcgaacgcag | cactggatag | ccaggtgatt | 1980 |
| tacgaaggtt | ttagcaactt | ccaagcattt | gcaacgaata | cggaagatta | cactaacgct | 2040 |
| gtgatcgcca | aaaacggcca | gctgttcaag | gattggggca | tcacctcgtt | ccagctggct | 2100 |
| ccgcagtatc | gcagctccac | cgatacgagc | ttcctggata | gcattattca | gaacggctat | 2160 |
| gccttcacgg | accgttatga | cctgggctat | ggcacccccga | cgaagtatgg | caccgtggac | 2220 |

```
cagctgcgcg atgcaatcaa ggctctgcac gccaatggca tccaagcaat tgccgactgg    2280
gttccggacc agatctacaa cctgccgggt caggagctgg ccacggtgac ccgtacgaac    2340
tcctatggtg ataaagacac caatagcgat attgatcaga gcttgtacgt gatccaatcg    2400
cgcggtggcg gtaagtatca agcccaatac ggtggtgcat tcctgagcga cattcaaaag    2460
aagtatccgg ctctgttcga gactaaacag atcagcacgg gtctgccgat ggacccgagc    2520
caaaagatta ccgagtggag cggcaagtac ttcaacggta gcaatattca aggtaagggc    2580
gctggttacg tcctgaagga cagcggcacc gaccagtact ataaagtgac gagcaacaat    2640
aacaaccgtg atttcctgcc gaaacagctg acggatgatc tgtctgaaac cggttttgtg    2700
cgtgacaata ttggcatggt ctattacacc ctgtctggct acctggcacg caataccttc    2760
atccaggacg acaacggtaa ctattactac tttgatagca ccggtcacct ggttacgggt    2820
ttccagaaca ttaacaacca ccactacttt ttcttgccga acggcattga actggttcag    2880
agctttctgc aaaacgctga tggtagcacg atctacttcg atcaaaaggg tcgtcaagtt    2940
ttcaaccagt atatcactga tcagactggt accgcgtact acttccagaa cgacggcacc    3000
atggtcactt ctggctttac tgagatcgat ggccacaagc agtatttcta taagaatggc    3060
actcaggtta agggtcagtt tgtgagcgac accgatggtc acgtcttttta cctggaagcg    3120 ggtaatggta atgtcgccac gcaacgtttc gcacagaaca gccagggtca atggttctac    3180
ttgggtaatg atggcattgc gttgacgggt ttgcagacga tcaacggtgt tcagaactac    3240 tttatgcgg acggtcatca aagcaaggg gacttcatca ccatccagaa tcatgtcctg    3300
tacaccaacc cgctgacggg tgccatcacg accggcatgc aacagatcgg cgacaaaatc    3360
ttcgtgtttg ataatacggg taatatgctg acgaaccagt attatcagac gctggatggt    3420
cagtggctgc acctgagcac ccagggtcca gcagatacgg gtctggtcaa tatcaatggt    3480
aatctgaagt attttcaggc aaatggtcgt caggtgaaag gccaattcgt caccgacccg    3540
attaccaacg tcagctacta catgaacgcg acggacggta gcgcagtgtt caatgactat    3600
ttcacctatc agggccaatg gtatttgacg gactccaact atcagttggt caaaggcttc    3660
aaagtggtga acaacaaact gcaacatttc gatgaaatca ccggtgtgca aaccaagagc    3720
gctcacatta ttgttaacaa tcgtacctac attttttgacg accagggcta ttttgtcagc    3780
gtggcataa                                                             3789
```

<210> SEQ ID NO 54
<211> LENGTH: 1262
<212> TYPE: PRT
<213> ORGANISM: Leuconostoc citreum

<400> SEQUENCE: 54

Met Ile Asn Gly His Asn Tyr Tyr Phe Asp Ser Leu Gly Gln Leu Lys
1               5                   10                  15

Lys Gly Phe Thr Gly Val Ile Asp Gly Gln Val Arg Tyr Phe Asp Gln
            20                  25                  30

Glu Ser Gly Gln Glu Val Ser Thr Thr Asp Ser Gln Ile Lys Glu Gly
        35                  40                  45

Leu Thr Ser Gln Thr Thr Asp Tyr Thr Ala His Asn Ala Val His Ser
    50                  55                  60

Thr Asp Ser Ala Asp Phe Asp Asn Phe Asn Gly Tyr Leu Thr Ala Ser
65                  70                  75                  80

Ser Trp Tyr Arg Pro Lys Asp Val Leu Arg Asn Gly Gln His Trp Glu

-continued

```
                85                  90                  95
Ala Thr Thr Ala Asn Asp Phe Arg Pro Ile Val Ser Val Trp Trp Pro
            100                 105                 110
Ser Lys Gln Thr Gln Val Asn Tyr Leu Asn Tyr Met Ser Gln Met Gly
            115                 120                 125
Leu Ile Asp Asn Arg Gln Met Phe Ser Leu Lys Asp Asn Gln Ala Met
130                 135                 140
Leu Asn Ile Ala Cys Thr Thr Val Gln Gln Ala Ile Glu Thr Lys Ile
145                 150                 155                 160
Gly Val Ala Asn Ser Thr Ala Trp Leu Lys Thr Ala Ile Asp Asp Phe
                165                 170                 175
Ile Arg Thr Gln Pro Gln Trp Asn Met Ser Ser Glu Asp Pro Lys Asn
                180                 185                 190
Asp His Leu Gln Asn Gly Ala Leu Thr Phe Val Asn Ser Pro Leu Thr
                195                 200                 205
Pro Asp Thr Asn Ser Asn Phe Arg Leu Leu Asn Arg Thr Pro Thr Asn
210                 215                 220
Gln Thr Gly Val Pro Lys Tyr Thr Ile Asp Gln Ser Lys Gly Gly Phe
225                 230                 235                 240
Glu Leu Leu Leu Ala Asn Asp Val Asp Asn Ser Asn Pro Val Val Gln
                245                 250                 255
Ala Glu Gln Leu Asn Trp Leu His Tyr Leu Met Asn Phe Gly Ser Ile
                260                 265                 270
Thr Ala Asn Asp Ser Ala Ala Asn Phe Asp Gly Ile Arg Val Asp Ala
                275                 280                 285
Val Asp Asn Val Asp Ala Asp Leu Leu Gln Ile Ala Ala Asp Tyr Phe
                290                 295                 300
Lys Ala Ala Tyr Gly Val Asp Lys Asn Asp Ala Thr Ala Asn Gln His
305                 310                 315                 320
Leu Ser Ile Leu Glu Asp Trp Ser His Asn Asp Pro Glu Tyr Val Lys
                325                 330                 335
Asp Phe Gly Asn Asn Gln Leu Thr Met Asp Asp Tyr Met His Thr Gln
                340                 345                 350
Leu Ile Trp Ser Leu Thr Lys Asp Met Arg Met Arg Gly Thr Met Gln
                355                 360                 365
Arg Phe Met Asp Tyr Tyr Leu Val Asn Arg Asn His Asp Ser Thr Glu
                370                 375                 380
Asn Thr Ala Ile Pro Asn Tyr Ser Phe Val Arg Ala His Asp Ser Glu
385                 390                 395                 400
Val Gln Thr Val Ile Ala Gln Ile Ile Ser Glu Leu His Pro Asp Val
                405                 410                 415
Lys Asn Ser Leu Ala Pro Thr Ala Asp Gln Leu Ala Glu Ala Phe Lys
                420                 425                 430
Ile Tyr Asn Asn Asp Glu Lys Gln Ala Asp Lys Lys Tyr Thr Gln Tyr
                435                 440                 445
Asn Met Pro Ser Ala Tyr Ala Met Leu Leu Thr Asn Lys Asp Thr Val
            450                 455                 460
Pro Arg Val Tyr Tyr Gly Asp Leu Tyr Thr Asp Asp Gly Gln Tyr Met
465                 470                 475                 480
Ala Asn Lys Ser Pro Tyr Phe Asp Ala Ile Asn Gly Leu Leu Lys Ser
                485                 490                 495
Arg Ile Lys Tyr Val Ala Gly Gly Gln Ser Met Ala Val Asp Gln Asn
            500                 505                 510
```

```
Asp Ile Leu Thr Asn Val Arg Tyr Gly Lys Gly Ala Met Ser Val Thr
            515                 520                 525

Asp Ser Gly Asn Ala Asp Thr Arg Thr Gln Gly Ile Gly Val Ile Val
        530                 535                 540

Ser Asn Lys Glu Asn Leu Ala Leu Lys Ser Gly Asp Thr Val Thr Leu
545                 550                 555                 560

His Met Gly Ala Ala His Lys Asn Gln Ala Phe Arg Leu Leu Leu Gly
                565                 570                 575

Thr Thr Ala Asp Asn Leu Ser Tyr Tyr Asp Asn Asp Asn Ala Pro Val
            580                 585                 590

Lys Tyr Thr Asn Asp Gln Gly Asp Leu Ile Phe Asp Asn Thr Glu Ile
        595                 600                 605

Tyr Gly Val Arg Asn Pro Gln Val Ser Gly Phe Leu Ala Val Trp Val
    610                 615                 620

Pro Val Gly Ala Asp Ser His Gln Asp Ala Arg Thr Leu Ser Asp Asp
625                 630                 635                 640

Thr Ala His His Asp Gly Lys Thr Phe His Ser Asn Ala Ala Leu Asp
                645                 650                 655

Ser Gln Val Ile Tyr Glu Gly Phe Ser Asn Phe Gln Ala Phe Ala Thr
            660                 665                 670

Asn Thr Glu Asp Tyr Thr Asn Ala Val Ile Ala Lys Asn Gly Gln Leu
        675                 680                 685

Phe Lys Asp Trp Gly Ile Thr Ser Phe Gln Leu Ala Pro Gln Tyr Arg
    690                 695                 700

Ser Ser Thr Asp Thr Ser Phe Leu Asp Ser Ile Ile Gln Asn Gly Tyr
705                 710                 715                 720

Ala Phe Thr Asp Arg Tyr Asp Leu Gly Tyr Gly Thr Pro Thr Lys Tyr
                725                 730                 735

Gly Thr Val Asp Gln Leu Arg Asp Ala Ile Lys Ala Leu His Ala Asn
            740                 745                 750

Gly Ile Gln Ala Ile Ala Asp Trp Val Pro Asp Gln Ile Tyr Asn Leu
        755                 760                 765

Pro Gly Gln Glu Leu Ala Thr Val Thr Arg Thr Asn Ser Tyr Gly Asp
    770                 775                 780

Lys Asp Thr Asn Ser Asp Ile Asp Gln Ser Leu Tyr Val Ile Gln Ser
785                 790                 795                 800

Arg Gly Gly Gly Lys Tyr Gln Ala Gln Tyr Gly Gly Ala Phe Leu Ser
                805                 810                 815

Asp Ile Gln Lys Lys Tyr Pro Ala Leu Phe Glu Thr Lys Gln Ile Ser
            820                 825                 830

Thr Gly Leu Pro Met Asp Pro Ser Gln Lys Ile Thr Glu Trp Ser Gly
        835                 840                 845

Lys Tyr Phe Asn Gly Ser Asn Ile Gln Gly Lys Gly Ala Gly Tyr Val
    850                 855                 860

Leu Lys Asp Ser Gly Thr Asp Gln Tyr Tyr Lys Val Thr Ser Asn Asn
865                 870                 875                 880

Asn Asn Arg Asp Phe Leu Pro Lys Gln Leu Thr Asp Leu Ser Glu
                885                 890                 895

Thr Gly Phe Val Arg Asp Asn Ile Gly Met Val Tyr Tyr Thr Leu Ser
            900                 905                 910

Gly Tyr Leu Ala Arg Asn Thr Phe Ile Gln Asp Asp Asn Gly Asn Tyr
        915                 920                 925
```

| | | | | | | | | | | | |
|---|---|---|---|---|---|---|---|---|---|---|---|
Tyr | Tyr | Phe | Asp | Ser | Thr | Gly | His | Leu | Val | Thr | Gly | Phe | Gln | Asn | Ile
930 | | | | | 935 | | | | 940

Asn Asn His His Tyr Phe Phe Leu Pro Asn Gly Ile Glu Leu Val Gln
945             950                 955                 960

Ser Phe Leu Gln Asn Ala Asp Gly Ser Thr Ile Tyr Phe Asp Gln Lys
            965                 970                 975

Gly Arg Gln Val Phe Asn Gln Tyr Ile Thr Asp Gln Thr Gly Thr Ala
        980                 985                 990

Tyr Tyr Phe Gln Asn Asp Gly Thr  Met Val Thr Ser Gly  Phe Thr Glu
        995             1000                1005

Ile Asp Gly His Lys Gln Tyr  Phe Tyr Lys Asn Gly  Thr Gln Val
    1010            1015                1020

Lys Gly Gln Phe Val Ser Asp  Thr Asp Gly His Val  Phe Tyr Leu
    1025            1030                1035

Glu Ala Gly Asn Gly Asn Val  Ala Thr Gln Arg Phe  Ala Gln Asn
    1040            1045                1050

Ser Gln Gly Gln Trp Phe Tyr  Leu Gly Asn Asp Gly  Ile Ala Leu
    1055            1060                1065

Thr Gly Leu Gln Thr Ile Asn  Gly Val Gln Asn Tyr  Phe Tyr Ala
    1070            1075                1080

Asp Gly His Gln Ser Lys Gly  Asp Phe Ile Thr Ile  Gln Asn His
    1085            1090                1095

Val Leu Tyr Thr Asn Pro Leu  Thr Gly Ala Ile Thr  Thr Gly Met
    1100            1105                1110

Gln Gln Ile Gly Asp Lys Ile  Phe Val Phe Asp Asn  Thr Gly Asn
    1115            1120                1125

Met Leu Thr Asn Gln Tyr Tyr  Gln Thr Leu Asp Gly  Gln Trp Leu
    1130            1135                1140

His Leu Ser Thr Gln Gly Pro  Ala Asp Thr Gly Leu  Val Asn Ile
    1145            1150                1155

Asn Gly Asn Leu Lys Tyr Phe  Gln Ala Asn Gly Arg  Gln Val Lys
    1160            1165                1170

Gly Gln Phe Val Thr Asp Pro  Ile Thr Asn Val Ser  Tyr Tyr Met
    1175            1180                1185

Asn Ala Thr Asp Gly Ser Ala  Val Phe Asn Asp Tyr  Phe Thr Tyr
    1190            1195                1200

Gln Gly Gln Trp Tyr Leu Thr  Asp Ser Asn Tyr Gln  Leu Val Lys
    1205            1210                1215

Gly Phe Lys Val Val Asn Asn  Lys Leu Gln His Phe  Asp Glu Ile
    1220            1225                1230

Thr Gly Val Gln Thr Lys Ser  Ala His Ile Ile Val  Asn Asn Arg
    1235            1240                1245

Thr Tyr  Ile Phe Asp Asp Gln  Gly Tyr Phe Val Ser  Val Ala
    1250            1255                1260

<210> SEQ ID NO 55
<211> LENGTH: 4284
<212> TYPE: DNA
<213> ORGANISM: Streptococcus salivarius

<400> SEQUENCE: 55
atgaaagacg gcaagtacta ttacctgttg gaggacggta gccacaagaa aaactttgcg    60
atcacggtca acggccaagt gctgtatttc gatgagaacg gtgcactgag cagcacgtct   120
acctattcgt ttacccagga gactaccaac ctggttaccg atttcactaa gaataatgct   180

```
gcgtacgaca gcaccaaggc ttccttcgag ctggttgatg gctacctgac tgcggacagc    240
tggtatcgtc cgaaggaaat cctggaggct ggcaccacct ggaaagcgag caccgagaaa    300
gactttcgtc cgctgctgat gagctggtgg ccggataaag acacccaggt tgcgtacctg    360
aattacatga cgaaggcgct gagcaatggc gaggaaacga agacgtgtt tacgatcgag     420 aactcccaag catctctgaa cgcagccgct cagatcatcc aacgcaagat cgaggtcaag    480
attgcagcga acaaaagcac ggactggctg cgccagagca tcgaggcgtt cgtgaaagat    540
caagacaagt ggaatatcaa ttcggagagc ccgggtaaag agcatttcca aaaggtgct   600 ctgctgttcg ttaacagcga cctgaccaaa tgggcgaata gcgactatcg taaactggac    660
caaacggcga ccagccgtct gccgaaagac aagattaaga gcggcagcga tgcgggctac    720 gagttttgc tgtcctctga cattgataac agcaacccga ttgttcaggc ggagatgctg    780
aaccaactgt actatttcat gaactggggt cagattgtgt ttggcgacaa agataaggat    840
gcccatttcg acggtatccg cgtcgacgcc gtagacaacg ttagcattga tatgctgcaa    900
ctggttagct cttatatgaa ggcggcatac aaagttaatg aaagcgaagc gcgtgcactg    960
gcaaacattt ccattctgga ggcttggagc cagaacgatc cgtactacgt tgatgaacac    1020
aacacggctg cgctgtctat ggacaacggt ctgcgcctga gcatcgttca cggtttgacc    1080
cgtccggtta ctaacaaggg taccggtgcc cgtaatgcaa gcatgaaaga cctgatcaac    1140
ggtggctact tcggcttgtc caatcgtgca gaagttacga gctacgatca gctgggcttc    1200
gccacctacc tgtttgtgcg tgcccatgac tctgaagttc agaccgttat cgcggacatt    1260
atctcgaaga aaatcgatcc aaccacggac ggtttcacgt tcaccctgga ccagttgaaa    1320
caagccttcg acatctacaa cgccgatatg ctgaaggttg ataaggagta cacgcacagc    1380
aacatcccgg ctgcgtatgc cctgatgctg caaaactatg gtgcggctac gcgcgtgtat    1440
tatggtgatt tgtatacgga caatggccag tacatggcga aaaagagccc gtactttgat    1500
cagatcacga ccctgctgaa ggcgcgtagc aagtacgttg cgggtggcca gaccagctac    1560
atccataacc tggcgggtga tggtgtcagc agcgcgaagg ataacaaaga ggtgttggtc    1620
agcgtccgct acggtcagga tttgatgagc aaaaccgaca ccgagggtgg taagtatggt    1680
cgtaacagcg gtatgctgac cctgatcgcc aacaaccctg atctgaagct ggcagacggt    1740
gaaaccatca ccgtcaacat gggcgcagcg cacaagaatc aagcatatcg tccgttgttg    1800
ctgggcaccg aaaagggcat tgtgagcagc ctgaatgatt ccgacacgaa aattgttaag    1860
tataccgacg cgcaaggcaa tctggttttt accgctgatg agatcaaagg tttcaaaacc    1920
gtggatatga gcggttacct gtccgtgtgg gtgccggttg gcgcgaccga ggaccaaaac    1980
gtgctggcca agccgagcac gaaggtctac aaagaggggta ataagtttta tcgagcagc    2040 gcggcactgg aagcacaggt gatctacgag ggttttagca attttcaaga cttcgtgaag    2100
gaagatagcc agtataccaa caagctgatt gcggccaatg cggacctgtt caaaagctgg    2160
ggtattacga gctttgaaat cgctccgcag tatgttagct ccaaggatgg caccttcctg    2220
gatagcatca ttgagaatgg ctacgcgttt accgatcgtt acgacttcgc gatgtcgaaa    2280
aacaataagt acgctccaa agaggatctg cgtgacgcgt tgaaagccct gcacaaacaa    2340
ggcattcaag ttattgcaga ttgggtcccg gaccagctgt acaccctgcc gggtaaggaa    2400
gtggtcacgg cgacccgcac ggacacccac ggtaaagtcc tggatgacac ctccctggtc    2460
aataaactgt acgttaccaa taccaaatct agcggtaacg acttccaggc gcaatacggc    2520
```

| | |
|---|---|
| ggtgcattcc tggacaaact gcaaaagttg tacccggaga ttttcaagga agtgatggag | 2580 |
| gctagcggca aaaccattga tccgtccgtc aaaatcaagc agtgggaggc aaagtatttc | 2640 |
| aacggtacga acattcagaa acgcggtagc gactacgttc tgagcgacgg caaactgtat | 2700 |
| ttcacggtaa acgacaaagg taccttcttg ccggcagctc tgaccggtga cacgaaggca | 2760 |
| aagaccggtt tcgcctatga cggtactggc gtcacttact atacgacctc cggcacgcag | 2820 |
| gcaaagagcc aatttgtcac ctacaatggc aagcagtact atttcaatga caaggttat | 2880 |
| ctggtcacgg gtgaacaggc gattgacggt agcaactact tcttcctgcc gaacggcgtt | 2940 |
| atgtttacgg acggtgtgat caaaaatgct aaaggtcagt ctctggtcta cggcaaatct | 3000 |
| ggtaagctga ccacgcaaac cggttggaag gaagttacgg tgaaggatga tagcggcaag | 3060 |
| gaagagaaat ctaccaata cttctttaag ggtggcatta tggcgacggg tctgaccgag | 3120 |
| gttgaaggta aagagaaata cttttatgat aatggttatc aggctaaagg tattttcatc | 3180 |
| cctaccaaag acggccatct gatgttttc tgcggtgata gcggtgagcg taaatacagc | 3240 |
| ggtttcttcg aacaagacgg taactggtat tacgcaaacg ataaaggtta cgtcgcgacc | 3300 |
| ggttttacca aagtgggtaa gcagaacttg tactttaacg agaaaggtgt gcaggtcaag | 3360 |
| aaccgtttct tcaggttgg tgatgctact tattacgcga ataacgaggg tgatgtactg | 3420 |
| cgtggtgcac agacgatcaa cggcgacgaa ctgtacttcg acgaaagcgg caagcaagtc | 3480 |
| aaaggtgaat ttgtgaataa cccggacggt accacgagct attatgacgc aattaccggt | 3540 |
| gtgaaactgg tggacaccag cttggtcgtt aatggtcaaa cgttcaacat tgacgctaaa | 3600 |
| ggcgttgtca ccaaggcgca cacgccgggt ttctatacca ctggcgacaa caattggttt | 3660 |
| tatgcagata gccacggtcg caatgtcact ggcgcacaga tcattaacgg ccaacacctg | 3720 |
| tatttcgatg cgaatggccg tcaggtgaag ggcggctttg ttatgaacac tgatggttct | 3780 |
| cgttcgttct atcattggaa taccggtgat aaactggtga gcacgttctt tacgaccggc | 3840 |
| cacgatcgtt ggtactacgc cgacgacaaa ggtaacgtgg tgaccggcgc acaagtcatc | 3900 |
| aacggtcaga aattgttctt cgcgaccgac ggtaaacaag ttaagggcga tttcgcgacc | 3960 |
| aacgcaaatg gttcccgttc ttactatcac ggtgccacgg gtaataagct ggtcagcacc | 4020 |
| ttcttaccac cgggcgataa caactggtac tatgcagacg cgaagggcga ggttgtcgtt | 4080 |
| ggtgaacaaa cgattaacgg tcaaaatctg tattttgatc agaccggtaa gcaagtgaaa | 4140 |
| ggtgcgaccg cgaccaatcc agatggcagc atttcttatt acgatgttca cacgggcgag | 4200 |
| aaggtcatca ccgctgggt caaaattccg agcggtcaat gggtgtactt caacgcgcag | 4260 |
| ggtaagggtt acgtcagcaa ttaa | 4284 |

<210> SEQ ID NO 56
<211> LENGTH: 1427
<212> TYPE: PRT
<213> ORGANISM: Streptococcus salivarius

<400> SEQUENCE: 56

Met Lys Asp Gly Lys Tyr Tyr Tyr Leu Leu Glu Asp Gly Ser His Lys
1               5                   10                  15

Lys Asn Phe Ala Ile Thr Val Asn Gly Gln Val Leu Tyr Phe Asp Glu
            20                  25                  30

Asn Gly Ala Leu Ser Ser Thr Ser Thr Tyr Ser Phe Thr Gln Glu Thr
        35                  40                  45

Thr Asn Leu Val Thr Asp Phe Thr Lys Asn Asn Ala Ala Tyr Asp Ser
    50                  55                  60

```
Thr Lys Ala Ser Phe Glu Leu Val Asp Gly Tyr Leu Thr Ala Asp Ser
 65                  70                  75                  80

Trp Tyr Arg Pro Lys Glu Ile Leu Glu Ala Gly Thr Thr Trp Lys Ala
                 85                  90                  95

Ser Thr Glu Lys Asp Phe Arg Pro Leu Leu Met Ser Trp Trp Pro Asp
            100                 105                 110

Lys Asp Thr Gln Val Ala Tyr Leu Asn Tyr Met Thr Lys Ala Leu Ser
            115                 120                 125

Asn Gly Glu Glu Thr Lys Asp Val Phe Thr Ile Glu Asn Ser Gln Ala
130                 135                 140

Ser Leu Asn Ala Ala Ala Gln Ile Ile Gln Arg Lys Ile Glu Val Lys
145                 150                 155                 160

Ile Ala Ala Asn Lys Ser Thr Asp Trp Leu Arg Gln Ser Ile Glu Ala
                165                 170                 175

Phe Val Lys Asp Gln Asp Lys Trp Asn Ile Asn Ser Glu Ser Pro Gly
            180                 185                 190

Lys Glu His Phe Gln Lys Gly Ala Leu Leu Phe Val Asn Ser Asp Leu
            195                 200                 205

Thr Lys Trp Ala Asn Ser Asp Tyr Arg Lys Leu Asp Gln Thr Ala Thr
210                 215                 220

Ser Arg Leu Pro Lys Asp Lys Ile Lys Ser Gly Ser Asp Ala Gly Tyr
225                 230                 235                 240

Glu Phe Leu Leu Ser Ser Asp Ile Asp Asn Ser Asn Pro Ile Val Gln
                245                 250                 255

Ala Glu Met Leu Asn Gln Leu Tyr Tyr Phe Met Asn Trp Gly Gln Ile
            260                 265                 270

Val Phe Gly Asp Lys Asp Lys Asp Ala His Phe Asp Gly Ile Arg Val
            275                 280                 285

Asp Ala Val Asp Asn Val Ser Ile Asp Met Leu Gln Leu Val Ser Ser
290                 295                 300

Tyr Met Lys Ala Ala Tyr Lys Val Asn Glu Ser Glu Ala Arg Ala Leu
305                 310                 315                 320

Ala Asn Ile Ser Ile Leu Glu Ala Trp Ser Gln Asn Asp Pro Tyr Tyr
                325                 330                 335

Val Asp Glu His Asn Thr Ala Ala Leu Ser Met Asp Asn Gly Leu Arg
            340                 345                 350

Leu Ser Ile Val His Gly Leu Thr Arg Pro Val Thr Asn Lys Gly Thr
            355                 360                 365

Gly Ala Arg Asn Ala Ser Met Lys Asp Leu Ile Asn Gly Gly Tyr Phe
370                 375                 380

Gly Leu Ser Asn Arg Ala Glu Val Thr Ser Tyr Asp Gln Leu Gly Phe
385                 390                 395                 400

Ala Thr Tyr Leu Phe Val Arg Ala His Asp Ser Glu Val Gln Thr Val
                405                 410                 415

Ile Ala Asp Ile Ile Ser Lys Lys Ile Asp Pro Thr Thr Asp Gly Phe
            420                 425                 430

Thr Phe Thr Leu Asp Gln Leu Lys Gln Ala Phe Asp Ile Tyr Asn Ala
            435                 440                 445

Asp Met Leu Lys Val Asp Lys Glu Tyr Thr His Ser Asn Ile Pro Ala
            450                 455                 460

Ala Tyr Ala Leu Met Leu Gln Thr Met Gly Ala Ala Thr Arg Val Tyr
465                 470                 475                 480
```

-continued

Tyr Gly Asp Leu Tyr Thr Asp Asn Gly Gln Tyr Met Ala Lys Lys Ser
            485                 490                 495

Pro Tyr Phe Asp Gln Ile Thr Thr Leu Leu Lys Ala Arg Ser Lys Tyr
        500                 505                 510

Val Ala Gly Gly Gln Thr Ser Tyr Ile His Asn Leu Ala Gly Asp Gly
            515                 520                 525

Val Ser Ser Ala Lys Asp Asn Lys Glu Val Leu Val Ser Val Arg Tyr
530                 535                 540

Gly Gln Asp Leu Met Ser Lys Thr Asp Thr Glu Gly Gly Lys Tyr Gly
545                 550                 555                 560

Arg Asn Ser Gly Met Leu Thr Leu Ile Ala Asn Asn Pro Asp Leu Lys
                565                 570                 575

Leu Ala Asp Gly Glu Thr Ile Thr Val Asn Met Gly Ala Ala His Lys
            580                 585                 590

Asn Gln Ala Tyr Arg Pro Leu Leu Leu Gly Thr Glu Lys Gly Ile Val
        595                 600                 605

Ser Ser Leu Asn Asp Ser Asp Thr Lys Ile Val Lys Tyr Thr Asp Ala
    610                 615                 620

Gln Gly Asn Leu Val Phe Thr Ala Asp Glu Ile Lys Gly Phe Lys Thr
625                 630                 635                 640

Val Asp Met Ser Gly Tyr Leu Ser Val Trp Val Pro Val Gly Ala Thr
                645                 650                 655

Glu Asp Gln Asn Val Leu Ala Lys Pro Ser Thr Lys Val Tyr Lys Glu
            660                 665                 670

Gly Asp Lys Val Tyr Ser Ser Ala Ala Leu Glu Ala Gln Val Ile
        675                 680                 685

Tyr Glu Gly Phe Ser Asn Phe Gln Asp Phe Val Lys Glu Asp Ser Gln
    690                 695                 700

Tyr Thr Asn Lys Leu Ile Ala Ala Asn Ala Asp Leu Phe Lys Ser Trp
705                 710                 715                 720

Gly Ile Thr Ser Phe Glu Ile Ala Pro Gln Tyr Val Ser Ser Lys Asp
                725                 730                 735

Gly Thr Phe Leu Asp Ser Ile Ile Glu Asn Gly Tyr Ala Phe Thr Asp
            740                 745                 750

Arg Tyr Asp Phe Ala Met Ser Lys Asn Asn Lys Tyr Gly Ser Lys Glu
        755                 760                 765

Asp Leu Arg Asp Ala Leu Lys Ala Leu His Lys Gln Gly Ile Gln Val
    770                 775                 780

Ile Ala Asp Trp Val Pro Asp Gln Leu Tyr Thr Leu Pro Gly Lys Glu
785                 790                 795                 800

Val Val Thr Ala Thr Arg Thr Asp Thr His Gly Lys Val Leu Asp Asp
                805                 810                 815

Thr Ser Leu Val Asn Lys Leu Tyr Val Thr Asn Thr Lys Ser Ser Gly
            820                 825                 830

Asn Asp Phe Gln Ala Gln Tyr Gly Gly Ala Phe Leu Asp Lys Leu Gln
        835                 840                 845

Lys Leu Tyr Pro Glu Ile Phe Lys Glu Val Met Glu Ala Ser Gly Lys
    850                 855                 860

Thr Ile Asp Pro Ser Val Lys Ile Lys Gln Trp Glu Ala Lys Tyr Phe
865                 870                 875                 880

Asn Gly Thr Asn Ile Gln Lys Arg Gly Ser Asp Tyr Val Leu Ser Asp
                885                 890                 895

Gly Lys Leu Tyr Phe Thr Val Asn Asp Lys Gly Thr Phe Leu Pro Ala

-continued

```
                900             905             910
Ala Leu Thr Gly Asp Thr Lys Ala Lys Thr Gly Phe Ala Tyr Asp Gly
            915             920             925

Thr Gly Val Thr Tyr Tyr Thr Thr Ser Gly Thr Gln Ala Lys Ser Gln
            930             935             940

Phe Val Thr Tyr Asn Gly Lys Gln Tyr Tyr Phe Asn Asp Lys Gly Tyr
945             950             955             960

Leu Val Thr Gly Glu Gln Ala Ile Asp Gly Ser Asn Tyr Phe Phe Leu
            965             970             975

Pro Asn Gly Val Met Phe Thr Asp Gly Val Ile Lys Asn Ala Lys Gly
            980             985             990

Gln Ser Leu Val Tyr Gly Lys Ser Gly Lys Leu Thr Thr Gln Thr Gly
            995             1000            1005

Trp Lys Glu Val Thr Val Lys Asp Asp Ser Gly Lys Glu Glu Lys
            1010            1015            1020

Phe Tyr Gln Tyr Phe Phe Lys Gly Gly Ile Met Ala Thr Gly Leu
            1025            1030            1035

Thr Glu Val Glu Gly Lys Glu Lys Tyr Phe Tyr Asp Asn Gly Tyr
            1040            1045            1050

Gln Ala Lys Gly Ile Phe Ile Pro Thr Lys Asp Gly His Leu Met
            1055            1060            1065

Phe Phe Cys Gly Asp Ser Gly Glu Arg Lys Tyr Ser Gly Phe Phe
            1070            1075            1080

Glu Gln Asp Gly Asn Trp Tyr Tyr Ala Asn Asp Lys Gly Tyr Val
            1085            1090            1095

Ala Thr Gly Phe Thr Lys Val Gly Lys Gln Asn Leu Tyr Phe Asn
            1100            1105            1110

Glu Lys Gly Val Gln Val Lys Asn Arg Phe Phe Gln Val Gly Asp
            1115            1120            1125

Ala Thr Tyr Tyr Ala Asn Asn Glu Gly Asp Val Leu Arg Gly Ala
            1130            1135            1140

Gln Thr Ile Asn Gly Asp Glu Leu Tyr Phe Asp Glu Ser Gly Lys
            1145            1150            1155

Gln Val Lys Gly Glu Phe Val Asn Pro Asp Gly Thr Thr Ser
            1160            1165            1170

Tyr Tyr Asp Ala Ile Thr Gly Val Lys Leu Val Asp Thr Ser Leu
            1175            1180            1185

Val Val Asn Gly Gln Thr Phe Asn Ile Asp Ala Lys Gly Val Val
            1190            1195            1200

Thr Lys Ala His Thr Pro Gly Phe Tyr Thr Thr Gly Asp Asn Asn
            1205            1210            1215

Trp Phe Tyr Ala Asp Ser His Gly Arg Asn Val Thr Gly Ala Gln
            1220            1225            1230

Ile Ile Asn Gly Gln His Leu Tyr Phe Asp Ala Asn Gly Arg Gln
            1235            1240            1245

Val Lys Gly Gly Phe Val Met Asn Thr Asp Gly Ser Arg Ser Phe
            1250            1255            1260

Tyr His Trp Asn Thr Gly Asp Lys Leu Val Ser Thr Phe Phe Thr
            1265            1270            1275

Thr Gly His Asp Arg Trp Tyr Tyr Ala Asp Asp Lys Gly Asn Val
            1280            1285            1290

Val Thr Gly Ala Gln Val Ile Asn Gly Gln Lys Leu Phe Phe Ala
            1295            1300            1305
```

```
Thr Asp Gly Lys Gln Val Lys Gly Asp Phe Ala Thr Asn Ala Asn
    1310            1315                1320
Gly Ser Arg Ser Tyr Tyr His Gly Ala Thr Gly Asn     Lys Leu Val
    1325            1330                1335
Ser Thr Phe Phe Thr Thr Gly Asp Asn Asn Trp Tyr     Tyr Ala Asp
    1340            1345                1350
Ala Lys Gly Glu Val Val Val Gly Glu Gln Thr Ile     Asn Gly Gln
    1355            1360                1365
Asn Leu Tyr Phe Asp Gln Thr Gly Lys Gln Val Lys     Gly Ala Thr
    1370            1375                1380
Ala Thr Asn Pro Asp Gly Ser Ile Ser Tyr Tyr Asp     Val His Thr
    1385            1390                1395
Gly Glu Lys Val Ile Asn Arg Trp Val Lys Ile Pro     Ser Gly Gln
    1400            1405                1410
Trp Val Tyr Phe Asn Ala Gln Gly Lys Gly Tyr Val     Ser Asn
    1415            1420                1425

<210> SEQ ID NO 57
<211> LENGTH: 5208
<212> TYPE: DNA
<213> ORGANISM: Lactobacillus reuteri

<400> SEQUENCE: 57
atggatcagc aagtacaaag cagcaccacc caggagcaga cgagcacggt taacgcggac      60
acgactaaaa ccgtcaatct ggataccaac actgaccagc cggctcagac gaccgataag     120
aatcaggtcg cgaatgatac caccaccaac caaagcaaga cggacagcac cagcacgacg     180
gttaagaatc cgacgtttat tcctgttagc actttgtcca gctccgataa cgaaaagcag     240
agccagaatt acaataaacc agataacggt aattacggta atgttgatgc ggcctacttc     300
aataacaatc agctgcacat tagcggttgg cacgcaacca acgcgagcca gggtacggat     360
agccgccaag taatcgtacg cgacattacc accaagaccg agctgggtcg tactaatgtg     420
accaacaatg ttctgcgtcc ggacgtgaaa aatgttcaca cgtctacaa cgctgacaac     480 agcggctttg atgtgaatat caatattgat ttcagcaaga tgaaagacta tcgtgacagc     540
atcgagatcg tttctcgtta tagcggcaac ggcaagagcg ttgactggtg gtcgcagccg     600
atcacgtttg acaaaaacaa ttatgcttat ctggacactt tcgaggtgaa gaacggtgaa     660
ctgcatgcaa cgggctggaa tgccaccaac aaggctatca attacaatca ccacttcgtt     720
attctgtttg atcgtacgaa tggcaaagaa gtcacccgcc aagaggtgcg tgatggtcaa     780
agccgtccgg atgtggcgaa ggtatacccg caagtcgttg cgcgaacaa tagcggtttt     840 gacgttacgt ttaacattgg tgatttggac tacacccatc agtaccagat cctgtctcgt     900
tacagcaacg cagacaacgg tgaaggcgat tatgtgacct attggtttgc gccgcagagc     960
atcgctccgg cgaatcaaag caaccaaggt tacctggaca gcttcgatat ttcgaaaaac    1020
ggtgaggtga ccgtgacggg ttggaatgcg acggatctga gcgagttgca aacgaatcac    1080
tacgtgatcc tgtttgatca gacggcgggt caacaggttg catccgctaa ggtcgacctg    1140
atcagccgtc cagacgtcgc gaaggcgtac cctaccgtta aaacggcaga aacctccggt    1200
ttcaaggtca cgtttaaggt tagcaatctg caaccgggcc accaatacag cgtcgttagc    1260
cgctttagcg ccgatgaaaa cggtaatggc aacgacaaac gccacacgga ctactggtac    1320
tctccggtta ccctgaacca aacggctagc aacattgaca ctatcaccat gacttccaac    1380
```

```
ggtctgcaca tcaccggctg gatggcgagc gataatagca ttaacgaagc gaccccgtac    1440
gcgattatcc tgaacaacgg tcgcgaggtg acgcgccaga aactgaccct gatcgcgcgt    1500
ccggatgttg cggcagtgta tccgagcctg tacaatagcg cggttagcgg cttcgacacc    1560
accatcaagc tgactaacgc gcaatatcaa gcattgaacg ccagctgca agtgctgctg    1620 cgctttagca aggcggtgga cggtaacccg aatggtacca ataccgtcac ggatcaattt    1680
agcaaaaact acgcaacgac cggtggtaat ttcgattacg tcaaggttaa tggtaaccaa    1740
attgagtttt ctggctggca cgcgacgaat cagagcaatg ataagaacag ccaatggatt    1800
atcgtcttgg ttaacggtaa agaggtcaaa cgccagctgg tcaatgacac gaaagacggc    1860
gcagccggct tcaatcgtaa tgatgtgtat aaagtgaacc cagcgatcga aaatagcatt    1920
atgtctggct tccagggcat tatcacgttg ccggttacgg tgaaagacga aaacgtgcag    1980
ctggtgcacc gcttctccaa tgacgcaaaa acgggtgagg gcaattatgt cgatttctgg    2040
agcgaggtga tgtctgtgaa ggactctttc caaaagggta atggtccgct gaaccagttt    2100
ggcctgcaaa ccatcaacgg ccaacaatac tatattgacc cgacgaccgg ccagccgcgt    2160
aagaatttcc tgctgcaaaa cggcaacgat tggatttact tcgacaaaga cactggcgca    2220
ggcaccaacg cgctgaaatt gcagtttgat aagggcacga ttagcgctga cgaacaatac    2280
cgtcgcggca acgaggcgta ctcctacgat gataagagca ttgaaaatgt caacggttac    2340
ttgacggcgg acacgtggta ccgcccgaag cagatcctga aggatggcac cacttggacc    2400
gattccaaag aaaccgatat gcgtccgatc ttgatggtct ggtggccaaa cacggtgact    2460
caggcgtact atctgaacta catgaaacaa tatggcaatc tgctgccggc gagcctgccg    2520
agctttagca ccgacgccga tagcgcggag ttgaatcatt attccgagct ggtccaacag    2580
aatatcgaga aacgtattag cgagactggt agcactgatt ggctgcgtac cctgatgcac    2640
gagttcgtga cgaagaatag catgtggaac aaagatagcg agaacgttga ctacggtggc    2700
ctgcaactgc aaggtggttt cctgaagtac gttaacagcg acctgacgaa gtacgcaaac    2760
tctgattggc gtctgatgaa ccgtaccgcg acgaacattg acggtaagaa ttacggtggt    2820
gccgagtttc tgctggcgaa tgacatcgac aactctaacc cggtggtgca ggccgaagaa    2880
ttgaattggc tgtattatct gatgaacttc ggtaccatca ccggtaacaa cccagaagct    2940
aacttcgacg gcatccgtgt cgacgcggtc gataatgtgg atgttgatct gctgagcatt    3000
gcccgtgact actttaatgc agcgtataac atggaacaaa gcgatgctag cgcgaataag    3060
cacatcaata ttctggaaga ttgggggctgg gacgatccgg cgtacgtgaa caaaatcggc    3120
aatccacagt tgaccatgga tgaccgcctg cgtaatgcaa ttatggacac cctgagcggt    3180
gcgccggata agaaccaagc gctgaacaag ctgattactc agtctctggt gaatcgcgca    3240
aatgataata ctgaaaacgc ggtgatccct tcctacaact ttgtccgcgc tcatgacagc    3300
aatgcccagg accagatccg tcaagcgatc caggcggcaa ccggcaaacc ttatggcgag    3360
ttcaacttgg atgatgagaa aaagggtatg gaggcttaca tcaatgacca aaatagcacc    3420
aataagaaat ggaacctgta caacatgccg agcgcatata ccatcctgct gacgaataag    3480
gactcggtcc cgcgtgtcta ctatggcgac ttgtaccagg atggtggcca gtacatggaa    3540
cacaaaactc gttactttga caccatcacg aatctgctga aaacccgcgt caagtatgtc    3600
gcaggcggcc agaccatgtc tgtggataag aatggcattt tgactaatgt ccgtttcggt    3660
aagggtgcga tgaacgcaac tgacacgggt accgatgaaa cccgcaccga aggtatcggc    3720
gttgttatca gcaacaatac gaatttgaaa ctgaatgacg gcgaaagcgt tgtgctgcac    3780
```

-continued

```
atgggcgctg cccataagaa tcagaagtat cgtgcagtga tcctgaccac ggaggacggt    3840
gtgaagaatt acaccaacga caccgatgcg ccggtcgcat acaccgacgc gaacggcgat    3900
ttgcatttca ccaatactaa cctggacggt cagcaatata ccgccgttcg tggctacgca    3960
aacccggacg ttacgggtta tctggccgtc tgggttcctg ctggtgccgc cgatgaccaa    4020
gacgcacgta ccgctccgag cgacgaggcc cacaccacga aaacggcgta tcgttccaat    4080
gcggcattgg actccaacgt catctacgaa ggcttttcga actttatcta ttggccgacg    4140
accgagagcg agcgcacgaa tgtccgcatc gcgcagaacg cggatctgtt caaatcgtgg    4200
ggtatcacca ccttcgagct ggcgccacag tacaatagca gcaaggacgg tacgtttctg    4260
gattcgatca ttgacaatgg ttacgcgttt accgatcgtt atgacctggg tatgtctacc    4320
ccgaacaagt acggtagcga tgaggatctg cgtaacgccc tgcaagcact gcacaaggcc    4380
ggtctgcaag ccatcgcaga ttgggttccg gaccaaatct acaatctgcc gggcaaagag    4440
gctgtcacgg ttactcgtag cgatgaccac ggcactacct gggaggttag cccgatcaag    4500
aatgtggtgt atatcactaa taccatcggt ggtggcgaat accagaaaaa gtatggtggt    4560
gaatttctgg acaccttgca aaagaatat ccgcagctgt ttagccaagt ttacccggtg    4620
acccaaacga cgattgaccc tagcgttaag attaaagagt ggtccgcgaa gtacttcaat    4680
ggtactaata tcctgcatcg cggtgcgggt tacgtcctgc gtagcaatga tggtaagtat    4740
tacaacctgg gtactagcac ccagcagttc ctgccgagcc agctgagcgt tcaagataat    4800
gagggttacg gtttcgttaa agagggtaac aactatcact attatgacga gaacaaacaa    4860
atggttaagg acgcgtttat ccaggatagc gtcggcaatt ggtactattt tgataagaac    4920
ggcaatatgg ttgcaaacca aagcccggtt gaaatcagca gcaacggtgc gagcggcacc    4980
tacttgtttt tgaataatgg taccagcttc cgcagcggcc tggtcaaaac ggatgcaggc    5040
acctattact acgatggtga cggtcgcatg gttcgtaatc aaacggtttc tgacggtgcc    5100
atgacgtacg ttctggacga aaatggtaaa ctggtcagcg aatcttttga tagcagcgcg    5160
accgaggccc atccgctgaa accgggcgat ctgaacggtc aaaagtaa               5208
```

<210> SEQ ID NO 58
<211> LENGTH: 1735
<212> TYPE: PRT
<213> ORGANISM: Lactobacillus reuteri

<400> SEQUENCE: 58

```
Met Asp Gln Gln Val Gln Ser Ser Thr Thr Gln Glu Gln Thr Ser Thr
1               5                   10                  15

Val Asn Ala Asp Thr Thr Lys Thr Val Asn Leu Asp Thr Asn Thr Asp
            20                  25                  30

Gln Pro Ala Gln Thr Thr Asp Lys Asn Gln Val Ala Asn Asp Thr Thr
        35                  40                  45

Thr Asn Gln Ser Lys Thr Asp Ser Thr Thr Val Lys Asn Pro
    50                  55                  60

Thr Phe Ile Pro Val Ser Thr Leu Ser Ser Asp Asn Glu Lys Gln
65                  70                  75                  80

Ser Gln Asn Tyr Asn Lys Pro Asp Asn Gly Asn Tyr Gly Asn Val Asp
                85                  90                  95

Ala Ala Tyr Phe Asn Asn Asn Gln Leu His Ile Ser Gly Trp His Ala
            100                 105                 110

Thr Asn Ala Ser Gln Gly Thr Asp Ser Arg Gln Val Ile Val Arg Asp
```

```
              115                 120                 125
Ile Thr Thr Lys Thr Glu Leu Gly Arg Thr Asn Val Thr Asn Asn Val
    130                 135                 140

Leu Arg Pro Asp Val Lys Asn Val His Asn Val Tyr Asn Ala Asp Asn
145                 150                 155                 160

Ser Gly Phe Asp Val Asn Ile Asn Ile Asp Phe Ser Lys Met Lys Asp
                165                 170                 175

Tyr Arg Asp Ser Ile Glu Ile Val Ser Arg Tyr Ser Gly Asn Gly Lys
            180                 185                 190

Ser Val Asp Trp Trp Ser Gln Pro Ile Thr Phe Asp Lys Asn Asn Tyr
        195                 200                 205

Ala Tyr Leu Asp Thr Phe Glu Val Lys Asn Gly Glu Leu His Ala Thr
    210                 215                 220

Gly Trp Asn Ala Thr Asn Lys Ala Ile Asn Tyr Asn His His Phe Val
225                 230                 235                 240

Ile Leu Phe Asp Arg Thr Asn Gly Lys Glu Val Thr Arg Gln Glu Val
                245                 250                 255

Arg Asp Gly Gln Ser Arg Pro Asp Val Ala Lys Val Tyr Pro Gln Val
            260                 265                 270

Val Gly Ala Asn Asn Ser Gly Phe Asp Val Thr Phe Asn Ile Gly Asp
        275                 280                 285

Leu Asp Tyr Thr His Gln Tyr Gln Ile Leu Ser Arg Tyr Ser Asn Ala
    290                 295                 300

Asp Asn Gly Glu Gly Asp Tyr Val Thr Tyr Trp Phe Ala Pro Gln Ser
305                 310                 315                 320

Ile Ala Pro Ala Asn Gln Ser Asn Gln Gly Tyr Leu Asp Ser Phe Asp
                325                 330                 335

Ile Ser Lys Asn Gly Glu Val Thr Val Thr Gly Trp Asn Ala Thr Asp
            340                 345                 350

Leu Ser Glu Leu Gln Thr Asn His Tyr Val Ile Leu Phe Asp Gln Thr
        355                 360                 365

Ala Gly Gln Gln Val Ala Ser Ala Lys Val Asp Leu Ile Ser Arg Pro
    370                 375                 380

Asp Val Ala Lys Ala Tyr Pro Thr Val Lys Thr Ala Glu Thr Ser Gly
385                 390                 395                 400

Phe Lys Val Thr Phe Lys Val Ser Asn Leu Gln Pro Gly His Gln Tyr
                405                 410                 415

Ser Val Val Ser Arg Phe Ser Ala Asp Glu Asn Gly Asn Gly Asn Asp
            420                 425                 430

Lys Arg His Thr Asp Tyr Trp Tyr Ser Pro Val Thr Leu Asn Gln Thr
        435                 440                 445

Ala Ser Asn Ile Asp Thr Ile Thr Met Thr Ser Asn Gly Leu His Ile
    450                 455                 460

Thr Gly Trp Met Ala Ser Asp Asn Ser Ile Asn Glu Ala Thr Pro Tyr
465                 470                 475                 480

Ala Ile Ile Leu Asn Asn Gly Arg Glu Val Thr Arg Gln Lys Leu Thr
                485                 490                 495

Leu Ile Ala Arg Pro Asp Val Ala Val Tyr Pro Ser Leu Tyr Asn
            500                 505                 510

Ser Ala Val Ser Gly Phe Asp Thr Thr Ile Lys Leu Thr Asn Ala Gln
        515                 520                 525

Tyr Gln Ala Leu Asn Gly Gln Leu Gln Val Leu Leu Arg Phe Ser Lys
    530                 535                 540
```

```
Ala Val Asp Gly Asn Pro Asn Gly Thr Asn Thr Val Thr Asp Gln Phe
545                 550                 555                 560

Ser Lys Asn Tyr Ala Thr Thr Gly Gly Asn Phe Asp Tyr Val Lys Val
                565                 570                 575

Asn Gly Asn Gln Ile Glu Phe Ser Gly Trp His Ala Thr Asn Gln Ser
            580                 585                 590

Asn Asp Lys Asn Ser Gln Trp Ile Ile Val Leu Val Asn Gly Lys Glu
        595                 600                 605

Val Lys Arg Gln Leu Val Asn Asp Thr Lys Asp Gly Ala Ala Gly Phe
610                 615                 620

Asn Arg Asn Asp Val Tyr Lys Val Asn Pro Ala Ile Glu Asn Ser Ile
625                 630                 635                 640

Met Ser Gly Phe Gln Gly Ile Ile Thr Leu Pro Val Thr Val Lys Asp
                645                 650                 655

Glu Asn Val Gln Leu Val His Arg Phe Ser Asn Asp Ala Lys Thr Gly
            660                 665                 670

Glu Gly Asn Tyr Val Asp Phe Trp Ser Glu Val Met Ser Val Lys Asp
        675                 680                 685

Ser Phe Gln Lys Gly Asn Gly Pro Leu Asn Gln Phe Gly Leu Gln Thr
690                 695                 700

Ile Asn Gly Gln Gln Tyr Tyr Ile Asp Pro Thr Thr Gly Gln Pro Arg
705                 710                 715                 720

Lys Asn Phe Leu Leu Gln Asn Gly Asn Asp Trp Ile Tyr Phe Asp Lys
                725                 730                 735

Asp Thr Gly Ala Gly Thr Asn Ala Leu Lys Leu Gln Phe Asp Lys Gly
            740                 745                 750

Thr Ile Ser Ala Asp Glu Gln Tyr Arg Arg Gly Asn Glu Ala Tyr Ser
        755                 760                 765

Tyr Asp Asp Lys Ser Ile Glu Asn Val Asn Gly Tyr Leu Thr Ala Asp
770                 775                 780

Thr Trp Tyr Arg Pro Lys Gln Ile Leu Lys Asp Gly Thr Thr Trp Thr
785                 790                 795                 800

Asp Ser Lys Glu Thr Asp Met Arg Pro Ile Leu Met Val Trp Trp Pro
                805                 810                 815

Asn Thr Val Thr Gln Ala Tyr Tyr Leu Asn Tyr Met Lys Gln Tyr Gly
            820                 825                 830

Asn Leu Leu Pro Ala Ser Leu Pro Ser Phe Ser Thr Asp Ala Asp Ser
        835                 840                 845

Ala Glu Leu Asn His Tyr Ser Glu Leu Val Gln Gln Asn Ile Glu Lys
850                 855                 860

Arg Ile Ser Glu Thr Gly Ser Thr Asp Trp Leu Arg Thr Leu Met His
865                 870                 875                 880

Glu Phe Val Thr Lys Asn Ser Met Trp Asn Lys Asp Ser Glu Asn Val
                885                 890                 895

Asp Tyr Gly Gly Leu Gln Leu Gln Gly Gly Phe Leu Lys Tyr Val Asn
            900                 905                 910

Ser Asp Leu Thr Lys Tyr Ala Asn Ser Asp Trp Arg Leu Met Asn Arg
        915                 920                 925

Thr Ala Thr Asn Ile Asp Gly Lys Asn Tyr Gly Gly Ala Glu Phe Leu
930                 935                 940

Leu Ala Asn Asp Ile Asp Asn Ser Asn Pro Val Val Gln Ala Glu Glu
945                 950                 955                 960
```

```
Leu Asn Trp Leu Tyr Tyr Leu Met Asn Phe Gly Thr Ile Thr Gly Asn
            965                 970                 975

Asn Pro Glu Ala Asn Phe Asp Gly Ile Arg Val Asp Ala Val Asp Asn
        980                 985                 990

Val Asp Val Asp Leu Leu Ser Ile Ala Arg Asp Tyr Phe Asn Ala Ala
        995                 1000                1005

Tyr Asn Met Glu Gln Ser Asp Ala Ser Ala Asn Lys His Ile Asn
    1010                1015                1020

Ile Leu Glu Asp Trp Gly Trp Asp Asp Pro Ala Tyr Val Asn Lys
    1025                1030                1035

Ile Gly Asn Pro Gln Leu Thr Met Asp Asp Arg Leu Arg Asn Ala
    1040                1045                1050

Ile Met Asp Thr Leu Ser Gly Ala Pro Asp Lys Asn Gln Ala Leu
    1055                1060                1065

Asn Lys Leu Ile Thr Gln Ser Leu Val Asn Arg Ala Asn Asp Asn
    1070                1075                1080

Thr Glu Asn Ala Val Ile Pro Ser Tyr Asn Phe Val Arg Ala His
    1085                1090                1095

Asp Ser Asn Ala Gln Asp Gln Ile Arg Gln Ala Ile Gln Ala Ala
    1100                1105                1110

Thr Gly Lys Pro Tyr Gly Glu Phe Asn Leu Asp Asp Glu Lys Lys
    1115                1120                1125

Gly Met Glu Ala Tyr Ile Asn Asp Gln Asn Ser Thr Asn Lys Lys
    1130                1135                1140

Trp Asn Leu Tyr Asn Met Pro Ser Ala Tyr Thr Ile Leu Leu Thr
    1145                1150                1155

Asn Lys Asp Ser Val Pro Arg Val Tyr Tyr Gly Asp Leu Tyr Gln
    1160                1165                1170

Asp Gly Gly Gln Tyr Met Glu His Lys Thr Arg Tyr Phe Asp Thr
    1175                1180                1185

Ile Thr Asn Leu Leu Lys Thr Arg Val Lys Tyr Val Ala Gly Gly
    1190                1195                1200

Gln Thr Met Ser Val Asp Lys Asn Gly Ile Leu Thr Asn Val Arg
    1205                1210                1215

Phe Gly Lys Gly Ala Met Asn Ala Thr Asp Thr Gly Thr Asp Glu
    1220                1225                1230

Thr Arg Thr Glu Gly Ile Gly Val Val Ile Ser Asn Asn Thr Asn
    1235                1240                1245

Leu Lys Leu Asn Asp Gly Glu Ser Val Val Leu His Met Gly Ala
    1250                1255                1260

Ala His Lys Asn Gln Lys Tyr Arg Ala Val Ile Leu Thr Thr Glu
    1265                1270                1275

Asp Gly Val Lys Asn Tyr Thr Asn Asp Thr Asp Ala Pro Val Ala
    1280                1285                1290

Tyr Thr Asp Ala Asn Gly Asp Leu His Phe Thr Asn Thr Asn Leu
    1295                1300                1305

Asp Gly Gln Gln Tyr Thr Ala Val Arg Gly Tyr Ala Asn Pro Asp
    1310                1315                1320

Val Thr Gly Tyr Leu Ala Val Trp Val Pro Ala Gly Ala Ala Asp
    1325                1330                1335

Asp Gln Asp Ala Arg Thr Ala Pro Ser Asp Glu Ala His Thr Thr
    1340                1345                1350

Lys Thr Ala Tyr Arg Ser Asn Ala Ala Leu Asp Ser Asn Val Ile
```

```
            1355                1360                1365
Tyr Glu Gly Phe Ser Asn Phe Ile Tyr Trp Pro Thr Thr Glu Ser
        1370                1375                1380
Glu Arg Thr Asn Val Arg Ile Ala Gln Asn Ala Asp Leu Phe Lys
        1385                1390                1395
Ser Trp Gly Ile Thr Thr Phe Glu Leu Ala Pro Gln Tyr Asn Ser
        1400                1405                1410
Ser Lys Asp Gly Thr Phe Leu Asp Ser Ile Ile Asp Asn Gly Tyr
        1415                1420                1425
Ala Phe Thr Asp Arg Tyr Asp Leu Gly Met Ser Thr Pro Asn Lys
        1430                1435                1440
Tyr Gly Ser Asp Glu Asp Leu Arg Asn Ala Leu Gln Ala Leu His
        1445                1450                1455
Lys Ala Gly Leu Gln Ala Ile Ala Asp Trp Val Pro Asp Gln Ile
        1460                1465                1470
Tyr Asn Leu Pro Gly Lys Glu Ala Val Thr Val Thr Arg Ser Asp
        1475                1480                1485
Asp His Gly Thr Thr Trp Glu Val Ser Pro Ile Lys Asn Val Val
        1490                1495                1500
Tyr Ile Thr Asn Thr Ile Gly Gly Gly Glu Tyr Gln Lys Lys Tyr
        1505                1510                1515
Gly Gly Glu Phe Leu Asp Thr Leu Gln Lys Glu Tyr Pro Gln Leu
        1520                1525                1530
Phe Ser Gln Val Tyr Pro Val Thr Gln Thr Thr Ile Asp Pro Ser
        1535                1540                1545
Val Lys Ile Lys Glu Trp Ser Ala Lys Tyr Phe Asn Gly Thr Asn
        1550                1555                1560
Ile Leu His Arg Gly Ala Gly Tyr Val Leu Arg Ser Asn Asp Gly
        1565                1570                1575
Lys Tyr Tyr Asn Leu Gly Thr Ser Thr Gln Gln Phe Leu Pro Ser
        1580                1585                1590
Gln Leu Ser Val Gln Asp Asn Glu Gly Tyr Gly Phe Val Lys Glu
        1595                1600                1605
Gly Asn Asn Tyr His Tyr Tyr Asp Glu Asn Lys Gln Met Val Lys
        1610                1615                1620
Asp Ala Phe Ile Gln Asp Ser Val Gly Asn Trp Tyr Tyr Phe Asp
        1625                1630                1635
Lys Asn Gly Asn Met Val Ala Asn Gln Ser Pro Val Glu Ile Ser
        1640                1645                1650
Ser Asn Gly Ala Ser Gly Thr Tyr Leu Phe Leu Asn Asn Gly Thr
        1655                1660                1665
Ser Phe Arg Ser Gly Leu Val Lys Thr Asp Ala Gly Thr Tyr Tyr
        1670                1675                1680
Tyr Asp Gly Asp Gly Arg Met Val Arg Asn Gln Thr Val Ser Asp
        1685                1690                1695
Gly Ala Met Thr Tyr Val Leu Asp Glu Asn Gly Lys Leu Val Ser
        1700                1705                1710
Glu Ser Phe Asp Ser Ser Ala Thr Glu Ala His Pro Leu Lys Pro
        1715                1720                1725
Gly Asp Leu Asn Gly Gln Lys
        1730                1735

<210> SEQ ID NO 59
```

```
<211> LENGTH: 1242
<212> TYPE: PRT
<213> ORGANISM: Unknown
<220> FEATURE:
<223> OTHER INFORMATION: unknown Streptococcus species

<400> SEQUENCE: 59

Met Ile Asn Gly Lys Glu Tyr Tyr Val Glu Asp Asp Gly Thr Val Arg
1               5                   10                  15

Lys Asn Tyr Val Leu Glu Arg Asn Gly Gly Ser Gln Tyr Phe Asn Ala
            20                  25                  30

Glu Thr Gly Glu Leu Ser Asn Gln Lys Asp Tyr Arg Phe Asp Lys Asn
        35                  40                  45

Gly Gly Thr Gly Ser Ala Ala Asp Ser Thr Thr Asn Thr Asn Val Thr
    50                  55                  60

Val Asn Gly Asp Lys Asn Ala Phe Tyr Gly Thr Thr Glu Lys Asp Ile
65                  70                  75                  80

Glu Leu Val Asp Gly Tyr Phe Thr Ala Asn Thr Trp Tyr Arg Pro Lys
                85                  90                  95

Glu Ile Leu Lys Asp Gly Lys Glu Trp Thr Ala Ser Thr Glu Asn Asp
            100                 105                 110

Lys Arg Pro Leu Leu Thr Val Trp Trp Pro Ser Lys Ala Ile Gln Ala
        115                 120                 125

Ser Tyr Leu Asn Tyr Met Arg Glu Glu Gly Leu Gly Thr Asn Gln Thr
    130                 135                 140

Phe Thr Ser Tyr Ser Ser Gln Thr Gln Met Asp Gln Ala Ala Leu Glu
145                 150                 155                 160

Val Gln Lys Arg Ile Glu Glu Arg Ile Ala Arg Glu Gly Asn Thr Asp
                165                 170                 175

Trp Leu Arg Thr Thr Ile Lys Asn Phe Val Lys Thr Gln Pro Gly Trp
            180                 185                 190

Asn Ser Thr Ser Glu Asn Leu Asp Asn Ser Asp His Leu Gln Gly Gly
        195                 200                 205

Ala Leu Leu Tyr Asn Asn Ser Asn Arg Thr Ser Tyr Ala Asn Ser Asp
    210                 215                 220

Tyr Arg Leu Leu Asn Arg Thr Pro Thr Gln Gln Asp Gly Thr Arg Arg
225                 230                 235                 240

Tyr Phe Lys Asp Asn Ser Ser Gly Gly Phe Glu Phe Leu Leu Ala Asn
                245                 250                 255

Asp Ile Asp Asn Ser Asn Pro Ala Val Gln Ala Glu Gln Leu Asn Trp
            260                 265                 270

Leu His Tyr Ile Met Asn Ile Gly Ser Leu Thr Gly Gly Ser Glu Asp
        275                 280                 285

Glu Asn Phe Asp Gly Val Arg Val Asp Ala Val Asp Asn Val Asn Ala
    290                 295                 300

Asp Leu Leu Gln Ile Ala Ser Asp Tyr Phe Lys Ala Lys Tyr Gly Val
305                 310                 315                 320

Glu Lys Ser Glu Glu Glu Ala Ile Lys His Leu Ser Ile Leu Glu Ala
                325                 330                 335

Trp Ser His Asn Asp Ala Tyr Tyr Asn Glu Asp Thr Lys Gly Ala Gln
            340                 345                 350

Leu Pro Met Asp Asp Pro Leu Arg Leu Ala Met Val Phe Ser Phe Leu
        355                 360                 365

Arg Pro Ile Gly Asn Arg Ser Gly Leu Glu Pro Leu Ile Thr Asn Ser
    370                 375                 380
```

-continued

```
Leu Asn Asp Arg Ser Glu Ser Lys Lys Asn Thr Lys Arg Met Ala Asn
385                 390                 395                 400

Tyr Thr Phe Val Arg Ala His Asp Ser Glu Val Gln Ser Val Ile Gly
                405                 410                 415

Gln Ile Ile Lys Asn Glu Ile Asn Pro Gln Ser Thr Gly Asn Thr Phe
            420                 425                 430

Thr Leu Asp Glu Met Lys Lys Ala Phe Lys Ile Tyr Asn Ala Asp Met
        435                 440                 445

Arg Ser Ala Asn Lys Arg Tyr Thr Gln Tyr Asn Ile Pro Ser Ala Tyr
    450                 455                 460

Ala Phe Met Leu Thr Asn Lys Asp Thr Val Pro Arg Val Tyr Tyr Gly
465                 470                 475                 480

Asp Leu Tyr Thr Asp Asp Gly Gln Tyr Met Ala Gln Lys Ser Pro Tyr
                485                 490                 495

His Asp Ala Ile Ser Thr Leu Leu Gln Ala Arg Ile Arg Tyr Ala Ala
            500                 505                 510

Gly Gly Gln Asp Met Lys Met Ser Tyr Val Gly Ser Gly Asn Thr Asn
        515                 520                 525

Gly Trp Asp Ala Ser Gly Val Leu Thr Ser Val Arg Tyr Gly Lys Gly
    530                 535                 540

Ala Asn Asn Ala Ser Asp Ala Gly Thr Ala Glu Thr Arg Asn Gln Gly
545                 550                 555                 560

Met Ala Val Ile Leu Ser Asn Gln Pro Ala Leu Arg Leu Asn Ser Asn
                565                 570                 575

Leu Thr Ile Asn Met Gly Ala Ala His Arg Asn Gln Ala Tyr Arg Pro
            580                 585                 590

Leu Leu Leu Thr Thr Ser Asn Gly Val Ala Ser Tyr Leu Asn Asp Gly
        595                 600                 605

Asp Ala Asn Gly Ile Val Lys Tyr Thr Asp Ala Asn Gly Tyr Leu Thr
    610                 615                 620

Phe Asn Pro Gly Glu Ile Ser Gly Val Arg Asn Ala Gln Val Asp Gly
625                 630                 635                 640

Tyr Leu Ala Val Trp Val Pro Leu Gly Ala Ser Glu Asn Gln Asp Val
                645                 650                 655

Arg Val Ala Ala Ser Lys Ser Lys Asn Ser Ser Gly Leu Val Tyr Asp
            660                 665                 670

Ser Ser Ala Ala Leu Asp Ser Gln Val Ile Tyr Glu Gly Phe Ser Asn
        675                 680                 685

Phe Gln Asp Phe Val Gln Asp Pro Ser Gln Tyr Thr Asn Lys Lys Ile
    690                 695                 700

Ala Glu Asn Ala Asn Leu Phe Lys Ser Trp Gly Ile Thr Ser Phe Glu
705                 710                 715                 720

Phe Ala Pro Gln Tyr Val Ser Ser Asp Gly Thr Phe Leu Asp Ser
                725                 730                 735

Val Ile Gln Asn Gly Tyr Ala Phe Ser Asp Arg Tyr Asp Ile Gly Met
            740                 745                 750

Ser Lys Asp Asn Lys Tyr Gly Ser Leu Ala Asp Leu Lys Ala Ala Leu
        755                 760                 765

Lys Ser Leu His Ala Val Gly Ile Ser Ala Ile Ala Asp Trp Val Pro
    770                 775                 780

Asp Gln Ile Tyr Asn Leu Pro Gly Asp Glu Val Val Thr Ala Thr Arg
785                 790                 795                 800
```

```
Val Asn Asn Tyr Gly Glu Thr Lys Asp Gly Ala Ile Ile Asp His Ser
                805                 810                 815

Leu Tyr Val Ala Lys Thr Arg Thr Phe Gly Asn Asp Tyr Gln Gly Lys
            820                 825                 830

Tyr Gly Gly Ala Tyr Leu Asp Glu Leu Lys Arg Leu Tyr Pro Gln Phe
        835                 840                 845

Phe Asp Arg Val Gln Ile Ser Thr Gly Lys Leu Thr Thr Asp Glu
850                 855                 860

Lys Ile Thr Lys Trp Ser Ala Lys Tyr Met Asn Gly Thr Asn Ile Leu
865                 870                 875                 880

Asp Arg Gly Ser Glu Tyr Val Leu Lys Asn Gly Leu Ser Gly Tyr Tyr
                885                 890                 895

Gly Thr Asn Gly Gly Lys Val Ser Leu Pro Lys Val Val Gly Ser Asn
            900                 905                 910

Gln Ser Thr Asn Asn Asn Gln Asn Gly Asp Gly Ser Gly Arg Phe
        915                 920                 925

Glu Lys Ser Trp Gly Ser Val Tyr Tyr Arg Tyr Asn Asp Gly Gln Arg
    930                 935                 940

Ala Arg Asn Ala Phe Ile Lys Asp Asn Asp Gly Asn Val Tyr Tyr Phe
945                 950                 955                 960

Asp Asn Thr Gly Arg Met Ala Ile Gly Glu Lys Thr Ile Asp Gly Lys
                965                 970                 975

Gln Tyr Phe Phe Leu Ala Asn Gly Val Gln Leu Arg Asp Gly Tyr Arg
            980                 985                 990

Gln Asn Arg Arg Gly Gln Val Phe Tyr Tyr Asp Glu Asn Gly Ile Met
        995                 1000                1005

Ser Gln Thr Gly Lys Pro Ser Pro Lys Pro Glu Pro Lys Pro Asp
    1010                1015                1020

Asn Asn Thr Phe Ser Arg Asn Gln Phe Ile Gln Ile Gly Asn Asn
    1025                1030                1035

Val Trp Ala Tyr Tyr Asp Gly Asn Gly Lys Arg Val Ile Gly Arg
    1040                1045                1050

Gln Asn Ile Asn Gly Gln Glu Leu Phe Phe Asp Asn Asn Gly Val
    1055                1060                1065

Gln Val Lys Gly Arg Thr Ala Gln Val Asp Gly Val Thr Arg Tyr
    1070                1075                1080

Phe Asp Ala Asn Ser Gly Glu Met Ala Arg Asn Arg Phe Ala Glu
    1085                1090                1095

Val Glu Pro Gly Val Trp Ala Tyr Phe Asn Asn Asp Gly Ala Ala
    1100                1105                1110

Val Thr Gly Ser Gln Asn Ile Asn Gly Gln Thr Leu Tyr Phe Asp
    1115                1120                1125

Gln Asn Gly His Gln Val Lys Gly Ala Leu Val Thr Val Asp Gly
    1130                1135                1140

Asn Leu Arg Tyr Tyr Asp Ala Asn Ser Gly Asp Leu Tyr Arg Asn
    1145                1150                1155

Arg Phe Gln Glu Val Asn Gly Ser Trp Tyr Tyr Phe Asp Gly Asn
    1160                1165                1170

Gly Asn Ala Val Lys Gly Met Val Asn Ile Asn Gly Gln Asn Leu
    1175                1180                1185

Leu Phe Asp Asn Asp Gly Lys Gln Val Lys Gly His Leu Val Arg
    1190                1195                1200

Val Asn Gly Val Ile Arg Tyr Tyr Asp Pro Asn Ser Gly Glu Met
```

```
                1205                1210                1215
Ala Val Asn Arg Trp Val Glu Ile Ser Ser Gly Trp Trp Val Tyr
        1220                1225                1230

Phe Asp Gly Glu Gly Arg Gly Gln Ile
        1235                1240

<210> SEQ ID NO 60
<211> LENGTH: 1518
<212> TYPE: PRT
<213> ORGANISM: Streptococcus salivarius

<400> SEQUENCE: 60

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
            20                  25                  30

Leu Ser Val Thr Thr Ser Ser Val Ser Ala Asp Glu Thr Gln Asp Lys
        35                  40                  45

Thr Val Thr Gln Ser Asn Ser Gly Thr Thr Ala Ser Leu Val Thr Ser
    50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335
```

-continued

Glu Lys Ser Thr Gln Trp Leu Arg Glu Thr Ile Ser Ala Phe Val Lys
               340                 345                 350
Thr Gln Pro Gln Trp Asn Lys Glu Thr Glu Asn Tyr Ser Lys Gly Gly
           355                 360                 365
Gly Glu Asp His Leu Gln Gly Gly Ala Leu Leu Tyr Val Asn Asp Ser
       370                 375                 380
Arg Thr Pro Trp Ala Asn Ser Asp Tyr Arg Arg Leu Asn Arg Thr Ala
385                 390                 395                 400
Thr Asn Gln Thr Gly Thr Ile Asp Lys Ser Ile Leu Asp Glu Gln Ser
               405                 410                 415
Asp Pro Asn His Met Gly Gly Phe Asp Phe Leu Leu Ala Asn Asp Val
           420                 425                 430
Asp Leu Ser Asn Pro Val Val Gln Ala Glu Gln Leu Asn Gln Ile His
       435                 440                 445
Tyr Leu Met Asn Trp Gly Ser Ile Val Met Gly Asp Lys Asp Ala Asn
       450                 455                 460
Phe Asp Gly Ile Arg Val Asp Ala Val Asp Asn Val Asp Ala Asp Met
465                 470                 475                 480
Leu Gln Leu Tyr Thr Asn Tyr Phe Arg Glu Tyr Tyr Gly Val Asn Lys
               485                 490                 495
Ser Glu Ala Asn Ala Leu Ala His Ile Ser Val Leu Glu Ala Trp Ser
           500                 505                 510
Leu Asn Asp Asn His Tyr Asn Asp Lys Thr Asp Gly Ala Ala Leu Ala
       515                 520                 525
Met Glu Asn Lys Gln Arg Leu Ala Leu Leu Phe Ser Leu Ala Lys Pro
       530                 535                 540
Ile Lys Glu Arg Thr Pro Ala Val Ser Pro Leu Tyr Asn Asn Thr Phe
545                 550                 555                 560
Asn Thr Thr Gln Arg Asp Glu Lys Thr Asp Trp Ile Asn Lys Asp Gly
               565                 570                 575
Ser Lys Ala Tyr Asn Glu Asp Gly Thr Val Lys Gln Ser Thr Ile Gly
           580                 585                 590
Lys Tyr Asn Glu Lys Tyr Gly Asp Ala Ser Gly Asn Tyr Val Phe Ile
       595                 600                 605
Arg Ala His Asp Asn Asn Val Gln Asp Ile Ile Ala Glu Ile Ile Lys
       610                 615                 620
Lys Glu Ile Asn Pro Lys Ser Asp Gly Phe Thr Ile Thr Asp Ala Glu
625                 630                 635                 640
Met Lys Gln Ala Phe Glu Ile Tyr Asn Lys Asp Met Leu Ser Ser Asp
               645                 650                 655
Lys Lys Tyr Thr Leu Asn Asn Ile Pro Ala Ala Tyr Ala Val Met Leu
           660                 665                 670
Gln Asn Met Glu Thr Ile Thr Arg Val Tyr Tyr Gly Asp Leu Tyr Thr
       675                 680                 685
Asp Asp Gly His Tyr Met Glu Thr Lys Ser Pro Tyr Tyr Asp Thr Ile
       690                 695                 700
Val Asn Leu Met Lys Ser Arg Ile Lys Tyr Val Ser Gly Gly Gln Ala
705                 710                 715                 720
Gln Arg Ser Tyr Trp Leu Pro Thr Asp Gly Lys Met Asp Asn Ser Asp
               725                 730                 735
Val Glu Leu Tyr Arg Thr Asn Glu Val Tyr Thr Ser Val Arg Tyr Gly
           740                 745                 750
Lys Asp Ile Met Thr Ala Asn Asp Thr Glu Gly Ser Lys Tyr Ser Arg

-continued

```
            755                 760                 765
Thr Ser Gly Gln Val Thr Leu Val Ala Asn Asn Pro Lys Leu Asn Leu
770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                    805                 810                 815

Phe Thr Ser Asp Ala Asp Ala Ile Ala Ala Gly Tyr Val Lys Glu Thr
                    820                 825                 830

Asp Ser Asn Gly Val Leu Thr Phe Gly Ala Asn Asp Ile Lys Gly Tyr
                    835                 840                 845

Glu Thr Phe Asp Met Ser Gly Phe Val Ala Val Trp Val Pro Val Gly
                    850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                    885                 890                 895

Leu Ile Tyr Glu Gly Phe Ser Asn Phe Gln Thr Ile Pro Asp Gly Ser
                    900                 905                 910

Asp Pro Ser Val Tyr Thr Asn Arg Lys Ile Ala Glu Asn Val Asp Leu
                    915                 920                 925

Phe Lys Ser Trp Gly Val Thr Ser Phe Glu Met Ala Pro Gln Phe Val
                    930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                    965                 970                 975

Gly Ser Lys Glu Asp Leu Arg Asp Ala Leu Lys Ala Leu His Lys Ala
                    980                 985                 990

Gly Ile Gln Ala Ile Ala Asp Trp Val Pro Asp Gln Ile Tyr Gln Leu
                    995                 1000                1005

Pro Gly Lys Glu Val Val Thr Ala Thr Arg Thr Asp Gly Ala Gly
            1010                1015                1020

Arg Lys Ile Ala Asp Ala Ile Ile Asp His Ser Leu Tyr Val Ala
            1025                1030                1035

Asn Ser Lys Ser Ser Gly Lys Asp Tyr Gln Ala Lys Tyr Gly Gly
            1040                1045                1050

Glu Phe Leu Ala Glu Leu Lys Ala Lys Tyr Pro Glu Met Phe Lys
            1055                1060                1065

Val Asn Met Ile Ser Thr Gly Lys Pro Ile Asp Asp Ser Val Lys
            1070                1075                1080

Leu Lys Gln Trp Lys Ala Glu Tyr Phe Asn Gly Thr Asn Val Leu
            1085                1090                1095

Glu Arg Gly Val Gly Tyr Val Leu Ser Asp Glu Ala Thr Gly Lys
            1100                1105                1110

Tyr Phe Thr Val Thr Lys Glu Gly Asn Phe Ile Pro Leu Gln Leu
            1115                1120                1125

Thr Gly Lys Glu Lys Val Ile Thr Gly Phe Ser Ser Asp Gly Lys
            1130                1135                1140

Gly Ile Thr Tyr Phe Gly Thr Ser Gly Thr Gln Ala Lys Ser Ala
            1145                1150                1155

Phe Val Thr Phe Asn Gly Asn Thr Tyr Tyr Phe Asp Ala Arg Gly
            1160                1165                1170
```

-continued

His Met Val Thr Asn Ser Glu Tyr Ser Pro Asn Gly Lys Asp Val
    1175            1180                1185

Tyr Arg Phe Leu Pro Asn Gly Ile Met Leu Ser Asn Ala Phe Tyr
    1190            1195                1200

Ile Asp Ala Asn Gly Asn Thr Tyr Leu Tyr Asn Ser Lys Gly Gln
    1205            1210                1215

Met Tyr Lys Gly Gly Tyr Thr Lys Phe Asp Val Ser Glu Thr Asp
    1220            1225                1230

Lys Asp Gly Lys Glu Ser Lys Val Val Lys Phe Arg Tyr Phe Thr
    1235            1240                1245

Asn Glu Gly Val Met Ala Lys Gly Val Thr Val Ile Asp Gly Phe
    1250            1255                1260

Thr Gln Tyr Phe Gly Glu Asp Gly Phe Gln Ala Lys Asp Lys Leu
    1265            1270                1275

Val Thr Phe Lys Gly Lys Thr Tyr Tyr Phe Asp Ala His Thr Gly
    1280            1285                1290

Asn Gly Ile Lys Asp Thr Trp Arg Asn Ile Asn Gly Lys Trp Tyr
    1295            1300                1305

Tyr Phe Asp Ala Asn Gly Val Ala Ala Thr Gly Ala Gln Val Ile
    1310            1315                1320

Asn Gly Gln Lys Leu Tyr Phe Asn Glu Asp Gly Ser Gln Val Lys
    1325            1330                1335

Gly Gly Val Val Lys Asn Ala Asp Gly Thr Tyr Ser Lys Tyr Lys
    1340            1345                1350

Glu Gly Phe Gly Glu Leu Val Thr Asn Glu Phe Phe Thr Thr Asp
    1355            1360                1365

Gly Asn Val Trp Tyr Tyr Ala Gly Ala Asn Gly Lys Thr Val Thr
    1370            1375                1380

Gly Ala Gln Val Ile Asn Gly Gln His Leu Tyr Phe Asn Ala Asp
    1385            1390                1395

Gly Ser Gln Val Lys Gly Gly Val Val Lys Asn Ala Asp Gly Thr
    1400            1405                1410

Tyr Ser Lys Tyr Asn Ala Ser Thr Gly Glu Arg Leu Thr Asn Glu
    1415            1420                1425

Phe Phe Thr Thr Gly Asp Asn Asn Trp Tyr Tyr Ile Gly Ala Asn
    1430            1435                1440

Gly Lys Ser Val Thr Gly Glu Val Lys Ile Gly Asp Asp Thr Tyr
    1445            1450                1455

Phe Phe Ala Lys Asp Gly Lys Gln Val Lys Gly Gln Thr Val Ser
    1460            1465                1470

Ala Gly Asn Gly Arg Ile Ser Tyr Tyr Tyr Gly Asp Ser Gly Lys
    1475            1480                1485

Arg Ala Val Ser Thr Trp Ile Glu Ile Gln Pro Gly Val Tyr Val
    1490            1495                1500

Tyr Phe Asp Lys Asn Gly Leu Ala Tyr Pro Pro Arg Val Leu Asn
    1505            1510                1515

<210> SEQ ID NO 61
<211> LENGTH: 1528
<212> TYPE: PRT
<213> ORGANISM: Streptococcus salivarius

<400> SEQUENCE: 61

Met Thr Asn Lys Ile Thr Gly Lys Ile Ile Met Glu Asn Lys Val His

-continued

```
  1               5                  10                 15
Tyr Lys Leu His Lys Val Lys Lys Gln Trp Val Thr Ile Ala Val Ala
                 20                  25                 30
Ser Ala Ala Leu Ala Thr Val Val Gly Gly Leu Ser Ala Thr Thr Ser
                 35                  40                 45
Ser Val Ser Ala Asp Glu Thr Gln Asp Lys Ile Val Thr Gln Pro Asn
 50                                  55                 60
Leu Asp Thr Thr Ala Asp Leu Val Thr Ser Thr Glu Ala Thr Lys Glu
 65                  70                  75                 80
Val Asp Lys Arg Thr Asn Thr Lys Glu Ala Asp Val Leu Thr Pro Ala
                 85                  90                 95
Lys Glu Thr Asn Ala Val Glu Thr Ala Thr Thr Asn Thr Gln Ala
                 100                 105                110
Thr Ala Glu Ala Ala Thr Thr Ala Thr Thr Ser Asp Val Ala Val Ala
                 115                 120                125
Ala Val Pro Asn Lys Glu Ala Val Val Thr Thr Asp Ala Pro Ala Val
                 130                 135                140
Thr Thr Glu Lys Ala Glu Glu Gln Pro Ala Thr Val Lys Ala Glu Val
145                 150                 155                160
Val Asn Thr Glu Val Lys Ala Pro Gln Ala Ala Leu Lys Asp Ser Glu
                 165                 170                175
Val Glu Ala Ala Leu Ser Leu Lys Asn Ile Lys Tyr Thr Asp Gly Lys
                 180                 185                190
Tyr Tyr Tyr Val Asn Glu Asp Gly Ser His Lys Glu Asn Phe Ala Ile
                 195                 200                205
Thr Val Asn Gly Gln Leu Leu Tyr Phe Gly Lys Asp Gly Ala Leu Thr
                 210                 215                220
Ser Ser Ser Thr His Ser Phe Thr Pro Gly Thr Thr Asn Ile Val Asp
225                 230                 235                240
Gly Phe Ser Ile Asn Asn Arg Ala Tyr Asp Ser Ser Glu Ala Ser Phe
                 245                 250                255
Glu Leu Ile Asn Gly Tyr Leu Thr Ala Asp Ser Trp Tyr Arg Pro Val
                 260                 265                270
Ser Ile Ile Lys Asp Gly Val Thr Trp Gln Ala Ser Thr Ala Glu Asp
                 275                 280                285
Phe Arg Pro Leu Leu Met Ala Trp Trp Pro Asn Val Asp Thr Gln Val
                 290                 295                300
Asn Tyr Leu Asn Tyr Met Ser Lys Val Phe Asn Leu Glu Ala Lys Tyr
305                 310                 315                320
Thr Ser Thr Asp Lys Gln Ala Asp Leu Asn Arg Ala Ala Lys Asp Ile
                 325                 330                335
Gln Val Lys Ile Glu Gln Lys Ile Gln Ala Glu Lys Ser Thr Gln Trp
                 340                 345                350
Leu Arg Glu Thr Ile Ser Ala Phe Val Lys Thr Gln Pro Gln Trp Asn
                 355                 360                365
Lys Glu Thr Glu Asn Tyr Ser Lys Gly Gly Gly Glu Asp His Leu Gln
                 370                 375                380
Gly Gly Ala Leu Leu Tyr Val Asn Asp Ser Arg Thr Pro Trp Ala Asn
385                 390                 395                400
Ser Asn Tyr Arg Leu Leu Asn Arg Thr Ala Thr Asn Gln Thr Gly Thr
                 405                 410                415
Ile Asn Lys Ser Val Leu Asp Glu Gln Ser Asp Pro Asn His Met Gly
                 420                 425                430
```

-continued

```
Gly Phe Asp Phe Leu Leu Ala Asn Asp Val Asp Leu Ser Asn Pro Val
            435                 440                 445

Val Gln Ala Glu Gln Leu Asn Gln Ile His Tyr Leu Met Asn Trp Gly
    450                 455                 460

Ser Ile Val Met Gly Asp Lys Asp Ala Asn Phe Asp Gly Ile Arg Val
465                 470                 475                 480

Asp Ala Val Asp Asn Val Asn Ala Asp Met Leu Gln Leu Tyr Thr Asn
                485                 490                 495

Tyr Phe Arg Glu Tyr Tyr Gly Val Asn Lys Ser Glu Ala Gln Ala Leu
            500                 505                 510

Ala His Ile Ser Val Leu Glu Ala Trp Ser Leu Asn Asp Asn His Tyr
            515                 520                 525

Asn Asp Lys Thr Asp Gly Ala Ala Leu Ala Met Glu Asn Lys Gln Arg
            530                 535                 540

Leu Ala Leu Leu Phe Ser Leu Ala Lys Pro Ile Lys Asp Arg Thr Pro
545                 550                 555                 560

Ala Val Ser Pro Leu Tyr Asn Asn Thr Phe Asn Thr Thr Gln Arg Asp
                565                 570                 575

Phe Lys Thr Asp Trp Ile Asn Lys Asp Gly Ser Thr Ala Tyr Asn Glu
            580                 585                 590

Asp Gly Thr Ala Lys Gln Ser Thr Ile Gly Lys Tyr Asn Glu Lys Tyr
            595                 600                 605

Gly Asp Ala Ser Gly Asn Tyr Val Phe Ile Arg Ala His Asp Asn Asn
            610                 615                 620

Val Gln Asp Ile Ile Ala Glu Ile Ile Lys Lys Glu Ile Asn Lys Lys
625                 630                 635                 640

Ser Asp Gly Phe Thr Ile Ser Asp Ser Glu Met Lys Gln Ala Phe Glu
                645                 650                 655

Ile Tyr Asn Lys Asp Met Leu Ser Ser Asn Lys Lys Tyr Thr Leu Asn
            660                 665                 670

Asn Ile Pro Ala Ala Tyr Ala Val Met Leu Gln Asn Met Glu Thr Ile
            675                 680                 685

Thr Arg Val Tyr Tyr Gly Asp Leu Tyr Thr Asp Asp Gly His Tyr Met
            690                 695                 700

Glu Thr Lys Ser Pro Tyr His Asp Thr Ile Val Asn Leu Met Lys Asn
705                 710                 715                 720

Arg Ile Lys Tyr Val Ser Gly Gln Ala Gln Arg Ser Tyr Trp Leu
            725                 730                 735

Pro Thr Asp Gly Lys Met Asp Asn Ser Asp Val Glu Leu Tyr Arg Thr
            740                 745                 750

Ser Glu Val Tyr Thr Ser Val Arg Tyr Gly Lys Asp Ile Met Thr Ala
            755                 760                 765

Asp Asp Thr Glu Gly Ser Lys Tyr Ser Arg Thr Ser Gly Gln Val Thr
            770                 775                 780

Leu Val Val Asn Asn Pro Lys Leu Thr Leu His Glu Ser Ala Lys Leu
785                 790                 795                 800

Asn Val Glu Met Gly Lys Ile His Ala Asn Gln Lys Tyr Arg Ala Leu
                805                 810                 815

Ile Val Gly Thr Ala Asp Gly Ile Lys Asn Phe Thr Ser Asp Ala Glu
            820                 825                 830

Ala Ile Ala Ala Gly Tyr Val Lys Glu Thr Asp Ser Asn Gly Val Leu
            835                 840                 845
```

```
Thr Phe Gly Ala Asn Asp Ile Lys Gly Tyr Glu Thr Phe Asp Met Ser
850                 855                 860

Gly Phe Val Ala Val Trp Val Pro Val Gly Ala Ser Asp Asp Gln Asp
865                 870                 875                 880

Ile Arg Val Ala Pro Ser Thr Glu Ala Lys Lys Glu Gly Leu Thr
                885                 890                 895

Leu Lys Ala Thr Glu Ala Tyr Asp Ser Gln Leu Ile Tyr Glu Gly Phe
                900                 905                 910

Ser Asn Phe Gln Thr Ile Pro Asp Gly Ser Asp Pro Ser Val Tyr Thr
                915                 920                 925

Asn Arg Lys Ile Ala Glu Asn Val Asp Leu Phe Lys Ser Trp Gly Val
                930                 935                 940

Thr Ser Phe Glu Met Ala Pro Gln Phe Val Ser Ala Asp Gly Thr
945                 950                 955                 960

Phe Leu Asp Ser Val Ile Gln Asn Gly Tyr Ala Phe Ala Asp Arg Tyr
                965                 970                 975

Asp Leu Ala Met Ser Lys Asn Asn Lys Tyr Gly Ser Lys Glu Asp Leu
                980                 985                 990

Arg Asp Ala Leu Lys Ala Leu His  Lys Ala Gly Ile Gln  Ala Ile Ala
                995                 1000                1005

Asp Trp Val Pro Asp Gln Ile  Tyr Gln Leu Pro Gly  Lys Glu Val
1010                1015                1020

Val Thr Ala Thr Arg Thr Asp  Gly Ala Gly Arg Lys  Ile Ala Asp
1025                1030                1035

Ala Ile Ile Asp His Ser Leu  Tyr Val Ala Asn Ser  Lys Ser Ser
1040                1045                1050

Gly Arg Asp Tyr Gln Ala Gln  Tyr Gly Gly Glu Phe  Leu Ala Glu
1055                1060                1065

Leu Lys Ala Lys Tyr Pro Lys  Met Phe Thr Glu Asn  Met Ile Ser
1070                1075                1080

Thr Gly Lys Pro Ile Asp Asp  Ser Val Lys Leu Lys  Gln Trp Lys
1085                1090                1095

Ala Lys Tyr Phe Asn Gly Thr  Asn Val Leu Asp Arg  Gly Val Gly
1100                1105                1110

Tyr Val Leu Ser Asp Glu Ala  Thr Gly Lys Tyr Phe  Thr Val Thr
1115                1120                1125

Lys Glu Gly Asn Phe Ile Pro  Leu Gln Leu Thr Gly  Asn Glu Lys
1130                1135                1140

Ala Val Thr Gly Phe Ser Asn  Asp Gly Lys Gly Ile  Thr Tyr Phe
1145                1150                1155

Gly Thr  Ser Gly Asn Gln Ala  Lys Ser Ala Phe Val  Thr Phe Asn
1160                1165                1170

Gly Asn  Thr Tyr Tyr Phe Asp  Ala Arg Gly His Met  Val Thr Asn
1175                1180                1185

Gly Glu  Tyr Ser Pro Asn Gly  Lys Asp Val Tyr Arg  Phe Leu Pro
1190                1195                1200

Asn Gly  Ile Met Leu Ser Asn  Ala Phe Tyr Val Asp  Ala Asn Gly
1205                1210                1215

Asn Thr  Tyr Leu Tyr Asn Tyr  Lys Gly Gln Met Tyr  Lys Gly Gly
1220                1225                1230

Tyr Thr  Lys Phe Asp Val Thr  Glu Thr Asp Lys Asp  Gly Asn Glu
1235                1240                1245

Ser Lys  Val Val Lys Phe Arg  Tyr Phe Thr Asn Glu  Gly Val Met
```

```
              1250                1255                1260

Ala Lys Gly Leu Thr Val Ile Asp Gly Ser Thr Gln Tyr Phe Gly
    1265                1270                1275

Glu Asp Gly Phe Gln Thr Lys Asp Lys Leu Ala Thr Tyr Lys Gly
    1280                1285                1290

Lys Thr Tyr Tyr Phe Glu Ala His Thr Gly Asn Ala Ile Lys Asn
    1295                1300                1305

Thr Trp Arg Asn Ile Asp Gly Lys Trp Tyr His Phe Asp Glu Asn
    1310                1315                1320

Gly Val Ala Ala Thr Gly Ala Gln Val Ile Asn Gly Gln Lys Leu
    1325                1330                1335

Tyr Phe Asn Glu Asp Gly Ser Gln Val Lys Gly Gly Val Val Lys
    1340                1345                1350

Asn Ala Asp Gly Thr Tyr Ser Lys Tyr Lys Glu Gly Ser Gly Glu
    1355                1360                1365

Leu Val Thr Asn Glu Phe Phe Thr Thr Asp Gly Asn Val Trp Tyr
    1370                1375                1380

Tyr Ala Gly Ala Asp Gly Lys Thr Val Thr Gly Ala Gln Val Ile
    1385                1390                1395

Asn Gly Gln His Leu Tyr Phe Lys Glu Asp Gly Ser Gln Val Lys
    1400                1405                1410

Gly Gly Val Val Lys Asn Ala Asp Gly Thr Tyr Ser Lys Tyr Asp
    1415                1420                1425

Ala Ala Thr Gly Glu Arg Leu Thr Asn Glu Phe Phe Thr Thr Gly
    1430                1435                1440

Asp Asn Asn Trp Tyr Tyr Ile Gly Ser Asn Gly Lys Thr Val Thr
    1445                1450                1455

Gly Glu Val Lys Ile Gly Ala Asp Thr Tyr Tyr Phe Ala Lys Asp
    1460                1465                1470

Gly Lys Gln Val Lys Gly Gln Thr Val Thr Ala Gly Asn Gly Arg
    1475                1480                1485

Ile Ser Tyr Tyr Tyr Gly Asp Ser Gly Lys Lys Ala Ile Ser Thr
    1490                1495                1500

Trp Ile Glu Ile Gln Pro Gly Ile Tyr Val Tyr Phe Asp Lys Thr
    1505                1510                1515

Gly Ile Ala Tyr Pro Pro Arg Val Leu Asn
    1520                1525

<210> SEQ ID NO 62
<211> LENGTH: 1518
<212> TYPE: PRT
<213> ORGANISM: Streptococcus salivarius

<400> SEQUENCE: 62

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
        35                  40                  45

Thr Val Thr Gln Ser Asn Ser Gly Thr Thr Ala Ser Leu Val Thr Ser
    50                  55                  60

Pro Glu Ala Thr Lys Glu Ala Asp Lys Arg Thr Asn Thr Lys Glu Ala
65                  70                  75                  80
```

```
Asp Val Leu Thr Pro Ala Lys Glu Thr Asn Ala Val Glu Thr Ala Thr
            85                  90                  95

Thr Thr Asn Thr Gln Ala Thr Ala Glu Ala Ala Thr Thr Ala Thr Thr
        100                 105                 110

Ala Asp Val Ala Val Ala Ala Val Pro Asn Lys Glu Ala Val Val Thr
        115                 120                 125

Thr Asp Ala Pro Ala Val Thr Thr Glu Lys Ala Glu Glu Gln Pro Ala
        130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Val Asn Glu Asp Gly Ser His
                180                 185                 190

Lys Glu Asn Phe Ala Ile Thr Val Asn Gly Gln Leu Leu Tyr Phe Gly
                195                 200                 205

Lys Asp Gly Ala Leu Thr Ser Ser Thr Tyr Ser Phe Thr Pro Gly
        210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
                260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
        340                 345                 350

Thr Gln Pro Gln Trp Asn Lys Glu Thr Glu Asn Tyr Ser Lys Gly Gly
        355                 360                 365

Gly Glu Asp His Leu Gln Gly Gly Ala Leu Leu Tyr Val Asn Asp Ser
        370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
                420                 425                 430

Asp Leu Ser Asn Pro Val Val Gln Ala Glu Gln Leu Asn Gln Ile His
        435                 440                 445

Tyr Leu Met Asn Trp Gly Ser Ile Val Met Gly Asp Lys Asp Ala Asn
        450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
```

-continued

```
                500                 505                 510
Leu Asn Asp Asn His Tyr Asn Asp Lys Thr Asp Gly Ala Ala Leu Ala
            515                 520                 525
Met Glu Asn Lys Gln Arg Leu Ala Leu Leu Phe Ser Leu Ala Lys Pro
        530                 535                 540
Ile Lys Glu Arg Thr Pro Ala Val Ser Pro Leu Tyr Asn Asn Thr Phe
545                 550                 555                 560
Asn Thr Thr Gln Arg Asp Glu Lys Thr Asp Trp Ile Asn Lys Asp Gly
            565                 570                 575
Ser Lys Ala Tyr Asn Glu Asp Gly Thr Val Lys Gln Ser Thr Ile Gly
            580                 585                 590
Lys Tyr Asn Glu Lys Tyr Gly Asp Ala Ser Gly Asn Tyr Val Phe Ile
        595                 600                 605
Arg Ala His Asp Asn Asn Val Gln Asp Ile Ile Ala Glu Ile Ile Lys
        610                 615                 620
Lys Glu Ile Asn Pro Lys Ser Asp Gly Phe Thr Ile Thr Asp Ala Glu
625                 630                 635                 640
Met Lys Gln Ala Phe Glu Ile Tyr Asn Lys Asp Met Leu Ser Ser Asp
            645                 650                 655
Lys Lys Tyr Thr Leu Asn Asn Ile Pro Ala Ala Tyr Ala Val Met Leu
            660                 665                 670
Gln Asn Met Glu Thr Ile Thr Arg Val Tyr Tyr Gly Asp Leu Tyr Thr
        675                 680                 685
Asp Asp Gly His Tyr Met Glu Thr Lys Ser Pro Tyr Tyr Asp Thr Ile
        690                 695                 700
Val Asn Leu Met Lys Ser Arg Ile Lys Tyr Val Ser Gly Gly Gln Ala
705                 710                 715                 720
Gln Arg Ser Tyr Trp Leu Pro Thr Asp Gly Lys Met Asn Ser Asp
            725                 730                 735
Val Glu Leu Tyr Arg Thr Asn Glu Val Tyr Thr Ser Val Arg Tyr Gly
            740                 745                 750
Lys Asp Ile Met Thr Ala Asn Asp Thr Glu Gly Ser Lys Tyr Ser Arg
        755                 760                 765
Thr Ser Gly Gln Val Thr Leu Val Ala Asn Asn Pro Lys Leu Thr Leu
        770                 775                 780
Asp Gln Ser Ala Lys Leu Asn Val Glu Met Gly Lys Ile His Ala Asn
785                 790                 795                 800
Gln Lys Tyr Arg Ala Leu Ile Val Gly Thr Ala Asp Gly Ile Lys Asn
            805                 810                 815
Phe Thr Ser Asp Ala Asp Ala Ile Ala Ala Gly Tyr Val Lys Glu Thr
            820                 825                 830
Asp Ser Asn Gly Val Leu Thr Phe Gly Ala Asn Asp Ile Lys Gly Tyr
        835                 840                 845
Glu Thr Phe Asp Met Ser Gly Phe Val Ala Val Trp Val Pro Val Gly
        850                 855                 860
Ala Ser Asp Asp Gln Asp Ile Arg Val Ala Pro Ser Thr Glu Ala Lys
865                 870                 875                 880
Lys Glu Gly Glu Leu Thr Leu Lys Ala Thr Glu Ala Tyr Asp Ser Gln
            885                 890                 895
Leu Ile Tyr Glu Gly Phe Ser Asn Phe Gln Thr Ile Pro Asp Gly Ser
            900                 905                 910
Asp Pro Ser Val Tyr Thr Asn Arg Lys Ile Ala Glu Asn Val Asp Leu
        915                 920                 925
```

Phe Lys Ser Trp Gly Val Thr Ser Phe Glu Met Ala Pro Gln Phe Val
    930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Ala Leu His Lys Ala
            980                 985                 990

Gly Ile Gln Ala Ile Ala Asp Trp Val Pro Asp Gln Ile Tyr Gln Leu
        995                 1000                1005

Pro Gly Lys Glu Val Val Thr Ala Thr Arg Thr Asp Gly Ala Gly
    1010                1015                1020

Arg Lys Ile Ala Asp Ala Ile Ile Asp His Ser Leu Tyr Val Ala
    1025                1030                1035

Asn Thr Lys Ser Ser Gly Lys Asp Tyr Gln Ala Lys Tyr Gly Gly
    1040                1045                1050

Glu Phe Leu Ala Glu Leu Lys Ala Lys Tyr Pro Glu Met Phe Lys
    1055                1060                1065

Val Asn Met Ile Ser Thr Gly Lys Pro Ile Asp Asp Ser Val Lys
    1070                1075                1080

Leu Lys Gln Trp Lys Ala Glu Tyr Phe Asn Gly Thr Asn Val Leu
    1085                1090                1095

Glu Arg Gly Val Gly Tyr Val Leu Ser Asp Glu Ala Thr Gly Lys
    1100                1105                1110

Tyr Phe Thr Val Thr Lys Asp Gly Asn Phe Ile Pro Leu Gln Leu
    1115                1120                1125

Thr Gly Asn Glu Lys Val Val Thr Gly Phe Ser Asn Asp Gly Lys
    1130                1135                1140

Gly Ile Thr Tyr Phe Gly Thr Ser Gly Thr Gln Ala Lys Ser Ala
    1145                1150                1155

Phe Val Thr Phe Asn Gly Asn Thr Tyr Tyr Phe Asp Ala Arg Gly
    1160                1165                1170

His Met Val Thr Asn Gly Glu Tyr Ser Pro Asn Gly Lys Asp Val
    1175                1180                1185

Tyr Arg Phe Leu Pro Asn Gly Ile Met Leu Ser Asn Ala Phe Tyr
    1190                1195                1200

Val Asp Ala Asn Gly Asn Thr Tyr Leu Tyr Asn Ser Lys Gly Gln
    1205                1210                1215

Met Tyr Lys Gly Gly Tyr Thr Lys Phe Asp Val Thr Glu Thr Asp
    1220                1225                1230

Lys Asp Gly Lys Glu Ser Lys Val Val Lys Phe Arg Tyr Phe Thr
    1235                1240                1245

Asn Glu Gly Val Met Ala Lys Gly Val Thr Val Ile Asp Gly Phe
    1250                1255                1260

Thr Gln Tyr Phe Gly Glu Asp Gly Phe Gln Ala Lys Asp Lys Leu
    1265                1270                1275

Val Thr Phe Lys Gly Lys Thr Tyr Tyr Phe Asp Ala His Thr Gly
    1280                1285                1290

Asn Ala Ile Lys Asp Thr Trp Arg Asn Ile Asn Gly Lys Trp Tyr
    1295                1300                1305

His Phe Asp Ala Asn Gly Val Ala Ala Thr Gly Ala Gln Val Ile
    1310                1315                1320

```
Asn Gly Gln Lys Leu Tyr Phe Asn Glu Asp Gly Ser Gln Val Lys
    1325                1330                1335

Gly Gly Val Val Lys Asn Ala Asp Gly Thr Tyr Ser Lys Tyr Lys
    1340                1345                1350

Glu Gly Ser Gly Glu Leu Val Thr Asn Glu Phe Phe Thr Thr Asp
    1355                1360                1365

Gly Asn Val Trp Tyr Tyr Ala Gly Ala Asn Gly Lys Thr Val Thr
    1370                1375                1380

Gly Ala Gln Val Ile Asn Gly Gln His Leu Tyr Phe Asn Ala Asp
    1385                1390                1395

Gly Ser Gln Val Lys Gly Val Val Lys Asn Ala Asp Gly Thr
    1400                1405                1410

Tyr Ser Lys Tyr Asp Ala Ser Thr Gly Glu Arg Leu Thr Asn Glu
    1415                1420                1425

Phe Phe Thr Thr Gly Asp Asn Asn Trp Tyr Tyr Ile Gly Ala Asn
    1430                1435                1440

Gly Lys Ser Val Thr Gly Glu Val Lys Ile Gly Asp Asp Thr Tyr
    1445                1450                1455

Phe Phe Ala Lys Asp Gly Lys Gln Val Lys Gly Gln Thr Val Ser
    1460                1465                1470

Ala Gly Asn Gly Arg Ile Ser Tyr Tyr Tyr Gly Asp Ser Gly Lys
    1475                1480                1485

Arg Ala Val Ser Thr Trp Ile Glu Ile Gln Pro Gly Val Tyr Val
    1490                1495                1500

Tyr Phe Asp Lys Asn Gly Ile Ala Tyr Pro Pro Arg Val Leu Asn
    1505                1510                1515

<210> SEQ ID NO 63
<211> LENGTH: 1431
<212> TYPE: PRT
<213> ORGANISM: Streptococcus salivarius

<400> SEQUENCE: 63

Met Thr Lys Glu Thr Asn Thr Val Asp Ala Ala Thr Thr Asn Thr
1               5                   10                  15

Gln Ala Ala Asp Ala Ala Thr Lys Thr Ala Asp Ala Ala Val Thr
                20                  25                  30

Ala Leu Pro Asn Lys Glu Ala Val Val Thr Thr Asp Ala Pro Ala Val
                35                  40                  45

Thr Thr Glu Lys Ala Ala Glu Gln Pro Ala Thr Val Lys Ser Glu Val
50                  55                  60

Val Asn Thr Glu Val Lys Ala Pro Glu Ala Ala Leu Lys Asp Ser Glu
65                  70                  75                  80

Val Glu Ala Ala Leu Ser Leu Lys Asn Ile Lys Asn Ile Asp Gly Lys
                85                  90                  95

Tyr Tyr Tyr Val Asn Lys Asp Gly Ser His Lys Glu Asn Phe Ala Ile
                100                 105                 110

Thr Val Asn Gly Gln Leu Leu Tyr Phe Gly Lys Asp Gly Ala Leu Thr
                115                 120                 125

Ser Ser Thr Tyr Ser Phe Thr Gln Gly Thr Thr Asn Ile Val Asp
                130                 135                 140

Gly Phe Ser Lys Asn Asn Arg Ala Tyr Asp Ser Ser Glu Ala Ser Phe
145                 150                 155                 160

Glu Leu Ile Asp Gly Tyr Leu Thr Ala Asp Ser Trp Tyr Arg Pro Val
                165                 170                 175
```

-continued

```
Ser Ile Ile Lys Asp Gly Val Thr Trp Gln Ala Ser Thr Lys Glu Asp
            180                 185                 190

Phe Arg Pro Leu Leu Met Ala Trp Trp Pro Asn Val Asp Thr Gln Val
        195                 200                 205

Asn Tyr Leu Asn Tyr Met Ser Lys Val Phe Asn Leu Asp Ala Lys Tyr
    210                 215                 220

Thr Ser Thr Asp Lys Gln Val Asp Leu Asn Arg Ala Ala Lys Asp Ile
225                 230                 235                 240

Gln Val Lys Ile Glu Gln Lys Ile Gln Ala Glu Lys Ser Thr Gln Trp
                245                 250                 255

Leu Arg Glu Ala Ile Ser Ala Phe Val Lys Thr Gln Pro Gln Trp Asn
            260                 265                 270

Lys Glu Thr Glu Asn Phe Ser Lys Gly Gly Glu Asp His Leu Gln
        275                 280                 285

Gly Gly Ala Leu Leu Tyr Val Asn Asp Pro Arg Thr Pro Trp Ala Asn
    290                 295                 300

Ser Asn Tyr Arg Leu Leu Asn Arg Thr Ala Thr Asn Gln Thr Gly Thr
305                 310                 315                 320

Ile Asp Lys Ser Val Leu Asp Glu Gln Ser Asp Pro Asn His Met Gly
                325                 330                 335

Gly Phe Asp Phe Leu Leu Ala Asn Asp Val Asp Thr Ser Asn Pro Val
            340                 345                 350

Val Gln Ala Glu Gln Leu Asn Gln Ile His Tyr Leu Met Asn Trp Gly
        355                 360                 365

Ser Ile Val Met Gly Asp Lys Asp Ala Asn Phe Asp Gly Ile Arg Val
    370                 375                 380

Asp Ala Val Asp Asn Val Asp Ala Asp Met Leu Gln Leu Tyr Thr Asn
385                 390                 395                 400

Tyr Phe Arg Glu Tyr Tyr Gly Val Asn Lys Ser Glu Ala Asn Ala Leu
                405                 410                 415

Ala His Ile Ser Val Leu Glu Ala Trp Ser Leu Asn Asp Asn His Tyr
            420                 425                 430

Asn Asp Lys Thr Asp Gly Ala Ala Leu Ala Met Glu Asn Lys Gln Arg
        435                 440                 445

Leu Ala Leu Leu Phe Ser Leu Ala Lys Pro Ile Lys Glu Arg Thr Pro
    450                 455                 460

Ala Val Ser Pro Leu Tyr Asn Asn Thr Phe Asn Thr Thr Gln Arg Asp
465                 470                 475                 480

Glu Lys Thr Asp Trp Ile Asn Lys Asp Gly Ser Lys Ala Tyr Asn Glu
                485                 490                 495

Asp Gly Thr Val Lys Gln Ser Thr Ile Gly Lys Tyr Asn Glu Lys Tyr
            500                 505                 510

Gly Asp Ala Ser Gly Asn Tyr Val Phe Ile Arg Ala His Asp Asn Asn
        515                 520                 525

Val Gln Asp Ile Ile Ala Glu Ile Ile Lys Lys Glu Ile Asn Pro Lys
    530                 535                 540

Ser Asp Gly Phe Thr Ile Thr Asp Ala Glu Met Lys Lys Ala Phe Glu
545                 550                 555                 560

Ile Tyr Asn Lys Asp Met Leu Ser Ser Asp Lys Lys Tyr Thr Leu Asn
                565                 570                 575

Asn Ile Pro Ala Ala Tyr Ala Val Met Leu Gln Asn Met Glu Thr Ile
            580                 585                 590
```

```
Thr Arg Val Tyr Tyr Gly Asp Leu Tyr Thr Asp Gly His Tyr Met
        595                 600             605
Glu Thr Lys Ser Pro Tyr Tyr Asp Thr Ile Val Asn Leu Met Lys Asn
610                 615                 620
Arg Ile Lys Tyr Val Ser Gly Gly Gln Ala Gln Arg Ser Tyr Trp Leu
625                 630                 635                 640
Pro Thr Asp Gly Lys Met Asp Lys Ser Asp Val Glu Leu Tyr Arg Thr
                645                 650                 655
Asn Glu Val Tyr Thr Ser Val Arg Tyr Gly Lys Asp Ile Met Thr Ala
                660                 665                 670
Asp Asp Thr Gln Gly Ser Lys Tyr Ser Arg Thr Ser Gly Gln Val Thr
                675                 680                 685
Leu Val Val Asn Asn Pro Lys Leu Ser Leu Asp Lys Ser Ala Lys Leu
        690                 695                 700
Asp Val Glu Met Gly Lys Ile His Ala Asn Gln Lys Tyr Arg Ala Leu
705                 710                 715                 720
Ile Val Gly Thr Pro Asn Gly Ile Lys Asn Phe Thr Ser Asp Ala Glu
                725                 730                 735
Ala Ile Ala Ala Gly Tyr Val Lys Glu Thr Asp Gly Asn Gly Val Leu
                740                 745                 750
Thr Phe Gly Ala Asn Asp Ile Lys Gly Tyr Glu Thr Phe Asp Met Ser
        755                 760                 765
Gly Phe Val Ala Val Trp Val Pro Val Gly Ala Ser Asp Asp Gln Asp
        770                 775                 780
Ile Arg Val Ala Ala Ser Thr Ala Ala Lys Lys Glu Gly Glu Leu Thr
785                 790                 795                 800
Leu Lys Ala Thr Glu Ala Tyr Asp Ser Gln Leu Ile Tyr Glu Gly Phe
                805                 810                 815
Ser Asn Phe Gln Thr Ile Pro Asp Gly Ser Asp Pro Ser Val Tyr Thr
                820                 825                 830
Asn Arg Lys Ile Ala Glu Asn Val Asp Leu Phe Lys Ser Trp Gly Val
        835                 840                 845
Thr Ser Phe Glu Met Ala Pro Gln Phe Val Ser Ala Asp Asp Gly Thr
        850                 855                 860
Phe Leu Asp Ser Val Ile Gln Asn Gly Tyr Ala Phe Ala Asp Arg Tyr
865                 870                 875                 880
Asp Leu Ala Met Ser Lys Asn Lys Tyr Gly Ser Lys Glu Asp Leu
                885                 890                 895
Arg Asn Ala Leu Lys Ala Leu His Lys Ala Gly Ile Gln Ala Ile Ala
        900                 905                 910
Asp Trp Val Pro Asp Gln Ile Tyr Gln Leu Pro Gly Lys Glu Val Val
        915                 920                 925
Thr Ala Thr Arg Thr Asp Gly Ala Gly Arg Lys Ile Ser Asp Ala Ile
        930                 935                 940
Ile Asp His Ser Leu Tyr Val Ala Asn Ser Lys Ser Ser Gly Lys Asp
945                 950                 955                 960
Tyr Gln Ala Lys Tyr Gly Gly Glu Phe Leu Ala Glu Leu Lys Ala Lys
                965                 970                 975
Tyr Pro Glu Met Phe Lys Val Asn Met Ile Ser Thr Gly Lys Pro Ile
                980                 985                 990
Asp Asp Ser Val Lys Leu Lys Gln Trp Lys Ala Glu Tyr Phe Asn Gly
        995                 1000                1005
Thr Asn Val Leu Asp Arg Gly Val Gly Tyr Val Leu Ser Asp Glu
```

-continued

```
            1010                1015                1020
Ala Thr Gly Lys Tyr Phe Thr Val Thr Lys Glu Gly Asn Phe Ile
            1025                1030                1035
Pro Leu Gln Leu Lys Gly Asn Glu Lys Val Ile Thr Gly Phe Ser
            1040                1045                1050
Ser Asp Gly Lys Gly Ile Thr Tyr Phe Gly Thr Ser Gly Asn Gln
            1055                1060                1065
Ala Lys Ser Ala Phe Val Thr Phe Asn Gly Asn Thr Tyr Tyr Phe
            1070                1075                1080
Asp Ala Arg Gly His Met Val Thr Asn Gly Glu Tyr Ser Pro Asn
            1085                1090                1095
Gly Lys Asp Val Tyr Arg Phe Leu Pro Asn Gly Ile Met Leu Ser
            1100                1105                1110
Asn Ala Phe Tyr Val Asp Gly Asn Gly Asn Thr Tyr Leu Tyr Asn
            1115                1120                1125
Ser Lys Gly Gln Met Tyr Lys Gly Gly Tyr Ser Lys Phe Asp Val
            1130                1135                1140
Thr Glu Thr Lys Asp Gly Lys Glu Ser Lys Val Val Lys Phe Arg
            1145                1150                1155
Tyr Phe Thr Asn Glu Gly Val Met Ala Lys Gly Val Thr Val Val
            1160                1165                1170
Asp Gly Phe Thr Gln Tyr Phe Asn Glu Asp Gly Ile Gln Ser Lys
            1175                1180                1185
Asp Glu Leu Val Thr Tyr Asn Gly Lys Thr Tyr Tyr Phe Glu Ala
            1190                1195                1200
His Thr Gly Asn Ala Ile Lys Asn Thr Trp Arg Asn Ile Lys Gly
            1205                1210                1215
Lys Trp Tyr His Phe Asp Ala Asn Gly Val Ala Ala Thr Gly Ala
            1220                1225                1230
Gln Val Ile Asn Gly Gln His Leu Tyr Phe Asn Glu Asp Gly Ser
            1235                1240                1245
Gln Val Lys Gly Gly Val Val Lys Asn Ala Asp Gly Thr Phe Ser
            1250                1255                1260
Lys Tyr Lys Asp Gly Ser Gly Asp Leu Val Val Asn Glu Phe Phe
            1265                1270                1275
Thr Thr Gly Asp Asn Val Trp Tyr Tyr Ala Gly Ala Asn Gly Lys
            1280                1285                1290
Thr Val Thr Gly Ala Gln Val Ile Asn Gly Gln His Leu Phe Phe
            1295                1300                1305
Lys Glu Asp Gly Ser Gln Val Lys Gly Asp Phe Val Lys Asn Ser
            1310                1315                1320
Asp Gly Thr Tyr Ser Lys Tyr Asp Ala Ala Ser Gly Glu Arg Leu
            1325                1330                1335
Thr Asn Glu Phe Phe Thr Thr Gly Asp Asn His Trp Tyr Tyr Ile
            1340                1345                1350
Gly Ala Asn Gly Lys Thr Val Thr Gly Glu Val Lys Ile Gly Asp
            1355                1360                1365
Asp Thr Tyr Phe Phe Ala Lys Asp Gly Lys Gln Leu Lys Gly Gln
            1370                1375                1380
Ile Val Thr Thr Arg Ser Gly Arg Ile Ser Tyr Tyr Phe Gly Asp
            1385                1390                1395
Ser Gly Lys Lys Ala Ile Ser Thr Trp Val Glu Ile Gln Pro Gly
            1400                1405                1410
```

```
Val Phe Val Phe Phe Asp Lys Asn Gly Leu Ala Tyr Pro Pro Glu
    1415                1420                1425

Asn Met Asn
    1430

<210> SEQ ID NO 64
<211> LENGTH: 1532
<212> TYPE: PRT
<213> ORGANISM: Unknown
<220> FEATURE:
<223> OTHER INFORMATION: unknown Streptococcus species

<400> SEQUENCE: 64

Met Glu Asn Lys Val His Tyr Lys Leu His Lys Val Lys Lys Gln Trp
1               5                   10                  15

Val Thr Ile Ala Val Ala Ser Ala Ala Leu Ala Thr Val Val Gly Gly
            20                  25                  30

Leu Ser Ala Thr Thr Ser Ser Val Ser Ala Asp Glu Thr Gln Asp Lys
        35                  40                  45

Thr Val Thr Gln Pro Asn Ser Asp Thr Thr Ala Asp Leu Val Thr Ser
    50                  55                  60

Thr Glu Ala Thr Lys Glu Val Asp Lys Arg Thr Asn Thr Lys Glu Ala
65                  70                  75                  80

Asp Val Leu Thr Pro Ala Lys Glu Thr Asn Thr Val Glu Thr Ala Ala
                85                  90                  95

Thr Thr Asn Thr Gln Ala Thr Ala Glu Ala Ala Lys Thr Ala Thr Thr
            100                 105                 110

Thr Asn Thr Gln Ala Thr Ala Glu Val Ala Lys Thr Ala Thr Thr Ala
        115                 120                 125

Asp Val Ala Val Ala Val Pro Asn Lys Glu Ala Val Val Thr Thr
    130                 135                 140

Asp Ala Pro Ala Val Thr Thr Glu Lys Ala Glu Glu Gln Pro Ala Thr
145                 150                 155                 160

Val Lys Ala Glu Val Val Asn Thr Glu Val Lys Ala Pro Glu Ala Ala
                165                 170                 175

Leu Lys Asp Ser Glu Val Glu Ala Ala Leu Ser Leu Lys Asn Ile Lys
            180                 185                 190

Asn Ile Asp Gly Lys Tyr Tyr Val Asn Glu Asp Gly Ser His Lys
        195                 200                 205

Glu Asn Phe Ala Ile Thr Val Asn Gly Gln Leu Leu Tyr Phe Gly Lys
    210                 215                 220

Asp Gly Ala Leu Thr Ser Ser Thr Tyr Ser Phe Thr Gln Gly Thr
225                 230                 235                 240

Thr Asn Ile Val Asp Gly Phe Ser Ile Asn Asn Arg Ala Tyr Asp Ser
                245                 250                 255

Ser Glu Ala Ser Phe Glu Leu Ile Asp Gly Tyr Leu Thr Ala Asp Ser
            260                 265                 270

Trp Tyr Arg Pro Ala Ser Ile Ile Lys Asp Gly Val Thr Trp Gln Ala
        275                 280                 285

Ser Thr Ala Glu Asp Phe Arg Pro Leu Leu Met Ala Trp Trp Pro Asn
    290                 295                 300

Val Asp Thr Gln Val Asn Tyr Leu Asn Tyr Met Ser Lys Val Phe Asn
305                 310                 315                 320

Leu Asp Ala Lys Tyr Ser Ser Thr Asp Lys Gln Glu Thr Leu Lys Val
                325                 330                 335
```

```
Ala Ala Lys Asp Ile Gln Ile Lys Ile Glu Gln Lys Ile Gln Ala Glu
            340                 345                 350
Lys Ser Thr Gln Trp Leu Arg Glu Thr Ile Ser Ala Phe Val Lys Thr
        355                 360                 365
Gln Pro Gln Trp Asn Lys Glu Thr Glu Asn Tyr Ser Lys Gly Gly Gly
    370                 375                 380
Glu Asp His Leu Gln Gly Gly Ala Leu Leu Tyr Val Asn Asp Ser Arg
385                 390                 395                 400
Thr Pro Trp Ala Asn Ser Asn Tyr Arg Leu Leu Asn Arg Thr Ala Thr
                405                 410                 415
Asn Gln Thr Gly Thr Ile Asp Lys Ser Ile Leu Asp Glu Gln Ser Asp
            420                 425                 430
Pro Asn His Met Gly Gly Phe Asp Phe Leu Leu Ala Asn Asp Val Asp
        435                 440                 445
Leu Ser Asn Pro Val Val Gln Ala Glu Gln Leu Asn Gln Ile His Tyr
    450                 455                 460
Leu Met Asn Trp Gly Ser Ile Val Met Gly Asp Lys Asp Ala Asn Phe
465                 470                 475                 480
Asp Gly Ile Arg Val Asp Ala Val Asp Asn Val Asp Ala Asp Met Leu
                485                 490                 495
Gln Leu Tyr Thr Asn Tyr Phe Arg Glu Tyr Tyr Gly Val Asn Lys Ser
            500                 505                 510
Glu Ala Asn Ala Leu Ala His Ile Ser Val Leu Glu Ala Trp Ser Leu
        515                 520                 525
Asn Asp Asn His Tyr Asn Asp Lys Thr Asp Val Ala Ala Leu Ala Met
    530                 535                 540
Glu Asn Lys Gln Arg Leu Ala Leu Leu Phe Ser Leu Ala Lys Pro Ile
545                 550                 555                 560
Lys Glu Arg Thr Pro Ala Val Ser Pro Leu Tyr Asn Asn Thr Phe Asn
                565                 570                 575
Thr Thr Gln Arg Asp Glu Lys Thr Asp Trp Ile Asn Lys Asp Gly Ser
            580                 585                 590
Lys Ala Tyr Asn Glu Asp Gly Thr Val Lys Lys Ser Thr Ile Gly Lys
        595                 600                 605
Tyr Asn Glu Lys Tyr Gly Asp Ala Ser Gly Asn Tyr Val Phe Ile Arg
    610                 615                 620
Ala His Asp Asn Asn Val Gln Asp Ile Ile Ala Glu Ile Ile Lys Lys
625                 630                 635                 640
Glu Ile Asn Glu Lys Ser Asp Gly Phe Thr Ile Thr Asp Ser Glu Met
                645                 650                 655
Lys Arg Ala Phe Glu Ile Tyr Asn Lys Asp Met Leu Ser Asn Asp Lys
            660                 665                 670
Lys Tyr Thr Leu Asn Asn Ile Pro Ala Ala Tyr Ala Val Met Leu Gln
        675                 680                 685
Asn Met Glu Thr Ile Thr Arg Val Tyr Tyr Gly Asp Leu Tyr Thr Asp
    690                 695                 700
Asp Gly Asn Tyr Met Glu Ala Lys Ser Pro Tyr Tyr Asp Thr Ile Val
705                 710                 715                 720
Asn Leu Met Lys Ser Arg Ile Lys Tyr Val Ser Gly Gly Gln Ala Gln
                725                 730                 735
```

```
Arg Ser Tyr Trp Leu Pro Thr Asp Gly Lys Met Asp Lys Ser Asp Val
            740                 745                 750

Glu Leu Tyr Arg Thr Asn Glu Val Tyr Thr Ser Val Arg Tyr Gly Lys
            755                 760                 765

Asp Ile Met Thr Ala Asp Thr Gln Gly Ser Lys Tyr Ser Arg Thr
770             775                 780

Ser Gly Gln Val Thr Leu Val Val Asn Asn Pro Lys Leu Thr Leu Asp
785                 790                 795                 800

Gln Ser Ala Lys Leu Asn Val Val Met Gly Lys Ile His Ala Asn Gln
                805                 810                 815

Lys Tyr Arg Ala Leu Ile Val Gly Thr Pro Asn Gly Ile Lys Asn Phe
            820                 825                 830

Thr Ser Asp Ala Glu Ala Ile Ala Ala Gly Tyr Val Lys Glu Thr Asp
            835                 840                 845

Gly Asn Gly Val Leu Thr Phe Gly Ala Asn Asp Ile Lys Gly Tyr Glu
850                 855                 860

Thr Phe Asp Met Ser Gly Phe Val Ala Val Trp Val Pro Val Gly Ala
865                 870                 875                 880

Ser Asp Asp Gln Asp Ile Arg Val Ala Ala Ser Thr Ala Ala Lys Lys
                885                 890                 895

Glu Gly Glu Leu Thr Leu Lys Ala Thr Glu Ala Tyr Asp Ser Gln Leu
            900                 905                 910

Ile Tyr Glu Gly Phe Ser Asn Phe Gln Thr Ile Pro Asp Gly Ser Asp
            915                 920                 925

Pro Ser Val Tyr Thr Asn Arg Lys Ile Ala Glu Asn Val Asp Leu Phe
            930                 935                 940

Lys Ser Trp Gly Val Thr Ser Phe Glu Met Ala Pro Gln Phe Val Ser
945                 950                 955                 960

Ala Asp Asp Gly Thr Phe Leu Asp Ser Val Ile Gln Asn Gly Tyr Ala
                965                 970                 975

Phe Ala Asp Arg Tyr Asp Leu Ala Met Ser Lys Asn Asn Lys Tyr Gly
            980                 985                 990

Ser Lys Glu Asp Leu Arg Asn Ala  Leu Lys Ala Leu His  Lys Ala Gly
            995                 1000                1005

Ile Gln  Ala Ile Ala Asp Trp  Val Pro Asp Gln Ile  Tyr Gln Leu
1010                1015                1020

Pro Gly  Lys Glu Val Val Thr  Ala Thr Arg Thr Asp  Gly Ala Gly
1025                1030                1035

Arg Lys  Ile Ser Asp Ala Ile  Ile Asp His Ser Leu  Tyr Val Ala
1040                1045                1050

Asn Ser  Lys Ser Ser Gly Lys  Asp Tyr Gln Ala Lys  Tyr Gly Gly
1055                1060                1065

Glu Phe  Leu Ala Glu Leu Lys  Ala Lys Tyr Pro Glu  Met Phe Lys
1070                1075                1080

Val Asn  Met Ile Ser Thr Gly  Lys Pro Ile Asp Asp  Ser Val Lys
1085                1090                1095

Leu Lys  Gln Trp Lys Ala Glu  Tyr Phe Asn Gly Thr  Asn Val Leu
1100                1105                1110

Asp Arg  Gly Val Gly Tyr Val  Leu Ser Asp Glu Ala  Thr Gly Lys
1115                1120                1125

Tyr Phe  Thr Val Thr Lys Glu  Gly Asn Phe Ile Pro  Leu Gln Leu
1130                1135                1140
```

-continued

```
Lys Gly Asn Lys Lys Val Ile Thr Gly Phe Ser Ser Asp Gly Lys
    1145                1150                1155

Gly Ile Thr Tyr Phe Gly Thr Ser Gly Asn Gln Ala Lys Ser Ala
    1160                1165                1170

Phe Val Thr Phe Asn Gly Asn Thr Tyr Tyr Phe Asp Ala Arg Gly
    1175                1180                1185

His Met Val Thr Asn Gly Glu Tyr Ser Pro Asn Gly Lys Asp Val
    1190                1195                1200

Tyr Arg Phe Leu Pro Asn Gly Ile Met Leu Ser Asn Ala Phe Tyr
    1205                1210                1215

Val Asp Gly Asn Gly Asn Thr Tyr Leu Tyr Asn Ser Lys Gly Gln
    1220                1225                1230

Met Tyr Lys Gly Gly Tyr Ser Lys Phe Asp Val Thr Glu Thr Lys
    1235                1240                1245

Asp Gly Lys Glu Ser Lys Val Val Lys Phe Arg Tyr Phe Thr Asn
    1250                1255                1260

Glu Gly Val Met Ala Lys Gly Val Thr Val Val Asp Gly Phe Thr
    1265                1270                1275

Gln Tyr Phe Asn Glu Asp Gly Ile Gln Ser Lys Asp Glu Leu Val
    1280                1285                1290

Thr Tyr Asn Gly Lys Thr Tyr Tyr Phe Glu Ala His Thr Gly Asn
    1295                1300                1305

Ala Ile Lys Asn Thr Trp Arg Asn Ile Lys Gly Lys Trp Tyr His
    1310                1315                1320

Phe Asp Ala Asn Gly Val Ala Ala Thr Gly Ala Gln Val Ile Asn
    1325                1330                1335

Gly Gln His Leu Tyr Phe Asn Glu Asp Gly Ser Gln Val Lys Gly
    1340                1345                1350

Ser Ile Val Lys Asn Ala Asp Gly Thr Phe Ser Lys Tyr Lys Asp
    1355                1360                1365

Ser Ser Gly Asp Leu Val Val Asn Glu Phe Phe Thr Thr Gly Asp
    1370                1375                1380

Asn Val Trp Tyr Tyr Ala Gly Ala Asn Gly Lys Thr Val Thr Gly
    1385                1390                1395

Ala Gln Val Ile Asn Gly Gln His Leu Phe Phe Lys Glu Asp Gly
    1400                1405                1410

Ser Gln Val Lys Gly Asp Phe Val Lys Asn Ser Asp Gly Thr Tyr
    1415                1420                1425

Ser Lys Tyr Asp Ala Ala Ser Gly Glu Arg Leu Thr Asn Glu Phe
    1430                1435                1440

Phe Thr Thr Gly Asp Asn His Trp Tyr Tyr Ile Gly Ala Asn Gly
    1445                1450                1455

Lys Thr Val Thr Gly Glu Val Lys Ile Gly Asp Thr Tyr Phe
    1460                1465                1470

Phe Ala Lys Asp Gly Lys Gln Leu Lys Gly Gln Ile Val Thr Thr
    1475                1480                1485

Arg Ser Gly Arg Ile Ser Tyr Tyr Phe Gly Asp Ser Gly Lys Lys
    1490                1495                1500

Ala Ile Ser Thr Trp Val Glu Ile Gln Pro Gly Val Phe Val Phe
    1505                1510                1515

Phe Asp Lys Asn Gly Leu Ala Tyr Pro Pro Glu Asn Met Asn
    1520                1525                1530
```

GLUCOSYLTRANSFERASE ENZYMES FOR PRODUCTION OF GLUCAN POLYMERS

This application is a divisional of pending application Ser. No. 14/036,049, filed Sep. 25, 2013, which claims the benefit of U.S. Provisional Application Nos. 61/705,177; 61/705,178; 61/705,179; 61/705,180 and 61/705,181, each filed Sep. 25, 2012. All of these prior applications are incorporated herein by reference in their entirety.

FIELD OF INVENTION

The invention is in the field of enzyme catalysis. Specifically, this invention pertains to producing high molecular weight, insoluble poly alpha-1,3-glucan using a glucosyltransferase enzyme.

BACKGROUND

Driven by a desire to find new structural polysaccharides using enzymatic syntheses or genetic engineering of microorganisms or plant hosts, researchers have discovered polysaccharides that are biodegradable and can be made economically from renewably sourced feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase (gtf) enzyme isolated from *Streptococcus salivarius* (Simpson et al., *Microbiology* 141:1451-1460, 1995). Films prepared from poly alpha-1,3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber using an *S. salivarius* gtfJ enzyme. At least 50% of the hexose units within the polymer of this fiber were linked via alpha-1,3-glycosidic linkages. *S. salivarius* gtfJ enzyme utilizes sucrose as a substrate in a polymerization reaction producing poly alpha-1,3-glucan and fructose as end-products (Simpson et al., 1995). The disclosed polymer formed a liquid crystalline solution when it was dissolved above a critical concentration in a solvent or in a mixture comprising a solvent. Continous, strong, cotton-like fibers were obtained from this solution that could be spun and used in textile applications.

Not all glucosyltransferase enzymes can produce glucan with a molecular weight and percentage of alpha-1,3 glycosidic linkages suitable for use in spinning fibers. For example, most glucosyltransferase enzymes do not produce glucan having at least 50% alpha-1,3 glycosidic linkages and a number average degree of polymerization of at least 100. Therefore, it is desirable to identify glucosyltransferase enzymes that can convert sucrose to glucan polymers having a high percentage of alpha-1,3 glycosidic linkages and high molecular weight.

SUMMARY OF INVENTION

In one embodiment, the invention concerns a reaction solution comprising water, sucrose and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34.

In a second embodiment, the glucosyltransferase enzyme in the reaction solution synthesizes poly alpha-1,3-glucan having at least 50% alpha-1,3 glycosidic linkages and a number average degree of polymerization of at least 100. In a third embodiment, the glucosyltransferase synthesizes poly alpha-1,3-glucan having 100% alpha-1,3 glycosidic linkages and a number average degree of polymerization of at least 100. In a fourth embodiment, the glucosyltransferase enzyme synthesizes poly alpha-1,3-glucan having 100% alpha-1,3 glycosidic linkages and a number average degree of polymerization of at least 250.

In a fifth embodiment, the reaction solution comprises a primer. In a sixth embodiment, this primer can be dextran or hydrolyzed glucan.

In a seventh embodiment, the invention concerns a method for producing poly alpha-1,3-glucan comprising the step of contacting at least water, sucrose, and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. The poly alpha-1,3-glucan produced in this method can optionally be isolated.

In an eighth embodiment, the glucosyltransferase enzyme used in the method synthesizes poly alpha-1,3-glucan having at least 50% alpha-1,3 glycosidic linkages and a number average degree of polymerization of at least 100. In a ninth embodiment, the glucosyltransferase enzyme synthesizes poly alpha-1,3-glucan having 100% alpha-1,3 glycosidic linkages and a number average degree of polymerization of at least 100. In a tenth embodiment, the glucosyltransferase enzyme synthesizes poly alpha-1,3-glucan having 100% alpha-1,3 glycosidic linkages and a number average degree of polymerization of at least 250.

In an eleventh embodiment, the contacting step of the method further comprises contacting a primer with the water, sucrose, and glucosyltransferase enzyme. In a twelfth embodiment, this primer can be dextran or hydrolyzed glucan.

BRIEF DESCRIPTION OF THE SEQUENCES

TABLE 1

Summary of Nucleic Acid and Protein SEQ ID Numbers

| Description | Nucleic acid SEQ ID NO. | Protein SEQ ID NO. |
|---|---|---|
| "0874 gtf", *Streptococcus sobrinus*. DNA codon-optimized for expression in *E. coli*. The first 156 amino acids of the protein are deleted compared to GENBANK Identification No. 450874, which discloses "glucosyltransferase-I". | 1 | 2 (1435 aa) |

TABLE 1-continued

Summary of Nucleic Acid and Protein SEQ ID Numbers

| Description | Nucleic acid SEQ ID NO. | Protein SEQ ID NO. |
|---|---|---|
| "6855 gtf", *Streptococcus salivarius* SK126. DNA codon-optimized for expression in *E. coli*. The first 178 amino acids of the protein are deleted compared to GENBANK Identification No. 228476855, which discloses "glucosyltransferase-SI". | 3 | 4 (1341 aa) |
| "2379 gtf", *Streptococcus salivarius*. DNA codon-optimized for expression in *E. coli*. The first 203 amino acids of the protein are deleted compared to GENBANK Identification No. 662379, which discloses "glucosyltransferase". | 5 | 6 (1247 aa) |
| "7527" or "gtfJ", *Streptococcus salivarius*. DNA codon-optimized for expression in *E. coli*. The first 42 amino acids of the protein are deleted compared to GENBANK Identification No. 47527, which discloses "glucosyltransferase-I". | 7 | 8 (1477 aa) |
| "1724 gtf", *Streptococcus downei*. DNA codon-optimized for expression in *E. coli*. The first 162 amino acids of the protein are deleted compared to GENBANK Identification No. 121724, which discloses "glucosyltransferase-I". | 9 | 10 (1436 aa) |
| "0544 gtf", *Streptococcus mutans*. DNA codon-optimized for expression in *E. coli*. The first 164 amino acids of the protein are deleted compared to GENBANK Identification No. 290580544, which discloses "glucosyltransferase-I". | 11 | 12 (1313 aa) |
| "5926 gtf", *Streptococcus dentirousetti*. DNA codon-optimized for expression in *E. coli*. The first 144 amino acids of the protein are deleted compared to GENBANK Identification No. 167735926, which discloses "glucosyltransferase-I". | 13 | 14 (1323 aa) |
| "4297 gtf", *Streptococcus oralis*. DNA codon-optimized for expression in *E. coli*. The first 228 amino acids of the protein are deleted compared to GENBANK Identification No. 7684297, which discloses "glucosyltransferase". | 15 | 16 (1348 aa) |
| "5618 gtf", *Streptococcus sanguinis*. DNA codon-optimized for expression in *E. coli*. The first 223 amino acids of the protein are deleted compared to GENBANK Identification No. 328945618, which discloses "glucosyltransferase-S". | 17 | 18 (1348 aa) |
| "2765 gtf", unknown *Streptococcus* sp. C150. DNA codon-optimized for expression in *E. coli*. The first 193 amino acids of the protein are deleted compared to GENBANK Identification No. 322372765, which discloses "glucosyltransferase-S". | 19 | 20 (1340 aa) |
| "4700 gtf", *Leuconostoc mesenteroides*. DNA codon-optimized for expression in *E. coli*. The first 36 amino acids of the protein are deleted compared to GENBANK Identification No. 21654700, which discloses "dextransucrase DsrD". | 21 | 22 (1492 aa) |
| "1366 gtf", *Streptococcus criceti*. DNA codon-optimized for expression in *E. coli*. The first 139 amino acids of the protein are deleted compared to GENBANK Identification No. 146741366, which discloses "glucosyltransferase". | 23 | 24 (1323 aa) |
| "0427 gtf", *Streptococcus sobrinus*. DNA codon-optimized for expression in *E. coli*. The first 156 amino acids of the protein are deleted compared to GENBANK Identification No. 940427, which discloses "GTF-I". | 25 | 26 (1435 aa) |
| "2919 gtf", *Streptococcus salivarius* PS4. DNA codon-optimized for expression in *E. coli*. The first 92 amino acids of the protein are deleted compared to GENBANK Identification No. 383282919, which discloses "putative glucosyltransferase". | 27 | 28 (1340 aa) |
| "2678 gtf", *Streptococcus salivarius* K12. DNA codon-optimized for expression in *E. coli*. The first 188 amino acids of the protein are deleted compared to GENBANK Identification No. 400182678, which discloses "dextransucrase-S". | 29 | 30 (1341 aa) |
| "2381 gtf", *Streptococcus salivarius*. DNA codon-optimized for expression in *E. coli*. The first 273 amino acids of the protein are deleted compared to GENBANK Identification No. 662381, which discloses "glucosyltransferase". | 31 | 32 (1305 aa) |

TABLE 1-continued

Summary of Nucleic Acid and Protein SEQ ID Numbers

| Description | Nucleic acid SEQ ID NO. | Protein SEQ ID NO. |
|---|---|---|
| "3929 gtf", *Streptococcus salivarius* JIM8777. DNA codon-optimized for expression in *E. coli*. The first 178 amino acids of the protein are deleted compared to GENBANK Identification No. 387783929, which discloses "glucosyltransferase-S precursor (GTF-S) (Dextransucrase) (Sucrose 6-glucosyltransferase)". | 33 | 34 (1341 aa) |
| "6907 gtf", *Streptococcus salivarius* SK126. DNA codon-optimized for expression in *E. coli*. The first 161 amino acids of the protein are deleted compared to GENBANK Identification No. 228476907, which discloses "glucosyltransferase-SI". | 35 | 36 (1331 aa) |
| "6661 gtf", *Streptococcus salivarius* SK126. DNA codon-optimized for expression in *E. coli*. The first 265 amino acids of the protein are deleted compared to GENBANK Identification No. 228476661, which discloses "glucosyltransferase-SI". | 37 | 38 (1305 aa) |
| "0339 gtf", *Streptococcus gallolyticus* ATCC 43143. DNA codon-optimized for expression in *E. coli*. The first 213 amino acids of the protein are deleted compared to GENBANK Identification No. 334280339, which discloses "glucosyltransferase". | 39 | 40 (1310 aa) |
| "0088 gtf", *Streptococcus mutans*. DNA codon-optimized for expression in *E. coli*. The first 189 amino acids of the protein are deleted compared to GENBANK Identification No. 3130088, which discloses "glucosyltransferase-SI". | 41 | 42 (1267 aa) |
| "9358 gtf", *Streptococcus mutans* UA159. DNA codon-optimized for expression in *E. coli*. The first 176 amino acids of the protein are deleted compared to GENBANK Identification No. 24379358, which discloses "glucosyltransferase-S". | 43 | 44 (1287 aa) |
| "8242 gtf", *Streptococcus gallolyticus* ATCC BAA-2069. DNA codon-optimized for expression in *E. coli*. The first 191 amino acids of the protein are deleted compared to GENBANK Identification No. 325978242, which discloses "glucosyltransferase-I". | 45 | 46 (1355 aa) |
| "3442 gtf", *Streptococcus sanguinis* SK405. DNA codon-optimized for expression in *E. coli*. The first 228 amino acids of the protein are deleted compared to GENBANK Identification No. 324993442, which discloses a " . . . signal domain protein". | 47 | 48 (1348 aa) |
| "7528 gtf", *Streptococcus salivarius*. DNA codon-optimized for expression in *E. coli*. The first 173 amino acids of the protein are deleted compared to GENBANK Identification No. 47528, which discloses "glucosyltransferase S". | 49 | 50 (1427 aa) |
| "3279 gtf", *Streptococcus* sp. C150. DNA codon-optimized for expression in *E. coli*. The first 178 amino acids of the protein are deleted compared to GENBANK Identification No. 322373279, which discloses "glucosyltransferase S". | 51 | 52 (1393 aa) |
| "6491 gtf", *Leuconostoc citreum* KM20. DNA codon-optimized for expression in *E. coli*. The first 244 amino acids of the protein are deleted compared to GENBANK Identification No. 170016491, which discloses "glucosyltransferase". | 53 | 54 (1262 aa) |
| "6889 gtf", *Streptococcus salivarius* SK126. DNA codon-optimized for expression in *E. coli*. The first 173 amino acids of the protein are deleted compared to GENBANK Identification No. 228476889, which discloses "glucosyltransferase-I". | 55 | 56 (1427 aa) |
| "4154 gtf", *Lactobacillus reuteri*. DNA codon-optimized for expression in *E. coli*. The first 38 amino acids of the protein are deleted compared to GENBANK Identification No. 51574154, which discloses "glucansucrase". | 57 | 58 (1735 aa) |
| "3298 gtf", *Streptococcus* sp. C150. The first 209 amino acids of the protein are deleted compared to GENBANK Identification No. 322373298, which discloses "glucosyltransferase-S". | | 59 (1242 aa) |
| "Wild type gtfJ", *Streptococcus salivarius*. GENBANK Identification No. 47527. | | 60 (1518 aa) |

TABLE 1-continued

Summary of Nucleic Acid and Protein SEQ ID Numbers

| Description | Nucleic acid SEQ ID NO. | Protein SEQ ID NO. |
|---|---|---|
| Wild type gtf corresponding to 2678 gtf, *Streptococcus salivarius* K12. GENBANK Identification No. 400182678, which discloses "dextransucrase-S". | | 61 (1528 aa) |
| Wild type gtf corresponding to 6855 gtf, *Streptococcus salivarius* SK126. GENBANK Identification No. 228476855, which discloses "glucosyltransferase-SI". | | 62 (1518 aa) |
| Wild type gtf corresponding to 2919 gtf, *Streptococcus salivarius* PS4. GENBANK Identification No. 383282919, which discloses "putative glucosyltransferase". | | 63 (1431 aa) |
| Wild type gtf corresponding to 2765 gtf, *Streptococcus* sp. C150. GENBANK Identification No. 322372765, which discloses "glucosyltransferase-S". | | 64 (1532 aa) |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least about 50% of the glycosidic linkages are alpha-1,3-glycosidic linkages. Poly alpha-1,3-glucan is a type of polysaccharide. The structure of poly alpha-1,3-glucan can be illustrated as follows:

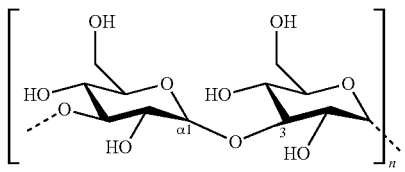

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. This linkage is illustrated in the poly alpha-1,3-glucan structure provided above. Herein, "alpha-D-glucose" will be referred to as "glucose".

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The "molecular weight" of the poly alpha-1,3-glucan herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements such as with high-pressure liquid chromatography (HPLC), size exclusion chromatography (SEC), or gel permeation chromatography (GPC).

The terms "glucosyltransferase enzyme", "gtf enzyme", "gtf enzyme catalyst", "gtf", and "glucansucrase" are used interchangeably herein. The activity of a gtf enzyme herein catalyzes the reaction of the substrate sucrose to make the products poly alpha-1,3-glucan and fructose. Other products (byproducts) of a gtf reaction can include glucose (where glucose is hydrolyzed from the glucosyl-gtf enzyme intermediate complex), various soluble oligosaccharides (DP2-DP7), and leucrose (where glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37: D233-238, 2009).

The terms "reaction" and "enzymatic reaction" are used interchangeably herein and refer to a reaction that is performed by a glucosyltransferase enzyme. A "reaction solution" as used herein generally refers to a solution comprising at least one active glucosyltransferase enzyme in a solution comprising sucrose and water, and optionally other components. It is in the reaction solution where the step of contacting water, sucrose and a glucosyltransferase enzyme is performed. The term "under suitable reaction conditions" as used herein, refers to reaction conditions that support conversion of sucrose to poly alpha-1,3-glucan via glucosyltransferase enzyme activity. The reaction herein is not naturally occurring.

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight", "weight percentage (wt %)" and "weight-weight percentage (% w/w)" are used interchangeably herein. Percent by weight refers to the percentage of a material on a mass basis as it is comprised in a composition, mixture, or solution.

The terms "increased", "enhanced" and "improved" are used interchangeably herein. These terms refer to a greater quantity or activity such as a quantity or activity slightly greater than the original quantity or activity, or a quantity or activity in large excess compared to the original quantity or activity, and including all quantities or activities in between. Alternatively, these terms may refer to, for example, a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a polynucleotide sequence that expresses a protein, and which may refer to the coding region alone or may include regulatory sequences upstream and/or downstream to the coding region (e.g., 5' untranslated regions upstream of the transcription start site of the coding region). A gene that is "native" or "endogenous" refers to a gene as found in nature with its own regulatory sequences; this gene is located in its natural location in the genome of an organism. "Chimeric gene" refers to any gene that is not a native gene, comprising regulatory and coding sequences that are not found together in nature. A "foreign" or "heterologous" gene refers to a gene that is introduced into the host organism by gene transfer. Foreign genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a transformation procedure. A "codon-optimized gene" is a gene having its frequency of codon usage designed to mimic the frequency of preferred codon usage of the host cell.

A native amino acid sequence or polynucleotide sequence is naturally occurring, whereas a non-native amino acid sequence or polynucleotide sequence does not occur in nature.

"Coding sequence" as used herein refers to a DNA sequence that codes for a specific amino acid sequence. "Regulatory sequences" as used herein refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include promoters, enhancers, silencers, 5' untranslated leader sequence, introns, polyadenylation recognition sequences, RNA processing sites, effector binding sites, stem-loop structures and other elements involved in regulation of gene expression.

The term "recombinant" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

The term "transformation" as used in certain embodiments refers to the transfer of a nucleic acid molecule into a host organism. The nucleic acid molecule may be a plasmid that replicates autonomously, or it may integrate into the genome of the host organism. Host organisms containing the transformed nucleic acid fragments are referred to as "transgenic" or "recombinant" or "transformed" organisms or "transformants".

The term "recombinant" or "heterologous" refers to an artificial combination of two otherwise separate segments of sequence, e.g., by chemical synthesis or by the manipulation of isolated segments of nucleic acids by genetic engineering techniques.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 85%, 86%, 87%, 88%, 89%, 90%, 91%, 92%, 93%, 94%, 95%, 96%, 97%, 98%, or 99% of the function/activity of the disclosed sequence.

The term "isolated" as used in certain embodiments refers to any cellular component that has been completely or partially purified from its native source (e.g., an isolated polynucleotide or polypeptide molecule). In some instances, an isolated polynucleotide or polypeptide molecule is part of a greater composition, buffer system or reagent mix. For example, the isolated polynucleotide or polypeptide molecule can be comprised within a cell or organism in a heterologous manner. Another example is an isolated glucosyltransferase enzyme.

Embodiments of the disclosed invention concern a reaction solution comprising water, sucrose and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. Significantly, these glucosyltransferase enzymes can synthesize poly alpha-1,3-glucan having at least 50% alpha-1,3 glycosidic linkages and a number average degree of polymerization of at least 100. Such glucan is suitable for use in spinning fibers and in other industrial applications.

The molecular weight of the poly alpha-1,3-glucan produced by the glucosyltransferase enzymes herein can be measured as $DP_n$ (number average degree of polymerization). Alternatively, the molecular weight of the poly alpha-1,3-glucan can be measured in terms of Daltons, grams/mole, or as $DP_w$ (weight average degree of polymerization). The poly alpha-1,3-glucan in certain embodiments of the invention can have a molecular weight in $DP_n$ or $DP_w$ of at least about 100. The molecular weight of the poly alpha-1,3-glucan can alternatively be at least about 250 $DP_n$ or $DP_w$. Alternatively still, the $DP_n$ or $DP_w$ of the poly alpha-1,3-glucan can be at least about 100, 150, 200, 250, 300, 350, 400, 450, 500, 550, 600, 650, 700, 750, 800, 850, 900, 950, or 1000 (or any integer between 100 and 1000).

The molecular weight of the poly alpha-1,3-glucan herein can be measured using any of several means known in the art. For example, glucan polymer molecular weight can be measured using high-pressure liquid chromatography (HPLC), size exclusion chromatography (SEC), or gel permeation chromatography (GPC).

The poly alpha-1,3-glucan herein is preferably linear/unbranched. The percentage of glycosidic linkages between the glucose monomer units of the poly alpha-1,3-glucan that are alpha-1,3 is at least about 50%, 60%, 70%, 80%, 90%, 95%, 96%, 97%, 98%, 99%, or 100%. In such embodiments, accordingly, the poly alpha-1,3-glucan has less than about 50%, 40%, 30%, 20%, 10%, 5%, 4%, 3%, 2%, 1%, or 0% of glycosidic linkages that are not alpha-1,3.

It is understood that the higher the percentage of alpha-1,3-glycosidic linkages present in the poly alpha-1,3-glucan, the greater the probability that the poly alpha-1,3-glucan is linear, since there are lower occurrences of certain glycosidic linkages forming branch points in the polymer. In certain embodiments, the poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

The glycosidic linkage profile of the poly alpha-1,3-glucan can be determined using any method known in the art. For example, the linkage profile can be determined using methods that use nuclear magnetic resonance (NMR) spectroscopy (e.g., $^{13}C$ NMR or $^1H$ NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The poly alpha-1,3-glucan herein may be characterized by any combination of the aforementioned percentages of alpha-1,3 linkages and molecular weights. For example, the poly alpha-1,3-glucan produced in a reaction solution herein can have at least 50% alpha-1,3 glycosidic linkages and a $DP_n$ or $DP_w$ of at least 100. As another example, the poly alpha-1,3-glucan can have 100% alpha-1,3 glycosidic linkages and a $DP_n$ or $DP_w$ of at least 100. The poly alpha-1,3-glucan in still another example can have 100% alpha-1,3 glycosidic linkages and a $DP_n$ or $DP_w$ of at least 250.

The glucosyltransferase enzyme in certain embodiments of the invention may be derived from a *Streptococcus* species, *Leuconostoc* species or *Lactobacillus* species, for example. Examples of *Streptococcus* species from which the glucosyltransferase may be derived include *S. salivarius*, *S. sobrinus*, *S. dentirousetti*, *S. downei*, *S. mutans*, *S. oralis*, *S. gallolyticus* and *S. sanguinis*. Examples of *Leuconostoc* species from which the glucosyltransferase may be derived include *L. mesenteroides*, *L. amelibiosum*, *L. argentinum*, *L. carnosum*, *L. citreum*, *L. cremoris*, *L. dextranicum* and *L. fructosum*. Examples of *Lactobacillus* species from which the glucosyltransferase may be derived include *L. acidophilus*, *L. delbrueckii*, *L. helveticus*, *L. salivarius*, *L. casei*, *L. curvatus*, *L. plantarum*, *L. sakei*, *L. brevis*, *L. buchneri*, *L. fermentum* and *L. reuteri*.

The glucosyltransferase enzyme herein can comprise, or consist of, an amino acid sequence that is at least 90% identical to the amino acid sequence provided in SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34, wherein the glucosyltransferase enzyme has activity. Alternatively, the glucosyltransferase enzyme can comprise, or consist of, an amino acid sequence that is at least 90%, 91%, 92%, 93%, 94%, 95%, 96%, 97%, 98%, or 99% identical to SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34, wherein the glucosyltransferase enzyme has activity.

All the amino acid residues disclosed herein at each amino acid position of the glucosyltransferase enzyme sequences are examples. Given that certain amino acids share similar structural and/or charge features with each other (i.e., conserved), the amino acid at each position in the glucosyltransferase enzyme sequences can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

Examples of glucosyltransferase enzymes may be any of the amino acid sequences disclosed herein and that further include 1-300 (or any integer there between) residues on the N-terminus and/or C-terminus. Such additional residues may be from a corresponding wild type sequence from which the glucosyltransferase enzyme is derived, or may be another sequence such as an epitope tag (at either N- or C-terminus) or a heterologous signal peptide (at N-terminus), for example.

Thus, examples of glucosyltransferase enzymes include SEQ ID NOs:61, 62, 63 and 64, which represent the wild type sequences from which SEQ ID NOs:30, 4, 28 and 20 are derived, respectively.

The glucosyltransferase enzyme can be encoded by the polynucleotide sequence provided in SEQ ID NO:3, SEQ ID NO:9, SEQ ID NO:11, SEQ ID NO:13, SEQ ID NO:19, SEQ ID NO:25, SEQ ID NO:27, SEQ ID NO:29, or SEQ ID NO:33, for example. Alternatively, the glucosyltransferase enzyme can be encoded by a polynucleotide sequence that is at least 90%, 91%, 92%, 93%, 94%, 95%, 96%, 97%, 98%, or 99% identical to SEQ ID NO:3, SEQ ID NO:9, SEQ ID NO:11, SEQ ID NO:13, SEQ ID NO:19, SEQ ID NO:25, SEQ ID NO:27, SEQ ID NO:29, or SEQ ID NO:33.

The glucosyltransferase enzyme in certain embodiments synthesizes poly alpha-1,3-glucan in which at least about 50%, 60%, 70%, 80%, 90%, 95%, 96%, 97%, 98%, 99%, or 100% (or any integer between 50% and 100%) of the constituent glycosidic linkages are alpha-1,3 linkages. In such embodiments, accordingly, the glucosyltransferase enzyme synthesizes poly alpha-1,3-glucan in which there is less than about 50%, 40%, 30%, 20%, 10%, 5%, 4%, 3%, 2%, or 1% of glycosidic linkages that are not alpha-1,3.

In other aspects, the glucosyltransferase enzyme synthesizes poly alpha-1,3-glucan with no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

The glucosyltransferase enzyme can synthesize poly alpha-1,3-glucan having a molecular weight in $DP_n$ or $DP_w$ of at least about 100. Alternatively, the glucosyltransferase enzyme can synthesize poly alpha-1,3-glucan having a molecular weight in $DP_n$ or $DP_w$ of at least about 400. Alternatively still, the glucosyltransferase enzyme can synthesize poly alpha-1,3-glucan having a molecular weight in $DP_n$ or $DP_w$ of at least about 100, 150, 200, 250, 300, 350, 400, 450, 500, 550, 600, 650, 700, 750, 800, 850, 900, 950, or 1000 (or any integer between 100 and 1000).

One or more different glucosyltransferase enzymes may be used in the disclosed invention. The glucosyltransferase enzyme preferably does not have, or has very little (less than 1%), dextransucrase, reuteransucrase, or alternansucrase activity. The glucosyltransferase in certain embodiments does not comprise amino acid residues 2-1477 of SEQ ID NO:8 or amino acid residues 138-1477 of SEQ ID NO:8, which are derived from the glucosyltransferase identified in GENBANK under GI number 47527 (SEQ ID NO:60).

The glucosyltransferase enzyme herein can be primer-independent or primer-dependent. Primer-independent glucosyltransferase enzymes do not require the presence of a primer to perform glucan synthesis. A primer-dependent glucosyltransferase enzyme requires the presence of an initiating molecule in the reaction solution to act as a primer for the enzyme during glucan polymer synthesis. The term "primer" as used herein refers to any molecule that can act as the initiator for a glucosyltransferase enzyme. Oligosaccharides and polysaccharides can serve a primers herein, for example. Primers that can be used in certain embodiments include dextran and other carbohydrate-based primers, such as hydrolyzed glucan, for example. Hydrolyzed glucan can be prepared by acid hydrolysis of a glucan such as poly alpha-glucan. International Appl. Publ. No. WO2013/036918, which is incorporated herein by reference, discloses such preparation of hydrolyzed glucan using poly alpha-1,3-glucan as the starting material. Dextran for use as a primer herein can be dextran T10 (i.e., dextran having a molecular weight of 10 kD). Alternatively, the dextran can have a molecular weight of about 2, 4, 6, 8, 10, 12, 14, 16, 18, 20, or 25 kD, for example.

The glucosyltransferase enzyme used herein may be produced by any means known in the art (e.g., U.S. Pat. No. 7,000,000, which is incorporated herein by reference). For example, the glucosyltransferase enzyme may be produced recombinantly in any bacterial (e.g., *E. coli* such as TOP10, *Bacillus* sp.) or eukaryotic (e.g., yeasts such as *Pichia* sp. and *Saccharomyces* sp.) heterologous gene expression system. Any of the above-listed nucleic acid sequences can be used for this purpose, for example.

The glucosyltransferase enzyme used herein may be purified and/or isolated prior to its use, or may be used in the form of a cell lysate, for example. A cell lysate or extract may be prepared from a bacteria (e.g., *E. coli*) used to heterologously express the enzyme. For example, the bacteria may be subjected to disruption using a French pressure cell (French press). The glucosyltransferase enzyme is soluble in these type of preparations. The lysate or extract may be used at about 0.15-0.3% (v/v) in a reaction solution for producing poly alpha-1,3-glucan from sucrose. In certain embodiments, a bacterial cell lysate is first cleared of insoluble material by means such as centrifugation or filtration.

In certain embodiments, the heterologous gene expression system may be one that is designed for protein secretion. The glucosyltransferase enzyme comprises a signal peptide (signal sequence) in such embodiments. The signal peptide may be either its native signal peptide or a heterologous signal peptide.

The activity of the glucosyltransferase enzyme can be determined using any method known in the art. For example, glucosyltransferase enzyme activity can be determined by measuring the production of reducing sugars (fructose and glucose) in a reaction solution containing sucrose (50 g/L), dextran T10 (1 mg/mL) and potassium phosphate buffer (pH 6.5, 50 mM), where the solution is held at 22-25° C. for 24-30 hours. The reducing sugars can be measured by adding 0.01 mL of the reaction solution to a mixture containing 1 N NaOH and 0.1% triphenyltetrazolium chloride and then monitoring the increase in absorbance at $OD_{480\ nm}$ for five minutes.

The temperature of the reaction solution herein can be controlled, if desired. In certain embodiments, the solution has a temperature between about 5° C. to about 50° C. The temperature of the solution in certain other embodiments is between about 20° C. to about 40° C. Alternatively, the temperature of the solution may be about 20, 21, 22, 23, 24, 25, 26, 27, 28, 29, 30, 31, 32, 33, 34, 35, 36, 37, 38, 39, or 40° C.

The temperature of the reaction solution may be maintained using various means known in the art. For example, the temperature of reaction solution can be maintained by placing the vessel containing the reaction solution in an air or water bath incubator set at the desired temperature.

The initial concentration of the sucrose in the solution can be about 20 g/L to about 400 g/L, for example. Alternatively, the initial concentration of the sucrose can be about 75 g/L to about 175 g/L, or from about 50 g/L to about 150 g/L. Alternatively still, the initial concentration of the sucrose can be about 40, 50, 60, 70, 80, 90, 100, 110, 120, 130, 140, 150, or 160 g/L (or any integer between 40 and 160 g/L), for example. The "initial concentration of sucrose" refers to the sucrose concentration in the solution just after all the reaction solution components have been added (water, sucrose, gtf enzyme).

Sucrose used in the reaction solution can be highly pure (≥99.5%) or be of any other purity or grade. For example, the sucrose can have a purity of at least 99.0%, or be reagent grade sucrose. The sucrose may be derived from any renewable sugar source such as sugar cane, sugar beets, cassava, sweet sorghum, or corn. The sucrose can be provided in any form such as crystalline form or non-crystalline form (e.g., syrup or cane juice).

The pH of the reaction solution herein can be between about 4.0 to about 8.0. Alternatively, the pH can be about 4.0, 4.5, 5.0, 5.5, 6.0, 6.5, 7.0, 7.5, or 8.0. In certain embodiments, the pH of a solution containing water and sucrose may be set before adding the glucosyltransferase enzyme. The pH of the reaction solution can be adjusted or controlled by the addition or incorporation of a suitable buffer, including but not limited to: phosphate, tris, citrate, or a combination thereof. The concentration of the buffer can be from 0 mM to about 100 mM, or about 10, 20, or 50 mM, for example. A suitable amount of DTT (dithiothreitol, e.g., about 1.0 mM) can optionally be added to the reaction solution.

The disclosed invention also concerns a method for producing poly alpha-1,3-glucan comprising the step of contacting at least water, sucrose, and a glucosyltransferase enzyme that synthesizes poly alpha-1,3-glucan. The glucosyltransferase enzyme can comprise an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. The poly alpha-1,3-glucan produced in this method can optionally be isolated.

Water, sucrose, and a glucosyltransferase enzyme as described herein are contacted in a reaction solution. Thus, the method can comprise providing a reaction solution comprising water, sucrose and a glucosyltransferase enzyme as described herein. It will be understood that, as the glucosyltransferase enzyme synthesizes poly alpha-1,3-glucan, the reaction solution becomes a reaction mixture given that insoluble poly alpha-1,3-glucan falls out of solution as indicated by clouding of the reaction. The contacting step of the disclosed method can be performed in any number of ways. For example, the desired amount of sucrose can first be dissolved in water (optionally, other components may also be added at this stage of preparation, such as buffer components), followed by the addition of the glucosyltransferase enzyme. The solution may be kept still, or agitated via stirring or orbital shaking, for example. The reaction can be, and typically is, cell-free.

The glucosyltransferase enzyme can optionally be added to water or an aqueous solution (e.g., sucrose in water) that does not contain salt or buffer when initially preparing the reaction solution. The pH of such a preparation can then be modified as desired, such as to pH 5-6 for example. The reaction can be carried out to completion without any added buffer, if desired.

Completion of the reaction in certain embodiments can be determined visually (no more accumulation of precipitated poly alpha-1,3-glucan) and/or by measuring the amount of sucrose left in the solution (residual sucrose), where a percent sucrose consumption of over about 90% can indicate reaction completion. Typically, a reaction of the disclosed process will take about 12, 24, 36, 48, 60, 72, 84, or 96 hours to complete, depending on certain parameters such as the amount of sucrose and glucosyltransferase enzyme used in the reaction.

The percent sucrose consumption of a reaction in certain embodiments of the disclosed process is at least 90%, 91%, 92%, 93%, 94%, 95%, 96%, 97%, 98%, 99%, or 100%. Alternatively, the percent sucrose consumption may be >90% or >95%.

The yield of the poly alpha-1,3-glucan produced in the disclosed invention can be at least about 5%, 6%, 7%, 8%, 9%, 10%, 11%, 12%, 13%, 14%, 15%, 16%, 17%, 18%, 19%, or 20%, based on the weight of the sucrose used in the reaction solution.

The poly alpha-1,3-glucan produced in the disclosed method may optionally be isolated. For example, insoluble poly alpha-1,3-glucan may be separated by centrifugation or filtration. In doing so, the poly alpha-1,3-glucan is separated from the rest of the reaction solution, which may comprise water, fructose and certain byproducts (e.g., leucrose, soluble oligosaccharides DP2-DP7). This solution may also comprise residual sucrose and glucose monomer.

Poly alpha-1,3 glucan is a potentially low cost polymer which can be enzymatically produced from renewable resources containing sucrose using glucosyltransferase enzymes. It has been shown that this polymer can form ordered liquid crystalline solutions when the polymer is dissolved in a solvent under certain conditions (U.S. Pat. No. 7,000,000). Such solutions can be spun into continuous, high strength, cotton-like fibers. The poly alpha-1,3-glucan produced using the disclosed invention has comparable utilities.

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meanings of some of the abbreviations used herein are as follows: "g" means gram(s), "h" means hour(s), "mL" means milliliter(s), "psi" means pound(s) per square inch, "wt %" means weight percentage, "µm" means micrometer(s), "° C." means degrees Celsius, "mg" means milligram(s), "mm" means millimeter(s), "µL" means microliter(s), "mmol" means millimole(s), "min" means minute(s), "mol %" means mole percent, "M" means molar, "rpm" means revolutions per minute, "MPa" means megaPascals.

General Methods

Preparation of Crude Extracts of Glucosyltransferase (gtf) Enzymes

Gtf enzymes were prepared as follows. $E.\ coli$ TOP10® cells (Invitrogen, Carlsbad Calif.) were transformed with a pJexpress404®-based construct containing a particular gtf-encoding DNA sequence. Each sequence was codon-optimized to express the gtf enzyme in $E.\ coli$. Individual $E.\ coli$ strains expressing a particular gtf enzyme were grown in LB (Luria broth) medium (Becton, Dickinson and Company, Franklin Lakes, N.J.) with ampicillin (100 µg/mL) at 37° C. with shaking to $OD_{600}$=0.4-0.5, at which time IPTG (isopropyl beta-D-1-thiogalactopyranoside, Cat. No. 16758, Sigma-Aldrich, St. Louis, Mo.) was added to a final concentration of 0.5 mM. The cultures were incubated for 2-4 hours at 37° C. following IPTG induction. Cells were harvested by centrifugation at 5,000×g for 15 minutes and resuspended (20% w/v) in 50 mM phosphate buffer pH 7.0 supplemented with dithiothreitol (DTT, 1.0 mM). Resuspended cells were passed through a French Pressure Cell (SLM Instruments, Rochester, N.Y.) twice to ensure >95% cell lysis. Lysed cells were centrifuged for 30 minutes at 12,000×g at 4° C. The resulting supernatant was analyzed by the BCA (bicinchoninic acid)

protein assay (Sigma-Aldrich) and SDS-PAGE to confirm expression of the gtf enzyme, and the supernatant was stored at −20° C.

Determination of Gtf Enzymatic Activity

Gtf enzyme activity was confirmed by measuring the production of reducing sugars (fructose and glucose) in a gtf reaction solution. A reaction solution was prepared by adding a gtf extract (prepared as above) to a mixture containing sucrose (50 or 150 g/L), potassium phosphate buffer (pH 6.5, 50 mM), and optionally dextran (1 mg/mL, dextran T10, Cat. No. D9260, Sigma-Aldrich); the gtf extract was added to 2.5%-5% by volume. The reaction solution was then incubated at 22-25° C. for 24-30 hours, after which it was centrifuged. Supernatant (0.01 mL) was added to a mixture containing 1 N NaOH and 0.1% triphenyltetrazolium chloride (Sigma-Aldrich). The mixture was incubated for five minutes after which its $OD_{480\,nm}$ was determined using an ULTROSPEC spectrophotometer (Pharmacia LKB, New York, N.Y.) to gauge the presence of the reducing sugars fructose and glucose.

Determination of Glycosidic Linkages

Glycosidic linkages in the glucan product synthesized by a gtf enzyme were determined by $^{13}C$ NMR (nuclear magnetic resonance). Dry glucan polymer (25-30 mg) was dissolved in 1 mL of deuterated dimethyl sulfoxide (DMSO) containing 3% by weight of LiCl with stirring at 50° C. Using a glass pipet, 0.8 mL of the solution was transferred into a 5-mm NMR tube. A quantitative $^{13}C$ NMR spectrum was acquired using a Bruker Avance 500-MHz NMR spectrometer (Billerica, Mass.) equipped with a CPDUL cryoprobe at a spectral frequency of 125.76 MHz, using a spectral window of 26041.7 Hz. An inverse gated decoupling pulse sequence using waltz decoupling was used with an acquisition time of 0.629 second, an inter-pulse delay of 5 seconds, and 6000 pulses. The time domain data was transformed using an exponential multiplication of 2.0 Hz.

Determination of Number Average Degree of Polymerization DP

The $DP_n$ of a glucan product synthesized by a gtf enzyme was determined by size-exclusion chromatography (SEC). Dry glucan polymer was dissolved at 5 mg/mL in N,N-dimethyl-acetamide (DMAc) and 5% LiCl with overnight shaking at 100° C. The SEC system used was an Alliance™ 2695 separation module from Waters Corporation (Milford, Mass.) coupled with three on-line detectors: a differential refractometer 2410 from Waters, a multiangle light scattering photometer Heleos™ 8+ from Wyatt Technologies (Santa Barbara, Calif.), and a differential capillary viscometer ViscoStar™ from Wyatt. The columns used for SEC were four styrene-divinyl benzene columns from Shodex (Japan) and two linear KD-806M, KD-802 and KD-801 columns to improve resolution at the low molecular weight region of a polymer distribution. The mobile phase was DMAc with 0.11% LiCl. The chromatographic conditions used were 50° C. in the column and detector compartments, 40° C. in the sample and injector compartment, a flow rate of 0.5 mL/min, and an injection volume of 100 μL. The software packages used for data reduction were Empower™ version 3 from Waters (calibration with broad glucan polymer standard) and Astra® version 6 from Wyatt (triple detection method with column calibration).

Example 1

Production of Gtf Enzyme 0874 (SEQ ID NO:2)

This Example describes preparing an N-terminally truncated version of a *Streptococcus sobrinus* gtf enzyme identified in GENBANK under GI number 450874 (SEQ ID NO:2, encoded by SEQ ID NO:1; herein referred to as "0874").

A nucleotide sequence encoding gtf 0874 was synthesized using codons optimized for protein expression in *E. coli* (DNA2.0, Inc., Menlo Park, Calif.). The nucleic acid product (SEQ ID NO:1), encoding gtf 0874 (SEQ ID NO:2), was subcloned into pJexpress404® (DNA2.0, Inc.) to generate the plasmid construct identified as pMP57. This plasmid construct was used to transform *E. coli* TOP10 cells (Invitrogen, Carlsbad, Calif.) to generate the strain identified as TOP10/pMP57.

Production of gtf 0874 by bacterial expression and determination of its enzymatic activity were performed following the procedures disclosed in the General Methods section. The enzymatic activity of gtf 0874 is shown in Table 2 (see Example 18 below).

Example 2

Production of Gtf Enzyme 6855 (SEQ ID NO:4)

This Example describes preparing an N-terminally truncated version of a *Streptococcus salivarius* gtf enzyme identified in GENBANK under GI number 228476855 (SEQ ID NO:4, encoded by SEQ ID NO:3; herein referred to as "6855").

A nucleotide sequence encoding gtf 6855 was synthesized using codons optimized for protein expression in *E. coli* (DNA2.0, Inc.). The nucleic acid product (SEQ ID NO:3), encoding gtf 6855 (SEQ ID NO:4), was subcloned into pJexpress404® to generate the plasmid construct identified as pMP53. This plasmid construct was used to transform *E. coli* TOP10 cells to generate the strain identified as TOP10/pMP53.

Production of gtf 6855 by bacterial expression and determination of its enzymatic activity were performed following the procedures disclosed in the General Methods section. The enzymatic activity of gtf 6855 is shown in Table 2 (see Example 18 below).

Example 3

Production of Gtf Enzyme 2379 (SEQ ID NO:6)

This Example describes preparing an N-terminally truncated version of a *Streptococcus salivarius* gtf enzyme identified in GENBANK under GI number 662379 (SEQ ID NO:6, encoded by SEQ ID NO:5; herein referred to as "2379").

A nucleotide sequence encoding gtf 2379 was synthesized using codons optimized for protein expression in *E. coli* (DNA2.0, Inc.). The nucleic acid product (SEQ ID NO:5), encoding gtf 2379 (SEQ ID NO:6), was subcloned into pJexpress404® to generate the plasmid construct identified as pMP66. This plasmid construct was used to transform *E. coli* TOP10 cells to generate the strain identified as TOP10/pMP66.

Production of gtf 2379 by bacterial expression and determination of its enzymatic activity were performed following the procedures disclosed in the General Methods section. The enzymatic activity of gtf 2379 is shown in Table 2 (see Example 18 below).

Example 4

Production of Gtf Enzyme 7527 (GtfJ, SEQ ID NO:8)

This Example describes preparing an N-terminally truncated version of a *Streptococcus salivarius* gtf enzyme identified in GENBANK under GI number 47527 (SEQ ID NO:8, encoded by SEQ ID NO:7; herein referred to as "7527" or "GtfJ").

A nucleotide sequence encoding gtf 7527 was synthesized using codons optimized for protein expression in *E. coli* (DNA2.0, Inc.). The nucleic acid product (SEQ ID NO:7), encoding gtf 7527 (SEQ ID NO:8), was subcloned into pJexpress404® to generate the plasmid construct identified as pMP65. This plasmid construct was used to transform *E. coli* TOP10 cells to generate the strain identified as TOP10/pMP65.

Production of gtf 7527 by bacterial expression and determination of its enzymatic activity were performed following the procedures disclosed in the General Methods section. The enzymatic activity of gtf 7527 is shown in Table 2 (see Example 18 below).

Example 5

Production of Gtf Enzyme 1724 (SEQ ID NO:10)

This Example describes preparing an N-terminally truncated version of a *Streptococcus downei* gtf enzyme identified in GENBANK under GI number 121724 (SEQ ID NO:10, encoded by SEQ ID NO:9; herein referred to as "1724").

A nucleotide sequence encoding gtf 1724 was synthesized using codons optimized for protein expression in *E. coli* (DNA2.0, Inc.). The nucleic acid product (SEQ ID NO:9), encoding gtf 1724 (SEQ ID NO:10), was subcloned into pJexpress404® to generate the plasmid construct identified as pMP52. This plasmid construct was used to transform *E. coli* TOP10 cells to generate the strain identified as TOP10/pMP52.

Production of gtf 1724 by bacterial expression and determination of its enzymatic activity were performed following the procedures disclosed in the General Methods section. The enzymatic activity of gtf 1724 is shown in Table 2 (see Example 18 below).

Example 6

Production of Gtf Enzyme 0544 (SEQ ID NO:12)

This Example describes preparing an N-terminally truncated version of a *Streptococcus mutans* gtf enzyme identified in GENBANK under GI number 290580544 (SEQ ID NO:12, encoded by SEQ ID NO:11; herein referred to as "0544").

A nucleotide sequence encoding gtf 0544 was synthesized using codons optimized for protein expression in *E. coli* (DNA2.0, Inc.). The nucleic acid product (SEQ ID NO:11), encoding gtf 0544 (SEQ ID NO:12), was subcloned into pJexpress404® to generate the plasmid construct identified as pMP55. This plasmid construct was used to transform *E. coli* TOP10 cells to generate the strain identified as TOP10/pMP55.

Production of gtf 0544 by bacterial expression and determination of its enzymatic activity were performed following the procedures disclosed in the General Methods section. The enzymatic activity of gtf 0544 is shown in Table 2 (see Example 18 below).

Example 7

Production of Gtf Enzyme 5926 (SEQ ID NO:14)

This Example describes preparing an N-terminally truncated version of a *Streptococcus dentirousetti* gtf enzyme identified in GENBANK under GI number 167735926 (SEQ ID NO:14, encoded by SEQ ID NO:13; herein referred to as "5926").

A nucleotide sequence encoding gtf 5926 was synthesized using codons optimized for protein expression in *E. coli* (DNA2.0, Inc.). The nucleic acid product (SEQ ID NO:13), encoding gtf 5926 (SEQ ID NO:14), was subcloned into pJexpress404® to generate the plasmid construct identified as pMP67. This plasmid construct was used to transform *E. coli* TOP10 cells to generate the strain identified as TOP10/pMP67.

Production of gtf 5926 by bacterial expression and determination of its enzymatic activity were performed following the procedures disclosed in the General Methods section. The enzymatic activity of gtf 5926 is shown in Table 2 (see Example 18 below).

Example 8

Production of Gtf Enzyme 4297 (SEQ ID NO:16)

This Example describes preparing an N-terminally truncated version of a *Streptococcus oralis* gtf enzyme identified in GENBANK under GI number 7684297 (SEQ ID NO:16, encoded by SEQ ID NO:15; herein referred to as "4297").

A nucleotide sequence encoding gtf 4297 was synthesized using codons optimized for protein expression in *E. coli* (DNA2.0, Inc.). The nucleic acid product (SEQ ID NO:15), encoding gtf 4297 (SEQ ID NO:16), was subcloned into pJexpress404® to generate the plasmid construct identified as pMP62. This plasmid construct was used to transform *E. coli* TOP10 cells to generate the strain identified as TOP10/pMP62.

Production of gtf 4297 by bacterial expression and determination of its enzymatic activity were performed following the procedures disclosed in the General Methods section. The enzymatic activity of gtf 4297 is shown in Table 2 (see Example 18 below).

Example 9

Production of Gtf Enzyme 5618 (SEQ ID NO:18)

This Example describes preparing an N-terminally truncated version of a *Streptococcus sanguinis* gtf enzyme identified in GENBANK under GI number 328945618 (SEQ ID NO:18, encoded by SEQ ID NO:17; herein referred to as "5618").

A nucleotide sequence encoding gtf 5618 was synthesized using codons optimized for protein expression in *E. coli* (DNA2.0, Inc.). The nucleic acid product (SEQ ID NO:17), encoding gtf 5618 (SEQ ID NO:18), was subcloned into pJexpress404® to generate the plasmid construct identified as pMP56. This plasmid construct was used to transform *E. coli* TOP10 cells to generate the strain identified as TOP10/pMP56.

Production of gtf 5618 by bacterial expression and determination of its enzymatic activity were performed following the procedures disclosed in the General Methods section. The enzymatic activity of gtf 5618 is shown in Table 2 (see Example 18 below).

Example 10

Production of Gtf Enzyme 2765 (SEQ ID NO:20)

This Example describes preparing an N-terminally truncated version of a *Streptococcus* sp. gtf enzyme identified in GENBANK under GI number 322372765 (SEQ ID NO:20, encoded by SEQ ID NO:19; herein referred to as "2765").

A nucleotide sequence encoding gtf 2765 was synthesized using codons optimized for protein expression in *E. coli* (DNA2.0, Inc.). The nucleic acid product (SEQ ID NO:19), encoding gtf 2765 (SEQ ID NO:20), was subcloned into pJexpress404® to generate the plasmid construct identified as pMP73. This plasmid construct was used to transform *E. coli* TOP10 cells to generate the strain identified as TOP10/pMP73.

Production of gtf 2765 by bacterial expression and determination of its enzymatic activity were performed following the procedures disclosed in the General Methods section. The enzymatic activity of gtf 2765 is shown in Table 2 (see Example 18 below).

Example 11

Production of Gtf Enzyme 4700 (SEQ ID NO:22)

This Example describes preparing an N-terminally truncated version of a *Leuconostoc mesenteroides* gtf enzyme identified in GENBANK under GI number 21654700 (SEQ ID NO:22, encoded by SEQ ID NO:21; herein referred to as "4700").

A nucleotide sequence encoding gtf 2765 was synthesized using codons optimized for protein expression in *E. coli* (DNA2.0, Inc.). The nucleic acid product (SEQ ID NO:21), encoding gtf 4700 (SEQ ID NO:22), was subcloned into pJexpress404® to generate the plasmid construct identified as pMP83. This plasmid construct was used to transform *E. coli* TOP10 cells to generate the strain identified as TOP10/pMP83.

Production of gtf 4700 by bacterial expression and determination of its enzymatic activity were performed following the procedures disclosed in the General Methods section. The enzymatic activity of gtf 4700 is shown in Table 2 (see Example 18 below).

Example 12

Production of Gtf Enzyme 1366 (SEQ ID NO:24)

This Example describes preparing an N-terminally truncated version of a *Streptococcus criceti* gtf enzyme identified in GENBANK under GI number 146741366 (SEQ ID NO:24, encoded by SEQ ID NO:23; herein referred to as "1366").

A nucleotide sequence encoding gtf 1366 was synthesized using codons optimized for protein expression in *E. coli* (DNA2.0, Inc.). The nucleic acid product (SEQ ID NO:23), encoding gtf 1366 (SEQ ID NO:24), was subcloned into pJexpress404® to generate the plasmid construct identified as pMP86. This plasmid construct was used to transform *E. coli* TOP10 cells to generate the strain identified as TOP10/pMP86.

Production of gtf 1366 by bacterial expression and determination of its enzymatic activity were performed following the procedures disclosed in the General Methods section. The enzymatic activity of gtf 1366 is shown in Table 2 (see Example 18 below).

Example 13

Production of Gtf Enzyme 0427 (SEQ ID NO:26)

This Example describes preparing an N-terminally truncated version of a *Streptococcus sobrinus* gtf enzyme identified in GENBANK under GI number 940427 (SEQ ID NO:26, encoded by SEQ ID NO:25; herein referred to as "0427").

A nucleotide sequence encoding gtf 0427 was synthesized using codons optimized for protein expression in *E. coli* (DNA2.0, Inc.). The nucleic acid product (SEQ ID NO:25), encoding gtf 0427 (SEQ ID NO:26), was subcloned into pJexpress404® to generate the plasmid construct identified as pMP87. This plasmid construct was used to transform *E. coli* TOP10 cells to generate the strain identified as TOP10/pMP87.

Production of gtf 0427 by bacterial expression and determination of its enzymatic activity were performed following the procedures disclosed in the General Methods section. The enzymatic activity of gtf 0427 is shown in Table 2 (see Example 18 below).

Example 14

Production of Gtf Enzyme 2919 (SEQ ID NO:28)

This Example describes preparing an N-terminally truncated version of a *Streptococcus salivarius* gtf enzyme identified in GENBANK under GI number 383282919 (SEQ ID NO:28, encoded by SEQ ID NO:27; herein referred to as "2919").

A nucleotide sequence encoding gtf 2919 was synthesized using codons optimized for protein expression in *E. coli* (DNA2.0, Inc.). The nucleic acid product (SEQ ID NO:27), encoding gtf 2919 (SEQ ID NO:28), was subcloned into pJexpress404® to generate the plasmid construct identified as pMP88. This plasmid construct was used to transform *E. coli* TOP10 cells to generate the strain identified as TOP10/pMP88.

Production of gtf 2919 by bacterial expression and determination of its enzymatic activity were performed following the procedures disclosed in the General Methods section. The enzymatic activity of gtf 2919 is shown in Table 2 (see Example 18 below).

Example 15

Production of Gtf Enzyme 2678 (SEQ ID NO:30)

This Example describes preparing an N-terminally truncated version of a *Streptococcus salivarius* gtf enzyme identified in GENBANK under GI number 400182678 (SEQ ID NO:30 encoded by SEQ ID NO:29; herein referred to as "2678").

A nucleotide sequence encoding gtf 2678 was synthesized using codons optimized for protein expression in *E. coli* (DNA2.0, Inc.). The nucleic acid product (SEQ ID NO:29), encoding gtf 2678 (SEQ ID NO:30), was subcloned into pJexpress404® to generate the plasmid construct identified as pMP89. This plasmid construct was used to transform *E. coli* TOP10 cells to generate the strain identified as TOP10/pMP89.

Production of gtf 2678 by bacterial expression and determination of its enzymatic activity were performed following the procedures disclosed in the General Methods section. The enzymatic activity of gtf 2678 is shown in Table 2 (see Example 18 below).

Example 16

Production of Gtf Enzyme 2381 (SEQ ID NO:32)

This Example describes preparing an N-terminally truncated version of a *Streptococcus salivarius* gtf enzyme identified in GENBANK under GI number 662381 (SEQ ID NO:32 encoded by SEQ ID NO:31; herein referred to as "2381").

A nucleotide sequence encoding gtf 2381 was synthesized using codons optimized for protein expression in *E. coli* (DNA2.0, Inc.). The nucleic acid product (SEQ ID NO:31), encoding gtf 2381 (SEQ ID NO:32), was subcloned into pJexpress404® to generate the plasmid construct identified as pMP96. This plasmid construct was used to transform *E. coli* TOP10 cells to generate the strain identified as TOP10/pMP96.

Production of gtf 2381 by bacterial expression and determination of its enzymatic activity were performed following the procedures disclosed in the General Methods section. The enzymatic activity of gtf 2381 is shown in Table 2 (see Example 18 below).

Example 17

Production of Gtf Enzyme 3929 (SEQ ID NO:34) and Additional Gtf Enzymes

This Example describes preparing an N-terminally truncated version of a *Streptococcus salivarius* gtf enzyme identified in GENBANK under GI number 387783929 (SEQ ID NO:34 encoded by SEQ ID NO:33; herein referred to as "3929").

A nucleotide sequence encoding gtf 3929 was synthesized using codons optimized for protein expression in *E. coli* (DNA2.0, Inc.). The nucleic acid product (SEQ ID NO:33), encoding gtf 3929 (SEQ ID NO:34), was subcloned into pJexpress404® to generate the plasmid construct identified as pMP97. This plasmid construct was used to transform *E. coli* TOP10 cells to generate the strain identified as TOP10/pMP97.

Production of gtf 3929 by bacterial expression and determination of its enzymatic activity were performed following the procedures disclosed in the General Methods section. The enzymatic activity of gtf 3929 is shown in Table 2 (see Example 18 below).

Additional gtf enzymes were produced in a similar manner. Briefly, N-terminally truncated versions of enzymes identified in GENBANK under GI numbers 228476907 (a *Streptococcus salivarius* gtf, SEQ ID NO:36, herein referred to as "6907"), 228476661 (a *Streptococcus salivarius* gtf, SEQ ID NO:38, herein referred to as "6661"), 334280339 (a *Streptococcus gallolyticus* gtf, SEQ ID NO:40, herein referred to as "0339"), 3130088 (a *Streptococcus mutans* gtf, SEQ ID NO:42, herein referred to as "0088"), 24379358 (a *Streptococcus mutans* gtf, SEQ ID NO:44, herein referred to as "9358"), 325978242 (a *Streptococcus gallolyticus* gtf, SEQ ID NO:46, herein referred to as "8242"), 324993442 (a *Streptococcus sanguinis* gtf, SEQ ID NO:48, herein referred to as "3442"), 47528 (a *Streptococcus salivarius* gtf, SEQ ID NO:50, herein referred to as "7528"), 322373279 (a *Streptococcus* sp. gtf, SEQ ID NO:52, herein referred to as "3279"), 170016491 (a *Leuconostoc citreum* gtf, SEQ ID NO:54, herein referred to as "6491"), 228476889 (a *Streptococcus salivarius* gtf, SEQ ID NO:56, herein referred to as "6889"), 51574154 (a *Lactobacillus reuteri* gtf, SEQ ID NO:58, herein referred to as "4154"), and 322373298 (a *Streptococcus* sp. gtf, SEQ ID NO:59, herein referred to as "3298") were prepared and tested for enzymatic activity (Table 2, see Example 18 below).

Example 18

Production of Insoluble Glucan Polymer with Gtf Enzymes

This Example describes using the gtf enzymes prepared in the above Examples to synthesize glucan polymer.

Reactions were performed with each of the above gtf enzymes following the procedures disclosed in the General Methods section. Briefly, gtf reaction solutions were prepared comprising sucrose (50 g/L), potassium phosphate buffer (pH 6.5, 50 mM) and a gtf enzyme (2.5% extract by volume). After 24-30 hours at 22-25° C., insoluble glucan polymer product was harvested by centrifugation, washed three times with water, washed once with ethanol, and dried at 50° C. for 24-30 hours.

Following the procedures disclosed in the General Methods section, the glycosidic linkages in the insoluble glucan polymer product from each reaction were determined by $^{13}C$ NMR, and the $DP_n$ for each product was determined by SEC. The results of these analyses are shown in Table 2.

TABLE 2

Linkages and $DP_n$ of Glucan Produced by Various Gtf Enzymes

| Gtf | SEQ ID NO. | Reducing Sugars Produced? | Insoluble Glucan Produced? | Glucan Alpha Linkages %1,3 | %1,6 | $DP_n$ |
|---|---|---|---|---|---|---|
| 0874 | 2 | yes | yes | 100 | 0 | 60 |
| 6855 | 4 | yes | yes | 100 | 0 | 440 |
| 2379 | 6 | yes | yes | 37 | 63 | 310 |
| 7527 | 8 | yes | yes | 100 | 0 | 440 |
| 1724 | 10 | yes | yes | 100 | 0 | 250 |
| 0544 | 12 | yes | yes | 62 | 36 | 980 |
| 5926 | 14 | yes | yes | 100 | 0 | 260 |
| 4297 | 16 | yes | yes | 31 | 67 | 800 |
| 5618 | 18 | yes | yes | 34 | 66 | 1020 |
| 2765 | 20 | yes | yes | 100 | 0 | 280 |
| 4700 | 22 | yes | no | | | |
| 1366 | 24 | yes | no | | | |
| 0427 | 26 | yes | yes | 100 | 0 | 120 |
| 2919 | 28 | yes | yes | 100 | 0 | 250 |
| 2678 | 30 | yes | yes | 100 | 0 | 390 |
| 2381 | 32 | yes | no | | | |
| 3929 | 34 | yes | yes | 100 | 0 | 280 |
| 6907 | 36 | yes | no | | | |
| 6661 | 38 | yes | no | | | |
| 0339 | 40 | yes | no | | | |
| 0088 | 42 | yes | no | | | |
| 9358 | 44 | yes | no | | | |
| 8242 | 46 | yes | no | | | |
| 3442 | 48 | yes | no | | | |
| 7528 | 50 | yes | no | | | |
| 3279 | 52 | yes | no | | | |
| 6491 | 54 | yes | no | | | |
| 6889 | 56 | yes | no | | | |
| 4154 | 58 | yes | no | | | |
| 3298 | 59 | yes | no | | | |
| none | na | no | no | | | |

Several gtf enzymes produced insoluble glucan products (Table 2). However, only gtf enzymes 6855 (SEQ ID NO:4), 7527 (gtfJ, SEQ ID NO:8), 1724 (SEQ ID NO:10), 0544 (SEQ ID NO:12), 5926 (SEQ ID NO:14), 2765 (SEQ ID NO:20), 0427 (SEQ ID NO:26), 2919 (SEQ ID NO:28), 2678 (SEQ ID NO:30), and 3929 (SEQ ID NO:34) produced glucan comprising at least 50% alpha-1,3 linkages and having a $DP_n$ of at least 100. These enzymes are therefore suitable for producing glucan polymers for fiber applications.

Only gtfs 6855 (SEQ ID NO:4), 7527 (gtfJ, SEQ ID NO:8), 1724 (SEQ ID NO:10), 5926 (SEQ ID NO:14), 2765 (SEQ ID NO:20), 0427 (SEQ ID NO:26), 2919 (SEQ ID NO:28), 2678 (SEQ ID NO:30), and 3929 (SEQ ID NO:34) produced glucan polymer comprising 100% alpha-1,3 linkages and having a $DP_n$ of at least 100. These results, in which only nine out of thirty gtfs were able to produce glucan with 100% alpha-1,3 linkages and a $DP_n$ of at least 100, indicate that not all gtf enzymes are capable of producing high molecular weight, insoluble glucan with a high level of alpha-1,3 linkages.

Fewer gtf enzymes were able to produce glucan polymer comprising 100% alpha-1,3 linkages and having a $DP_n$ of at least 250.

Thus, gtf enzymes capable of producing glucan polymer comprising 100% alpha-1,3 linkages and a $DP_n$ of at least 100 were identified. These enzymes can be used to produce glucan suitable for producing fibers.

What is claimed is:

1. A reaction solution comprising water, sucrose and a glucosyltransferase enzyme that synthesizes poly alpha-1,3-glucan, wherein said glucosyltransferase enzyme consists of an amino acid sequence that is at least 93% identical to SEQ ID NO:26.

2. The reaction solution of claim 1, wherein said glucosyltransferase enzyme synthesizes poly alpha-1,3-glucan having at least 50% alpha-1,3 glycosidic linkages and a number average degree of polymerization of at least 100.

3. The reaction solution of claim 2, wherein said glucosyltransferase enzyme synthesizes poly alpha-1,3-glucan having 100% alpha-1,3 glycosidic linkages and a number average degree of polymerization of at least 100.

4. The reaction solution of claim 1, further comprising a primer.

5. The reaction solution of claim 4, wherein the primer is dextran.

6. The reaction solution of claim 4, wherein the primer is hydrolyzed glucan.

7. The reaction solution of claim 1, wherein said glucosyltransferase enzyme consists of an amino acid sequence that is at least 94% identical to SEQ ID NO:26.

8. The reaction solution of claim 7, wherein said glucosyltransferase enzyme consists of an amino acid sequence that is at least 95% identical to SEQ ID NO:26.

9. The reaction solution of claim 8, wherein said glucosyltransferase enzyme consists of an amino acid sequence that is at least 99% identical to SEQ ID NO:26.

10. The reaction solution of claim 1, wherein a heterologous amino acid sequence of 1-300 residues is at the N-terminus and/or C-terminus of said glucosyltransferase enzyme.

11. A method for producing poly alpha-1,3-glucan comprising:

a) contacting at least water, sucrose, and a glucosyltransferase enzyme that synthesizes poly alpha-1,3-glucan, wherein said glucosyltransferase enzyme consists of an amino acid sequence that is at least 93% identical to SEQ ID NO:26;
whereby poly alpha-1,3-glucan is produced; and
b) optionally, isolating the poly alpha-1,3-glucan produced in step (a).

12. The method of claim 11, wherein said glucosyltransferase enzyme synthesizes poly alpha-1,3-glucan having at least 50% alpha-1,3 glycosidic linkages and a number average degree of polymerization of at least 100.

13. The method of claim 12, wherein said glucosyltransferase enzyme synthesizes poly alpha-1,3-glucan having 100% alpha-1,3 glycosidic linkages and a number average degree of polymerization of at least 100.

14. The method of claim 11, wherein step (a) further comprises contacting a primer with the water, sucrose, and glucosyltransferase enzyme.

15. The method of claim 14, wherein the primer is dextran.

16. The method of claim 14, wherein the primer is hydrolyzed glucan.

17. The method of claim 11, wherein said glucosyltransferase enzyme consists of an amino acid sequence that is at least 94% identical to SEQ ID NO:26.

18. The method of claim 17, wherein said glucosyltransferase enzyme consists of an amino acid sequence that is at least 95% identical to SEQ ID NO:26.

19. The method of claim 18, wherein said glucosyltransferase enzyme consists of an amino acid sequence that is at least 99% identical to SEQ ID NO:26.

20. The method of claim 11, wherein a heterologous amino acid sequence of 1-300 residues is at the N-terminus and/or C-terminus of said glucosyltransferase enzyme.

* * * * *